(12) United States Patent
Liang et al.

(10) Patent No.: US 11,274,079 B2
(45) Date of Patent: Mar. 15, 2022

(54) 2-(2,2-DIARYLETHYL)-CYCLIC AMINE DERIVATIVE OR SALT, SYNTHESIS METHOD, APPLICATION AND COMPOSITION THEREOF

(71) Applicant: DALIAN INSTITUTE OF CHEMICAL PHYSICS, CHINESE ACADEMY OF SCIENCES, Liaoning (CN)

(72) Inventors: Xinmiao Liang, Liaoning (CN); Yaopeng Zhao, Liaoning (CN); Yanfang Liu, Liaoning (CN); Jixia Wang, Liaoning (CN); Changjian Wang, Liaoning (CN); Zhiwei Wang, Liaoning (CN); Nana Du, Liaoning (CN); Xiuli Zhang, Liaoning (CN); Zhimou Guo, Liaoning (CN); Chaoran Wang, Liaoning (CN)

(73) Assignee: Dalian Institute of Chemical Physics, Chinese Academy of Sciences, Liaoning (CN)

( * ) Notice: Subject to any disclaimer, the term of this patent is extended or adjusted under 35 U.S.C. 154(b) by 0 days.

(21) Appl. No.: 17/047,357

(22) PCT Filed: Apr. 11, 2019

(86) PCT No.: PCT/CN2019/082224
§ 371 (c)(1),
(2) Date: Oct. 13, 2020

(87) PCT Pub. No.: WO2019/196898
PCT Pub. Date: Oct. 17, 2019

(65) Prior Publication Data
US 2021/0155591 A1  May 27, 2021

(30) Foreign Application Priority Data
Apr. 12, 2018 (CN) .......................... 201810325578.2

(51) Int. Cl.
| C07D 211/22 | (2006.01) |
| A61P 11/06 | (2006.01) |
| C07D 207/08 | (2006.01) |
| C07D 211/14 | (2006.01) |
| C07D 409/06 | (2006.01) |

(52) U.S. Cl.
CPC ............ *C07D 211/22* (2013.01); *A61P 11/06* (2018.01); *C07D 207/08* (2013.01); *C07D 211/14* (2013.01); *C07D 409/06* (2013.01)

(58) Field of Classification Search
None
See application file for complete search history.

(56) References Cited

U.S. PATENT DOCUMENTS

| 2,769,812 A | 11/1956 | Ruddy |
| 3,252,982 A | 5/1966 | Mizzoni et al. |
| 3,252,983 A * | 5/1966 | Renat .................. C07D 207/27 546/231 |
| 3,446,901 A | 5/1969 | Geraint |
| 4,125,531 A | 11/1978 | Yen |
| 5,382,600 A | 1/1995 | Joensson et al. |
| 5,559,269 A | 9/1996 | Johansson et al. |
| 6,313,132 B1 | 11/2001 | Johansson et al. |
| 2003/0158176 A1 | 8/2003 | Richards et al. |

FOREIGN PATENT DOCUMENTS

| CN | 107129453 A | 9/2017 |
| DE | 1216318 B | 5/1966 |
| GB | 1169944 A | 11/1969 |
| GB | 1169945 A | 11/1969 |
| SE | 215499 C1 | 9/1967 |
| WO | 8906644 A1 | 7/1989 |
| WO | 9316044 A1 | 8/1993 |
| WO | 9411337 A1 | 5/1994 |
| WO | 9745423 A1 | 12/1997 |
| WO | 0234245 A2 | 5/2002 |
| WO | 03035599 A1 | 5/2003 |
| WO | 2004091607 A1 | 10/2004 |

OTHER PUBLICATIONS

Hans Postlind et al, "Tolterodine, A New Muscarinic Receptor Antagonist, Is Metabolized by Cytochromes P450 2D6 and 3A in Human Liver Microsomes", Drug Metabolism and Disposition, vol. 26 Issue 4, pp. 289-293, Apr. 1, 1998.

Charles H. Tilford et al., "Diuretics. α, α-Disubstituted 2-Piperidine-ethanols and 3, 3-Disubstituted Octahydropyrid[1,2-c]ozazines", Journal of the American Chemical Society, vol. 76, issue 9, pp. 2431-2441, May 1, 1954.

* cited by examiner

*Primary Examiner* — Samantha L Shterengarts
(74) *Attorney, Agent, or Firm* — Novick, Kim & Lee, PLLC; Allen Xue

(57) ABSTRACT

The disclosure relates to a 2-(2,2-diarylethyl)-cyclic amine derivative or salt, a synthesis method, an application and a composition thereof. Biological activity test shows that this kind of 2-(2,2-diarylethyl)-cyclic amine derivative has good M-receptor antagonistic activity; and can be used as an active component of drugs for the treatment of the diseases mediated or regulated by muscarinic receptors, such as asthma, chronic obstructive pulmonary disease (COPD), overactive bladder (OAB), bronchospasm with chronic obstructive pulmonary disease, visceral spasm, irritable bowel syndrome, Parkinson's disease, depression or anxiety, schizophrenia and related mental diseases.

26 Claims, 3 Drawing Sheets

US 11,274,079 B2

2-(2,2-DIARYLETHYL)-CYCLIC AMINE DERIVATIVE OR SALT, SYNTHESIS METHOD, APPLICATION AND COMPOSITION THEREOF

TECHNICAL FIELD

The present invention relates to the field of drug components for the treatment or prevention of diseases associated with M-receptor antagonism, particularly to a 2-(2,2-diarylethyl)cyclic amine derivative and preparation method thereof.

BACKGROUND

Muscarinic acetylcholine receptors (M-receptors) are widely distributed in smooth muscles, cardiac muscles, central and peripheral nerve tissues and various glands, and are divided into 5 subtypes (M1-M5). Studies show that the occurrence and pathological process of many major diseases, such as COPD, asthma, OAB and Parkinson's disease, are closely related to the dysfunction of different subtypes of M-receptor. Therefore, the study of M-receptor antagonists has become one of the hotspots in pharmaceutical research.

3,3-diarylpropylamine derivatives are a kind of widely studied drug intermediates with M-receptor antagonism, which can be used for the treatment of a variety of neuropathic disorders related to M-receptor regulation. WO 2004/091607 and US 2003/0158176 have reported that 3,3-diarylpropylamine derivatives have therapeutic effects on asthma, allergic rhinitis, runny nose caused by common cold, COPD and OAB. Tolterodine, a common commercially available drug for the treatment of urinary incontinence, is also a typical 3,3-diarylpropylamine compound, and synthesis and M-receptor thereof were first reported in U.S. Pat. No. 5,382,600. Drug Metabolism and Disposition, 26(4), 289-293 (1998) and U.S. Pat. No. 5,559,269 reported that the main active metabolite of tolterodine is hydroxytolterodine, which also has a strong M-receptor antagonistic activity and can be used for the treatment of OAB. Patent WO 02/34245 reported that tolterodine can be used for the treatment of asthma, COPD and allergic rhinitis. SE 215499 reported that a secondary amine type 3,3-diphenylpropylamine compound is beneficial to the heart and circulatory system. At the same time, some tertiary amine intermediate compounds with N-aromatic ring substituents were also reported. Patent DE 1216318 reported a diphenylalkylamine compound that is beneficial to the heart and circulatory system. U.S. Pat. No. 3,446,901, GB 1,169,944 and GB 1,169,945 reported that certain 3,3-diphenylpropylamine compounds have antidepressant activity. Patents WO 89/06644 and WO 94/11337 reported that tertiary amine type 3,3-diphenylpropylamine compounds have M-receptor antagonistic activity and can be used for the treatment of OAB. In addition to the structural framework of diphenylpropylamine, U.S. Pat. No. 6,313,132 also replaced one of the benzene rings with various heterocyclic rings, and the resulting 3,3-diarylpropylamine compound also has M-receptor antagonistic activity and can be used for the treatment of urinary incontinence.

In addition to the above-mentioned diaryl propyl type organic amine compounds, similar organic amine compounds with asymmetric ring structure have also been reported. U.S. Pat. No. 4,125,531 reported that 2-(2,2-diphenylethyl)-1-azabicyclo[2.2.2]octane derivative is a useful antidiarrheal agent. Journal of the American Chemical Society, 76(9), 2431-2441 (1954) has reported a series of α,α-diaryl-2-piperidinyl-ethanol compounds, which have diuretic and antifungal properties. However, there is no report about the antagonistic activity of similar diaryl cyclic amine derivatives on M-receptors.

SUMMARY

One of the purposes of the present invention is to propose a 2-(2,2-diarylethyl)-cyclic amine derivative and preparation method therefor, which are suitable for the preparation of pharmaceutical compositions for the treatment of asthma, COPD, OAB, bronchospasm with chronic obstructive pulmonary disease, visceral spasm, irritable bowel syndrome, Parkinson's disease, depression or anxiety, schizophrenia and related mental diseases. In some embodiments, the present invention connects the propyl group in a 3,3-diarylpropylamine derivative with another substituent on a nitrogen atom to form a ring to obtain a kind of 2-(2,2-diarylethyl)-cyclic amine compound with a novel structure, which has the structural characteristics of 3,3-diarylpropylamine and piperidine and other cyclic amines, and exhibits excellent M-receptor antagonistic activity.

One of the advantages of the present invention is that the present invention proposes a kind of 2-(2,2-diarylethyl)-cyclic amine derivative with a novel structure or salt thereof, and the aryl substituent thereof has hydroxyl or hydroxyl derivative functional group at the ortho position of the ethyl group. Biological activity test shows that this kind of compound has good M-receptor antagonistic activity, and the structure-activity relationship shows that the ortho hydroxyl group can significantly enhance this antagonistic activity. Relevant studies and in vitro tracheal activity tests show that this kind of compound can be used as an active component of drugs for the treatment of diseases mediated or regulated by M-receptors.

As shown in the experimental part of the present invention, representative compound of the present invention has highly effective antimuscarinic activity, such as M1 and/or M3 receptor antagonistic activity, and in vitro experiments have shown that this compound has a good diastolic effect on tracheal smooth muscle and has a diastolic effect equal to or better than that of tiotropium bromide ($IC_{50}$=33.0 nM). Therefore, in some aspects, the compound of the present invention can be used for the diastole of tracheal smooth muscle as well as the treatment of diseases related to tracheal smooth muscle. In some aspects, the compound of the present invention can be used for the treatment of asthma, COPD, OAB, bronchospasm with chronic obstructive pulmonary disease, visceral spasm, irritable bowel syndrome, Parkinson's disease, depression or anxiety, schizophrenia and related mental diseases.

The present invention proposes a 2-(2,2-diarylethyl)-cyclic amine derivative. The general formula of the 2-(2,2-diarylethyl)-cyclic amine derivative or pharmaceutically acceptable salt thereof is:

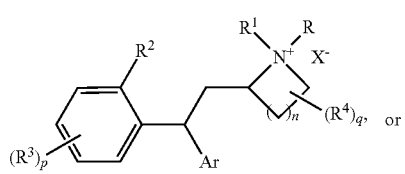

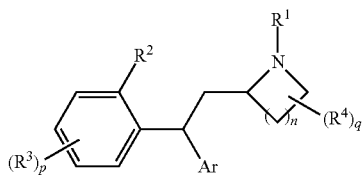

where,

X⁻ is an anion (for example, Cl⁻, Br⁻, I⁻ or the like);

R is hydrogen, substituted or unsubstituted $C_{1-10}$ alkyl;

$R^1$ is substituted or unsubstituted $C_{1-10}$ alkyl;

n is 1, 2, 3, 4 or 5;

$R^2$ is independently hydrogen, —OH, —$CF_3$, —CN, halogen, nitro, amino, substituted or unsubstituted $C_{1-10}$ alkyl, or —O-Pg, wherein Pg refers to an oxygen protective group (for example, the oxygen protective group as described herein);

$R^3$ is independently hydrogen, —OH, —$CF_3$, —CN, halogen, substituted or unsubstituted $C_{1-10}$ alkyl, —O-Pg', substituted or unsubstituted $C_{1-10}$ alkoxy, substituted or unsubstituted $C_{3-10}$ cycloalkyl, substituted or unsubstituted $C_{3-10}$ cycloalkyloxy at each occurrence, wherein Pg' refers to an oxygen protective group (for example, the oxygen protective group as described herein);

p is 0, 1, 2, 3 or 4;

$R^4$ is independently halogen, or substituted or unsubstituted $C_{1-10}$ alkyl at each occurrence;

q is 0, 1, 2, 3 or 4;

Ar is substituted or unsubstituted aryl or substituted or unsubstituted heterocyclic aryl. In some embodiments, when Ar is unsubstituted phenyl, the compound of formula II satisfies at least one of the following conditions: (1) $R^2$ is not hydrogen, (2) p is not 0, (3) q is not 0, (4) n is not 2, and (5) $R^1$ is not methyl. For example, in some embodiments, when Ar is phenyl, at least one of $R^2$, $R^3$, and $R^4$ is not hydrogen. Variables in general formula I or II, such as $R^1$, $R^2$, $R^3$, $R^4$, n, p, q, Ar and the like, can be independently selected from the definitions and preferences described herein, for example, $R^1$ in general formula I or II can be the same or different.

In some preferred embodiments, the general formula I or II may have the following structure:

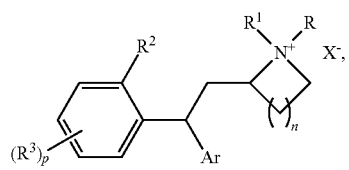

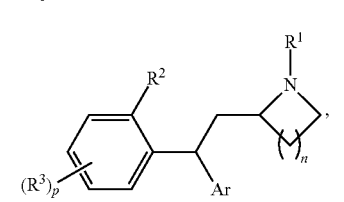

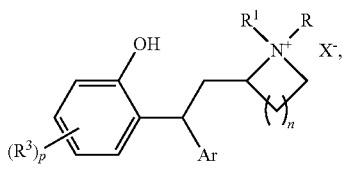

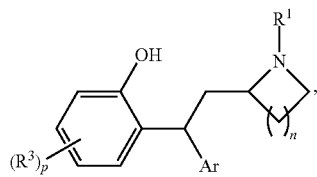

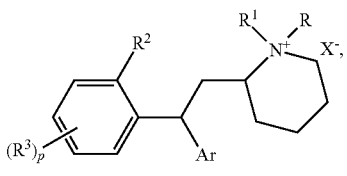

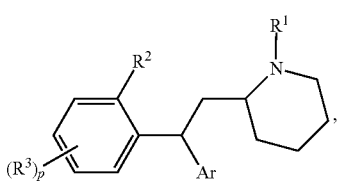

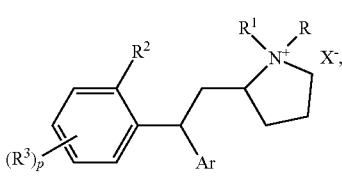

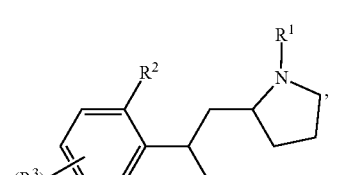

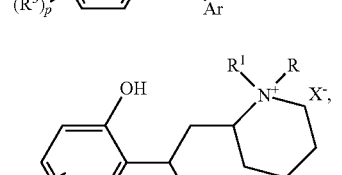

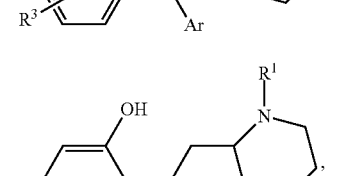

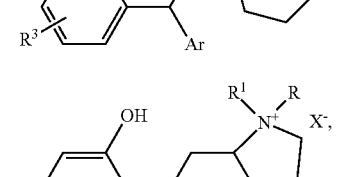

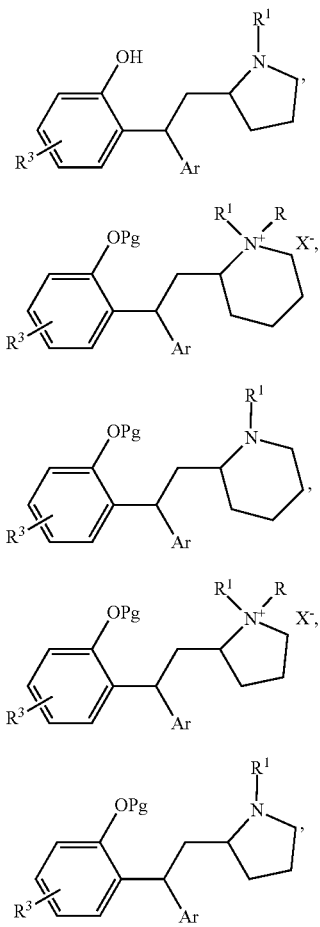

where applicable R, $R^1$, $R^2$, $R^3$, Pg, n, p, q, Ar, $X^-$ can be any definition and preference herein.

In some embodiments, $R^2$ can be hydrogen, —OH, —$CF_3$, —CN, halogen, nitro, amino, substituted or tin substituted $C_{1-10}$ alkyl, or —O-Pg. In some embodiments, Pg can be selected from $C_{1-10}$ alkyl, substituted or substituted phenyl, $C_{1-4}$ alkyl, —$C_{1-4}$ alkylene-($C_{1-4}$ alkoxy), —$SiR^{2a}R^{2a'}R^{2a''}$, —$COR^{2b}$, —CO—$OR^{2b}$, —CO—$NR^{2b}R^{2b'}$, —$SO_2$—$NR^{2b}R^{2b'}$, —COAr' and —CO—OAr'; wherein, $R^{2a}$, $R^{2a'}$, and $R^{2a''}$ are each independently —$C_{1-4}$ alkyl or phenyl; $R^{2b}$ and $R^{2b'}$ are each independently hydrogen, or substituted or unsubstituted —$C_{1-4}$ alkyl, provided that $R^{2b}$ is not hydrogen when directly connected to an oxygen atom; or $R^{2b}$, $R^{2b'}$, together with the nitrogen atom connected thereto, form a 4-8 membered substituted or unsubstituted heterocyclic ring; Ar' is substituted or unsubstituted phenyl, or substituted or unsubstituted naphthyl. In some embodiments, substituted refers to the substitution by one or more (for example, 1, 2, or 3) substituents, wherein each substituent can be independently selected from $C_{1-4}$ alkoxy, —NH—($C_{1-4}$ alkyl), —N($C_{1-4}$ alkyl)($C_{1-4}$ alkyl), $C_{2-4}$ alkenyl, $C_{2-4}$ alkynyl, —CN, halogen, phenyl, and phenoxy. In this article, without a clear definition, the $C_{1-4}$ alkyl in the term "—N($C_{1-4}$ alkyl)($C_{1-4}$ alkyl)" can be independently selected from the same or different groups.

Further, in some embodiments, $R^2$ is hydrogen, —OH, —CN, halogen, substituted or unsubstituted $C_{1-10}$ alkyl, or —O-Pg. In some embodiments, Pg can be selected from $C_{1-10}$ alkyl, methoxymethyl, benzyl, —$Si(CH_3)_2C(CH_3)_3$, —$Si(CH_3)_3$, —$Si(Ph)_2C(CH_3)_3$, —$COR^{2b}$, CO—$OR^{2b}$, —CO—$NR^{2b}R^{2b'}$, —$SO_2$—$NR^{2b}R^{2b'}$, —COAr', and —COOAr'.

Further, in some embodiments, $R^2$ is hydrogen, —OH, halogen, substituted or unsubstituted $C_{1-10}$ alkyl, or —O-Pg. In some embodiments, Pg can be selected from methyl, ethyl, methoxymethyl, —$Si(CH_3)_2C(CH_3)_3$, —$Si(CH_3)_3$, —$COR^{2b}$, —CO—$OR^{2b}$, —COAr' and —CO—OAr'. In some embodiments, $R^2$ is —OH or —O-Pg, wherein Pg can be selected from methyl, ethyl, methoxymethyl, —$Si(CH_3)_2C(CH_3)_3$, —$Si(CH_3)_3$, —$COR^{2b}$, —CO—$OR^{2b}$, —COAr' and —CO—OAr'.

In some embodiments, $R^{2a}$, $R^{2a'}$, and $R^{2a''}$ are each independently —$C_{1-4}$ alkyl or phenyl.

In some embodiments, $R^{2b}$ and $R^{2b'}$ are each independently hydrogen, or optionally substituted —$C_{1-10}$ alkyl, for example, optionally substituted by one or more (for example, 1, 2, or 3) substituents, wherein each substituent can be independently $C_{1-4}$ alkoxy, —NH—($C_{1-4}$ alkyl), —N($C_{1-4}$ alkyl)($C_{1-4}$ alkyl), $C_{2-4}$ alkenyl, $C_{2-4}$ alkynyl, —CN, halogen, phenyl, or phenoxy, provided that $R^{2b}$ is not hydrogen when directly connected to an oxygen atom. In some embodiments, $R^{2b}$, $R^{2b'}$, together with the nitrogen atom, form a substituted or unsubstituted 4-8 membered heterocyclic ring.

In some embodiments, Ar' can be optionally substituted phenyl or optionally substituted naphthyl; further, Ar' can be phenyl optionally substituted by one or more (for example, 1, 2, or 3) substituents, wherein each substituent can be independently selected from —$CF_3$, —CN, halogen, nitro, $C_{1-10}$ alkyl, $C_{2-4}$ alkenyl, $C_{2-4}$ alkynyl, $C_{1-10}$ alkoxy, —$NHSO_2R^{2b}$, —$COOR^{2b}$, —$SO_2R^{2b}$, —$SO_2NR^{2b}R^{2b'}$, —$NR^{2b}R^{2b'}$ or —$CONR^{2b}R^{2b'}$, and $R^{2b}$ and $R^{2b'}$ are as defined and preferred herein; furthermore, Ar' is phenyl optionally substituted by one or more (for example, 1, 2, or 3) substituents, wherein each substituent can be independently selected from —$CF_3$, —CN, —F, —Cl, —Br, nitro, $C_{1-10}$ alkyl, $C_{2-4}$ alkenyl, $C_{2-4}$ alkynyl, and $C_{1-10}$ alkoxy; and more further, Ar' is phenyl optionally substituted by one or more (for example, 1, 2, or 3) substituents, wherein each substituent can be independently selected from $CF_3$, —F, —Cl, $C_{1-4}$ alkyl, and $C_{1-4}$ alkoxy.

In some embodiments, $R^2$ is —O-Pg, wherein the oxygen protective group Pg can be selected from methyl, ethyl, allyl, benzyl, substituted benzyl (such as 4-methoxybenzyl), methoxymethyl (MOM), benzyloxymethyl (BOM), 2-methoxyethoxymethyl (MEM), trimethylsilyl (TMS), triethylsilyl (TES), triisopropylsilyl (TIPS), TBS t-butyldimethylsilyl (TBDMS), —$Si(Ph)_2C(CH_3)_3$, tetrahydropyranyl (THP), formyl, acetyl, chloracetyl, dichloroacetyl, trichloroacetyl, trifluoroacetyl, propionyl, methoxyacetyl, benzoyl, methylsulfonyl, —CO—$OCH_3$, —CO—$OCH_2CH_3$, —CO—OPh, benzenesulfonyl, and p-toluenesulfonyl.

Preferably, $R^2$ is hydroxyl.

Preferably, $R^2$ is hydroxyl, methoxyl, formyloxy, acetoxy, propionyloxy, benzoyloxy, —O—CO—$OCH_3$, —O—CO—$OCH_2CH_3$, or —O—CO—OPh.

In some embodiments, p is 0, that is, $R^3$ is not present. In some preferred embodiments, p can be 1. When present, $R^3$ can be independently —OH, —$CF_3$, —CN, halogen, $C_{1-10}$ alkyl, $C_{1-10}$ alkoxy, —($C_{1-4}$ alkylene)-OH, —($C_{1-4}$ alkylene)-O—CO—($C_{1-10}$ alkyl), —($C_{1-4}$ alkylene)-O—($C_{1-10}$ alkyl), —O—$COR^{2b}$, —O—CO—$OR^{2b}$, —O—CO—$NR^{2b}R^{2b'}$, —$OSO_2$—$NR^{2b}R^{2b'}$, —O—COAr' or —OCO—OAr' at each occurrence, wherein $R^{2b}$, $R^{2b'}$ and Ar' are as defined herein. In some embodiments, $R^{2b}$ and $R^{2b'}$ are each independently hydrogen, or optionally substituted $C_{1-4}$ alkyl, provided that $R^{2b}$ is not hydrogen when directly connected to an oxygen atom, or $R^{2b}$, $R^{2b'}$, together with the nitrogen atom connected thereto, form a 4-8 membered substituted or unsubstituted heterocyclic ring. In some embodiments, Ar' is substituted or unsubstituted phenyl, or substituted or unsubstituted naphthyl. Further definitions of $R^{2b}$, $R^{2b'}$ and Ar' are as described herein.

In some embodiments, $R^3$ can be independently —OH; —F; —CF$_3$; —CN; $C_{1-4}$ alkyl optionally substituted by one or more (for example, 1, 2, or 3) substituents, wherein each substituent is independently selected from —F, —OH and $C_{1-4}$ alkoxy; $C_{1-4}$ alkoxy optionally substituted by one or more (for example, 1, 2, or 3 A) substituents, wherein each substituent is independently selected from —F, —OH and $C_{1-4}$ alkoxy; $C_{3-6}$ cycloalkyl; or $C_{3-6}$ cycloalkyloxy at each occurrence.

In some embodiments, $R^3$ can be independently —OH, —F, —CF$_3$, —CN, —C$_{1-10}$ alkyl, —C$_{1-10}$ alkoxy, hydroxymethyl, hydroxyethyl, or —(C$_{1-2}$ alkyl)-O—CO—(C$_{1-10}$ alkyl) at each occurrence; further, $R^3$ can be independently —OH, —F, —CF$_3$, —CN, methyl, ethyl, propyl, butyl, isopropyl, isobutyl, tert-butyl, methoxyl, ethoxyl, hydroxymethyl, or 2-hydroxyethyl at each occurrence; furthermore, $R^3$ can be independently —OH, —F, —CF$_3$, —CN, —C$_{1-4}$ alkyl, or —C$_{1-4}$ alkoxy at each occurrence; and still further, $R^3$ can be independently —OH, —F, CF$_3$, methyl, ethyl, propyl, butyl, isopropyl, isobutyl, tert-butyl, methoxyl, or hydroxymethyl at each occurrence.

Preferably, p is 1; further, p is 1, and $R^3$ is connected to the meta or para position of $R^2$; and preferably, p is 1, and $R^3$ is connected to the para position of $R^2$,

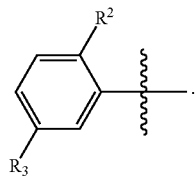

In some embodiments, p is 1, and $R^3$ is connected to the meta position of $R^2$, preferably

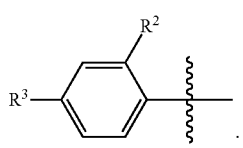

The definitions of $R^2$ and $R^3$ are as described and preferred herein.

Preferably, the

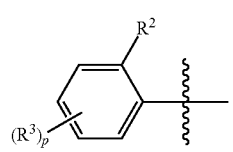

groups in formulas I and II are selected from:

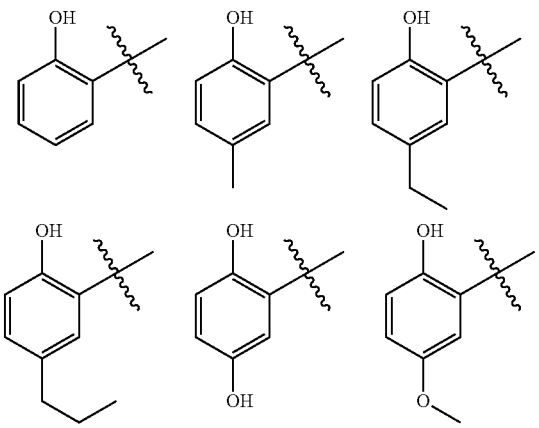

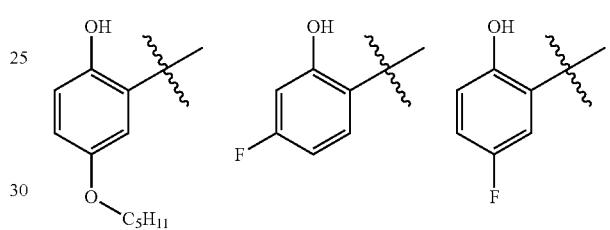

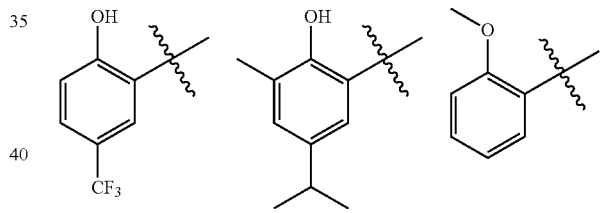

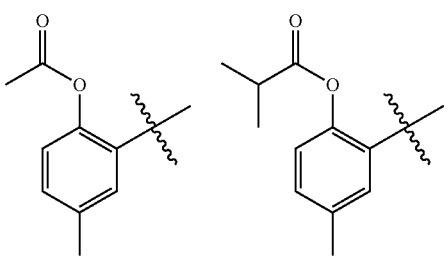

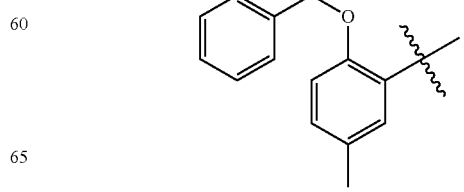

-continued

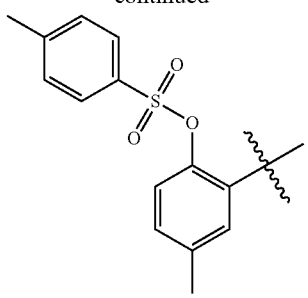

Preferably, n is 2 or 3.

Preferably, $R^4$ is independently F, or $C_{1-4}$ alkyl at each occurrence.

Preferably, q is 0, 1, or 2. In some embodiments, q is 0, that is, $R^4$ is not present.

Preferably, R, if present, is hydrogen, or substituted or unsubstituted $C_{1-10}$ alkyl; $R^1$ is substituted or unsubstituted $C_{1-10}$ alkyl. In some embodiments, substituted or unsubstituted $C_{1-10}$ alkyl means that $C_{1-10}$ alkyl is optionally substituted by one or more (for example, 1, 2, or 3) substituents, wherein each substituent is independently selected from $C_{3-6}$ cycloalkyl, $C_{1-4}$ alkoxy, —OH, halogen, or substituted or unsubstituted phenyl (for example, phenyl optionally substituted by one or more substituents independently selected from $C_{1-3}$ alkyl, $C_{1-3}$ alkoxy or halogen). In some embodiments, substituted or unsubstituted $C_{1-10}$ alkyl means that $C_{1-10}$ alkyl is optionally substituted by one or more (for example, 1, 2, or 3) substituents, wherein each substituent is independently selected from $C_{3-6}$ cycloalkyl, $C_{1-6}$ alkoxy, —OH, —F, —Cl, —Br, phenyl and phenoxy.

In some embodiments, R, if present, is hydrogen, methyl, ethyl, propyl, isopropyl, benzyl, 2-phenoxyethyl, 3-phenoxypropyl, 2-hydroxyethyl, 3-hydroxypropyl, 2-fluoroethyl, or 3-fluoropropyl; and preferably, $R^3$ can be methyl, ethyl, propyl, or isopropyl.

In some embodiments, R, if present, is preferably hydrogen, methyl, ethyl, propyl, or 3-phenoxypropyl; and preferably, $R^1$ is methyl or ethyl.

In some embodiments, Ar is aryl or heterocyclic aryl optionally substituted by one or more (for example, 1, 2, or 3) substituents. In some embodiments, each of the substituents is independently selected from —OH, —$CF_3$, —CN, halogen, $C_{1-10}$ alkyl, $C_{3-10}$ cycloalkyl, and $C_{1-10}$ alkoxy.

In some embodiments, Ar is phenyl, thienyl or furyl optionally substituted by one or more (for example, 1, 2, or 3) substituents. In some embodiments, Ar is unsubstituted phenyl, thienyl, or furyl. In some embodiments, Ar is substituted phenyl, thienyl or furyl, wherein each of the substituents is independently selected from —OH, —$CF_3$, —CN, —F, $C_{1-10}$ alkyl, and $C_{1-10}$ alkoxy. In some embodiments, each of the substituents is independently selected from —OH, —$CF_3$, —CN, —F, $C_{1-4}$ alkyl, and $C_{1-4}$ alkoxy.

In some preferred embodiments, Ar is phenyl or thienyl optionally substituted by one or more (for example, 1, 2, or 3) substituents. When phenyl or thienyl is substituted, preferably, each of the substituents is independently selected from methyl, ethyl and —F.

In some preferred embodiments, Ar is selected from:

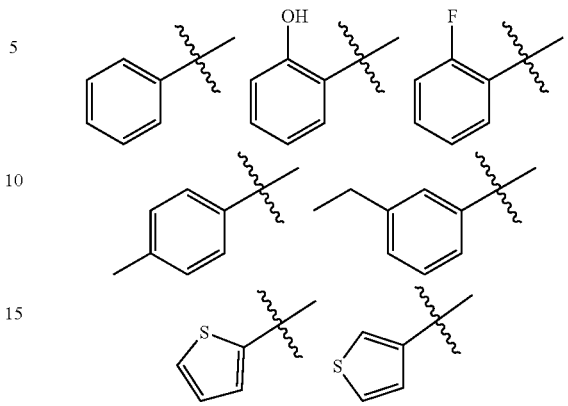

$X^-$ can be any anion. In some embodiments, preferably, $X^-$ is a pharmaceutically acceptable anion.

Preferably, the salts, hydrates, solvates and various crystals of 2-(2,2-diarylethyl)-cyclic amine derivatives I and II can be: diastereomer mixtures or individual diastereomer monomers when the compound is in the form of diastereomers, or enantiomer mixtures or individual enantiomer monomers when the compound is in the form, of enantiomers.

Further, in the absence of obvious conflict, the compound referred to in any embodiment of the present invention can be selected from the specific embodiment compounds I-2, I-3, I-4, I-5, I-6, I-7, I-8, I-9, I-10, I-14, I-15 I-19, I-20, I-22, I-23, I-25 and I-26 and compounds II-1, II-2, II-3, II-4, II-5, II-6, II-7, II-8, II-9, II-10, II-11, II-12, II-13, II-14, II-15, II-16, II-17, II-18, II-19, II-20, II-21, II-22, II-23, II-24, II-25 and II-26 shown in Table 1, or pharmaceutically acceptable salts, diastereomer mixtures, diastereomer monomers, enantiomer mixtures, and enantiomer monomers thereof, or hydrates, solvates or crystals of various crystal forms of the above-mentioned compounds.

In some embodiments, the present invention proposes a pharmaceutical composition. In some embodiments, the pharmaceutical composition may contain one or more compounds of the present invention (for example, the compound that has the general formula I or II, such as I-A to I-H or II-A to II-H, or any of the specific embodiments (see Table 1), or a pharmaceutically acceptable salt thereof), and any pharmaceutically acceptable excipients.

Preferably, physiologically applicable excipients, carriers, diluents and the like can be combined with the compounds of the present invention, such as the quaternary ammonium salts, free alkalis, and salts formed by the addition of add of the 2-(2,2-diarylethyl)-cyclic amine derivative, and stereoisomers, hydrates, solvates or crystals to form the pharmaceutical composition for the treatment or prevention of diseases related to M-receptor (such as M1 and/or M3) antagonism.

Preferably, the salts generated by the acid include HCl and HBr salts and the like.

Preferably, the diseases related to M-receptor (such as M1 and/or M3) antagonism include asthma, COPD, OAB, bronchospasm with chronic obstructive pulmonary disease, visceral spasm, irritable bowel syndrome, Parkinson's disease, depression or anxiety, schizophrenia and related mental diseases.

In some embodiments, the present invention also proposes a method of treating or preventing diseases related to M-receptor antagonism. Preferably, the method of treating the diseases comprises making the receptor come into contact with the compound of the present invention, such as the 2-(2,2-diarylethyl)-cyclic amine derivative. Preferably, the diseases related to M-receptor (such as M1 and/or M3) antagonism are asthma, COPD, OAB, bronchospasm with chronic obstructive pulmonary disease, visceral spasm, irritable bowed syndrome, Parkinson's disease, depression or anxiety, schizophrenia and related mental diseases. In some embodiments, the diseases are asthma, COPD, and/or bronchospasm with chronic obstructive pulmonary disease. In some embodiments, the disease is OAB. In some embodiments, the diseases are Parkinson's disease, visceral spasm, irritable bowel syndrome, depression or anxiety, and/or schizophrenia and related mental diseases. Preferably, the method of treating the diseases comprises administering to the subject of treatment an effective dose of one or more of the compounds of the present invention (for example, the compound that has the general formula I or II, such as I-A to I-H or II-A to II-H, or any of the specific embodiments (see Table 1), or a pharmaceutically acceptable salt thereof), or the pharmaceutical composition described herein.

In some aspects, the present invention also proposes a synthetic method of 2-(2,2-diarylethyl)-cyclic amine derivatives I and II. The synthetic route is as follows:

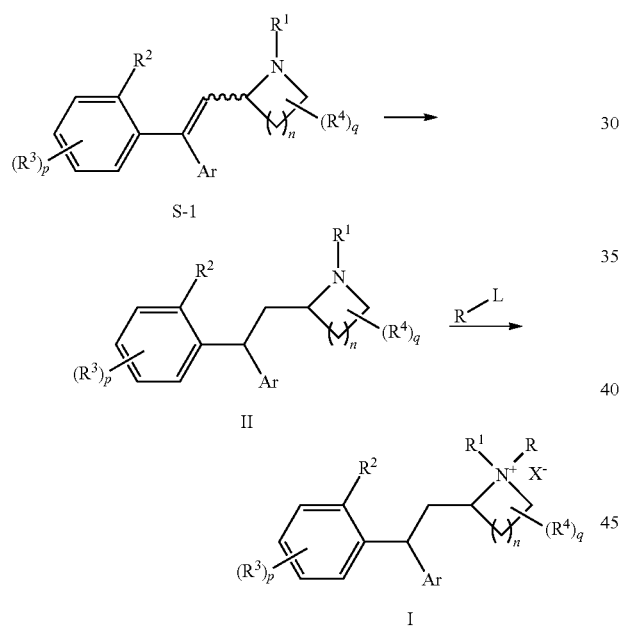

where R, $R^1$, $R^2$, $R^3$, $R^4$, n, p, q, Ar, L and $X^-$ are preferably the same as the above definitions, and $R^1$, $R^2$, $R^3$, and $R^4$ in general formula compounds S-1, II, and I can be independently the same or different.

As mentioned above, the general formula compound S-1 can be hydrogenated and reduced to form the general formula compound II. Then, if necessary, II can be reacted with an appropriate reagent R-L to form the general formula compound I, wherein L is a leaving group. Hydrogenation reduction and quaternary animation or salt formation reactions can be similar reactions known in the art, and some representative reaction conditions are also described in tins article.

In some embodiments, R-L can be an organic or inorganic acid; and the above-mentioned reaction can produce a salt of compound II. Preferably, the organic or inorganic acid is suitable for producing a pharmaceutically acceptable salt.

In some embodiments, R-L is an alkylating agent, selected from, for example, an organic halide, dialkyl sulfate, or dialkyl carbonate, and preferably, L is —Cl, —Br, or —I.

In some embodiments, $R^1$, $R^2$, $R^3$, and $R^4$ in general formula compounds S-1, II, and I are respectively the same.

In some embodiments, $R^1$, $R^3$, and $R^4$ in general formula compounds II and I are respectively the same, but $R^2$ is different, wherein $R^2$ in general formula compound II is —O-Pg, Pg refers to the oxygen protective group, and Pg is removed to obtain compound S-2; an oxygen protective group is optionally added to compound S-2 to convert S-2 into compound S-2A, wherein $R^{2A}$ is —O-$Pg^A$, and $Pg^A$ refers to an oxygen protective group; and then, compound S-2 or S-2A is optionally reacted with a suitable organic reagent R-L to produce general formula compound I, wherein $R^2$ in I is —OH or the same as $R^{2A}$ in S-2A;

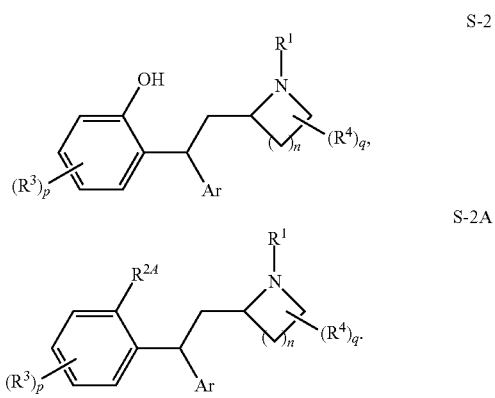

In some embodiments, $R^1$, $R^3$, and $R^4$ in general formula compounds II and I are respectively the same, but $R^2$ is different, wherein $R^2$ in general formula compound II is —OH; an oxygen protective group is added to $R^2$ in general formula compound II to obtain compound S-3, wherein $R^{2B}$ is —O-$Pg^B$, and $Pg^B$ refers to an oxygen protective group; and then, compound S-3 is optionally reacted with a suitable organic reagent R-L to produce general formula compound I, wherein $R^2$ in general formula compound I is the same as $R^{2B}$ in compound S-3.

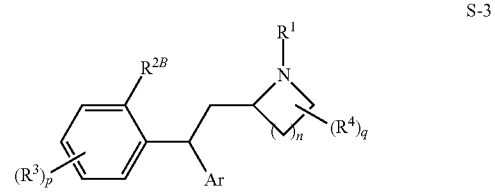

Oxygen protective groups suitable for use in the above-mentioned synthesis reactions include any of the oxygen protective groups described herein. Moreover, in the absence of a specific definition, oxygen protective groups (if any) in different general formula compounds or the same general formula described herein can be independently selected, and can be the same or different.

DETAILED DESCRIPTION

Figure 1:
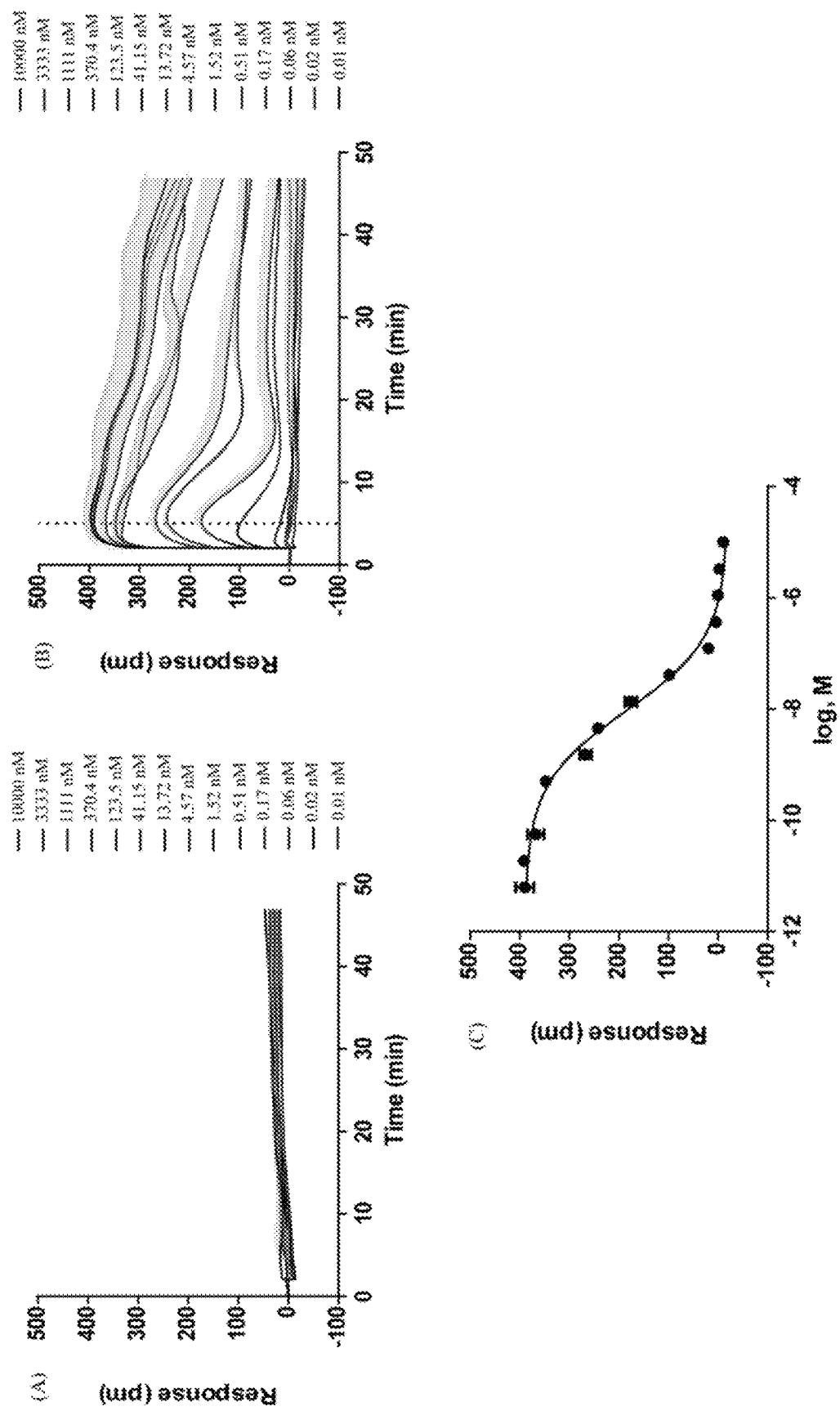
FIG. 1 shows the DMR signal of compound II-5 on CHO-K1-M1 cells (A), the effect of the compound on DMR response signal of acetylcholine (B) and the corresponding dose curves (C).

To make the object, the technical solution and the advantages of the present invention more clear, the technical solution of the present invention will be further described below.

The present invention proposes a 2-(2,2-diarylethyl)-cyclic amine derivative. The general formula of the 2-(2,2-diarylethyl)-cyclic amine derivative or pharmaceutically acceptable salt thereof is:

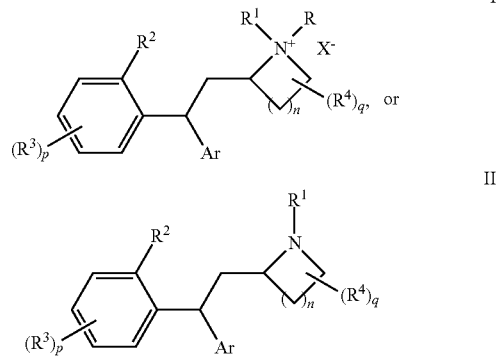

where R, $R^1$, $R^2$, $R^3$, $R^4$, n, p, q, Ar, and $X^-$ are the same as the definitions and preferences described herein.

In some specific embodiments, according to the present invention, preferred I and II compounds are as shown in Table 1:

TABLE 1

Preferred Compounds I-A and II-A in Embodiments of the Present Invention

| Compound | R | $R^1$ | $R^2$ | $R^3$ | p | Ar | n | $X^-$ |
|---|---|---|---|---|---|---|---|---|
| II-1 | — | —$CH_3$ | —H | — | 0 | —Ph | 3 | — |
| II-2a, and chiral monomers II-2a-1 and II-2a-2 thereof | — | —$CH_3$ | —OH | — | 0 | —Ph | 3 | — |
| I-2a-Cl | —H | —$CH_3$ | —OH | — | 0 | —Ph | 3 | $Cl^-$ |
| I-2a-Br, and chiral monomers I-2a-1-Br and I-2a-2-Br thereof | —$CH_3$ | —$CH_3$ | —OH | — | 0 | —Ph | 3 | $Br^-$ |
| I-2a-I | —$CH_3$ | —$CH_3$ | —OH | — | 0 | —Ph | 3 | $I^-$ |
| II-3, and chiral monomers II-3-1 and II-3-2 thereof | — | —$CH_3$ | —OH | — | 0 | 2-OH—Ph | 3 | — |
| I-3-Cl | —H | —$CH_3$ | —OH | — | 0 | 2-OH—Ph | 3 | $Cl^-$ |
| I-3-Br, and chiral monomers I-3-1-Br and I-3-2-Br thereof | —$CH_3$ | —$CH_3$ | —OH | — | 0 | 2-OH—Ph | 3 | $Br^-$ |
| I-3-I | —$CH_3$ | —$CH_3$ | —OH | — | 0 | 2-OH—Ph | 3 | $I^-$ |
| II-4a, and chiral monomers II-4a-1 and II-4a-2 thereof | — | —$CH_3$ | —OH | 5-$CH_3$ | 1 | —Ph | 3 | — |
| II-4b, and chiral monomers II-4b-1 and II-4b-2 thereof | — | —$CH_3$ | —OH | 5-$CH_3$ | 1 | —Ph | 3 | — |
| I-4a-Cl | —H | —$CH_3$ | —OH | 5-$CH_3$ | 1 | —Ph | 3 | $Cl^-$ |
| I-4a-HBr | —H | —$CH_3$ | —OH | 5-$CH_3$ | 1 | —Ph | 3 | $Br^-$ |
| I-4a-Br, and chiral monomers I-4a-1-Br and I-4a-2-Br | —$CH_3$ | —$CH_3$ | —OH | 5-$CH_3$ | 1 | —Ph | 3 | $Br^-$ |

TABLE 1-continued

Preferred Compounds I-A and II-A in Embodiments of the Present Invention

I-A

[Chemical structure of Compound I-A: aromatic ring with $R^2$ substituent, $(R^3)_p$ substituents, connected via CH-Ar group to a CH$_2$-linked azetidinium ring with $R^1$, R substituents on $N^+$, ring size $n$, and counterion $X^-$]

II-A

[Chemical structure of Compound II-A: aromatic ring with $R^2$ substituent, $(R^3)_p$ substituents, connected via CH-Ar group to a CH$_2$-linked azetidine ring with $R^1$ on N, ring size $n$]

| Compound | R | $R^1$ | $R^2$ | $R^3$ | p | Ar | n | $X^-$ |
|---|---|---|---|---|---|---|---|---|
| I-4b-Br, and chiral monomers I-4b-1-Br and I-4b-2-Br | —CH$_3$ | —CH$_3$ | —OH | 5-CH$_3$ | 1 | —Ph | 3 | Br$^-$ |
| I-4a-I, and chiral monomers I-4a-1-I and I-4a-2-I thereof | —CH$_3$ | —CH$_3$ | —OH | 5-CH$_3$ | 1 | —Ph | 3 | I$^-$ |
| I-4a-PrOPh, and chiral monomers I-4a-1-PrOPh and I-4a-2-PrOPh thereof | —PrOPh | —CH$_3$ | —OH | 5-CH$_3$ | 1 | —Ph | 3 | Br$^-$ |
| II-5 | — | —CH$_3$ | —OH | 5-CH$_2$CH$_3$ | 1 | —Ph | 3 | — |
| I-5-Cl | —H | —CH$_3$ | —OH | 5-CH$_2$CH$_3$ | 1 | —Ph | 3 | Cl$^-$ |
| I-5-Ac | —H | —CH$_3$ | —OH | 5-CH$_2$CH$_3$ | 1 | —Ph | 3 | Ac$^-$ |
| I-5-Br | —CH$_3$ | —CH$_3$ | —OH | 5-CH$_2$CH$_3$ | 1 | —Ph | 3 | Br$^-$ |
| I-5-I | —CH$_3$ | —CH$_3$ | —OH | 5-CH$_2$CH$_3$ | 1 | —Ph | 3 | I$^-$ |
| II-6 | — | —CH$_3$ | —OH | 5-(CH$_2$)$_2$CH$_3$ | 1 | —Ph | 3 | — |
| I-6 | —CH$_3$ | —CH$_3$ | —OH | 5-(CH$_2$)$_2$CH$_3$ | 1 | —Ph | 3 | Br$^-$ |
| II-7 | — | —CH$_3$ | —OH | 5-CH$_3$ | 1 | 2-F—Ph— | 3 | — |
| I-7 | —CH$_3$ | —CH$_3$ | —OH | 5-CH$_3$ | 1 | 2-F—Ph— | 3 | Br$^-$ |
| II-8 | — | —CH$_3$ | —OH | 4-F | 1 | —Ph | 3 | — |
| I-8 | —CH$_3$ | —CH$_3$ | —OH | 4-F | 1 | —Ph | 3 | Br$^-$ |
| II-9 | — | —CH$_3$ | —OH | 5-OCH$_3$ | 1 | —Ph | 3 | — |
| I-9 | —CH$_3$ | —CH$_3$ | —OH | 5-OCH$_3$ | 1 | —Ph | 3 | Br$^-$ |
| Diastereomer monomers II-10a and II-10b, and chiral monomers II-10a/b-1/-2 thereof | — | —CH$_3$ | —OH | 5-F | 1 | —Ph | 3 | — |
| Diastereomer monomers I-10a and I-10b, and chiral monomers I-10a/b-1/-2 thereof | —CH$_3$ | —CH$_3$ | —OH | 5-F | 1 | —Ph | 3 | Br$^-$ |
| II-11 | — | —CH$_3$ | —OH | —OH | 1 | —Ph | 3 | — |
| II-12 | — | —CH$_3$ | —OH | —OC$_5$H$_{11}$ | 1 | —Ph | 3 | — |
| II-13 | — | —CH$_3$ | —OH | —CF$_3$ | 1 | —Ph | 3 | — |
| II-14 | — | —CH$_3$ | —OH | —CH$_3$ | 1 | 4-Cl—Ph | 3 | — |
| I-14 | —CH$_3$ | —CH$_3$ | —OH | —CH$_3$ | 1 | 4-Cl—Ph | 3 | Br$^-$ |
| II-15 | — | —CH$_3$ | —OH | 5-CH$_3$ | 1 | 4-CH$_3$—Ph | 3 | — |
| I-15 | —CH$_3$ | —CH$_3$ | —OH | —CH$_3$ | 1 | 4-CH$_3$—Ph | 3 | Br$^-$ |
| II-16 | — | —CH$_3$ | —OH | 3-CH$_3$, 5-iPr | 2 | 3-Et—Ph | 3 | — |
| II-17 | — | —CH$_3$ | —OCH$_3$ | — | 0 | —Ph | 3 | — |
| II-18 | — | —CH$_2$CH$_3$ | —OH | 5-CH$_3$ | 1 | —Ph | 3 | — |
| II-19 | — | —CH$_3$ | —OH | 5-CH$_3$ | 1 | —Ph | 2 | — |
| I-19 | —CH$_3$ | —CH$_3$ | —OH | 5-CH$_3$ | 1 | —Ph | 2 | Br$^-$ |
| II-20 | — | —CH$_3$ | —OH | 5-CH$_2$CH$_3$ | 1 | —Ph | 2 | — |
| I-20 | —CH$_3$ | —CH$_3$ | —OH | 5-CH$_2$CH$_3$ | 1 | —Ph | 2 | Br$^-$ |
| II-21 | — | —CH$_3$ | —H | — | 0 | 2-Thienyl | 3 | — |
| II-22 | — | —CH$_3$ | —OH | 5-CH$_3$ | 1 | 3-Thienyl | 3 | — |
| I-22 | —CH$_3$ | —CH$_3$ | —OH | 5-CH$_3$ | 1 | 3-Thienyl | 3 | Br$^-$ |
| II-23 | — | —CH$_3$ | —OCOCH(CH$_3$)$_2$ | 5-CH$_3$ | 1 | —Ph | 3 | — |
| I-23 | —CH$_3$ | —CH$_3$ | —OCOCH(CH$_3$)$_2$ | 5-CH$_3$ | 1 | —Ph | 3 | Br$^-$ |
| II-24 | — | —CH$_3$ | —OAc | 5-CH$_3$ | 1 | —Ph | 3 | — |
| II-25 | — | —CH$_3$ | —OBz | 5-CH$_3$ | 1 | —Ph | 3 | — |
| I-25 | —CH$_3$ | —CH$_3$ | —OBz | 5-CH$_3$ | 1 | —Ph | 3 | Br$^-$ |
| II-26 | — | —CH$_3$ | —OTs | 5-CH$_3$ | 1 | —Ph | 3 | — |
| I-26 | —CH$_3$ | —CH$_3$ | —OTs | 5-CH$_3$ | 1 | —Ph | 3 | Br$^-$ |

In some embodiments, the hydrates, solvates and various crystals of 2-(2,2-diarylethyl)-cyclic amine derivatives and pharmaceutically acceptable salts thereof can be: diastereomer mixtures or individual diastereomer monomers when the compound is in the form of diastereomers, or enantiomer mixtures or individual enantiomer monomers when the compound is in the form of enantiomers.

In some embodiments, the 2-(2,2-diarylethyl)-cyclic amine derivatives and tire corresponding pharmaceutically acceptable salts thereof are used for the preparation of a pharmaceutical composition for the treatment or prevention of any diseases related to M-receptor antagonism, wherein the pharmaceutical composition includes free alkalis of physiologically applicable excipients, carriers, diluents and at least one 2-(2,2-diarylethyl)-cyclic amine derivative, pharmaceutically applicable salts, hydrates and solvates, or crystals. The pharmaceutical composition includes active substances of at least one 2-(2,2-diarylethyl)-cyclic amine derivative.

In some embodiments, the present invention also proposes a synthetic method of 2-(2,2-diarylethyl)-cyclic amine derivatives I and II. The synthetic route is as follows:

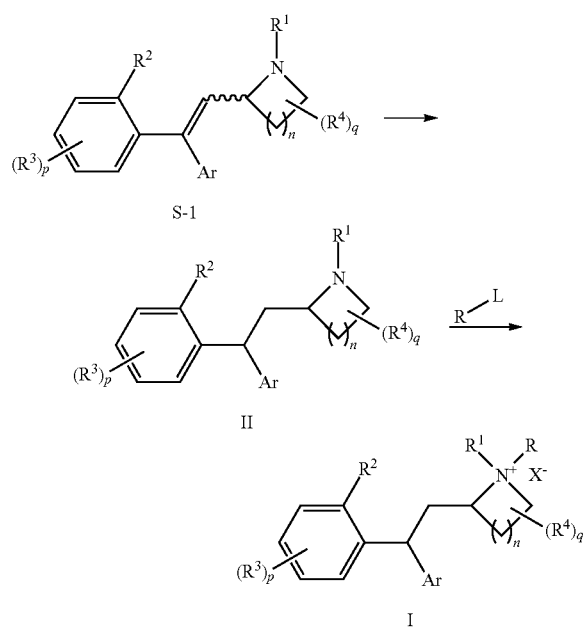

where R, $R^1$, $R^2$, $R^3$, $R^4$, n, p, q, Ar, L and $X^-$ are the same as the above definitions, and $R^1$, $R^2$, $R^3$, and $R^4$ in general formula compounds S-1, II, and I can be independently the same or different. According to the conditions disclosed in the present invention, experienced researchers can easily prepare the compounds represented by formulas I and II. Typically, compounds I and II can be prepared from the hydrogenation reaction of olefin compound S-1, followed by the optional formation of pharmaceutically acceptable acid salts or quaternary ammonium salts. In some embodiments, the order of hydrogenation and salt formation (for example, quaternary ammonium salt) can be reversed. For example, the olefin compound can be quaternized first, and then hydrogenated to obtain the compound I. The olefin compound S-1 can be prepared by β-diaryl allyl bromide and cyclic tertiary amine in the presence of dimethyl zinc, $MnCl_2$ and oxygen in reaction conditions (for specific methods, please refer to patent application 201810186605.2 (CN108383775A), Chem. Eur. J. 2015, 21, 16272-16279).

As shown by the present invention, in order to prevent some unnecessary side reactions, some functional groups need to be protected according to traditional methods. The present invention discloses appropriate protective groups and protection conditions for some functional groups, as well as deprotection conditions for some functional groups. For example, "Protective Groups in Organic Synthesis", 4th ed. P. G. M. Wuts; T. W. Greene, John Wiley, 2007 and a large number of protective groups described in the references. The reaction reagents used in the present invention are generally known compounds or can be prepared by known reaction conditions or simple modifications. For example, many reagents are commercially available from, such as Sinopharm Group Chemical Reagent Co., Ltd., and Shanghai Aladdin Bio-Chem Technology Co., Ltd. Other reagents can be prepared by known methods or simple modifications, such as Fieser and Fieser's Reagents for Organic Synthesis, Volumes 1-15 (John Wiley and Sons, 1991), Rodd's Chemistry of Carbon Compounds, Volumes 1-5 and Supplemental (Elsevier Science Publishers, 1989), Organic Reactions, Volumes 1-40 (John Wiley and Sons, 1991), March's Advanced Organic Chemistry, (Wiley, 7th Edition), and Larock's Comprehensive Organic Transformations (Wiley-VCH, 1999).

In some embodiments, compounds with a molecular structure of formula I can be converted into each other depending on $R^2$; and depending on $R^2$, compounds with a molecular structure of general formula II can be converted into each other.

For example, when $R^2$ is a methoxyl ether protective group. II-MOMO can be treated with hydrochloric acid to produce compound II-OH; and when $R^2$ is —OH, the reaction with methoxychloromethyl ether can produce compound II-MOMO.

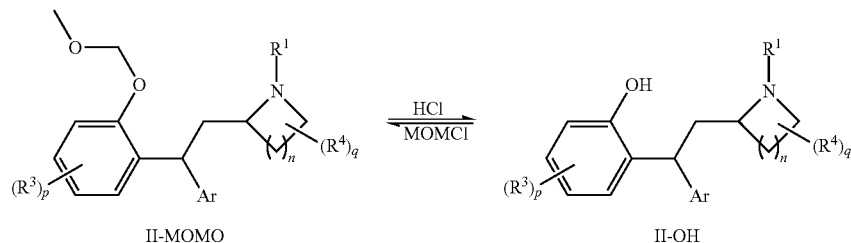

Similarly, when $R^2$ is a silyl ether protective group (including tert-butyl dimethyl silyl ether, tert-butyl diphenyl silyl ether, trimethyl silyl ether, etc.), II-OSi can be treated with tetrabutyl ammonium fluoride to produce compound II-OH; and when R² is —OH, the reaction between II-OH and tert-butyl dimethyl silicon chloride can produce compound II-OSi,

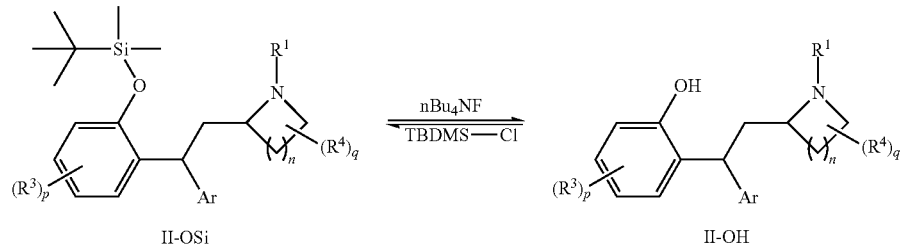

Similarly, depending on R², compounds with a molecular structure of general formula I can be converted into each other.

The separation of diastereomer mixtures can be achieved by chromatographic separation. The separation of enantiomer mixtures can be achieved by chiral chromatographic separation or by crystallization after the formation of a salt with a chiral acid.

The present invention also relates to a pharmaceutical composition containing one or more 2-(2,2-diarylethyl)-cyclic amine derivatives represented by the above-mentioned general formula I or II. In other words, the compounds of the present invention can be used as pharmaceutically active substances, especially as M-receptor antagonists.

The pharmaceutical composition can be used to prepare pharmaceutical preparations containing at least one of the compounds.

According to the present invention, the compounds represented by formulas I and II (including corresponding diastereomers and mixtures thereof, and enantiomers and mixtures thereof), or salts formed with physiologically acceptable acids, can be made into appropriate galenic dosage forms according to acceptable pharmaceutical procedures, such as for oral use, injection, and nasal spray. The pharmaceutical composition of the present invention contains a compound represented by general formula I or II, and compatible carrier materials or diluents that are pharmaceutically acceptable, which are well known in the art. Tire earner can be any inert material, organic or inorganic, suitable for enteral, transdermal or parenteral administration, for example, water, gelatin, gum arabic, lactose, microcrystalline cellulose starch, starch, sodium carboxymethyl starch, calcium hydrogen phosphate, magnesium stearate, talc, colloidal silicon dioxide, etc. The composition may also contain other pharmaceutically active agents, and conventional additives, for example, stabilizers, wetting agents, emulsifiers, flavoring agents, buffers and the like.

The composition of the present invention can be prepared into solid or liquid dosage forms for oral administration, such as tablets, capsules, powders, syrups and elixirs, and sterile solutions, suspensions or emulsions for parenteral administration.

The compound of the present invention can be used in a patch. The compound can be administered transdermally to reduce the side effects and improve individual compliance.

The compound or composition of the present invention can be used for the diastole of tracheal smooth muscle as well as the treatment of diseases related to tracheal smooth muscle.

The compound or composition of the present invention can also be used for the treatment of diseases related to M-receptor antagonism, such as asthma, COPD, OAB, bronchospasm with chronic obstructive pulmonary disease, visceral spasm, irritable bowel syndrome. Parkinson's disease, depression or anxiety, schizophrenia and related mental diseases. According to common sense, the dosage of a specific compound will vary depending on the potency, mode of administration, age and weight of the patient, and severity of the condition being treated. The daily dose, for example, can range from about 0.01 mg to 5 mg for a single administration, and for example, from about 0.05 mg to about 50 g per day for multiple administration.

In the compounds of formulas I and II (for example, I-A to I-H or II-A to II-H), the appropriate groups R, R¹, R², R³, R⁴, n, p, q, Ar, and X⁻, where applicable, are independently selected. The embodiments described in the present invention can be combined, and such combination remains within the scope of protection of the present invention. For example, where applicable, the definitions of any of the variables R, R¹, R², R³, R⁴, n, p, q, Ar, and X⁻ in general formula compounds I and II (for example, I-A to I-H or II-A to II-H) can be combined with the definitions of any other variables R, R¹, R², R³, R⁴, n, p, q, Ar, and X⁻ described herein. This combination is still within the scope of protection of the present invention.

"The compounds of the present invention" include any compound represented by general formula I or II (for example, the compound that has the general formula I or II, such as I-A to I-H or II-A to II-H, or any one or more of the compounds shown in Table 1), the compound represented by the general formula f or II, pharmaceutically acceptable salts thereof, stereoisomers, isotopic substituents, etc. The compounds of the present invention may also exist in the form of hydrates or solvates.

The compounds of the present invention may contain carbon or nitrogen atoms with asymmetrically substituted R. or S configuration. The compounds of the present invention are not limited to specific stereoisomers. For example, in some embodiments, the compounds of the present invention may be in a single R or S configuration for each chiral center, or a mixture of R and S in any ratio. Preferably, the compounds of the present invention are greater than 80% ee for each chiral center. For example, in some embodiments, the compounds of the present invention may, for each chiral center, be oversupplied in one configuration by about 85% to 90% over the other configuration, more preferably by about 95% to 99%, and more preferably by about 99%, or no other configuration can be detected. In some embodiments, the compounds of the present invention contain a chiral center, which can be a single (or enriched) enantiomer (R or S configuration), or a mixture of R. and S in any ratio (such as a racemic mixture). In some embodiments, the compounds of the present invention contain 2 or more chiral centers, which can be single (or enriched) diastereomers, or a diastereomer mixture (for example, greater than 80% de), and, in some embodiments, these single (or enriched) diastereomers can also be single (or enriched) enantiomers (for each chiral center, R or S configuration), or a mixture in any ratio (such as a racemic mixture).

The compounds of the present invention may be in the form of isotopic tracing or enrichment, which contain one or more atoms whose atomic weight or mass number is different from that of the most abundant atoms found in nature. Isotopes can be radioactive or non-radioactive. Isotopes of atoms such as hydrogen, carbon, phosphorus, sulfur, fluorine, chlorine, and iodine include, but not limited to: $^2H$, $^3H$, $^{13}C$, $^{14}C$, $^{15}N$, $^{18}O$, $^{32}P$, $^{35}S$, $^{18}F$, $^{16}Cl$, and $^{125}I$. Compounds containing these isotopes and/or other isotopes of other atoms are within the scope of the present invention.

In the present invention, the term "alkyl" by itself or as part of another group refers to straight or branched aliphatic hydrocarbons. The term "alkylene" by itself or as part of another group refers to a two-bonded alkyl bridged group —CH2-.

The term "$C_{1-4}$ alkylene" refers to a straight or branched two-chain alkyl bridged group —C1-4-having 1 to 4 carbon atoms. For example: methylene, ethylene, propylidene, butylene, or the like.

The term "cycloalkyl" preferably denotes an alicyclic group having 3-8 carbon atoms, such as cyclopropyl, cyclobutyl, cyclopentyl, cyclohexyl and the like.

The term "alkoxy" preferably denotes a straight or branched alkyl $C_{1-10}$ having 1 to 10 carbon atoms and bonded via oxygen atoms. The following are examples that may be mentioned: methoxy, ethoxy, propoxy, butoxy, pentyloxy, hexyloxy, heptyloxy, octyloxy, nonyloxy, decyloxy, and isomers thereof.

The term "halogen" means —F, —Cl, —Br and —I.

The terms "alkenyl" and "alkynyl" preferably refer to 2-4 carbon atom substituents containing one or two carbon-carbon double bonds or carbon-carbon triple bonds, for example: allyl, propargyl, isobutenyl, etc.

The term "aryl" refers to an aromatic hydrocarbon group —Ar, such as phenyl-($C_6H_5$), naphthyl-($C_{10}H_7$) and anthryl-($C_{14}C_9$). The preferred aryl according to the present invention is the phenyl and naphthyl, more preferably phenyl.

The term "heterocyclic aryl" refers to an optionally substituted five- or six-membered heterocyclic ring containing 1-3 heteroatoms, such as pyridyl, thienyl, furanyl, or optionally substituted benzohetercyclic ting, preferably thienyl and fund.

Unless a conflict is specifically mentioned, in the present invention, the combination of substituents and/or variables refers to the chemically permitted conditions that can produce stable compounds. A "stable" compound means that the compound can be prepared and separated, and structure and properties thereof remain unchanged for a period of time sufficient to allow same to be used for some purposes described in the present invention (for example, to administer medicine to a subject of treatment).

The term "optionally substituted" or a similar expression, such as optionally substituted alkyl, optionally substituted alkenyl, optionally substituted alkynyl, optionally substituted carboatomic radical, optionally substituted heterocyclic radical, optionally substituted aryl, and optionally substituted heterocyclic aryl, means that the group modified thereby may be substituted or unsubstituted. Generally speaking, the term "substituted" means that at least one hydrogen on a group (for example, a carbon or nitrogen atom) is replaced by a substituent. Unless otherwise indicated, when more than one site is substituted in a given structure, the substituents at each site can be the same or different. Typically, when substituted, the optionally substituted group may be substituted by 1 to 5 substituents, for example, $C_{1-4}$ alkyl, $C_{1-4}$ alkoxy, —OH, —F, —$CF_3$, —CN, hydroxymethyl, hydroxyethyl, methoxyphenyl, phenoxypropyl, 2-fluorophenyl, etc.

The term "anion" refers to any negatively charged group that maintains electrical neutrality.

The term "oxygen protective group" is a well-known group in the art, including the groups described in "*Protecting Groups in Organic Synthesis*, T. W. Greene, P. G. M. Wilts, $3^{rd}$ edition, John Wiley & Sons, 1999" and references cited therein. For example, oxygen protective groups include, but not limited to, substituted or unsubstituted alkyl ethers, such as methyl, allyl, benzyl, substituted benzyl (e.g., 4-methoxybenzyl), methoxymethyl (MOM), benzyloxymethyl (BOM), 2-methoxyethoxymethyl (MEM), etc.; silyl ethers, such as trimethylsilyl (IMS), triethylsilyl (TES), triisopropylsilyl (TIPS), TBS t-butyldimethylsilyl (TBDMS), etc.; acetal or ketal, such as tetrahydropyranyl (THP); esters, such as formate, acetate, chloroacetate, dichloroacetate, trichloroacetate, trifluoroacetate, methoxyacetate, etc.; carbonic esters; and sulfuric esters, such as mesylate, besilate, methyl p-toluenesulfonate, etc.

The term "leaving group" refers to the general meaning in synthetic organic chemistry, that is, an atom or group that can be substituted by a nucleophile. For example, see "Smith, *March Advanced Organic Chemistry* 6th ed. (501-502)". Examples of appropriate leaving groups include, but not limited to, halogens (e.g., F, Cl, Br, I), alkoxycarbonyloxy, aryloxycarbonyloxy, alkylsulfonyloxy, arylsulfonyloxy, alkylcarbonyloxy (for example, acetoxy), arylcarbonyloxy, aryloxy, methoxy, N,O-dimethylhydroxylamino, pixyl, etc.

The term "subject of treatment" (or "patient") refers to an animal, especially a mammal, subject to treatment, observation, or experimentation, preferably a human.

The term "effective dose" refers to the effective dose used in the treatment of one or more specified, diseases, such as asthma, COPD, OAB, bronchospasm with chronic obstructive pulmonary disease, visceral spasm, irritable bowel syndrome, Parkinson's disease, depression or anxiety, schizophrenia and related mental diseases, that can, for example, eliminate, reduce or ameliorate the disease or condition, and/or the symptoms related thereto.

In the present invention, the term "administration" refers to the administration of a certain amount of a compound or compound prodrug (for example, an ester prodrug) to an individual that needs treatment.

The terms "treatment" and "therapeutic" refer to a variety of treatments, especially for muscarinic receptor-related diseases. The terms "treatment" and "therapeutic" refer to the elimination, alleviation or amelioration of a disease or condition, and/or symptoms related thereto. Although not excluded, the treatment of a disease or condition does not require complete elimination of the disease, condition or symptom related thereto. The dosage of a specific compound in the present invention will vary depending on the potency, mode of administration, age and weight of the patient, and severity of the condition being treated. Tire preferred dosage range of the compound of the present invention for the treatment is 1 µg to 10 mg, and the number of times of administration per day is 1 to 4. The volume of the aerosol or intranasal spray of the compound of the present invention depends on the concentration of the compound in the aerosol or intranasal spray, where a higher concentration of the compound requires a smaller dose volume to achieve the therapeutically effective dose. Tire compound of the present invention can also be used in combination with other drugs.

The following non-limiting examples and pharmacological experiments will further illustrate the present invention.

NON-LIMITING EMBODIMENTS

In the following examples, the Chinese description of some groups is appended to tire functional groups, for example, —O—$C_{1-10}$ alkoxy, which refers to $C_{1-10}$ alkoxy. Other similar descriptions are explained similarly, for example, —O—$C_{1-4}$ alkyleneoxy-O—$C_{1-4}$ alkoxy, which refers to —O—$C_{1-4}$ alkylene-O—$C_{1-4}$ alkyl, and so on.

E1. A 2-(2,2-diarylethyl)-cyclic amine derivative, the 2-(2,2-diarylethyl)-cyclic amine derivative or pharmaceutically acceptable salt thereof having the general formula of:

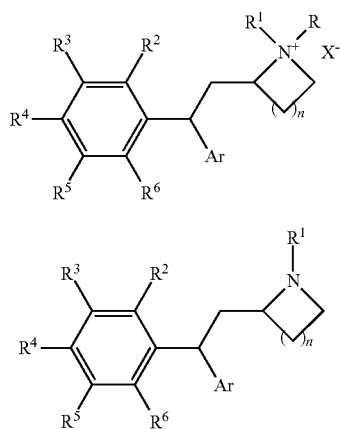

$X^-$ is an anion suitable for pharmaceutical use in a monovalent or polyvalent acid;

R is —$C_{1-10}$ alkyl or —$C_{1-10}$ alkyl derivative I;

$R^1$ is —$C_{1-10}$ alkyl or —$C_{1-10}$ alkyl derivative I;

$R^2$ is —H, —OH, —$CF_3$, —CN, halogen, nitro, amino, $C_{1-10}$ alkyl, —O—$C_{1-10}$ alkoxy, —$C_{1-4}$ alkylene-O—$C_{1-4}$ alkoxy, —O—$C_{1-4}$ alkyleneoxy-O—$C_{1-4}$ alkoxy, $C_{3-6}$ cycloalkyl, benzyloxy, —O—$SiR^{2a}R^{2a'}R^{2a''}$, —O—$COR^{2b}$ alkyl carboxylate, —O—CO—$OR^{2b}$ alkyl carbonate, —O—CO—$NR^{2b}R^{2b'}$ amino carbonate, —$OSO_2$—$NR^{2b}R^{2b'}$ amino sulfonate, —O—$COAr'$ aromatic ester or —OCO—$OAr'$ aryl carbonate;

$R^{2a}$ is —$C_{1-4}$ alkyl or phenyl;

$R^{2a'}$ is —$C_{1-4}$ alkyl or phenyl;

$R^{2a''}$ is —$C_{1-4}$ alkyl or phenyl;

$R^{2b}$ is H, —$C_{1-10}$ alkyl or —$C_{1-10}$ alkyl derivative II;

$R^{2b'}$ is H, —$C_{1-10}$ alkyl or —$C_{1-10}$ alkyl derivative II;

Ar' is phenyl, naphthyl, phenyl derivative I or naphthyl derivative;

$R^5$ is —H, —OH, —$CF_3$, —CN, halogen, $C_{1-10}$ alkyl, —O—$C_{1-10}$ alkoxy, —$C_{1-4}$—OH hydroxyalkyl, —$C_{1-4}$—O—CO—$C_{1-10}$ alkyl carboxylate alkyl, —$C_{1-4}$—O—$C_{1-10}$ alkoxyalkyl, —O—$COR^{2b}$ alkyl carboxylate, —O—CO—$OR^{2b}$ alkyl carbonate, —O—CO—$NR^{2b}R^{2b'}$ amino carbonate, —$OSO_2$—$NR^{2b}R^{2b'}$ amino sulfonate, —O—$COAr'$ aromatic ester or —OCO—$OAr'$ aryl carbonate;

$R^3$ is —H, —OH, —$CF_3$, —CN, halogen, —$C_{1-10}$ alkyl, —$C_{3-10}$ cycloalkyl, —O—$C_{1-10}$ alkoxy, —$C_{1-4}$—OH hydroxyalkyl or —$C_{1-4}$—O—$C_{1-4}$ alkoxyalkyl; $R^4$ is —H, —OH, —$CF_3$, —CN, halogen, —$C_{1-10}$ alkyl, —$C_{3-10}$ cycloalkyl, —O—$C_{1-10}$ alkoxy, —$C_{1-4}$—OH hydroxyalkyl or —$C_{1-4}$—O—$C_{1-4}$ alkoxyalkyl; $R^6$ is —H, —OH, —$CF_3$, —CN, halogen, —$C_{1-10}$ alkyl, —$C_{3-10}$ cycloalkyl, —O—$C_{1-10}$ alkoxy, —$C_{1-4}$—OH hydroxyalkyl or —$C_{1-4}$—O—$C_{1-4}$ alkoxyalkyl;

n is an integer between 1 and 5;

Ar is aryl, heterocyclic aryl, aryl derivative or heterocyclic aryl derivative, and the aryl includes phenyl, thienyl, furyl or a pyridyl.

E2. According to the 2-(2,2-diarylethyl)-cyclic amine derivative or pharmaceutically acceptable salt thereof of E1, the anions suitable for pharmaceutical use include: $Cl^-$, $Br^-$, $I^-$, succinate ion, fumarate ion, sulfate ion or mesylate ion;

The —$C_{1-10}$ alkyl derivative I comprises the —$C_{1-10}$ whose H is substituted by the group: —$C_{3-6}$ cycloalkyl, —O—$C_{1-6}$ alkoxy, hydroxy, halogen, phenyl, phenyl derivative II or phenoxy;

The —$C_{1-10}$ alkyl derivative II comprises the —$C_{1-10}$ whose H is substituted by the group: —O—$C_{1-10}$ alkoxy, —NH—$C_{1-10}$ alkylamino, —N—$(C_{1-10})_2$ alkyl amino, —$C_{2-4}$ alkenyl or alkynyl, —CN, halogen, phenyl or phenoxy;

The phenyl derivative I comprises the phenyl whose H is substituted by the group: —$CF_3$, —CN, halogen, nitro, —$C_{1-10}$ alkyl, —$C_{2-4}$ alkenyl or alkynyl, —O—$C_{1-10}$ alkoxy, —$NHSO_2R^{2b}$, —$COOR^{2b}$, —$SO_2R^{2b}$, —$SO_2NR^{2b}R^{2b'}$, —$NR^{2b}R^{2b'}$ or —$CONR^{2b}R^{2b'}$;

The aryl derivative comprises the aryl whose H is substituted by the group: —H, —OH, —$CF_3$, —CN, halogen, —$C_{1-10}$ alkyl, —$C_{3-10}$ cycloalkyl or —O—$C_{1-10}$ alkoxy;

The heterocyclic aryl derivative comprises the heterocyclic aryl whose H is substituted by the group: —H, —OH, —$CF_3$, —CN, halogen, —$C_{1-10}$ alkyl, —$C_{3-10}$ cycloalkyl or —O—$C_{1-10}$ alkoxy;

$R^{2b}$ and $R^{2b'}$ form a ring with the nitrogen atom.

E3. According to the 2-(2,2-diarylethyl)-cyclic amine derivative or pharmaceutically acceptable salt thereof of E2, the phenyl derivative II comprises the phenyl whose H is substituted by the group: —$C_{1-3}$ alkyl, —O—$C_{1-3}$ alkoxy or halogen.

E4. According to the 2-(2,2-diarylethyl)-cyclic amine derivative or pharmaceutically acceptable salt thereof of E1, $X^-$ is $Cl^-$, $Br^-$, $I^-$, citrate ion, succinate ion, fumarate ion, or sulfate ion;

R is —$C_{1-10}$ alkyl or —$C_{1-10}$ alkyl derivative III;

$R^1$ is —$C_{1-10}$ alkyl or —$C_{1-10}$ alkyl derivative III;

$R^2$ is —H, —OH, —$CF_3$, —CN, —F, $C_{1-10}$ alkyl, —O—$C_{1-10}$ alkoxy, —$OCH_2OCH_3$, benzyloxy, —$Si(CH_3)_2C(CH_3)_3$, —$Si(CH_3)_3$, —$Si(Ph)_2C(CH_3)_3$, —O—$COR^{2b}$ alkyl carboxylate, —O—CO—$OR^{2b}$ alkyl carbonate, —O—CO Ar' aromatic ester, —O—CO—O Ar' aryl carbonate, —O—CO—$NR^{2b}R^{2b'}$ amino carbonate or —$OSO_2$—$NR^{2b}R^{2b'}$ amino sulfonate;

$R^{2a}$ is —$C_{1-4}$ alkyl or phenyl;

$R^{2a'}$ is —$C_{1-4}$ alkyl or phenyl;

$R^{2a''}$ is —$C_{1-4}$ alkyl or phenyl;

$R^{2b}$ is H, —$C_{1-10}$ alkyl or —$C_{1-10}$ alkyl derivative IV;

$R^{2b'}$ is H, —$C_{1-10}$ alkyl or —$C_{1-10}$ alkyl derivative IV;

Ar' is phenyl, or phenyl derivative III;

$R^5$ is —H, —OH, —$CF_3$, —CN, —F, —$C_{1-10}$ alkyl, —O—$C_{1-10}$ alkoxy, —$C_{1-2}$—OH hydroxyalkyl or —$C_{1-2}$—O—CO—$C_{1-10}$ alkyl carboxylate alkyl;

$R^3$ is —H, —OH, —$CF_3$, —CN, —F, —$C_{1-10}$ alkyl, —O—$C_{1-10}$ alkoxy or —$C_{1-4}$—O—$C_{1-4}$ alkoxyalkyl;

$R^4$ is —H, —OH, —CF$_3$, —CN, —F, —C$_{1-10}$ alkyl, —O—C$_{1-10}$ alkoxy or —C$_{1-4}$—O—C$_{1-4}$ alkoxyalkyl;

$R^6$ is —H, —OH, —CF$_3$, —CN, —F, —C$_{1-10}$ alkyl, —O—C$_{1-10}$ alkoxy or —C$_{1-4}$—O—C$_{1-4}$ alkoxyalkyl;

n is an integer between 1 and 5;

Ar' is phenyl, thienyl, furyl, phenyl derivative IV, thienyl derivative I or furyl derivative I.

E5. According to the 2-(2,2-diarylethyl)-cyclic amine derivative or pharmaceutically acceptable salt thereof of E4, the —C$_{1-10}$ alkyl derivative III comprises the —C$_{1-10}$ alkyl whose H is substituted by the group: —C$_{3-6}$ cycloalkyl, —C$_{1-4}$ alkoxy, —OH, —F, —Cl, —Br, phenyl or phenoxy;

The —C$_{1-10}$ alkyl derivative IV comprises the —C$_{1-10}$ alkyl whose H is substituted by the groups: —C$_{2-4}$ alkenyl or alkynyl and —CN;

The phenyl derivative III comprises the phenyl whose H is substituted by the group: —CF$_3$, —CN, —F, —Cl, —Br, nitro, —C$_{1-10}$ alkyl, —C$_{2-4}$ alkenyl or alkynyl, or —O—C$_{1-10}$ alkoxy;

The phenyl derivative IV comprises the phenyl whose H is substituted by the group: —H, —OH, —CF$_3$, —CN, —F, —C$_{1-10}$ alkyl or —O—C$_{1-10}$ alkoxy;

The thienyl derivative I comprises the thienyl whose IT is substituted by the group: —H, —OH, —CF$_3$, —CN, —F, —C$_{1-10}$ alkyl or —O—C$_{1-10}$ alkoxy;

The furyl derivative I comprises the furyl whose H is substituted by the group: —H, —OH, —CF$_3$, —CN, —F, —C$_{1-10}$ alkyl or —O—C$_{1-10}$ alkoxy.

E6. According to the 2-(2,2-diarylethyl)-cyclic amine derivative or pharmaceutically acceptable salt thereof of E1, X$^-$ is Cl$^-$, Br$^-$ or I$^-$;

R is methyl, ethyl, propyl, isopropyl, benzyl, 2-phenoxyethyl, 3-phenoxypropyl, 2-hydroxyethyl, 3-hydroxypropyl, 2-fluoroethyl or 3-fluoropropyl;

$R^1$ is methyl, ethyl, propyl or isopropyl;

$R^2$ is —H, —OH, —CF$_3$, —CN, —F, methyl, ethyl, methoxyl, ethoxyl, —OCH$_2$OCH$_3$, —Si(CH$_3$)$_2$C(CH$_3$)$_3$, —Si(CH$_3$)$_3$, —O—COR$^{2b}$ alkyl carboxylate, —O—CO—OR$^{2b}$ alkyl carbonate, —O—COAr' aromatic ester, —O—CO—OAr' aryl carbonate;

$R^{2b}$ is H or C$_{1-6}$ alkyl;

Ar' is phenyl, or phenyl derivative V;

$R^5$ is —H, —OH, —CF$_3$, —CN, —F, methyl, ethyl, propyl, butyl, isopropyl, isobutyl, tert-butyl, methoxyl, ethoxyl, hydroxymethyl or 2-hydroxyethyl;

$R^3$ is —H, —OH, —CF$_3$, —CN, —F, —C$_{1-4}$ alkyl or —O—C$_{1-4}$ alkoxy;

$R^4$ is —H, —OH, —CF$_3$, —CN, —F, —C$_{1-4}$ alkyl or —O—C$_{1-4}$ alkoxy;

$R^6$ is —H, —OH, —CF$_3$, —CN, —F, —C$_{1-4}$ alkyl or —O—C$_{1-4}$ alkoxy;

n is 2 or 3;

Ar' is substituted or unsubstituted phenyl, thienyl, furyl, phenyl derivative IV, thienyl derivative II or furyl derivative II.

E7. According to the 2-(2,2-diarylethyl)-cyclic amine derivative or pharmaceutically acceptable salt thereof of E6, the phenyl derivative V comprises the phenyl whose H is substituted by the group: —CF$_3$, —F, —Cl, —C$_{1-4}$ alkyl or —O—C$_{1-4}$ alkoxy;

The phenyl derivative VI comprises the phenyl whose H is substituted by the group: —H, —OH, —CF$_3$, —CN, —F, —C$_{1-4}$ alkyl or —O—C$_{1-4}$ alkoxy;

The thienyl derivative II comprises the thienyl whose IT is substituted by the group: —H, —OH, —CF$_3$, —CN, —F, —C$_{1-4}$ alkyl or —O—C$_{1-4}$ alkoxy;

The furyl derivative II comprises the furyl whose H is substituted by the group: —H, —OH, —CF$_3$, —CN, —F, —C$_{1-4}$ alkyl or —O—C$_{1-4}$ alkoxy.

E8. According to the 2-(2,2-diarylethyl)-cyclic amine derivative or pharmaceutically acceptable salt thereof of E1, X$^-$ is Cl$^-$, Br$^-$ or I$^-$;

R is methyl, ethyl, propyl, 3-phenoxypropyl;

$R^1$ is methyl, ethyl;

$R^2$ is —H, —OH, —F, methoxyl, —O—COH, —O—COCH$_3$, —O—COCH$_2$CH$_3$, —O—COPh, —O—CO—OCH$_3$, —O—CO—OCH$_2$CH$_3$ or —O—CO-Oph;

$R^5$ is —H, —OH, —CF$_3$, —F, methyl, ethyl, propyl, butyl, isopropyl, isobutyl, tert-butyl, methoxyl or hydroxymethyl;

$R^3$ is —H, —OH, —F, methyl, ethyl, methoxyl or ethoxyl;

$R^4$ is —H, —OH, —F, methyl, ethyl, methoxyl or ethoxyl;

$R^6$ is —H, —OH, —F, methyl, ethyl, methoxyl or ethoxyl;

n is 2 or 3;

Ar is phenyl, thienyl, phenyl derivative VII or thienyl derivative III.

E9. According to tire 2-(2,2-diarylethyl)-cyclic amine derivative or pharmaceutically acceptable salt thereof of E8, the phenyl derivative VII comprises the phenyl whose H is substituted by the group: —H, —F, methyl or ethyl;

The thienyl derivative III comprises the thienyl whose IT is substituted by the group: —H, —F, methyl or ethyl.

E10. lire hydrates, solvates and various crystals of the 2-(2,2-diarylethyl)-cyclic amine derivative or pharmaceutically acceptable salt thereof of E1 are diastereomer mixtures and individual diastereomer monomers when the compound is in the form of diastereomers, and racemic mixtures and individual enantiomer monomers when the compound is in the form of enantiomers.

E11. According to the 2-(2,2-diarylethyl)-cyclic amine derivative or pharmaceutically acceptable salt thereof of E1, physiologically applicable excipients, earners, diluents, acid-generated salts and the quaternary ammonium salts, free alkalis, corresponding isomers, hydrates, solvates or crystals of the 2-(2,2-diarylethyl)-cyclic amine derivative form the pharmaceutical composition for the treatment or prevention of M-receptor mediated diseases.

E12. According to the 2-(2,2-diarylethyl)-cyclic amine derivative or pharmaceutically acceptable salt thereof of E11, the acid-generated salts include HCl, HBr, citric acid, succinate, fumarate, sulfate or mesylate.

E13. According to the 2-(2,2-diarylethyl)-cyclic amine derivative or pharmaceutically acceptable salt thereof of E11, the M-receptor mediated diseases include asthma, allergic rhinitis, runny nose caused by common cold, chronic obstructive pulmonary disease, urinary incontinence and Parkinson's disease.

E14. According to the 2-(2,2-diarylethyl)-cyclic amine derivative or pharmaceutically acceptable salt thereof of E11, the method of treating the anticholinergic diseases comprises making the receptor come into contact with the 2-(2,2-diarylethyl)-cyclic amine derivative.

E15. A synthesis method of the 2-(2,2-diarylethyl)-cyclic amine derivative or pharmaceutically acceptable salt thereof, the synthetic route being as follows:

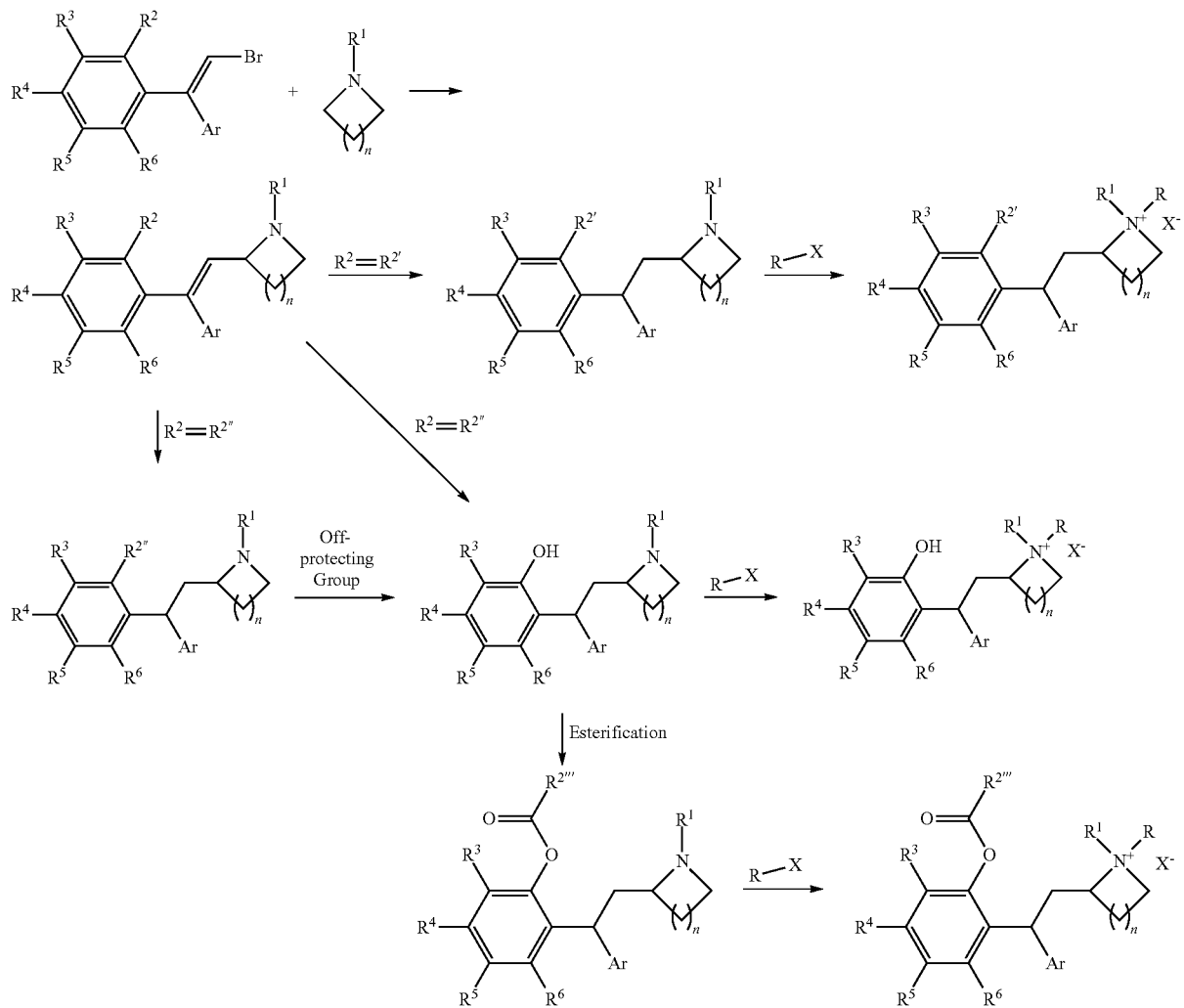

where $X^-$ is: $Cl^-$, $Br^-$, $I^-$, citrate ion, succinate ion, fumarate ion, sulfate ion or mesylate ion;

R is —$C_{1-10}$ alkyl or —$C_{1-10}$ alkyl derivative I;

$R^1$ is —$C_{1-10}$ alkyl or —$C_{1-10}$ alkyl derivative I;

$R^2$ can be "non-leaving group $R^{2''}$", "protected hydroxyl group $R^{2'''}$" or $R^{2'}$. $R^{2'}$ comprises —H, —OH, —$CF_3$, —CN, halogen, nitro, amino, —$C_{1-10}$ alkyl, —O—$C_{1-10}$ alkoxy, —$C_{1-4}$ alkylene-O—$C_{1-4}$ alkoxy, —$C_{3-6}$ cycloalkyl; $R^{2''}$ comprises —O—$C_{1-4}$ alkyleneoxy-O—$C_{1-4}$ alkoxy, benzyloxy, —O—$SiR^{2a}R^{2a'}R^{2a''}$, —O—$COR^{2b}$ alkyl carboxylate, —O—CO—$OR^{2b}$ alkyl carbonate, —O—$CONR^{2b}R^{2b'}$ amino carbonate, —$OSO_2$—$NR^{2b}R^{2b'}$ amino sulfonate, —O—COAr' aromatic ester or —OCO—OAr' aryl carbonate; $R^{2'''}$ comprises —$C_{1-10}$ alkyl or —$C_{1-10}$ alkyl derivative I, —$NR^{2b}R^{2b}$ amino, Ar' and or —OAr' aryloxy;

$R^{2a}$ is —$C_{1-4}$ alkyl or phenyl;

$R^{2a'}$ is —$C_{1-4}$ alkyl or phenyl;

$R^{2a''}$ is —$C_{1-4}$ alkyl or phenyl;

$R^{2b}$ is H, —$C_{1-10}$ alkyl or —$C_{1-10}$ alkyl derivative II;

$R^{2b'}$ is H, —$C_{1-10}$ alkyl or —$C_{1-10}$ alkyl derivative II;

Ar' is phenyl, naphthyl, phenyl derivative I or naphthyl derivative;

$R^5$ is —H, —OH, —$CF_3$, —CN, halogen, $C_{1-10}$ alkyl, —O—$C_{1-10}$ alkoxy, —$C_{1-4}$—OH hydroxyalkyl, —$C_{1-4}$—O—CO—$C_{1-10}$ alkyl carboxylate alkyl, —$C_{1-4}$—O—$C_{1-10}$ alkoxyalkyl, —O—$COR^{2b}$ alkyl carboxylate, —O—CO—$OR^{2b}$ alkyl carbonate, —O—CO—$NR^{2b}R^{2b'}$ amino carbonate, —$OSO_2$—$NR^{2b}R^{2b'}$ amino sulfonate, —O—COAr' aromatic ester or —OCO—OAr' aryl carbonate;

$R^3$ is —H, —OH, —$CF_3$, —CN, halogen, —$C_{1-10}$ alkyl, —$C_{3-10}$ cycloalkyl, —O—$C_{1-10}$ alkoxy, —$C_{1-4}$—OH hydroxyalkyl or —$C_{1-4}$—O—$C_{1-4}$ alkoxyalkyl; $R^4$ is —H, —OH, —$CF_3$, —CN, halogen, —$C_{1-10}$ alkyl, —$C_{3-10}$ cycloalkyl, —O—$C_{1-10}$ alkoxy, —$C_{1-4}$—OH hydroxyalkyl or —$C_{1-4}$—O—$C_{1-4}$ alkoxyalkyl; $R^6$ is —H, —OH, —$CF_3$, —CN, halogen, —$C_{1-10}$ alkyl, —$C_{3-10}$ cycloalkyl, —O—$C_{1-10}$ alkoxy, —$C_{1-4}$—OH hydroxyalkyl or —$C_{1-4}$—O—$C_{1-4}$ alkoxyalkyl;

n is an integer between 1 and 5;

Ar is aryl, heterocyclic aryl, aryl derivative or heterocyclic aryl derivative, and the and includes phenyl, thienyl, furyl or pyridyl.

E16. According to the synthetic method of 2-(2,2-diarylethyl)cyclic amine derivative or pharmaceutically acceptable salt thereof of E15, the —$C_{1-10}$ alkyl derivative I comprises the —$C_{1-10}$ whose H is substituted by the group: —$C_{3-6}$ cycloalkyl, —O—$C_{1-6}$ alkoxy, hydroxy, halogen, phenyl, phenyl derivative II or phenoxy;

The —$C_{1-10}$ alkyl derivative II comprises the —$C_{1-10}$ whose H is substituted by the group: —O—$C_{1-10}$ alkoxy, —NH—$C_{1-10}$ alkylamino, —N—$(C_{1-10})_2$ alkylamino, —$C_{2-4}$ alkenyl or alkynyl, —CN, halogen, phenyl or phenoxy;

The phenyl derivative I comprises the phenyl whose H is substituted by the group: —$CF_3$, —CN, halogen, nitro, —$C_{1-10}$ alkyl, —$C_{2-4}$ alkenyl or alkynyl, —O—$C_{1-10}$ alkoxy, —$NHSO_2R^{2b}$, —$COOR^{2b}$, —$SO_2R^{2b}$, —$SO_2NR^{2b}R^{2b'}$, —$NR^{2b}R^{2b'}$ or —$CONR^{2b}R^{2b'}$;

The aryl derivative comprises the aryl whose H is substituted by the group: —H, —OH, —$CF_3$, —CN, halogen, —$C_{1-10}$ alkyl, —$C_{3-10}$ cycloalkyl or —O—$C_{1-10}$ alkoxy;

The heterocyclic aryl derivative comprises the heterocyclic aryl whose H is substituted by the group: —H, —OH, $CF_3$, —CN, halogen, —$C_{1-10}$ alkyl, —$C_{3-10}$ cycloalkyl or —O—$C_{1-10}$ alkoxy;

$R^{2b}$ and $R^{2b'}$ form a ring with the nitrogen atom.

E17. According to the 2-(2,2-diarylethyl)-cyclic amine derivative or pharmaceutically acceptable salt thereof of E15, the phenyl derivative II comprises tire phenyl whose H is substituted by the group: —$C_{1-3}$ alkyl, —O—$C_{1-3}$ alkoxy or halogen.

Experiment Part

General Method

With reference to similar literature reports or specific examples shown below, experienced researchers can easily select appropriate reaction conditions for the chemical reaction. The materials necessary for such reaction can be purchased or prepared by conventional methods.

The $^1$H-NMR spectra of all compounds were collected on a Bracket AVANCE III 400 MHz instrument, and the spectra were obtained with tetraethylsilane (TMS) as the internal standard.

Liquid chromatography-mass spectrometry (LC-MS) analysis was performed on the Waters Alliance e2695-ZQ 2000 system, and the m/z value and relative abundance were reported. The chiral separation column is S-Chiral B (5 um, 10.0 mm*250 mm) of A China Chromatography Company.

Unless otherwise noted, all solvents are used directly. The ratio of all the mixed solvents refers to the volume ratio (v/v). All temperatures are in Degrees Centigrade (° C.).

The following non-limiting examples and pharmacological experiments will further illustrate the present invention. Unless otherwise specified, the compounds are mixtures of racemes or diastereomers.

Embodiment 1

2-(2,2-Diphenylethyl)-N-Methylpiperidine (II-1)

Synthetic Route:

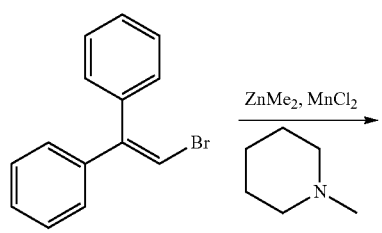

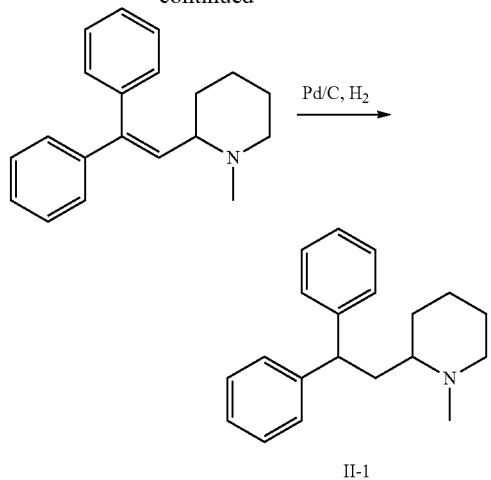

1.1 Synthesis of 2-(2,2-distyryl)-N-methylpiperidine 2-bromo-1,1-diphenylethylene (2.59 g, 10 mmol) is weighed and dissolved in 60 ml of N-methylpiperidine, $MnCl_2$ is added, and the above materials are stirred at room temperature. 40 ml of n-hexane solution of dimethyl zinc (1.0 M, 40 mmol) is added slowly, and the above materials are heated to 50 to 100° C. (usually 70° C.) and stirred for reaction. The reaction is monitored by TLC until the reaction is completed. The mixture is quenched with 20 to 100 ml of saturated sodium hydroxide solution, and is extracted with dichloromethane (3×100 ml). After being merged, the organic phase is dried with anhydrous sodium sulfate. The solvent is removed by rotary evaporation, and the residue obtained is separated and purified by silica column chromatography. 1.9 g of light brown oily product can be obtained (yield 69%). $^1$H NMR (400 MHz, $CDCl_3$), δ: 7.43-7.34 (m, 3H), 7.31-7.24 (m, 5H), 7.18-7.16 (m, 2H), 6.14 (d, J=8.0 Hz, 1H), 2.92-2.89 (m, 1H), 2.56-2.51 (m, 1H), 2.28 (s, 3H), 1.97-1.91 (m, 1H), 1.75-1.53 (m, 5H), 1.20-1.15 (m, 1H).

1.2 Synthesis of 2-(2,2-diphenylethyl)-N-methylpiperidine (II-1)

2-(2,2-distyryl)-1-methylpiperidine (277 mg) is weighed and placed in a 50 ml reaction bottle, 15 ml of absolute methanol is added to dissolve, and 20 mg of Pd/C (10%, dry type) is added. Hydrogen is used for replacement for three times, air in the reactor is removed, and reaction is performed at 40° C. for 12 h under normal pressure hydrogen atmosphere. TLC and LC-MS detection is performed. After the reaction of the materials is completed, the Pd/C is filtered with diatomite and washed with anhydrous methanol for three tunes. The solvent is removed by rotary evaporation to obtain a coarse product, and the coarse product is purified by silica column chromatography to obtain 240 mg of white solid product II-1 (yield 86%). MS (m/z): 280.3 [M+H]$^+$. $^1$H NMR (400 MHz, $CDCl_3$), δ: 7.24-7.15 (m, 8H), 7.15-7.05 (m, 2H), 3.98-3.94 (m, 1H), 2.74-2.70 (m, 1H), 2.54-2.48 (m, 1H), 2.20 (s, 3H), 2.02-1.94 (m, 1H), 1.87-1.76 (m, 2H), 1.72-1.65 (m, 1H), 1.60-1.55 (m, 1H), 1.50-1.43 (m, 2H), 1.25-1.16 (m, 2H).

Embodiment 2

2-[2-(2-hydroxy-phenyl)phenethyl]-N-methylpiperidine (II-2, and Chiral Monomers II-2a-1 and II-2a-2 Thereof), 2-[2-(2-hydroxy-phenyl)-phenethyl]-N,N-dimethylpiperidine Bromide (I-2a-Br, and Chiral Monomers I-2a-1-Br and I-2a-2-Br Thereof) and 2-[2-(2-hydroxy-phenyl)-phenethyl]N,N-dimethylpiperidine Iodide (I-2a-I)

Synthetic Route:

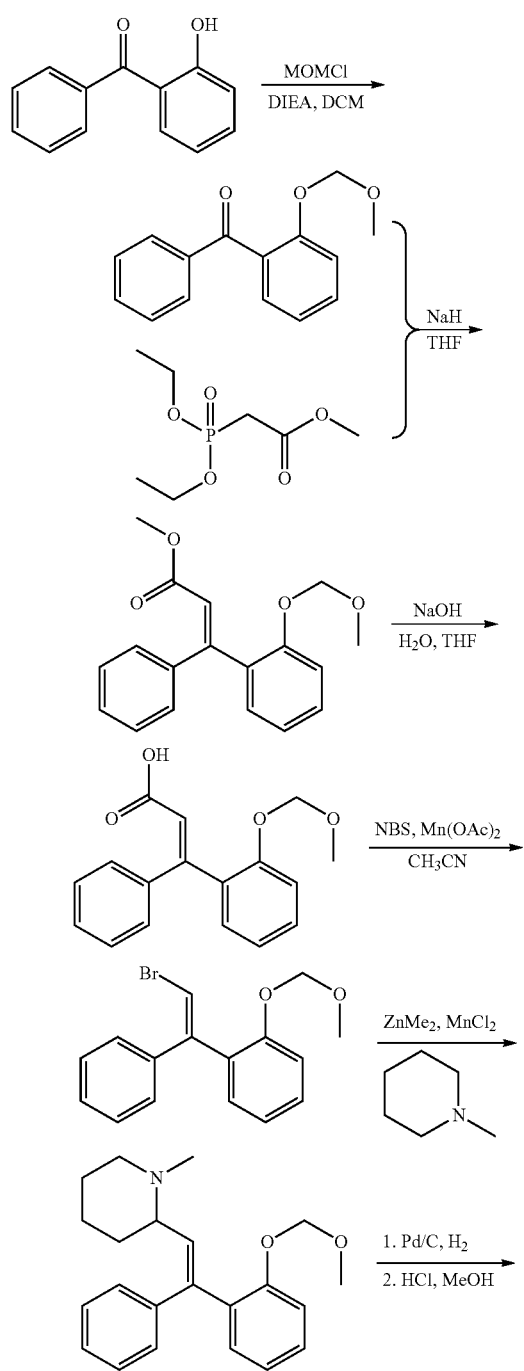

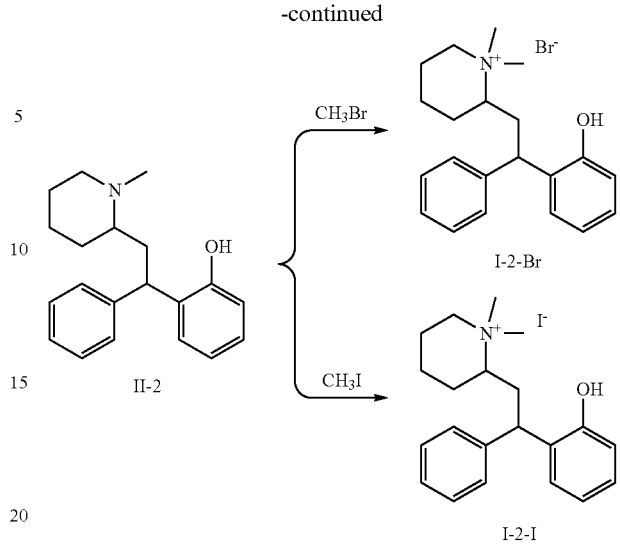

2.1 Synthesis of (2-methoxymethoxy-phenyl)(phenyl)methanone (2-hydroxy-phenyl)(phenyl)-methanone (1.98 g, 10 mmol) is dissolved in dichloromethane (50 ml), diisopropyl ethylamine (30 mmol) is added, the above materials are stirred at room temperature, and chloromethyl methyl ether (20 mmol) is added. The above materials are heated to reflux, for 12 hours, and the reaction is monitored by TLC until the reaction is completed. Tire reaction liquid is cooled to room temperature, the solvent is removed by rotary evaporation, and the product is purified by silica column chromatography to obtain 2.2 g of brown oily product of (2-methoxymethoxy-phenyl)(phenyl)-methanone (yield 91%). $^1$H NMR (400 MHz, CDCl$_3$), δ: 7.84-7.82 (m, 2H), 7.58-7.54 (m, 1H), 7.47-7.42 (m, 3H), 7.37 (q, J=12.0 Hz, 1H), 7.21 (d, J=8.0 Hz, 1H), 7.12-7.09 (m, 1H), 5.05 (s, 2H), 3.29 (s, 3H).

2.2 Synthesis of (E)-3-(2-methoxymethoxy-phenyl)-3-(phenyl)-methyl Acrylate

Methyl diethylphosphonoacetate (2.77 g, 2.43 ml, 13.2 mmol) is slowly dripped into anhydrous THF (20 ml) solution of NaH (60%, 0.527 g, 13.2 mmol), and the above materials are stirred for 10 minutes. Anhydrous THF (10 ml) solution of (2-methoxymethoxyphenyl)(phenyl)-methanone (2.66 g, 11 mmol) is dripped into the above solution, and the above materials are heated to reflux overnight. TLC is used for monitoring; after the reaction is completed, the materials are cooled to room temperature, 100 ml of water is added for quenching, and the mixture is extracted with ethyl acetate (3×30 mi). After being merged, the organic phase is washed with water and a saturated salt solution and dried with anhydrous sodium sulfate respectively. The solvent is removed by rotary evaporation, and the product is purified by silica column chromatography to obtain 3.01 g of brown oily product of (E)-3-(2-methoxymethoxy-phenyl)-3-(phenyl)-methyl acrylate (yield 92%). $^1$H-NMR spectrum shows that the product is E-isomer and no obvious Z-isomer is found. $^1$H NMR (400 MHz, CDCl$_3$), δ: 7.34-7.32 (m, 6H), 7.15 (d, J=8.0 Hz, 1H), 7.11-7.03 (m, 2H), 6.47 (s, 1H), 5.01 (s, 2H), 3.60 (s, 3H), 3.18 (s, 3H).

2.3 Synthesis of 3-(2-methoxymethoxyphenyl)-3-(phenyl)-acrylic Acid 2.98 g of 3-(2-methoxymethoxy-phenyl)-3-(phenyl)-methyl acrylate (10 mmol) is dissolved in 36 ml of THF, aqueous solution (12 ml) of NaOH (0.8 g, 20 mmol) is added at room temperature and the mixture is stirred to react for 4 h at 25 to 60° C. TLC is used for monitoring; after the reaction is completed, the materials are cooled to room temperature, adjusted to acidity with 2 M hydrochloric acid and extracted with ethyl acetate (3×30 ml). After being merged, the organic phase is washed with water and a saturated salt solution and dried with anhydrous sodium sulfate respectively. The solvent is removed by rotary evaporation, and the silica column chromatography is performed for purification to obtain 2.7 g of white solid product of 3-(2-methoxymethoxy-phenyl)-3-(phenyl)-acrylic acid (yield 95%). $^1$H-NMR spectrum show's that the product is the mixture of E,Z-isomers with E/Z=2.9/1. $^1$H NMR (400 MHz, CDCl$_3$), E-isomer δ: 7.33-7.24 (m, 6H), 7.18-7.12 (m, 1H), 7.07-7.00 (m, 2H), 6.42 (s, 1H), 5.00 (s, 2H), 3.18 (s, 3H). Z-isomer δ: 7.33-7.24 (m, 6H), 7.18-7.12 (m, 1H), 7.07-7.00 (m, 2H), 6.17 (s, 1H), 4.91 (s, 2H), 3.14 (s, 3H).

2.4 Synthesis of 2-bromo-1-(2-methoxymethoxy-phenyl)-styrene 2.84 g of 3-(2-methoxymethoxy-phenyl)-3-(phenyl)-acrylic acid (10 mmol) is weighed and dissolved in 30 mi of acetonitrile, and Mn(OAc)$_2$.4H$_2$O (0.49 g, 2 mmol) and NBS (2.67 g, 15 mmol) are added respectively. The mixture is stirred at room temperature for reaction, and TLC monitoring is performed. After the reaction is completed, the solvent is removed, 50 ml of dichloromethane is added to dissolve, water and saturated salt solution are used for washing, anhydrous sodium sulfate is added for drying, and the solvent is removed by rotary evaporation. The coarse product is purified by silica column chromatography to obtain 2.1 g of brown yellow oily product of target product 2-bromo-1-(2-methoxymethoxy phenyl)-styrene (yield 66%). (Refer to Shantanu Chowdhury, Sujit Roy, "Manganese (II) Catalysed Hunsdiecker Reaction: A Facile Entry to α-(Dibromomethyl) benzenemethanol", Tetrahedron Letters, 1996, 37(15), 2623-2624).

$^1$H-NMR spectrum shows that the product is the mixture of E,Z-isomers with E/Z=5.1/1. $^1$H NMR (400 MHz, CDCl$_3$), E-isomer δ: 7.38-7.72 (m, 2H), 7.29-7.24 (m, 4H), 7.22-7.20 (m, 1H), 7.19-7.17 (m, 1H), 7.10-7.06 (m, 1H), 6.88 (s, 1H), 5.05 (s, 2H), 3.23 (s, 3H). Z-isomer δ: 7.38-7.72 (m, 3H), 7.30-7.20 (m, 4H), 7.04-7.02 (m, 1H), 7.01-6.97 (m, 1H), 6.64 (s, 1H), 4.93 (s, 2H), 3.12 (s, 3H).

2.5 Synthesis of 2-[(E)-2-(2-methoxymethoxy-phenyl)-styryl]-N-methylpiperidine 2-bromo-1-(2-methoxymethoxy phenyl)-styrene (10 mmol) is weighed and dissolved in 60 ml of N-methylpiperidine, MnCl$_2$ is added, and the above materials are stirred at room temperature. 40 ml of n-hexane solution of dimethyl zinc (1.0 M, 40 mmol) is added slowly, the above materials are heated to 50 to 100° C. (usually 70° C.) and stirred for reaction. The reaction is monitored by TLC. After the reaction is completed, the mixture is quenched with 20 to 100 ml of saturated sodium hydroxide solution, and is extracted with dichloromethane (3×100 ml). After being merged, the organic phase is dried with anhydrous sodium sulfate. The solvent is removed by rotary evaporation, and the residue obtained is separated and purified by silica column chromatography. 1.4 g of light brown oily product of target compound 2-[(E)-2-(2-methoxymethoxy-phenyl)-styryl]-n-methylpiperidine can be obtained (yield 82%). $^1$H NMR (400 MHz, CDCl$_3$), δ: 7.45-7.30 (m, 3H), 7.20-7.00 (m, 4H), 6.95 (d, J=7.2 Hz, 1H), 6.80-6.65 (m, 1H), 6.67 (d, J=9.6 Hz, 1H), 3.40-3.25 (m, 1H), 3.04 (s, 2H), 2.63 (s, 3H), 2.36 (s, 3H), 2.26-2.21 (m, 1H), 2.10-2.01 (m, 1H), 2.01-1.80 (m, 2H), 1.80-1.70 (m, 2H), 1.49 (b, 1H), 1.06 (b, 1H).

2.6 Synthesis of 2-[2-(2-hydroxy-phenyl)-phenethyl]-N-methylpiperidine (II-2)

337 mg of 2-[2-(2-methoxymethoxy-phenyl)-styryl]-N-methylpiperidine (1.0 mmol) is weighed and placed in a 50 ml high pressure reactor, 15 ml of absolute methanol is added to dissolve, and 20 mg of Pd/C (10%, dry type) is added. The reactor is sealed, hydrogen is used for replacement for three times, air in the reactor is removed, the hydrogen pressure is adjusted to the normal pressure of 1.0 Mpa, and the above materials are stirred for reaction at 40° C. for 12 h. After the temperature is cooled to the room temperature, the pressure is released, and TLC and LC-MS detection is performed. After the reaction of the materials is completed, the Pd/C is filtered with diatomite and washed with anhydrous methanol for three times. The solvent is removed by rotary evaporation to obtain yellow brown oily coarse product 2-[2-(2-methoxymethoxy-phenyl)-phenethyl]-N-methylpiperidine. LC-MS (m/z): 340.3 [M+H]+.

The above coarse product 2-[2-(2-methoxymethoxy-phenyl)-phenethyl]-N-methylpiperidine is dissolved in 30 ml of methanol, 3.33 ml of concentrated hydrochloric acid is dripped, and the mixture is stirred at room temperature. The reaction is monitored by TLC. After the reaction is completed, the reaction mixture is adjusted to neutral with NaOH solution (2.0 M), extracted with dichloromethane (3×20 ml), and dried with anhydrous sodium sulfate. The solvent is removed by rotary evaporation. II-2 has two diastereomers, which can be prepared into white solid target product II-2A (92 mg) after purification by silica column chromatography (yield 81%). The yield of the other diastereomer II-2b is very low, which cannot be obtained by separation. MS (m/z): 296.5 [M+H]+. $^1$H NMR (400 MHz, CDCl$_3$), δ: 12.45 (b, 1H), 7.31-7.30 (m, 4H), 7.25-7.19 (m, 1H), 7.07-7.03 (m, 1H), 6.97 (d, J=8.0 Hz, 1H), 6.71-6.65 (m, 2H), 4.50 (dd, J=3.2 Hz, 12.8 Hz, 1H), 3.01-2.95 (m, 1H), 2.91-2.80 (m, 1H), 2.60-2.52 (m, 1H), 2.40 (s, 3H), 2.20-2.10 (m, 1H), 2.05-1.95 (m, 1H), 1.80-1.72 (m, 1H), 1.72-1.65 (m, 1H), 1.60-1.54 (m, 1H), 1.45-1.20 (m, 3H).

HPLC chiral resolution is conducted to produce the two chiral isomers II-2a-1 and II-2a-2 of the diastereomer II-2a (in the order of peak appearance). The resolution conditions are as follows: instrument: Waters 515-2996; chromatographic column: S-Chiral C (5 um, 10.0 mm*250 mm); mobile phase: N-hexane/methanol/diethylamine=98/2/0.1 (V/V/V); flow rate: 1 ml/min; column temperature: room temperature; detection wavelength: 2.80 nm; and retention time: 7.22 min for chiral monomer II-2a-1 and 10.20 min for chiral monomer II-2a-2.

2.7 Synthesis of 2-[2-(2-hydroxy-phenyl)-phenethyl]-N,N-dimethylpiperidine Bromide/Iodide (I-2a-Br/I-2a-I)

0.1 mmol of II-2a (or chiral monomer II-2a-1 or II-2a-2) is placed in a 25 ml round-bottom flask and dissolved by addition of 5 ml of dried THF (or dichloromethane). Bromomethane (or iodomethane) is dripped at room temperature, the mixture is stirred for reaction, and TLC is used for monitoring. After the reaction is completed, a solid product is separated out, the solvent is removed by suction filtration, and the product is washed with a small amount of THF (or dichloromethane). The obtained solid is detected by LC-MS and $^1$H NMR, which is the target product I-2a-Br or chiral monomer I-2a-1-Br or I-2a-2-Br (or I-2-I) thereof (yield 98%). MS (m/z): 310.6 [M+H]+. $^1$H NMR (400 MHz, CD$_3$OD) δ: 7.45 (d, J=8.0 Hz, 2H), 7.38 (t, J=8.0 Hz, 2H), 7.26 (t, J=8.0 Hz, 1H), 7.18-7.16 (m, 1H), 7.06-7.01 (m, 1H), 6.80-6.75 (m, 2H), 4.48 (dd, J=4.0 Hz, 12.0 Hz, 1H), 3.77-3.72 (m, 1H), 3.50-3.43 (m, 1H), 3.30-3.26 (m, 1H), 2.85 (t, J=12.0 Hz, 1H), 2.28-2.18 (m, 1H), 2.13-2.05 (m, 1H), 1.98-1.73 (m, 5H).

2.8 Synthesis of 2-[2-(2-hydroxy-phenyl)-phenethyl]-N-methylpiperidine hydrochloride (I-2a-Cl)

30 mg of compound II-2a is placed in a 25 ml round-bottom flask and dissolved by addition of 5 ml of absolute methanol. 0.1 ml of saturated ether solution of hydrogen chloride is dripped slowly, and the mixture is stirred at room temperature for reaction for 1 h. The solvent is removed by rotary evaporation, and the residue is dried under vacuum to obtain white solid product I-2a-Cl (yield 94%). LC-MS (m/z): 296.3 [M+H]$^+$.

Embodiment 3

2-[2,2-bis(2-hydroxy-phenyl)-ethyl]-N-methylpiperidine (II-3 Racemate and Chiral Monomers II-3-1, II-3-2 thereof), 2-[2,2-bis(2-hydroxy-phenyl)ethyl]-N,N-dimethylpiperidine Bromide (I-3-Br and Chiral Monomers I-3-1-Br, I-3-2-Br Thereof) and 2-[2,2-bis(2-hydroxy phenyl)ethyl]-N,N-dimethylpiperidine Iodide (I-3-I and Chiral Monomers I-3-1-I, I-3-2-I Thereof)

Synthetic Route:

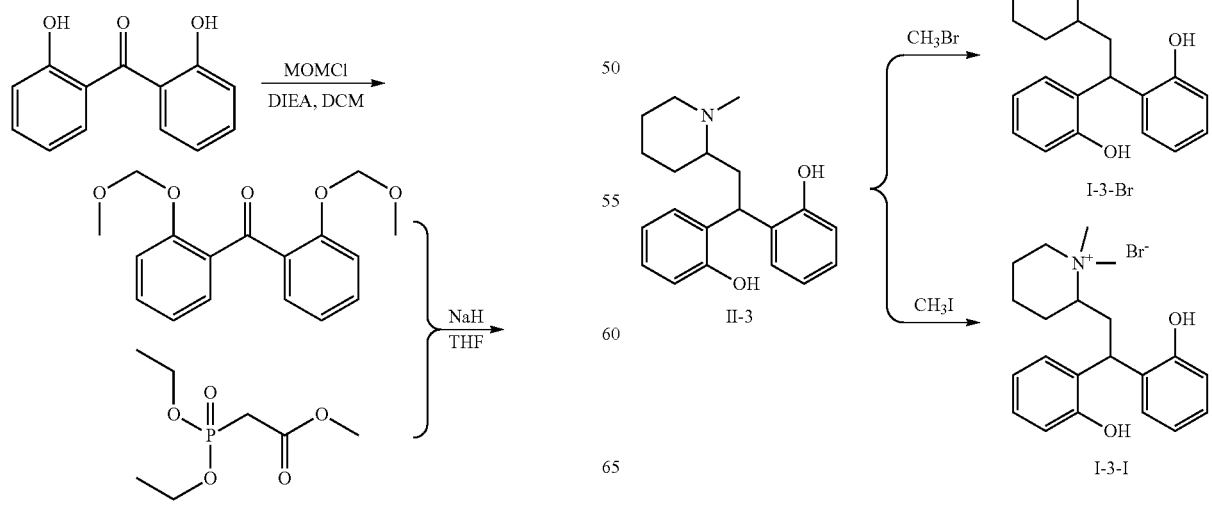

3.1 Synthesis of bis(2-methoxymethoxy-phenyl)-methanone

According to the steps described in 2.1 of embodiment 2, bis(2-hydroxy-phenyl)-methanone is used as the raw material and the amount of DIEA and chloromethyl methyl ether is doubled, which results in the brown oily product of bis(2-methoxymethoxy-phenyl)-methanone with a yield of 92%. $^1$H NMR (400 MHz, CDCl$_3$), δ: 7.54-7.52 (m, 2H), 7.43-7.39 (m, 2H), 7.12-7.04 (m, 4H), 4.98 (s, 4H), 3.26 (s, 6H).

3.2 Synthesis of 3,3-bis(2-methoxymethoxy-phenyl)methyl Acrylate

According to the steps described in 2.2 of embodiment 2, bis(2-methoxymethoxy-phenyl)-methanone is used as the raw material to produce the brown oily product of 3,3-bis(2-methoxymethoxy-phenyl)methyl acrylate with a yield of 81%. $^1$H NMR (400 MHz, CDCl$_3$), δ: 7.29-7.22 (m, 2H), 7.15 (d, J=8.0 Hz, 1H), 7.11-7.04 (m, 3H), 6.98-6.92 (m, 2H), 6.36 (s, 1H), 5.05 (s, 2H), 4.99 (s, 2H), 3.60 (s, 3H), 3.28 (s, 3H), 3.21 (s, 3H).

3.3 Synthesis of 3,3-bis(2-methoxymethoxy-phenyl)-acrylic Acid

According to the steps described in 2.3 of embodiment 2, 3,3-bis(2-methoxymethoxy-phenyl)-methyl acrylate is used as the raw material to produce the light brown solid product of 3,3-bis(2-methoxymethoxy-phenyl)-acrylic acid with a yield of 80%. $^1$H NMR (400 MHz, CDCl$_3$), δ: 10.48 (s, 1H), 7.28-7.21 (m, 2H), 7.18-7.16 (m, 1H), 7.11-7.05 (m, 3H), 6.98-6.92 (m, 2H), 6.36 (s, 1H), 5.05 (s, 2H), 4.99 (s, 2H), 3.28 (s, 3H), 3.21 (s, 3H).

3.4 Synthesis of 2-bromo-1-[2,2-bis(2-methoxymethoxy-phenyl)]-ethylene

According to the steps described in 2.4 of embodiment 2, 3,3-bis(2-methoxymethoxy-phenyl)-acrylic acid is used as the raw material to produce the brown yellow oily product of 2-bromo-1-[2,2-bis(2-methoxymethoxy-phenyl)]-ethylene with a yield of 60%. $^1$H NMR (400 MHz, CDCl$_3$), δ: 7.29-7.25 (m, 2H), 7.23-7.17 (m, 2H), 7.14-7.12 (m, 1H), 7.06-6.99 (m, 2H), 6.95-6.91 (m, 1H), 6.88 (s, 1H), 5.07 (s, 2H), 5.05 (s, 2H), 3.26 (s, 3H), 3.24 (s, 3H).

3.5 Synthesis of 2-[2,2-bis(2-methoxymethoxy-phenyl)-vinyl]-N-methylpiperidine According to the steps described in 2.5 of embodiment 2, 2-bromo-1-[2,2-bis(2-methoxymethoxy-phenyl)]-ethylene is used as the raw material to produce the light brown oily product of 2-[2,2-bis(2-methoxymethoxy-phenyl)-vinyl]-N-methylpiperidine with a yield of 40%. MS (m/z): 398.5 [M+H]$^+$. $^1$H NMR (400 MHz, CDCl$_3$), δ: 7.25-7.07 (m, 5H), 7.02-6.88 (m, 3H), 5.96-5.89 (m, 1H), 5.06-4.92 (m, 4H), 3.21-3.19 (m, 6H), 2.86-2.83 (m, 1H), 2.48-2.43 (m, 1H), 2.26-2.21 (m, 3H), 1.93-1.81 (m, 1H), 1.76-1.68 (m, 2H), 1.60-1.55 (m, 2H), 1.51-1.42 (m, 1H), 1.20-1.12 (m, 1H).

3.6 Synthesis of 2-[2,2-bis(2-hydroxy-phenyl)-ethyl]-N-methylpiperidine (II-3)

According to the steps described in 2.6 of embodiment 2, 2-[2,2-bis(2-methoxymethyl-phenyl)-vinyl]-N-methylpiperidine is used as the raw material to produce the white solid product of the target product II-3 by double-bond hydrogenation and deoxidation of protecting group with a yield of 88%. LC-MS (m/z): 312.3 [M+H]$^+$. $^1$H NMR (400 MHz, CDCl$_3$), δ: 7.33 (d, J=4 Hz, 1H), 7.18-7.14 (m, 1H), 7.12-7.09 (m, 1H), 6.97-6.92. (m, 2H), 6.85-6.80 (m, 2H), 6.78-6.73 (m, 1H), 4.52 (q, J=10.4 Hz, 1H), 2.99 (d, J=13.2 Hz, 1H), 2.74 (b, 1H), 2.54 (b, 1H), 2.39 (s, 3H), 2.17-2.08 (m, 2H), 1.76-1.60 (m, 2H), 1.50-1.30 (m, 4H).

Compound II-3 has a chiral carbon. HPLC chiral resolution is conducted to produce the two chiral isomers II-3-1 and II-3-2 of II-3 (in the order of peak appearance). Tire resolution conditions are as follows: instrument: Waters 515-2996; chromatographic column: S-Chiral C (5 um, 10.0 mm*250 mm); mobile phase: N-hexane/methanol/diethylamine=100/5/0.1 (V/V/V); flow rate: 1 ml/min; column temperature: room temperature; detection wavelength: 280 nm; and retention time: 14.9 min for chiral monomer II-3-1 and 21.2 min for chiral monomer II-3-2.

3.7 Synthesis of 2-[2,2-bis(2-hydroxy-phenyl)-ethyl]-N,N-dimethylpiperidine bromide/iodide (I-3-Br/I-3-I Racemate) and Chiral Monomers I-3-1-Br, I-3-2-Br, I-3-1-I and I-3-2-I Thereof According to the steps described in 2.7 of embodiment 2, II-3 (or chiral monomer II-3-1 or II-3-2) and bromomethane (or iodomethane) are used as the raw materials to produce the white solid target product I-3-Br or I-3-I, or the corresponding chiral monomers I-3-1-Br, I-3-2-Br or I-3-1-I, I-3-2-I, with a yield of 98%. MS (m/z): 326.3 [M+H]$^+$. $^1$H NMR (400 MHz, CD$_3$OD), δ: 7.27-7.21 (m, 3H), 7.14-7.05 (m, 2H), 6.92-6.83 (m, 3H), 4.67 (q, J=16 Hz, 1H), 3.33-3.31 (m, 1H), 3.21-3.14 (m, 1H), 3.02-2.96 (m, 1H), 2.92 (s, 3H), 2.87 (s, 3H), 2.78-2.72 (m, 1H), 2.12-2.11 (m, 1H), 2.01-1.97 (m, 1H), 1.86-1.77 (m, 2H), 1.73-1.66 (m, 2H), 1.39-1.34 (m, 1H).

3.8 Synthesis of 2-[2,2-bis(2-hydroxyphenyl)-ethyl]-N-methylpiperidine Hydrochloride (I-3-Cl)

According to the steps described in 2.8 of embodiment 2, 0.II-3 and the ethyl ether solution of HCl are used as the raw materials to produce the white solid product I-3-Cl with a yield of 98%.

Embodiment 4

2-[2-(2-hydroxy-5-methyl-phenyl)-phenethyl]-N-methylpiperidine (Diastereomers II-4a,-4b; Chiral Monomers II-4a-1-,2; Chiral Monomers II-4b-1-,2), 2-[2-(2-hydroxy-5-methyl-phenyl)-phenethyl]-N,N-dimethylpiperidine Bromide (Diastereomers I-4a-Br and I-4b-Br; Chiral Monomers I-4a-1-Br and I-4a-2-Br; I-4b-1-Br and I-4b-2-Br), 2-[2-(2-hydroxy-5-methyl-phenyl)-phenethyl]-N,N-dimethylpiperidine Iodide (I-4a-I, Chiral Monomers I-4a-1-I and I-4a-2-I) and 2-[2-(2-hydroxy-5-methyl-phenyl)-phenethyl]-N-methyl, N-phenoxypropyl Piperidine Bromide (I-4a-PrOPh Racemate, Chiral Monomers I-4a-1-PrOPh and I-4a-2-PrOPh)

Synthetic Route 1:

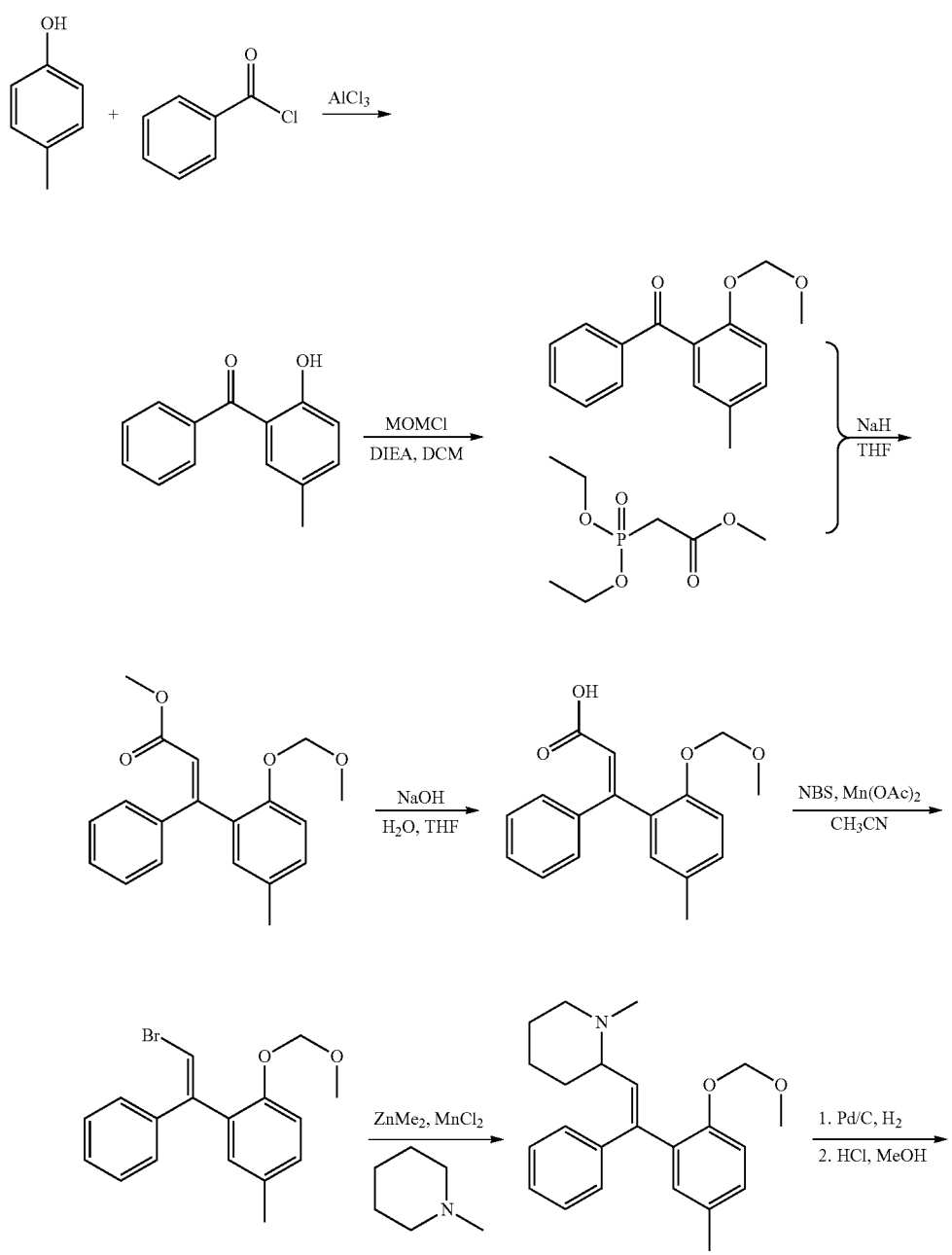

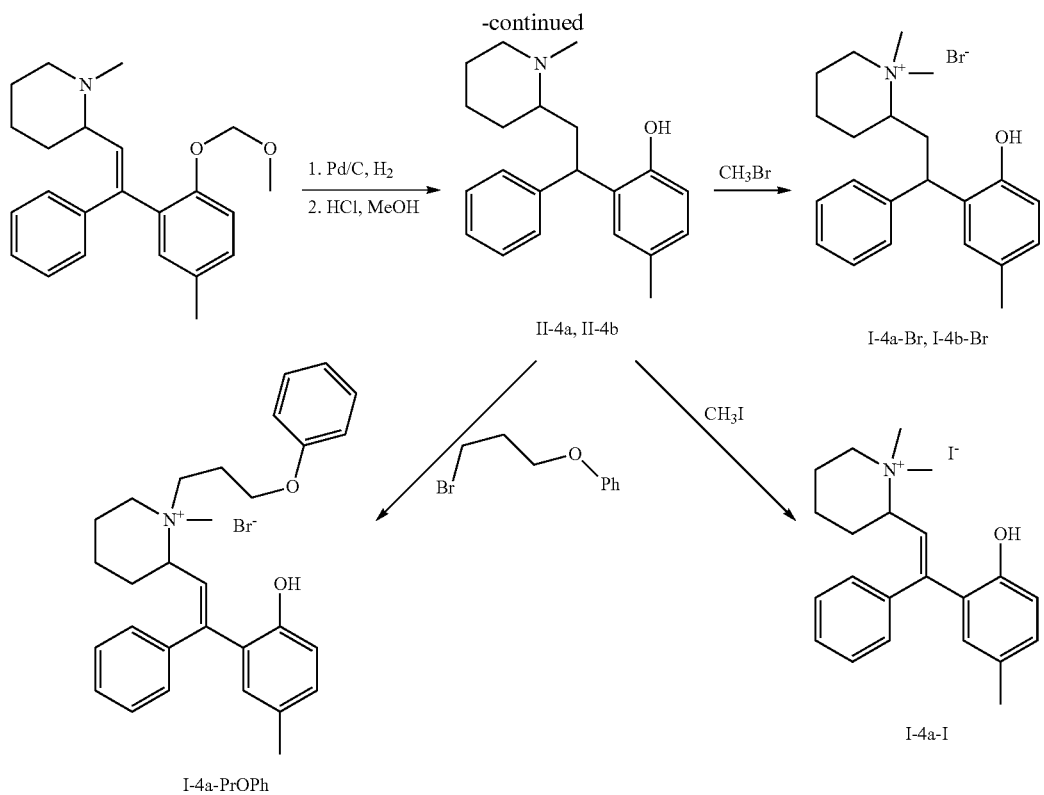

4.1.1 Synthesis of (2-hydroxy-5-methyl-phenyl)(phenyl)methanone 2.16 g (20 mmol) of p-methylphenol and anhydrous $AlCl_3$ (3.2 g, 24 mmol) are weighed and taken into a 250 ml round-bottom flask and heated to 120° C. After 20 minutes, 3.37 g (24 mmol) of benzoyl chloride is added in batches, kept at 120-140° C., stirred for reaction, and monitored by TLC. After reaction, 50 ml of ice water is poured into the flask, and then 10 ml of concentrated hydrochloric acid is added. Tire suspension is stirred for 10 minutes and extracted with dichloromethane (3×50 ml), and the organic phase thereof is merged, dried with anhydrous sodium sulfate, concentrated by a rotary evaporator, and purified by silicon oxide column chromatography, winch results in 3.4 g of yellow solid target product (2-hydroxy-5-methylphenyl)(phenyl)-methanone (with a yield of 80%). (References: Sunil V. Gaikwad, Beena R. Nawghare and Pradeep D. Lokhande, "Chemoselective C-Benzoylation of Phenols by Using AlCl3 Under Solvent-Free Conditions", Bull. Chem. Soc. Ethiop. 2015, 29(2), 319-325). $^1$H NMR (400 MHz, $CDCl_3$), δ: 11.78 (s, 1H), 7.61-7.59 (m, 2H), 7.53-7.51 (m, 1H), 7.46-7.44 (m, 2H), 7.29-7.25 (m, 2H), 6.93-6.90 (d, J=12 Hz, 1H), 2.18 (s, 3H).

4.1.2 Synthesis of (2-methoxymethoxy-5-methylphenyl)(phenyl)-methanone

According to the steps described in 2.1 of embodiment 2, (2-hydroxy-5-methyl-phenyl)(phenyl)-methanone is used as the raw material to produce 2.3 g of colorless oily product (2-methoxymethoxy-5-methyl-phenyl)(phenyl)methanone (with, a yield of 90%). $^1$H NMR (400 MHz, $CDCl_3$), δ: 7.76-7.74 (m, 2H), 7.47 (t, J=16 Hz, 1H), 7.35 (t, J=16 Hz, 2H), 7.18-7.15 (m, 1H), 7.10 (s, 1H), 7.02 (t, J=8 Hz, 1H), 4.92 (s, 2H), 3.20 (s, 3H), 2.25 (s, 3H).

4.1.3 Synthesis of 3-(2-methoxymethoxy-5-methylphenyl)-3-phenyl-methyl Acrylate According to the steps described in 2.2 of embodiment 2, (2-methoxymethoxy-5-methyl-phenyl)(phenyl)-methanone is used as the raw material to produce the colorless oily product 3-(2-methoxymethoxy-5-methyl-phenyl)-3-phenyl-methyl acrylate with a yield of 78%. $^1$H-NMR spectrum shows that the product is mainly E-isomer and no obvious Z-isomer is found. $^1$H NMR (400 MHz, $CDCl_3$), δ: 7.28-7.23 (m, 5H), 7.06-7.04 (m, 1H), 6.99-6.97 (m, 1H), 6.80 (s, 1H), 6.38 (s, 1H), 4.91 (s, 2H), 3.53 (s, 3H), 3.12 (s, 3H), 2.21 (s, 3H).

4.1.4 Synthesis of 3-(2-methoxymethoxy-5-methylphenyl)-3-phenyl-acrylic Acid According to the steps described in 2.3 of embodiment 2, 3-(2-methoxymethoxy-5-methyl-phenyl)-3-phenyl-methyl acrylate is used as the raw material to produce the white solid product 3-(2-methoxymethoxy-5-methyl-phenyl)-3-phenyl-acrylic acid with a yield of 85%. $^1$H-NMR spectrum shows that the product is the mixture of E,Z-isomers with E/Z=5.3/1. $^1$H NMR (400 MHz, $CDCl_3$), E-isomer δ: 7.28-7.25 (m, 3H), 7.21-7.19 (m, 2H), 7.06-7.04 (m, 1H), 6.97 (d, J=8 MHz, 1H), 6.80 (s, 1H), 6.36 (s, 1H), 4.91 (s, 2H), 3.14 (s, 3H), 2.21 (s, 3H). Z-isomer δ: 7.28-7.21 (m, 5H), 7.03-7.01 (m, 1H), 6.92-6.87 (m, 2H), 6.10 (s, 1H), 4.79 (s, 2H), 3.08 (s, 3H), 2.21 (s, 3H).

4.1.5 Synthesis of 2-bromo-1-(2-methoxymethoxy-5-methyl-phenyl)-1-phenyl-ethylene According to the steps described in 2.4 of embodiment 2, 3-(2-methoxymethoxy-5-methyl-phenyl)-3-phenyl-methyl acrylate is used as the raw material to produce the brown yellow oily product 2-bromo-1-(2-methoxymethoxy-5-methyl-phenyl)-1-phenyl-ethylene with a yield of 71%. $^1$H-NMR spectrum shows that the product is mainly E-isomer and no obvious Z-isomer is found. $^1$H NMR (400 MHz, CDCl$_3$), δ: 7.29-7.27 (m, 5H), 7.18-7.16 (m, 1H), 7.11 (d, J=8 MHz, 1H), 7.02 (s, 1H), 6.90 (s, 1H), 5.05 (s, 2H), 3.28 (s, 3H), 2.35 (s, 3H).

4.1.6 Synthesis of 2-[(E)-2-(2-methoxymethoxy-5-methyl-phenyl)-2-phenyl-vinyl]-N-methylpiperidine According to the steps described in 2.5 of embodiment 2, 2-bromo-1-(2-methoxymethoxy-5-methyl-phenyl)-1-phenyl-ethylene is used as the raw material to produce the light brown oily product 2-[(E)-2-(2-methoxymethoxy-5-methyl-phenyl)-2-phenyl-vinyl]-N-methylpiperidine with a yield of 90%. MS (m/z): 352.2 [M+H]$^+$. $^1$H NMR (400 MHz, CDCl$_3$), δ: 7.60-7.45 (m, 1H), 7.40-7.30 (m, 1H), 7.25-7.05 (m, 4H), 6.80-6.65 (m, 2H), 6.63 (d, J=10 Hz, 1H), 5.06-4.92 (m, 2H), 3.40-3.29 (m, 1H), 3.21-3.19 (m, 3H), 3.05 (b, 1H), 2.38 (s, 3H), 2.32 (s, 3H), 2.14-2.02 (m, 1H), 1.95-1.62 (m, 4H), 1.52-1.42 (m, 1H), 1.14-0.98 (m, 1H).

4.1.7 Synthesis of 2-[2-(2-hydroxy-5-methyl-phenyl)-phenethyl]-N-methylpiperidine (Diastereomers II-4a, b, and the Corresponding Chiral Monomers II-4a, b-1 and II-4a, b-2)

According to the steps described in 2.6 of embodiment 2, 2-[2-(2-methoxymethoxy-5-methyl-phenyl)-styryl-]-N-methylpiperidine is used as the raw material to produce tire white solid target product II-4 by double-bond hydrogenation reduction and deoxidation of protecting group and silica gel column separation. The product is a pair of diastereomers II-4a and II-4b with a ratio of approximately 18/1 and a total yield of 62%. LC-MS (m/z): 310.2 [M+H]$^+$. $^1$H NMR (400 MHz, CDCl$_3$), II-4a, δ: 12.03 (b, 1H), 7.34-7.30 (m, 4H), 7.24-7.20 (m, 1H), 6.87-6.82 (m, 2H), 6.46 (s, 1H), 4.47 (dd, J=4.0 Hz, 16 Hz, 1H), 2.97 (d, J=16.0 Hz, 1H), 2.84 (t, J=12.0 Hz, 1H), 2.60-2.53 (m, 1H), 2.38 (s, 3H), 2.17-2.10 (m, 1H), 2.09 (s, 3H), 2.01-1.93 (m, 1H), 1.80-1.50 (m, 4H), 1.45-1.34 (m, 2H).

II-4b, δ: 11.60 (b, 1H), 7.33-7.30 (m, 4H), 7.25-7.19 (m, 1H), 6.87-6.80 (m, 2H), 6.55 (d, J=1.6 Hz, 1H), 4.53 (dd, J=12.8 Hz, 3.2 Hz, 1H), 3.10 (d, J=11.2 Hz, 1H), 2.64-2.57 (m, 1H), 2.41 (s, 3H), 2.29-2.22 (m, 1H), 2.11 (s, 3H), 2.03-2.16 (m, 2H), 1.58-1.49 (m, 3H), 1.28-1.32 (m, 1H), 1.18-1.05 (m, 1H), 0.94-0.84 (m, 1H).

HPLC chiral resolution is conducted to produce the two chiral isomers II-4a, b-1 and II-4a, b-2 of II-4a, II-4b (in the order of peak appearance). The resolution conditions are as follows: instrument: Waters 515-2996; chromatographic column: S-Chiral B (5 um, 10.0 mm*250 mm); mobile phase: n-hexane/isopropanol/diethylamine=90/10/0.1; flow rate: ml/min; column temperature: room temperature; detection wavelength: 230 nm; and retention time: 5.194 mm for chiral isomer II-4a-1 and 7.812 min for chiral isomer II-4a-2; 9.376 min for chiral isomer II-4b-1 and 15.702 min for chiral isomer II-4b-2.

4.1.8 Synthesis of 2-[2-(2-hydroxy-5-methyl-phenyl)-phenethyl]-N,N-dimethylpiperidine Bromide/Iodide (Diastereomers I-4a,b-Br; I-4a-I), 2-[2-(2-hydroxy-5-methyl-phenyl)-phenethyl]-N-methyl,N-phenoxypropylpiperidine Bromide (I-4a-PrOPh) and the Corresponding Chiral Isomer Thereof According to the steps described in 2.7 of embodiment 2, II-4a or II-4b, or the corresponding chiral monomers I-4a-1,-2 and I-4b-1,-2 thereof are used as the raw materials to react with bromomethane or iodomethane to produce the white solid target product T4a,b-Br or I-4a-I, or the corresponding chiral monomers I-4a,b-1-Br or I-4a-1-I and I-4a, b-2-Br or I-4a-2-I thereof, with a yield of 95%.

LC-MS (m/z) of I-4a-Br, I-4a-1-Br or I-4a-2-Br: 324.3 [M+H]$^+$; $^1$H NMR (400 MHz, CD$_3$OD), δ: 7.43-7.40 (m, 2H), 7.37-7.33 (m, 2H), 7.26-7.22 (m, 1H), 6.96 (d, J=1.0 Hz, 1H), 6.80 (dd, J=8.0 Hz, 1.6 Hz, 1H), 6.66 (d, J=8.0 Hz, 1H), 4.28 (dd, J=11.2, 4.0 Hz, 1H), 3.74-3.71 (m, 1H), 3.45 (d, J=12.4 Hz, 1H), 3.24 (dd, J=12.4, 3.2 Hz, 1H), 3.03 (s, 3H), 3.0 (s, 3H), 2.83 (t, J=12.8 Hz, 1H), 2.22 (b, 1H), 2.17 (s, 3H), 2.08-2.01 (m, 1H), 1.97-1.90 (m, 1H), 1.89-1.83 (m, 2H), 1.82-1.71 (m, 1H), 1.48-1.38 (m, 1H).

LC-MS (m/z) of I-4b-Br, I-4b-1-Br or I-4b-2-Br: 324.3 [M+H]$^+$; $^1$H NMR (400 MHz, CD$_3$OD), δ: 7.40-7.37 (m, 2H), 7.31-7.27 (m, 2H), 7.21-7.16 (m, 1H), 6.99 (b, 1H), 6.91 (d, J=8.4 Hz, 1H), 6.75 (d, J=8.4 Hz, 1H), 4.49-4.47 (m, 1H), 3.45-3.49 (m, 1H), 3.36-3.27 (m, 1H), 3.05 (s, 3H), 3.03 (s, 3H), 3.0-2.94 (m, 1H), 2.27 (b, 1H), 2.21 (s, 3H), 2.2-2.1 (m, 1H), 1.98-1.93 (m, 1H), 1.93-1.85 (m, 1H), 1.84-1.74 (m, 2H), 1.48-1.40 (m, 1H), 1.35-1.31 (m, 1H).

LC-MS (m/z) of I-4a-I, I-4a-1-I or I-4a-2-I: 324.3 [M+H]$^+$. $^1$H NMR (400 MHz, DMSO-d$_6$) δ: 9.27 (s, 1H), 7.41 (d, J=4.0 Hz, 2H), 7.33 (t, J=8.0 Hz, 2H), 7.22 (t, J=8.0 Hz, 1H), 7.07 (b, 1H), 6.80 (q, I=4.0 Hz, 8 Hz, 1H), 6.66 (d, J=8 Hz, 1H), 4.28 (q, J=4.0 Hz, 12 Hz, 1H), 3.41-3.38 (m, 1H), 3.28 (m, 1H), 2.98 (s, 3H), 2.94 (s, 3H), 2.89-2.87 (m, 2H), 2.18 (s, 3H), 2.06-2.03 (m, 1H), 1.84-1.76 (m, 2H), 1.75-1.60 (m, 3H), 1.36-1.29 (m, 1H).

Synthesis of I-4a-PrOPh or I-4a-1-PrOPh or I-4a-2-PrOPh: In a 25 ml thick-walled pressure-resistant reaction flask, II-4 or II-4-1 or II-4-2 (120 mg, 0.39 mmol) is dissolved in 4 mi of acetonitrile, and 3-(bromopropoxy) benzene (123 ul, 4.0 equivalents) is added, sealed, heated to 120° C., and stirred for reaction for 12 hours. The TLC detection shows that the reaction is completed. The resultant is concentrated under reduced pressure, a small amount of ethyl acetate is added to dissolve, and petroleum ether is then added, which precipitates a white solid. The white solid is filtered, and washed with petroleum ether to produce 121 mg of the target product I-4a-PrOPh or I-4a-1-PrOPh or I-4a-2-PrOPh, with a yield of 70%. LC-MS (m/z): 444.3 [M+H]$^+$. $^1$H NMR (400 MHz, DMSO-d$_6$) δ: 9.28 (s, 1H), 7.40-7.17 (m, 8H), 7.0-6.94 (m, 3H), 6.82-6.80 (m, 1H), 6.70-6.65 (m, 1H), 4.28-4.25 (m, 1H), 4.07-3.89 (m, 2H), 3.60-3.41 (m, 2H), 3.0-2.84 (m, 5H), 2.20-1.98 (m, 6H), 1.84-1.67 (m, 5H), 1.52-1.23 (m, 3H).

4.1.9 Synthesis of 2-[2-(2-hydroxy-5-methyl-phenyl)-phenethyl]-N-methylpiperidine Hydrochloride or Hydrobromide (I-4a-Cl or I-4a-HBr)

According to the steps described in 2.8 of embodiment 2, 2-[2-(2-hydroxy-5-methyl-phenyl)-phenethyl]-N-methylpiperidine II-4a and the ether solution of HCl or HBr are used as the raw materials to produce the white solid product I-4a-Cl or I-4a-HBr with a yield of 98%. LC-MS (m/z): 310.2 [M+H]$^+$.

Synthetic Route 2:

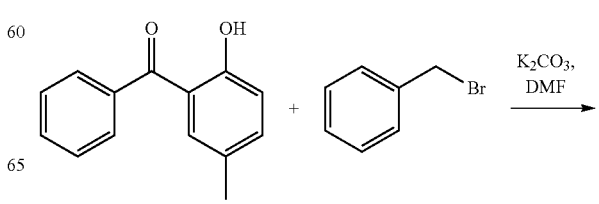

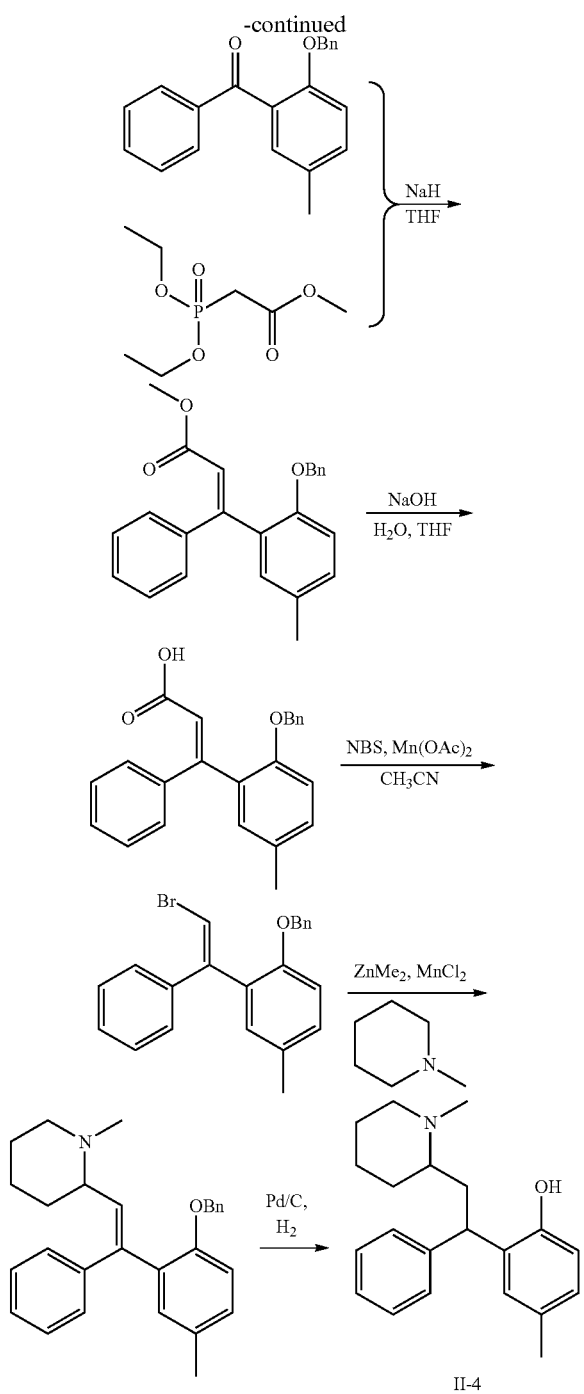

4.2.1 Synthesis of (2-benzyloxy-5-methyl-phenyl)(phenyl)-methanone

According to the steps described in 2.1 of embodiment 2, (2-hydroxy-5-methylphenyl)(phenyl)-methanone is used as the raw material to produce 2.3 g of colorless oily product (2-benzyloxy-5-methylphenyl)(phenyl)-methanone (with a yield of 90%). $^1$H NMR (400 MHz, CDCl$_3$), δ: 7.86-7.84 (m, 2H), 7.57 (t, J=7.6 Hz, 1H), 7.45 (t, J=7.6 Hz, 2H), 7.28-7.26 (m, 2H), 7.22-7.21 (m, 3H), 6.99-6.97 (m, 2H), 6.96-6.93 (m, 1H), 4.99 (s, 2H), 2.36 (s, 3H).

4.2.2 Synthesis of 3-(2-benzyloxy-5-methyl-phenyl)-3-phenyl-methyl Acrylate

According to the steps described in 2.2 of embodiment 2, (2-benzyloxy-5-methyl-phenyl)(phenyl)-methanone is used as the raw material to produce the colorless oily product 3-(2-benzyloxy-5-methyl-phenyl)-3-phenyl-methyl acrylate with a yield of 78%. $^1$H-NMR spectrum shows that the product is mainly E-isomer and no obvious Z-isomer is found. $^1$H NMR (400 MHz, CDCl$_3$), δ: 7.38-7.34 (m, 5H), 7.25-7.23 (m, 3H), 7.15-7.13 (m, 1H), 7.08-7.06 (m, 2H), 6.95 (s, 1H), 6.90 (d, J=8.4 Hz, 1H), 6.46 (s, 1H), 4.96 (s, 2H), 3.60 (s, 3H), 2.32 (s, 3H).

4.2.3 Synthesis of 3-(2-benzyloxy-5-methyl-phenyl)-3-phenyl-acrylic Acid

According to the steps described in 2.3 of embodiment 2, 3-(2-benzyloxy-5-methylphenyl)-3-phenyl-methyl acrylate is used as the raw material to produce the white solid product 3-(2-benzyloxy-5-methyl-phenyl)-3-phenyl-acrylic acid with a yield of 85%. $^1$H-NMR spectrum shows that the product is mainly E-isomer and no obvious Z-isomer is found. $^1$H NMR (400 MHz, CDCl$_3$), E-isomer δ: 7.38-7.34 (m, 5H), 7.24-7.21 (m, 3H), 7.15 (q, J=2.0, 8.4 Hz, 1H), 7.06-7.04 (m, 2H), 6.93 (s, 1H), 6.88 (d, J=8.4 Hz, 1H), 6.42 (s, 1H), 4.93 (s, 2H), 2.30 (s, 3H).

4.2.4 Synthesis of 2-bromo-1-(2-benzyloxy-5-methyl-phenyl)-1-phenyl-ethylene According to the steps described in 2.4 of embodiment 2, 3-(2-benzyloxy-5-methyl-phenyl)-3-phenyl-acrylic acid is used as the raw material to produce the brown yellow oily product 2-bromo-1-(2-benzyloxy-5-methyl-phenyl)-1-phenyl-ethylene with a yield of 71%. $^1$H-NMR spectrum shows that the product is mainly E-isomer and no obvious Z-isomer is found. $^1$H NMR (400 MHz, CDCl$_3$), δ: 7.32-7.30 (m, 3H), 7.29-7.28 (m, 2H), 7.27-7.25 (m, 3H), 7.17 (q, J=1.6, 8.4 Hz, 1H), 7.12-7.09 (m, 2H), 7.08-7.07 (m, 1H), 6.93 (d, J=8.4 Hz, 1H), 6.88 (s, 1H), 4.98 (s, 2H), 2.36 (s, 3H).

4.2.5 Synthesis of 2-[(E)-2-(2-benzyloxy-5-methyl-phenyl)-2-phenyl-vinyl]-N-methylpiperidine According to the steps described in 2.5 of embodiment 2, 2-bromo-1-(2-benzyloxy-5-methyl-phenyl)-1-phenyl-ethylene is used as the raw material to produce the light brown oily product 2-[(E)-2-(2-benzyloxy-5-methylphenyl)-2-phenyl-vinyl]-N-methylpiperidine with a yield of 88%. $^1$H NMR (400 MHz, CDCl$_3$), δ: 7.29-7.27 (m, 4H), 7.25-7.23 (m, 4H), 7.15-7.06 (m, 3H), 6.95 (s, 1H), 6.88 (d, J=8.4 Hz, 1H), 6.15 (d, J=9.2 Hz, 1H), 4.96 (s, 2H), 2.86-2.83 (m, 1H), 2.44-2.43 (m, 1H), 2.34 (s, 3H), 2.31-2.30 (m, 1H), 2.26 (s, 3H), 2.15-2.13 (m, 1H), 1.91-1.89 (m, 1H), 1.66-1.59 (m, 4H).

4.2.6 Synthesis of 2-[2-(2-hydroxy-5-methyl-phenyl)-phenethyl]-N-methylpiperidine (II-4a Racemate)

1.0 mmol of 2-[2-(2-benzyloxy-5-methyl-phenyl)-styryl-]-N-methylpiperidine is dissolved in 30 ml of methanol, and 20 mg Pd/C (10% or 5%, either dry or wet) is added. The mixture is stirred for reaction at room temperature and pressure under hydrogen atmosphere, and monitored by TLC. After the reaction is completed, the resultant is filtered with diatomite to remove Pd/C, the rotary evaporation of the filtrate is conducted under reduced pressure to remove the solvent, and the filtrate is purified by silicon oxide column chromatography, which results in the white solid target product II-4a. The product is a racemate with a yield of 56%. Due to a small proportion of tire other diastereomer II-4b, no product is obtained. LC-MS (m/z): 310.2 [M+H]+. 1H NMR (400 MHz, CDCl3), δ: 12.06 (b, 1H), 7.34-7.33 (m, 4H), 7.26-7.22 (m, 1H), 6.89-6.84 (m, 2H), 6.48 (s, 1H), 4.51 (dd, J=3.2 Hz, 13.2 Hz, 1H), 3.01-2.98 (m, 1H), 2.89-2.83 (m, 1H), 2.61-2.55 (m, 1H), 2.40 (s, 3H), 2.12 (3H, s), 2.03-1.95 (m, 1H), 1.81-1.77 (m, 1H), 1.72-1.65 (m, 1H), 1.60-1.53 (m, 2H), 1.47-1.39 (m, 1H), 1.36-1.26 (m, 2H).

Embodiment 5

2-[2-(2-hydroxy-5-ethyl-phenyl)-phenethyl]-N-methylpiperidine (II-5), 2-[2-(2-hydroxy-5-ethyl-phenyl)-phenethyl]-N,N-dimethylpiperidine Bromide (I-5-Br) and 2-[2-(2-hydroxy-5-ethyl-phenyl)-phenethyl]-N,N-dimethylpiperidine Iodide (I-5-I)

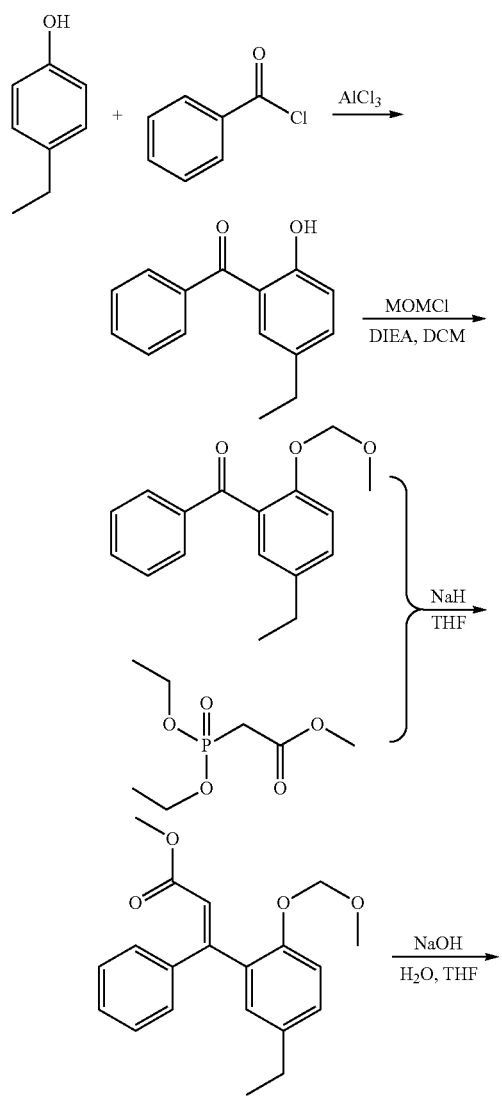

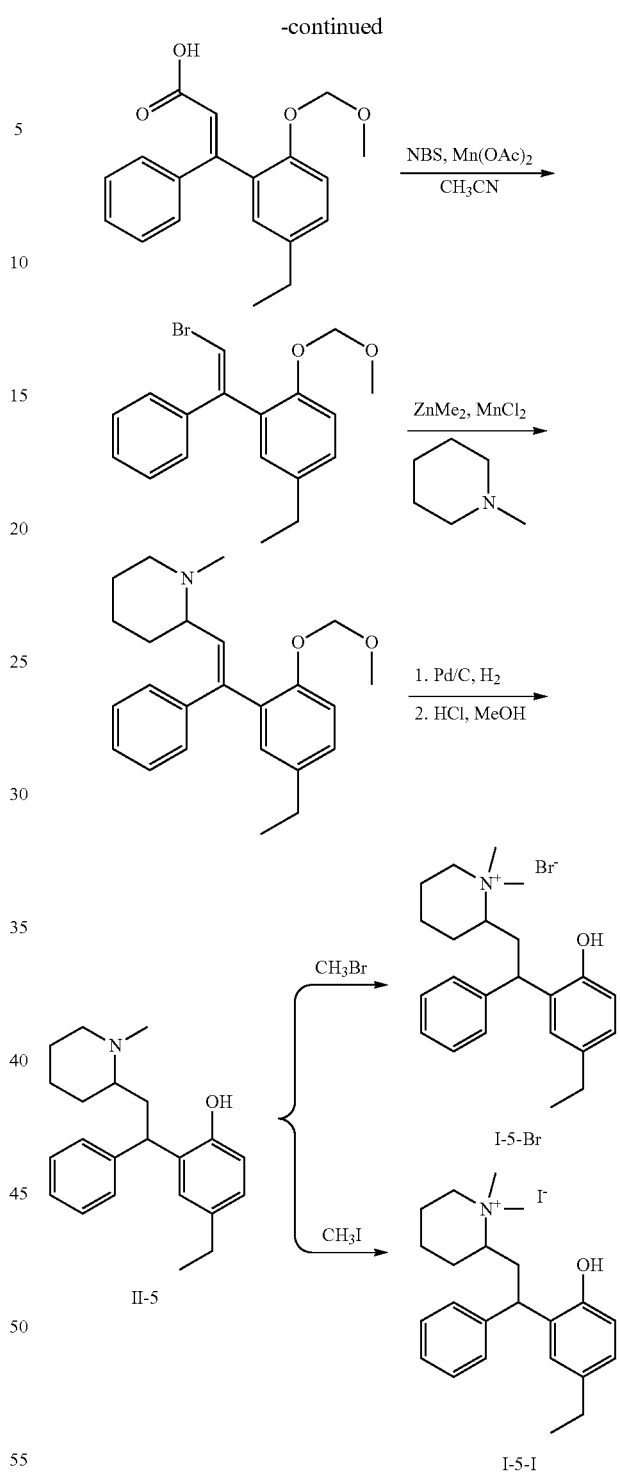

5.1 Synthesis of (2-hydroxy-5-ethyl-phenyl)(phenyl)-methanone

According to the steps described in 4.1.1 of embodiment 4, p-ethylphenol and benzoyl chloride are used as the raw materials to produce the brown yellow oily product (2-hydroxy-5-ethyl-phenyl)(phenyl)-methanone with a yield of 60%. 1H NMR (400 MHz, CDCl3), δ: 11.87 (s, 1H), 7.70-7.66 (m, 2H), 7.61-7.57 (m, 1H), 7.54-7.47 (m, 3H), 7.40-7.36 (m, 1H), 7.01 (d, J 8.0 Hz, 1H), 2.55 (q, J=8.0 Hz, 2H), 1.16 (t, J=8.0 Hz, 3H).

5.2 Synthesis of (2-methoxymethoxy-5-ethyl-phenyl)(phenyl)methanone

According to the steps described in 2.1 of embodiment 2, (2-hydroxy-5-ethyl-phenyl)(phenyl)-methanone is used as the raw material to produce the brown yellow oily product (2-methoxymethoxy-5-ethyl-phenyl)(phenyl)-methanone with a yield of 81%. $^1$H NMR (400 MHz, CDCl$_3$), δ: 7.86-7.80 (m, 2H), 7.58-7.52 (m, 1H), 7.46-7.40 (m, 2H), 7.29-7.25 (m, 1H), 7.21-7.19 (m, 1H), 7.12 (d, J=8.0 Hz, 1H), 5.01 (s, 2H), 3.28 (s, 3H), 2.63 (q, J=8.0 Hz, 2H), 1.23 (t, J=8.0 Hz, 3H).

5.3 Synthesis of 3-(2-methoxymethoxy-5-ethyl-phenyl)-3-phenyl-methyl acrylate According to the steps described in 2.2 of embodiment 2, (2-methoxymethoxy-5-ethyl-phenyl)(phenyl)-methanone is used as the raw material to produce the brown oily product 3-(2-methoxymethoxy-5-ethyl-phenyl)-3-phenyl-methyl acrylate with a yield of 78%. $^1$H-NMR spectrum shows that the product is mainly E-isomer. $^1$H NMR (400 MHz, CDCl$_3$), δ: 7.36-7.29 (m, 5H), 7.15 (q, J=8.4, 2.4 Hz, 1H), 7.08 (d, J=8.4 Hz, 1H), 6.90 (d, J=2.4 Hz, 1H), 6.46 (s, 1H), 4.98 (s, 2H), 3.59 (s, 3H), 3.19 (s, 3H), 2.59 (q, J=8.0 Hz, 2H), 1.20 (t, J=8.0 Hz, 3H).

5.4 Synthesis of 3-(2-methoxymethoxy-5-ethyl-phenyl)-3-phenyl-acrylic Acid

According to the steps described in 2.3 of embodiment 2, 3-(2-methoxymethoxy-5-ethyl-phenyl)-3-phenyl-methyl acrylate is used as the raw material to produce the white solid product 3-(2-methoxymethoxy-5-ethyl-phenyl)-3-phenyl-acrylic acid with a yield of 89%. $^1$H-NMR spectrum shows that the product is mainly E-isomer. $^1$H NMR (400 MHz, CDCl$_3$), δ: 10.88 (b, 1H), 7.35-7.30 (m, 5H), 7.15 (dd, J=8.4, 2.4 Hz, 1H), 7.06 (d, J=8.4 Hz, 1H), 6.89 (d, J=2.4 Hz, 1H), 6.41 (s, 1H), 4.97 (s, 2H), 3.18 (s, 3H), 2.58 (q, J=8 Hz, 2H), 1.19 (t, J=8 Hz, 3H).

5.5 Synthesis of 2-bromo-1-(2-methoxymethoxy-5-ethyl-phenyl)-1-phenyl-ethylene According to the steps described in 2.4 of embodiment 2,3-(2-methoxymethoxy-5-ethyl-phenyl)-3-phenyl-acrylic acid is used as the raw material to produce brown yellow oily product with a yield of 76%. $^1$H-NMR spectrum shows that the product is mainly E-isomer. $^1$H NMR (400 MHz, CDCl$_3$), δ: 7.28-7.23 (m, 5H), 7.17 (dd, J=8.8, 2.4 Hz, 1H), 7.10 (d, J 8.8 Hz, 1H), 7.02 (d, J=2.4 Hz, 1H), 6.88 (s, 1H), 5.02 (s, 2H), 3.24 (s, 3H), 2.63 (q, J=8.0 Hz, 2H), 1.23 (t, J=8.0 Hz, 3H).

5.6 Synthesis of 2-[2-(2-methoxymethoxy-5-ethyl-phenyl)-2-phenyl-vinyl]-N-methylpiperidine According to the steps described in 2.5 of embodiment 2, 2-bromo-1 (2-methoxymethoxy-5-ethyl-phenyl)-1-phenyl-ethylene is used as the raw material to produce light brown oily product with a yield of 81%. MS (m/z): 366.3 [M+H]$^+$. $^1$H NMR (400 MHz, CDCl$_3$), δ: 7.60-7.45 (m, 1H), 7.40-7.30 (m, 1H), 7.25-7.05 (m, 4H), 6.80-6.65 (m, 2H), 6.62 (d, J=10.0 Hz, 1H), 5.06-4.92 (m, 2H), 3.40-3.29 (m, 1H), 3.21-3.19 (m, 3H), 3.05 (b, 1H), 2.56 (q, J=8.0 Hz, 2H), 2.32 (s, 3H), 2.14-2.02 (m, 1H), 1.95-1.62 (m, 4H), 1.52-1.42, (m, 1H), 1.35-1.23 (m, 1H), 1.17 (t, J=8.0 Hz, 3H).

5.7 Synthesis of 2-[2-(2-hydroxy-5-ethyl-phenyl)-phenethyl]-N-methylpiperidine (II-5)

According to the steps described in 2.6 of embodiment 2, 2-[2-(2-methoxymethoxy-5-ethyl-phenyl)-styryl]-N-methylpiperidine is used as the raw material to produce the white solid product II-5 by double-bond hydrogenation and deoxidation of protecting group with a yield of 45%. Compound II-5 has two diastereomers, but only one diastereomer product is obtained from the separated product, which is possibly attributed to the low yield of the other. LC-MS (m/z): 324.6 [M+H]$^+$. $^1$H NMR (400 MHz, CDCl$_3$), δ: 12.18 (b, 1H), 7.31-7.30 (m, 4H), 7.23-7.19 (m, 1H), 6.90-6.84 (m, 2H), 6.48-6.46 (m, 1H), 4.48 (q, J=16.0 Hz, 4.0 Hz, 1H), 3.0-2.93 (m, 1H), 2.90-2.80 (m, 1H), 2.62-2.52 (m, 1H), 2.40 (q, J=8.0 Hz, 2H), 2.38 (s, 3H), 2.17-2.10 (m, 1H), 2.01-1.93 (m, 1H), 1.80-1.73 (m, 1H), 1.73-1.63 (m, 1H), 1.60-1.50 (m, 2H), 1.45-1.35 (m, 1H), 1.35-1.23 (m, 1H), 1.04 (t, J=8.0 Hz, 3H).

5.8 Synthesis of 2-[2-(2-hydroxy-5-ethyl-phenyl)-phenethyl]-N,N-dimethylpiperidine Bromide/Iodide (I-5-Br/I-5-I)

According to the steps described in 2.7 of embodiment 2, II-5 and bromomethane or iodomethane are used as the raw materials to produce the white solid target product I-5-Br or I-5-I with a yield of 96% or 97%, respectively. LC-MS (m/z): 338.3 [M+H]$^+$. $^1$H NMR (400 MHz, DMSO-d$_6$), δ: 9.29 (s, 1H), 7.41 (d, J=4.0 Hz, 3H), 7.33 (t, J=8.0 Hz, 3H), 7.22 (t, J=8.0 Hz, 1H), 7.07 (b, 1H), 6.80 (q, J=4.0 Hz, 8 Hz, 1H), 6.66 (d, J=8.0 Hz, 1H), 4.28 (q, J=4.0 Hz, 12 Hz, 1H), 3.41-3.38 (m, 1H), 3.31-3.28 (m, 1H), 2.98 (s, 3H), 2.94 (s, 3H), 2.89-2.87 (m, 2H), 2.46 (q, J=8.0 Hz, 2H), 2.06-2.03 (m, 1H), 1.84-1.76 (m, 2H), 1.75-1.60 (m, 3H), 1.36-1.29 (m, 1H), 1.10 (t, J=8.0 Hz, 3H).

5.9 Synthesis of 2-[2-(2-hydroxy-5-ethyl-phenyl)-phenethyl]-N-methylpiperidine Hydrochloride or Hydrobromide (I-5-Cl or I-5-Ac)

According to the steps described in 2.8 of embodiment 2, II-5 and the ethyl ether solution of HCl or glacial acetic add are used as the raw materials to produce the white solid product I-5-Cl or I-5-Ac with a yield of 100%. LC-MS (m/z): 324.6 [M+H]$^+$.

Embodiment 6

2-[2-(2-hydroxy-5-propyl-phenyl)-phenethyl]-N-methylpiperidine (II-6) and 2-[2-(2-hydroxy-5-propyl-phenyl)-phenethyl]-N,N-dimethylpiperidine Bromide (1-6)

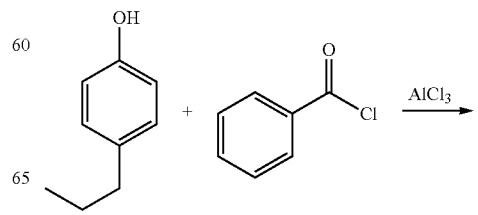

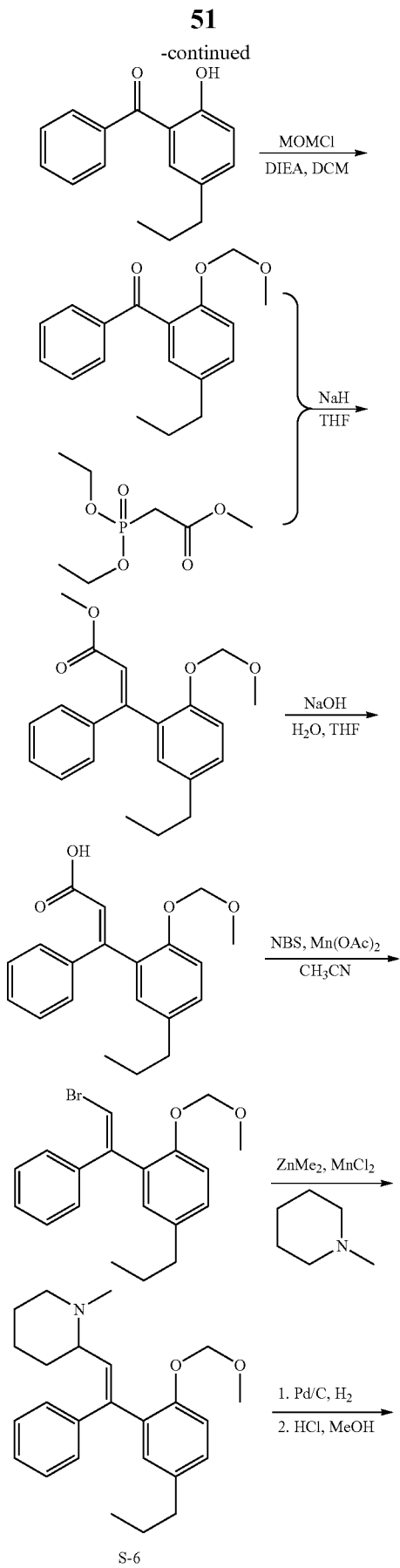

S-6

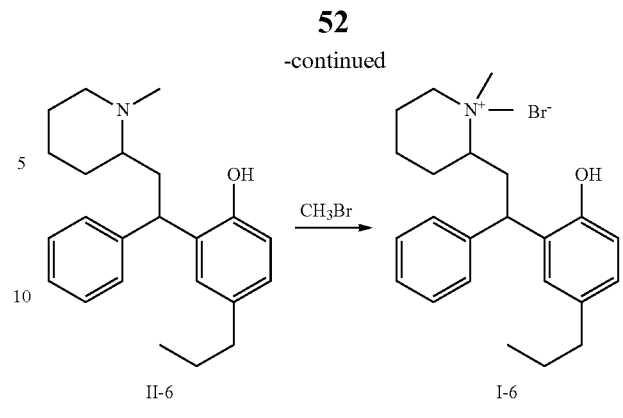

II-6     I-6

6.1 Synthesis of (2-hydroxy-5-propyl-phenyl)(phenyl)-methanone

According to the steps described in 4.1.1 of embodiment 4, p-propylphenol and benzoyl chloride are used as the raw materials to produce the brown oily product (2-hydroxy-5-propyl-phenyl)(phenyl)-methanone with a yield of 51%. $^1$H NMR (400 MHz, CDCl$_3$), δ: 11.85 (s, 1H), 7.69-7.67 (m, 2H), 7.62-7.58 (m, 1H), 7.53-7.49 (m, 2H), 7.36-7.33 (m, 2H), 7.01 (d, J=8.4 Hz, 1H), 2.49 (t, J=7.6 Hz, 2H), 1.57 (m, 2H), 0.90 (t, J=7.6 Hz, 3H).

6.2 Synthesis of (2-methoxymethoxy-5-propyl-phenyl)(phenyl)-methanone

According to the steps described in 2.1 of embodiment 2, (2-hydroxy-5-propyl-phenyl)(phenyl)-methanone is used as the raw material to produce the colorless oily product (2-methoxymethoxy-5-propyl-phenyl)(phenyl)-methanone with a yield of 71%. $^1$H NMR (400 MHz, CDCl$_3$), δ: 7.84-7.82 (m, 2H), 7.57-7.53 (m, 1H), 7.45-7.41 (m, 2H), 7.26-7.24 (m, 1H), 7.18-7.17 (m, 1H), 7.12 (d, J=8.8 Hz, 1H), 5.01 (s, 2H), 3.28 (s, 3H), 2.57 (t, J=7.6 Hz, 2H), 1.62 (m, 2H), 0.94 (t, J=7.6 Hz, 3H).

6.3 Synthesis of 3-(2-methoxymethoxy-5-propyl-phenyl)-3-phenyl-methyl Acrylate According to the steps described in 2.2 of embodiment 2, (2-methoxymethoxy-5-ethyl-phenyl)(phenyl)-methanone is used as the raw material to produce the brown oily product 3-(2-methoxymethoxy-5-propyl-phenyl)-3-phenyl-methyl acrylate with a yield of 61%. $^1$H-NMR spectrum show's that the product is E-isomer, and no obvious Z-isomer is found. $^1$H NMR (400 MHz, CDCl$_3$), δ: 7.36-7.26 (m, 5H), 7.15-7.12 (m, 1H), 7.07 (d, J=8.4 Hz, 1H), 6.88 (d, J=2.0 Hz, 1H), 6.45 (s, 1H), 4.98 (s, 2H), 3.59 (s, 3H), 3.19 (s, 3H), 2.53 (t, J=7.6 Hz, 2H), 1.59 (m, 2H), 0.91 (t, J=7.6 Hz, 3H).

6.4 Synthesis of 3-(2-methoxymethoxy-5-propyl-phenyl)-3-phenyl-acrylic Acid

According to the steps described in 2.3 of embodiment 2, 3-(2-methoxymethoxy-5-propyl-phenyl)-3-phenyl-methyl acrylate is used as the raw material to produce the white solid product 3-(2-methoxymethoxy-5-propyl-phenyl)-3-phenyl-acrylic acid with a yield of 92%. $^1$H-NMR spectrum shows that the product is the mixture of E and Z-isomers, and E/Z=1.8/1.0. $^1$H NMR (400 MHz, CDCl$_3$), E-isomer δ: 7.34-7.30 (m, 5H), 7.13-7.10 (m, 1H), 7.05 (d, J=8.4 Hz, 1H), 6.87 (d, J=2.0 Hz, 1H), 6.41 (s, 1H), 4.96 (s, 2H), 3.18 (s, 3H), 2.53-2.49 (m, 2H), 1.62-1.56 (m, 2H), 0.88 (t, J=7.6 Hz, 3H).

Z-isomer δ: 7.28-7.22 (m, 5H), 7.10-7.08 (m, 1H), 6.98-6.95 (m, 2H), 6.16 (s, 1H), 4.85 (s, 2H), 3.14 (s, 1.7H), 2.53-2.49 (m, 2H), 1.62-1.56 (m, 2H), 0.92 (t, J=7.6 Hz, 3H).

6.5 Synthesis of 2-bromo-1-(2-methoxymethoxy-5-propyl-phenyl)-1-phenyl-ethylene According to the steps described in 2.4 of embodiment 2, 3-(2-methoxymethoxy-5-propyl-phenyl)-3-phenyl-acrylic acid is used as the raw material to produce brown yellow oily product with a yield of 66%. $^1$H-NMR spectrum show's that the product is E-isomer, and no obvious Z-isomer is found. $^1$H NMR (400 MHz, CDCl$_3$), δ: 7.26-7.24 (m, 5H), 7.16-7.14 (m, 1H), 7.09-7.07 (m, 1H), 7.01 (d, J=2.4 Hz, 1H), 6.87 (s, 1H), 5.01 (s, 2H), 3.23 (s, 3H), 2.57 (m, 2H), 1.63 (m, 2H), 0.92 (m, 3H).

6.6 Synthesis of 2-[(E)-2-(2-methoxymethoxy-5-propyl-phenyl)-2-phenyl-vinyl]-N-methylpiperidine According to the steps described in 2.5 of embodiment 2, 2-bromo-1-(2-methoxymethoxy-5-propyl-phenyl)-1-phenyl-ethylene is used as the raw material to produce the light brown oily product 2-[(E)-2-(2-methoxymethoxy-5-propyl-phenyl)-2-phenyl-vinyl]-N-methylpiperidine (S-6) with a yield of 77%. LC-MS (m/z): 380.3 [M+H]$^+$. 1H NMR (400 MHZ, CDCl$_3$), δ: 7.60-7.45 (m, 1H), 7.40-7.32 (m, 1H), 7.25-7.05 (m, 4H), 6.80-6.65 (m, 2H), 6.63 (d, J=10.0 Hz, 1H), 5.06-4.92 (m, 2H), 3.40-3.29 (m, 1H), 3.23-3.19 (m, 3H), 3.05-3.03 (m, 1H), 2.56 (q, J=8.0 Hz, 2H), 2.32 (s, 3H), 2.14-2.02 (m, 1H), 1.95-1.62 (m, 4H), 1.52-1.42 (m, 3H), 3.35-1.23 (m, 1H), 1.01 (t, J=8.0 Hz, 3H).

6.7 Synthesis of 2-[2-(2-hydroxy-5-propyl-phenyl)-phenethyl]-N-methylpiperidine (II-6)

According to the steps described in 2.6 of embodiment 2, 2-[2-(2-methoxymethoxy-5-propyl-phenyl)-styryl-]N-methylpiperidine is used as the raw material to produce the white solid target product II-6 by double-bond hydrogenation and deoxidation of protecting group. $^1$H-NMR spectrum show's that the product is the mixture of two diastereomers with a total yield of 19%. II-6a/II-6b=1/0.35. LC-MS (m/z): 338.3 [M+H]$^{30}$. $^1$H NMR (400 MHz, CDCl$_3$): Isomer II-6a, δ: 12.15 (s, 1H), 7.33-7.29 (m, 4H), 7.24-7.18 (m, 1H), 6.88-6.80 (m, 2H), 6.43 (b, 1H), 4.49 (dd, J=2.8, 12.8 Hz, 1H), 2.95 (d, J=13.6 Hz, 1H), 2.88-2.82 (m, 1H), 2.63-2.54 (m, 1H), 2.38 (s, 3H), 2.34-2.30 (m, 2H), 2.18-2.09 (m, 1H), 2.02-1.92 (m, 1H), 1.80-1.73 (m, 1H), 1.73-1.63 (m, 1H), 1.60-1.50 (m, 2H), 1.45-1.35 (m, 2H), 1.35-1.20 (m, 2H), 0.78 (t, J=7.2 Hz, 3H).

Isomer II-6b, δ: 12.15 (s, 1H), 7.33-7.29 (m, 4H), 7.24-7.18 (m, 1H), 6.88-6.80 (m, 2H), 6.50 (b, 1H), 4.53 (dd, J=3.2, 12.8 Hz, 1H), 3.08 (d, J=12.0 Hz, 1H), 2.63-2.54 (m, 1H), 2.40 (s, 3H), 2.34-2.30 (m, 2H), 2.18-2.09 (m, 1H), 2.02-1.92 (m, 1H), 1.80-1.73 (m, 1H), 1.73-1.63 (m, 1H), 1.60-1.50 (m, 2H), 1.45-1.35 (m, 2H), 1.35-1.20 (m, 2H), 0.76 (t, J=7.2 Hz, 3H).

6.8 Synthesis of 2-[2-(2-hydroxy-5-propyl-phenyl)-phenethyl]-N,N-dimethylpiperidine Iodide (I-6)

According to the steps described in 2.7 of embodiment 2, II-6 and iodomethane are used as the raw materials to produce the white solid target product 1-6 with a yield of 97%. LC-MS (m/z): 352.3 [M+H]$^+$. $^1$H NMR (400 MHz, DMSO-d$_6$), isomer I-6a, δ: 9.28 (s, 1H), 7.42-7.39 (m, 2H), 7.36-7.32 (m, 2H), 7.23-7.21 (m, 1H), 7.08 (d, J=2.0 Hz, 1H), 6.81 (dd, J=8.4, 2.4 Hz, 1H), 6.67 (d, J=8.0 Hz, 1H), 4.30 (dd, J=11.2, 4.0 Hz, 1H), 3.4-3.3 (m, 1H), 2.96 (s, 3H), 2.93 (s, 3H), 2.88-2.85 (m, 2H), 2.40 (t, J=8.0 Hz, 2H), 2.08-1.96 (m, 1H), 1.83-1.77 (m, 2H), 1.75-1.60 (m, 3H), 1.54-1.46 (m, 2H), 1.36-1.24 (m, 2H), 0.85 (t, J=7.2 Hz, 3H).

Isomer I-6b, δ: 9.35 (s, 1H), 7.42-7.39 (m, 2H), 7.36-7.32 (m, 2H), 7.23-7.21 (m, 1H), 7.10 (d, J=2.0 Hz, 1H), 6.85 (dd, J=8.4, 2.4 Hz, 1H), 6.74 (d, J=8.0 Hz, 1H), 4.38 (dd, J=11.2, 4.0 Hz, 1H), 3.4-3.3 (m, 1H), 3.01 (s, 3H), 2.94 (s, 3H), 2.88-2.85 (m, 2H), 2.40 (t, J=8.0 Hz, 2H), 2.08-1.96 (m, 1H), 1.83-1.77 (m, 2H), 1.75-1.60 (m, 3H), 1.54-1.46 (m, 2H), 1.36-1.24 (m, 2H), 0.85 (t, J=7.2 Hz, 3H).

Embodiment 7

Synthesis of 2-[2-(2-fluorophenyl)-2-(2-hydroxy-5-methyl-phenyl)ethyl]-N-methylpiperidine (II-7) and 2-[2-(2-fluorophenyl)-2-(2-hydroxy-5-methyl-phenyl)-ethyl]-N,N-dimethylpiperidine Bromide (I-7)

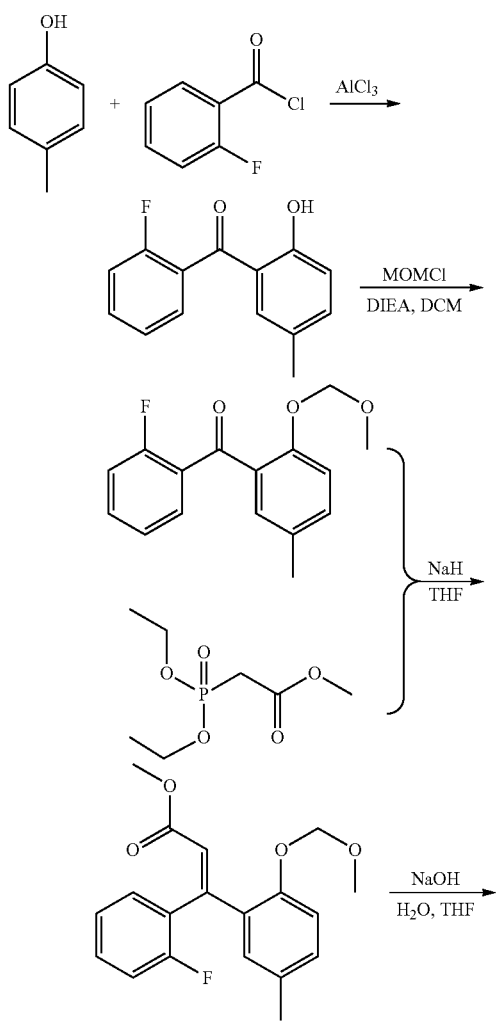

-continued

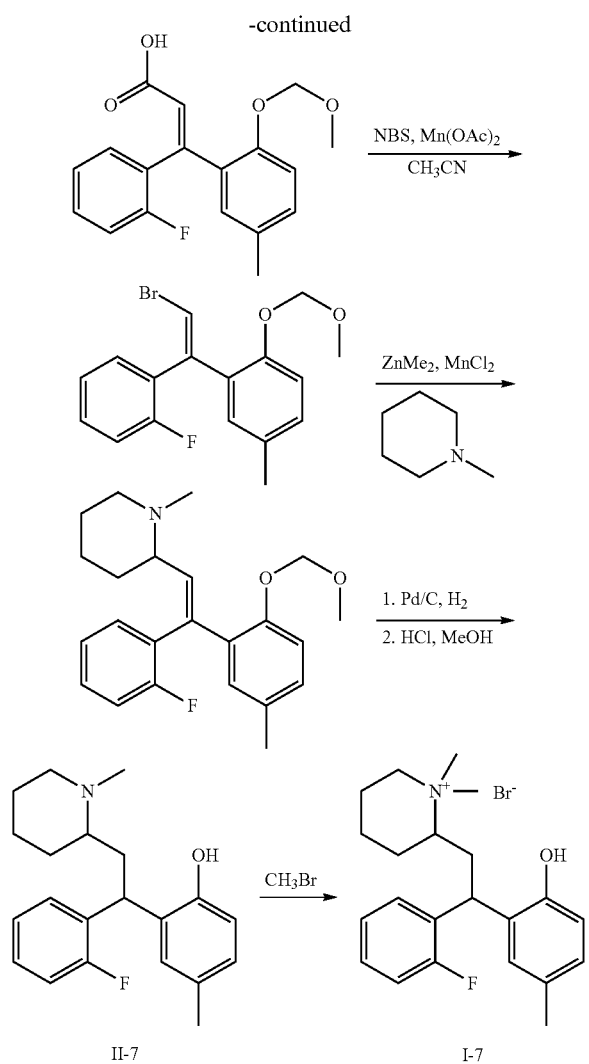

II-7     I-7

7.1 Synthesis of (2-fluorophenyl)(2-hydroxy-5-methyl-phenyl)-methanone

According to the steps described in 4.1.1 of embodiment 4, p-methylphenol and 2-fluorobenzoyl chloride are used as the raw materials to produce the brown solid pure product (2-fluorophenyl) (2-hydroxy-5-methyl-phenyl)-methanone with a yield of 80%. $^1$H NMR (400 MHz, CDCl$_3$), δ: 11.81 (s, 1H), 7.57-7.52 (m, 1H), 7.48-7.43 (m, 1H), 7.33 (dd, J=8.4, 2.4 Hz, 1H), 7.29 (dt, J=7.6, 0.8 Hz, 1H), 7.23-7.18 (m, 1H), 7.16 (b, 1H), 6.98 (d, J=8.4 Hz, 1H), 2.23 (s, 3H).

7.2 Synthesis of (2-fluorophenyl)(2-methoxymethoxy-5-methyl-phenyl)-methanone According to the steps described in 2.1 of embodiment 2, (2-fluorophenyl)(2-hydroxy-5-methyl-phenyl)-methanone is used as the raw material to produce the brown oily product (2-fluorophenyl) (2-methoxymethoxy-5-methyl-phenyl)-methanone with a yield of 82%. $^1$H NMR (400 MHz, CDCl$_3$), δ: 7.74-7.66 (m, 1H), 7.56-7.45 (m, 1H), 7.37-7.35 (m, 1H), 7.27-7.19 (m, 2H), 7.09-7.02 (m, 2H), 4.94 (s, 2H), 3.26 (s, 3H), 2.33 (s, 3H).

7.3 Synthesis of 3-(2-fluorophenyl)-3-(2-methoxymethoxy-5-methyl-phenyl)-methyl Acrylate According to the steps described in 2.2 of embodiment 2, (2-fluorophenyl)(2-methoxymethoxy-5-methyl-phenyl)-methanone is used as the raw material to produce the brown oily product 3-(2-fluorophenyl)-3-(2-methoxymethoxy-5-methyl-phenyl)-methyl acrylate with a yield of 92%. $^1$H-NMR spectrum shows that the product is mainly E-isomer. $^1$H NMR (400 MHz, CDCl$_3$), δ: 7.30-7.24 (m, 1H), 7.13-7.0 Cm. 5H), 6.91-6.89 (m, 1H), 6.45-6.44 (m, 1H), 5.02 (s, 2H), 3.61 (s, 3H), 3.24 (s, 3H), 2.27 (s, 3H).

7.4 Synthesis of 3-(2-fluorophenyl)-3-(2-methoxymethoxy-5-methyl-phenyl)-acrylic Acid According to the steps described in 2.3 of embodiment 2, 3-(2-fluorophenyl)-3-(2-methoxymethoxy-5-methyl-phenyl)-methyl acrylate is used as the raw material to produce the brown solid product 3-(2-fluorophenyl)-3-(2-methoxymethoxy-5-methyl-phenyl)-acrylic acid with a yield of 95%. $^1$H-NMR spectrum show's that the product is the mixture of E,Z-isomers with E/Z=1.5/1. $^1$H NMR (400 MHz, CDCl$_3$), E-isomer δ: 7.32-7.28 (m, 2H), 7.11-7.01 (m, 4H), 6.88 (b, 1H), 6.44 (s, 1H), 5.02 (s, 2H), 3.27 (s, 3H), 2.26 (s, 3H).

Z-isomer δ: 7.25-7.23 (m, 1H), 7.11-7.01 (m, 5H), 6.96 (d, J=8.0, 1H), 6.32 (s, 1H), 4.91 (s, 2H), 3.16 (s, 3H), 2.29 (s, 3H).

7.5 Synthesis of 2-bromo-1-(2-fluorophenyl)-1-(2-methoxymethoxy-5-methyl-phenyl)-ethylene According to the steps described in 2.4 of embodiment 2, 3-(2-fluorophenyl)-3-(2-methoxymethoxy-5-methyl-phenyl)-acrylic acid is used as the raw material to produce the brown yellow oily product 2-bromo-1-(2-fluorophenyl)-1-(2-methoxymethoxy-5-methyl-phenyl)-ethylene with a yield of 69%. $^1$H-NMR spectrum shows that the product is the mixture of E,Z-isomers with E/Z=2/1. $^1$H NMR (400 MHz, CDCl$_3$), E-isomer δ: 7.26-7.18 (m, 2H), 7.14-7.01 (m, 5H), 6.98 (s, 1H), 5.04 (s, 2H), 3.27 (s, 3H), 2.31 (s, 3H).

Z-isomer δ: 7.31-7.25 (m, 1H), 7.14-7.01 (m, 5H), 6.94 (d, J=8.0 Hz, 1H), 6.81 (s, 1H), 4.95 (s, 2H), 3.17 (s, 3H), 2.28 (s, 3H).

7.6 Synthesis of 2-[2-(2-methoxymethoxy-5-methyl-phenyl)-2-(2-fluorophenyl)vinyl]-N-methylpiperidine According to the steps described in 2.5 of embodiment 2, 2-bromo-1-(2-fluorophenyl)-1-(2-methoxymethoxy-5-methyl-phenyl)-ethylene is used as the raw material to produce the light brown oily product 2-[2-(2-methoxymethoxy-5-methyl-phenyl)-2-(2-fluorophenyl)-vinyl]-N-methylpiperidine with a yield of 79%. $^1$H-NMR spectrum shows that the product is the mixture of E,Z-isomers with E/Z=1.2/1. LC-MS (m/z): 370.3 [M+H]$^+$. $^1$H NMR (400 MHz, CDCl$_3$), E-isomer δ: 7.34-6.98 (m, 4H), 6.90 (d, J=8.2 Hz, 1H), 6.74-6.69 (m, 1H), 6.66-6.62 (m, 1H), 3.0-2.95 (m, 1H), 2.28 (s, 3H), 2.13 (s, 3H), 1.98-1.91 (m, 1H), 1.77-1.45 (m, 5H), 1.50-1.45 (m, 1H), 1.18-1.13 (m, 1H).

Z-isomer δ: 7.23-6.98 (m, 4H), 6.86 (d, J=8.0, 1H), 6.66-6.62 (m, 2H), 6.13 (d, J=8.8 Hz, 1H), 2.94-2.90 (m, 2H), 2.43-2.41 (m, 2H), 2.38 (s, 3H), 2.19 (s, 3H), 1.77-1.45 (m, 4H), 1.37-1.28 (m, 1H).

7.7 Synthesis of 2-[2-(2-fluorophenyl)-2-(2-hydroxy-5-methyl-phenyl)-ethyl]-N-methylpiperidine (II-7)

According to the steps described in 2.6 of embodiment 2, 2-[2-(2-fluorophenyl)-2-(2-methoxymethoxy-5-methyl-phenyl)-vinyl]-N-methylpiperidine is used as the raw material to produce two white solid target products by double-bond hydrogenation and deoxidation of protecting group. The products are the two diastereomer products II-7a and II-7b of II-7 with a total yield of 43%. LC-MS (m/z): 328.4 [M+H]$^+$. $^1$H NMR (400 MHz, CDCl$_3$), isomer II-7a, δ: 11.18 (b, 1H), 7.49-7.45 (m, 1H), 7.21-7.13 (m, 2H), 6.96 (t, J=9.6 Hz, 1H), 6.86 (d, J=8.0 Hz, 1H), 6.79 (d, J=8.0 Hz, 1H), 6.59 (s, 1H), 4.74 (dd, J=2.8, 12.8 Hz, 1H), 3.07 (d, J=10.8 Hz, 1H), 2.48-2.45 (m, 1H), 2.39 (s, 3H), 2.27-2.22 (m, 1H), 2.19-2.08 (m, 2H), 2.10 (s, 3H), 1.57-1.47 (m, 3H), 1.20-1.15 (m, 1H), 1.10-1.02 (m, 1H), 0.97-0.86 (m, 1H).

Isomer II-7b, δ: 1H NMR (400 MHz, CDCl$_3$), δ: 11.92 (b, 1H), 7.52-7.47 (m, 1H), 7.24-7.17 (m, 2H), 6.98 (t, J=9.6 Hz, 1H), 6.86 (d, J=8.0 Hz, 1H), 6.82 (d, J=8.0 Hz, 1H), 6.50 (s, 1H), 4.66 (m, 1H), 2.99 (d, J=13.6 Hz, 1H), 2.84 (t, J=12.8 Hz, 1H), 2.61-2.54 (m, 1H), 2.38 (s, 3H), 2.10 (s, 3H), 2.05-2.01 (m, 2H), 1.78-1.74 (m, 1H), 1.7-1.62 (m, 1H), 1.60-1.49 (m, 1H), 1.44-1.36 (m, 1H), 1.35-1.23 (m, 2H).

7.8 Synthesis of 2-[2-(2-fluorophenyl)-2-(2-hydroxy-5-methyl-phenyl)-ethyl]-N,N-dimethylpiperidine Bromide (I-7a)

According to the steps described in 2.7 of embodiment 2, II-7a and bromomethane are used as the raw materials to produce the white solid target product I-7a with a yield of 97%. LC-MS (m/z): 342.3 [M+H]$^+$. $^1$H NMR (400 MHz, CD$_3$OD), δ: 7.51 (t, J=7.6 Hz, 1H), 7.28 (q, J=6.8 Hz, 1H), 7.17 (t, J=7.6 Hz, 1H), 7.07-7.01 (m, 2H), 6.95 (d, J=8.4 Hz, 1H), 6.77 (d, J=8.4 Hz, 1H), 4.76 (dd, J=4.0, 12.0 Hz, 1H), 3.49-3.46 (m, 1H), 3.10-3.08 (m, 1H), 3.03 (s, 6H), 2.32-2.28 (m, 1H), 2.23 (s, 3H), 2.04-1.96 (m, 2H), 1.95-1.89 (m, 1H), 1.84-1.78 (m, 2H), 1.54-1.47 (m, 1H), 1.32 (b, 2H)

Embodiment 8

2-[2-(2-hydroxy-4-fluorophenyl)phenethyl]N-methylpiperidine (II-8) and 2-[2-(2-hydroxy-4-fluorophenyl)-phenethyl]-N,N-dimethylpiperidine bromide (I-8)

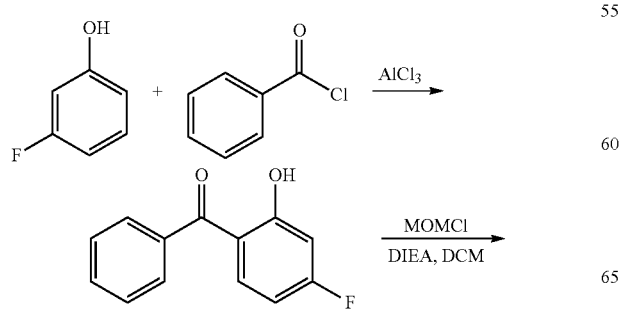

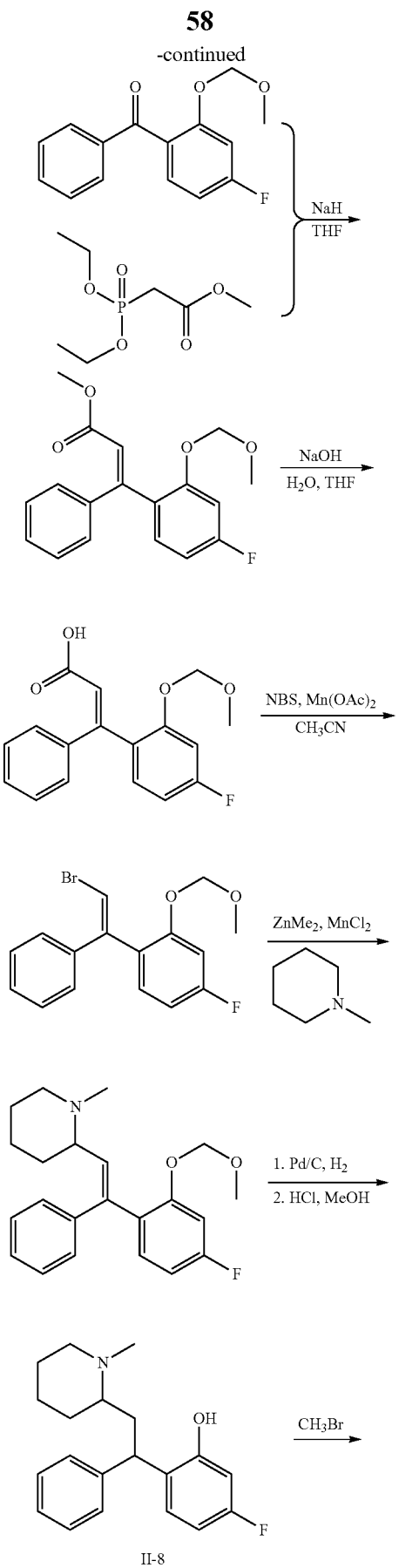

-continued

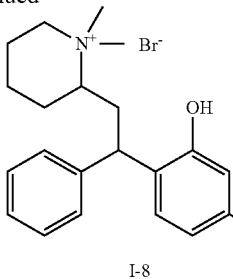

I-8

8.1 Synthesis of (2-hydroxy-4-fluorophenyl)(phenyl)-methanone

According to the steps described in 4.1.1 of embodiment 4, p-3-fluorophenol and benzoyl chloride are used as the raw materials to produce the brown solid pure product (2-hydroxy-4-fluorophenyl)(phenyl)-methanone with a yield of 83%. $^1$H NMR (400 MHz, CDCl$_3$), δ: 12.43 (s, 1H), 7.66-7.58 (m, 4H), 7.53-7.50 (m, 2H), 6.77 (dd, J=2.4, 10.4 Hz, 1H), 6.62-6.56 (m, 1H).

8.2 Synthesis of (2-methoxymethoxy-4-fluorophenyl)(phenyl)-methanone

According to the steps described in 2.1 of embodiment 2, (2-hydroxy-4-fluorophenyl)(phenyl)-methanone is used as the raw material to produce the brown oily product (2-methoxymethoxy-4-fluorophenyl)(phenyl)-methanone with a yield of 88%. $^1$H NMR (400 MHz, CDCl$_3$), δ: 7.81-7.78 (m, 2H), 7.58-7.53 (m, 1H), 7.46-7.37 (m, 3H), 6.98 (dd, J=2.4, 10.8 Hz, 1H), 6.81 (dt, I=2.4, 8.4 Hz, 1H), 5.03 (s, 2H), 3.31 (s, 3H).

8.3 Synthesis of 3-(2-methoxymethoxy-4-fluorophenyl)-3-phenyl-methyl Acrylate According to the steps described in 2.2 of embodiment 2, (2-methoxymethoxy-4-fluorophenyl)(phenyl)-methanone is used as the raw material to produce the brown oily product 3-(2-methoxymethoxy-4-fluorophenyl)-3-phenyl-methyl acrylate with a yield of 72%. $^1$H-NMR spectrum show's that the product is mainly E-isomer, $^1$H NMR (400 MHz, CDCl$_3$), δ: 7.34-7.28 (m, 5H), 7.05 (dd, J=6.4, 8.4 Hz, 1H), 6.93 (dd, J=2.4, 10.8 Hz, 1H), 6.78-6.73 (m, 1H), 6.46 (s, 1H), 5.0 (s, 2H), 3.18 (s, 3H), 3.14 (s, 3H).

8.4 Synthesis of 3-(2-methoxymethoxy-4-fluorophenyl)-3-phenyl-acrylic Acid

According to the steps described in 2.3 of embodiment 2, 3-(2-methoxymethoxy-4-fluorophenyl)-3-phenyl-methyl acrylate is used as the raw material to produce the brown solid product 3-(2-methoxymethoxy-4-fluorophenyl)-3-phenyl-acrylic acid with a yield of 91%. $^1$H-NMR spectrum shows that the product is the mixture of E,Z-isomers with E/Z=3/1. $^1$H NMR (400 MHz, CDCl$_3$), E-isomer δ: 7.37-7.28 (m, 5H), 7.04-7.0 (m, 1H), 6.92 (dd, J=2.4, 10.8 Hz, 1H), 6.76-6.71 (m, 1H), 6.42 (s, 1H), 4.99 (s, 2H), 3.19 (s, 3H).
Z-isomer δ: 7.37-7.28 (m, 3H), 7.23-7.21 (m, 2H), 7.14-7.1 (m, 1H), 6.84 (dd, J=2.4, 10.8, 1H), 6.69-6.67 (m, 1H), 6.17 (s, 1H), 4.92 (s, 2H), 3.15 (s, 3H).

8.5 Synthesis of 2-bromo-1-(2-methoxymethoxy-4-fluorophenyl)-1-(phenyl)-ethylene According to the steps described in 2.4 of embodiment 2, 3-(2-methoxymethoxy-4-fluorophenyl)-3-phenyl-acrylic acid is used as the raw material to produce the brown yellow oily product 2-bromo-1-(2-methoxymethoxy-4-fluorophenyl)-1-(phenyl)-ethylene with a yield of 66%. $^1$H-NMR spectrum show's that the product is mainly E-isomer. $^1$H NMR (400 MHz, CDCl$_3$), δ: 7.28-7.20 (m, 5H), 7.17-7.13 (m, 1H), 6.95-6.91 (m, 1H), 6.88 (s, 1H), 6.81-6.76 (m, 1H), 5.02 (s, 2H), 3.21 (s, 3H).

8.6 Synthesis of 2-[2-(2-methoxymethoxy-4-fluorophenyl)-2-phenyl-vinyl]-N-methylpiperidine According to the steps described in 2.5 of embodiment 2, 2-bromo-1-(2-methoxymethoxy-4-fluorophenyl)-1-(phenyl)-ethylene and N-methylpiperidine are used as the raw materials to produce the light brown oily product 2-[2-(2-methoxymethoxy-4-fluorophenyl)-2-phenyl-vinyl]-N-methylpiperidine with a yield of 75%. $^1$H-NMR spectrum show's that the product is mainly E-isomer, LC-MS (m/z): 356.4 [M+H]$^+$. $^1$H NMR (400 MHz, CDCl$_3$), δ: 7.29-7.23 (m, 5H), 7.06-7.02 (m, 1H), 6.93 (dd, J=2.4, 10.8 Hz, 1H), 6.78-6.73 (m, 1H), 6.34 (t, J=6.8 Hz, 1H), 4.99 (s, 2H), 3.21 (s, 3H), 3.0-2.95 (m, 1H), 2.28 (s, 3H), 1.98-1.91 (m, 1H), 1.77-1.45 (m, 5H), 1.50-1.45 (m, 1H), 1.18-1.13 (m, 1H).

8.7 Synthesis of 2-[2-(2-hydroxy-4-fluorophenyl)-2-phenyl-ethyl]-N-methylpiperidine (II-8)

According to the steps described in 2.6 of embodiment 2, 2-[2-(2-methoxymethoxy-4-fluorophenyl)-2-phenyl-vinyl]-N-methylpiperidine is used as the raw material to produce the white solid target product II-8 by double-bond hydrogenation and deoxidation of protecting group with a yield of 54%. LC-MS (m/z): 314.2 [M+H]$^+$. $^1$H NMR (400 MHz, CDCl$_3$), δ: 13.11 (b, 1H), 7.36-7.30 (m, 4H), 7.26-7.23 (m, 1H), 6.66 (dd, J=2.8, 10.8 Hz, 1H), 6.61-6.57 (m, 1H), 6.42-6.37 (dt, J=2.8, 8.4 Hz, 1H), 4.45 (dd, J=2.8, 13.2 Hz, 1H), 3.01 (d, J=13.6 Hz, 1H), 2.86 (t, J=12.8 Hz, 1H), 2.61-2.55 (m, 1H), 2.42 (s, 3H), 2.19-2.13 (m, 1H), 2.02-1.94 (m, 1H), 1.83-1.80 (m, 1H), 1.73-1.65 (m, 1H), 1.63-1.54 (m, 1H), 1.48-1.28 (m, 3H).

8.8 Synthesis of 2-[2-(2-hydroxy-4-fluorophenyl)-phenethyl]-N,N-dimethylpiperidine Bromide (I-8)

According to the steps described in 2.7 of embodiment 2, II-8 and bromomethane are used as the raw 1.0 materials to produce the white solid target product 1-8 by recrystallization of ethyl acetate with a yield of 83%. LC-MS (m/z): 328.3 [M+H]$^+$. $^1$H NMR (400 MHz, CD$_3$OD), δ: 7.44-7.42 (m, 2H), 7.40-7.36 (m, 2H), 7.30-7.26 (m, 1H), 7.18-7.14 (m, 1H), 6.55-6.49 (m, 2H), 4.43 (dd, J=4.0, 11.2 Hz, 1H), 3.47-3.44 (m, 1H), 3.30-3.27 (m, 1H), 3.03 (s, 3H), 3.02 (s, 3H), 2.88-2.82 (m, 1H), 2.27-2.21 (m, 1H), 2.09-2.02 (m, 1H), 1.98-1.94 (m, 1H), 1.91-1.84 (m, 1H), 1.81-1.76 (m, 1H), 1.52-1.45 (m, 1H), 1.32 (b, 2H).

Embodiment 9

2-[2-(2-hydroxy-5-methoxy-phenyl)-phenethyl]-N-methylpiperidine (II-9) and 2-[2-(2-hydroxy-5-methoxyphenyl)-phenethyl]-N,N-dimethylpiperidine Bromide (I-9)

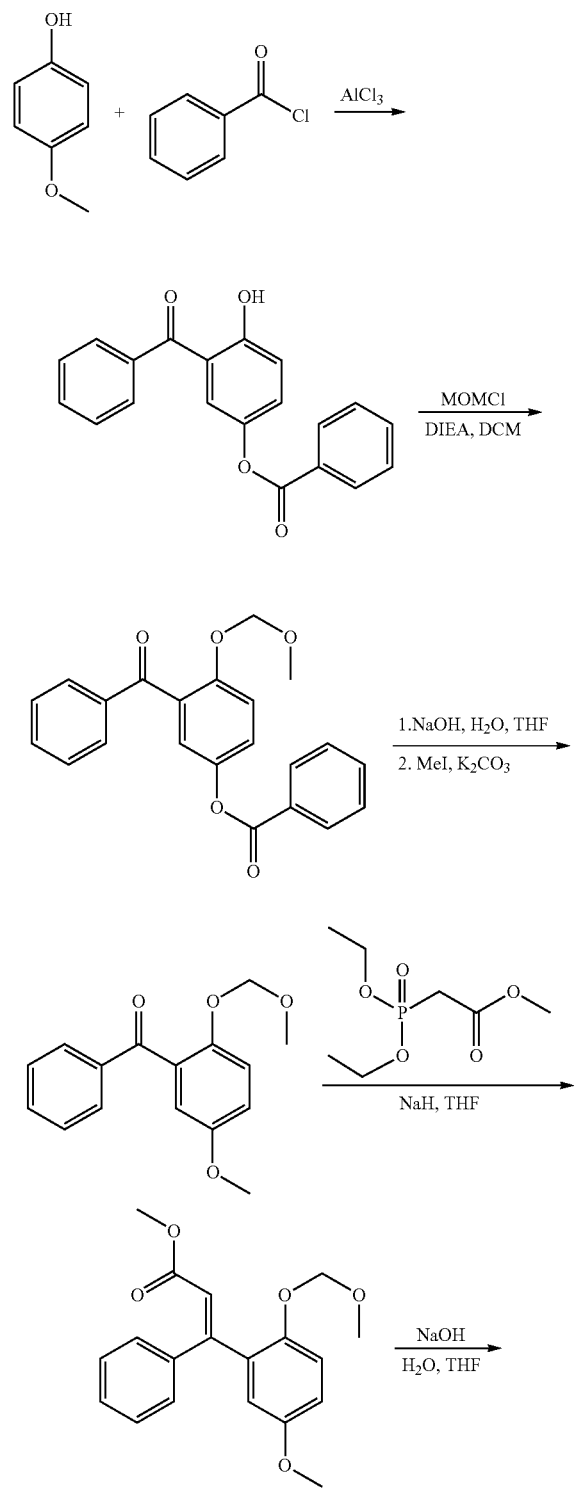

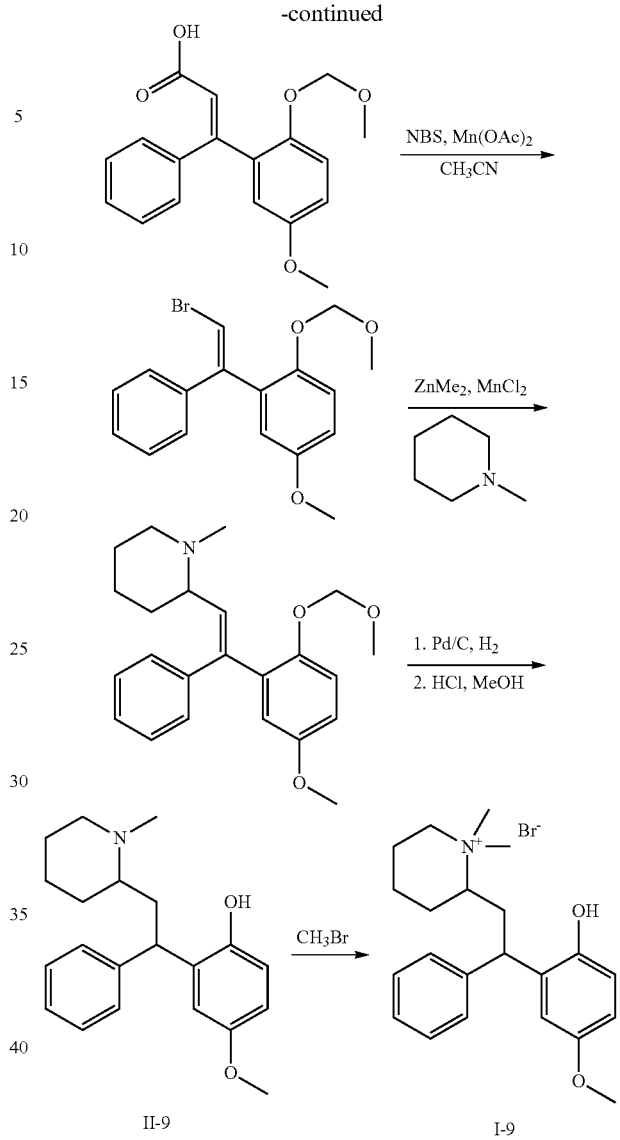

9.1 Synthesis of (2-hydroxy-5-benzoyloxy-phenyl)(phenyl)-methanone

According to the steps described in 4.1.1 of embodiment 4, p-methoxyphenol (2.28 g, 20 mmol) and benzoyl chloride (3.96 g, 25 mmol) are used as the raw materials to produce 1.6 g of brown solid product (2-hydroxy-5-benzoyloxy-phenyl)(phenyl)-methanone with a yield of 25% (calculated based on p-methoxyphenol). $^1$H NMR (400 MHz, CDCl$_3$), δ: 11.95 (s, 1H), 8.16 (d, J=7.2 Hz, 2H), 7.73 (d, J=7.2 Hz, 2H), 7.65-7.56 (m, 2H), 7.53-7.47 (m, 4H), 7.45 (d, J=3.2 Hz, 1H), 7.37 (dd, J=3.2, 8.8 Hz, 1H), 7.15 (d, J=8.8 Hz, 1H).

9.2 Synthesis of (2-methoxymethoxy-5-benzoyloxy-phenyl)(phenyl)-methanone

According to the steps described in 2.1 of embodiment 2, (2-hydroxy-5-benzoyloxy-phenyl)(phenyl)-methanone is used as the raw material to produce the brown oily product (2-methoxymethoxy-5-benzoyloxy-phenyl)(phenyl)-methanone with a yield of 77%. $^1$H NMR (400 MHz, CDCl$_3$), δ: 8.19 (d, J=8.4 Hz, 2H), 7.88 (m, 2H), 7.66-7.55 (m, 2H), 7.53-7.42 (m, 5H), 7.32-7.24 (m, 2H), 5.06 (s, 2H), 3.32 (s, 3H).

9.3 Synthesis of (2-methoxymethoxy-5-hydroxy-phenyl)(phenyl)-methanone (2-methoxymethoxy-5-benzoyloxy-phenyl)(phenyl)-methanone (3.62 g, 10 mmol) is dissolved in 36 ml of THF, aqueous solution (12 ml) of NaOH (0.8 g, 20 mmol) is added at room temperature and the mixture is stirred to react for 10 hours at 60° C. Tire TLC detection shows that the raw materials disappear. After cooling down to the room temperature, the mixture is adjusted to neutrality with 2 M hydrochloric acid and extracted with ethyl acetate (3×30 ml). After being merged, the organic phase is washed with water and a saturated salt solution respectively, and dried with anhydrous sodium, sulfate. The said organic phase is desolvated by a rotary evaporator, purified by silicon oxide column chromatography and eluted by dichloromethane/ methanol (10/1, v/v), which results in 2.4 g of the brown oily product (2-methoxymethoxy-5-hydroxy-phenyl)(phenyl)-methanone (with a yield of 93%). $^1$H NMR (400 MHz, CDCl$_3$), δ: 7.84 (m, 2H), 7.58-7.54 (m, 1H), 7.46-7.42 (m, 2H), 7.11 (d, 0.1=8.8 Hz, 1H), 6.93 (dd, J=3.2, 8.8 Hz, 1H), 6.85 (d, J=3.2 Hz, 1H), 4.95 (s, 2H), 3.29 (s, 3H).

9.4 Synthesis of (2-methoxymethoxy-5-methoxy-phenyl)(phenyl)-methanone (2-methoxymethoxy-5-hydroxy-phenyl)(phenyl)-methanone (2.58 g, 10 mmol) is weighed and dissolved into 20 ml of anhydrous THF, NaH (60%, 0.52 g, 1.3 mmol) is added in batches at room temperature, and after addition, the mixture is stirred for 10 minutes. At room temperature, iodomethane (1.85 g, 13 mmol) is added dropwise to the reaction solution. After addition, the mixture is heated to 40° C. for reaction for 3 hours. The TLC detection shows that the raw materials disappear. The mixture is quenched with water, extracted with dichloromethane (3×30 ml), dried with anhydrous sodium sulfate, concentrated by a rotary evaporator, purified by silicon oxide column chromatography and eluted by ligroin/dichloromethane (1/2), which results in 2.53 g of the brown oily product (2-methoxymethoxy-5-methoxy-phenyl)(phenyl)-methanone (with a yield of 93%). $^1$H NMR (400 MHz, CDCl$_3$), δ: 7.85-7.83 (m, 2H), 7.59-7.54 (m, 1H), 7.46-7.42 (m, 2H), 7.16 (d, J=9.2 Hz, 1H), 6.99 (dd, J=3.2, 9.2 Hz, 1H), 6.91 (d, J=3.2 Hz, 1H), 4.96 (s, 2H), 3.79 (s, 3H), 3.29 (s, 3H).

9.5 Synthesis of 3-(2-methoxymethoxy-5-methoxy-phenyl)-3-(phenyl)-methyl Acrylate According to the steps described in 2.2 of embodiment 2, (2-methoxymethoxy-5-methoxy-phenyl)(phenyl)-methanone is used as the raw material to produce the brown oily product 3-(2-methoxymethoxy-5-methoxy-phenyl)-3-(phenyl)-methyl acrylate with a yield of 73%. $^1$H NMR (400 MHz, CDCl$_3$), δ: 7.36-7.30 (m, 5H), 7.11 (d, J=8.8 Hz), 6.88-6.85 (m, 1H), 6.64 (s, 1H), 6.47 (s, 1H), 4.93 (s, 2H), 3.75 (s, 3H), 3.61 (s, 2H), 3.22 (s, 3H).

9.6 Synthesis of 3-(2-methoxymethoxy-5-methoxy-phenyl)-3-phenyl-acrylic Acid According to the steps described in 2.3 of embodiment 2, 3-(2-methoxymethoxy-5-methoxyphenyl)-3-(phenyl)-methyl acrylate is used as the raw material to produce the white solid product 3-(2-methoxymethoxy-5-methoxyphenyl)-3-phenylacrylic acid with a yield of 94%. $^1$H NMR (400 MHz, CDCl$_3$), δ: 7.37-7.33 (m, 2H), 7.30-7.27 (m, 3H), 7.24-7.21 (m, 2H), 6.91 (s, 1H), 6.75 (s, 1H), 4.95 (s, 2H), 3.85 (s, 3H), 3.26 (s, 3H).

9.7 Synthesis of 2-bromo-1-(2-methoxymethoxy-5-methoxy-phenyl)-1-phenyl-ethylene According to the steps described in 2.4 of embodiment 2, 3-(2-methoxymethoxy-5-methoxy-phenyl)-3-(phenyl)-acrylic acid is used as the raw material to produce the brown yellow oily product 2-bromo-1-(2-methoxymethoxy-5-methoxy-phenyl)-1-phenyl-ethylene with a yield of 41%. $^1$H NMR (400 MHz, CDCl$_3$), δ: 7.30-7.25 (m, 5H), 7.13 (d, J=8.0 Hz, 1H), 6.90-6.87 (m, 2H), 6.76 (s, 1H), 4.95 (s, 2H), 3.79 (s, 3H), 3.27 (s, 3H).

9.8 Synthesis of 2-[2-(2-methoxymethoxy-5-methoxy-phenyl)-styryl]-N-methylpiperidine According to the steps described in 2.5 of embodiment 2, 2-bromo-1 (2-methoxymethoxy-5-methoxy-phenyl)-1-phenyl-ethylene is used as the raw material to produce the light brown oily product 2-[2-(2-methoxymethoxy-5-methoxy-phenyl)-styryl]-N-methylpiperidine with a yield of 63%. LC-MS (m/z): 368.3 [M+H]$^+$. $^1$H NMR shows that the product is mainly E-isomer. $^1$H NMR (400 MHz, CDCl$_3$), δ: 7.29-7.17 (m, 5H), 7.12 (d, J=8.8 Hz, 1H), 6.85 (dd, J=3.2, 9.2 Hz, 1H), 6.66 (d, J=3.2 Hz, 1H), 6.17 (d, 9.2 Hz, 1H), 4.92-4.72 (m, 2H), 3.82-3.75 (m, 3H), 3.25 (s, 3H), 2.86 (d, J=11.2 Hz, 1H), 2.41-2.37 (m, 1H), 2.25 (s, 3H), 1.93-1.86 (m, 1H), 1.69-1.65 (m, 2H), 1.61-1.55 (m, 2H), 1.54-1.45 (m, 1H), 1.20-1.30 (m, 1H).

9.9 Synthesis of 2-[2-(2-hydroxy-5-methoxy-phenyl)phenethyl]-N-methylpiperidine (II-9)

According to the steps described in 2.6 of embodiment 2, 2-[2-(2-methoxymethoxy-5-methoxy-phenyl)-styryl-]-N-methylpiperidine is used as the raw material to produce the white solid target product II-9 by double-bond hydrogenation and deoxidation of protecting group with a yield of 22%. $^1$H NMR show's that the product is the mixture of two diastereomers with a ratio of 3.2/1. LC-MS (m/z): 326.2 [M+H]$^+$. $^1$H NMR (400 MHz, CDCl$_3$), isomer II-9a, δ: 11.91 (b, 1H), 7.31-7.29 (m, 4H), 7.23-7.18 (m, 1H), 6.88 (d, J=8.8 Hz, 1H), 6.63 (dd, J=3.2, 8.8 Hz, 1H), 6.32 (d, J=5.6 Hz, 1H), 4.50 (dd, J=3.2, 13.2 Hz, 1H), 3.59 (s, 3H), 2.98 (d, J=10.4 Hz, 1H), 2.85-2.78 (m, 1H), 2.58-2.50 (m, 1H), 2.37 (s, 3H), 2.16-2.10 (m, 1H), 2.02-1.95 (m, 1H), 1.78-1.75 (m, 1H), 1.69-1.66 (m, 1H), 1.60-1.50 (m, 2H), 1.35-1.20 (m, 2H).

Isomer II-9b, δ: 11.91 (b, 1H), 7.31-7.28 (m, 4H), 7.23-7.18 (m, 1H), 6.85 (d, J=8.8 Hz, 1H), 6.62 (dd, J=3.2, 8.8 Hz, 1H), 6.26 (d, J=3.2 Hz, 1H), 4.52 (dd, J=3.2, 13.2 Hz, 1H), 3.60 (s, 3H), 2.58-2.50 (m, 1H), 2.40 (s, 3H), 2.27-2.22 (m, 1H), 2.16-2.10 (m, 1H), 1.78-1.75 (m, 1H), 1.60-1.50 (m, 2H), 1.44-1.33 (m, 2H), 1.30-1.24 (m, 1H), 1.16-1.23 (m, 1H), 1.10-1.02 (m, 1H).

9.10 Synthesis of 2-[2-(2-hydroxy-5-methoxy-phenyl)-phenethyl]-N,N-dimethylpiperidine Bromide (I-9a)

According to the steps described in 2.7 of embodiment 2, II-9a and bromomethane are used as the raw materials to produce the white solid target product I-9a with a yield of 97%. LC-MS (m/z): 350.3 [M+H]+. 1H NMR (400 MHz, CD3OD), isomer I-9a, δ: 7.41-7.38 (m, 2H), 7.35-7.30 (m, 2H), 7.23-7.20 (m, 1H), 6.90-6.86 (m, 1H), 6.8-6.78 (m, 1H), 6.67 (b, 1H), 4.27 (dd, J=11.2, 4.0 Hz, 1H), 3.81 (s, 3H), 3.69-3.65 (m, 1H), 3.46-3.44 (m, 1H), 3.27-3.23 (m, 1H), 2.99 (s, 3H), 2.95 (s, 3H), 2.88-2.85 (m, 1H), 2.23-2.20 (m, 1H), 2.08-1.96 (m, 1H), 1.98-1.72 (m, 4H), 1.47-1.34 (m, 1H).

Embodiment 10

2-[2-(2-hydroxy-5-fluorophenyl)-phenethyl]-N-methylpiperidine (II-10) and 2-[2-(2-hydroxy-5-fluorophenyl)-phenylethyl]-N,N-dimethylpiperidine bromide (I-10)

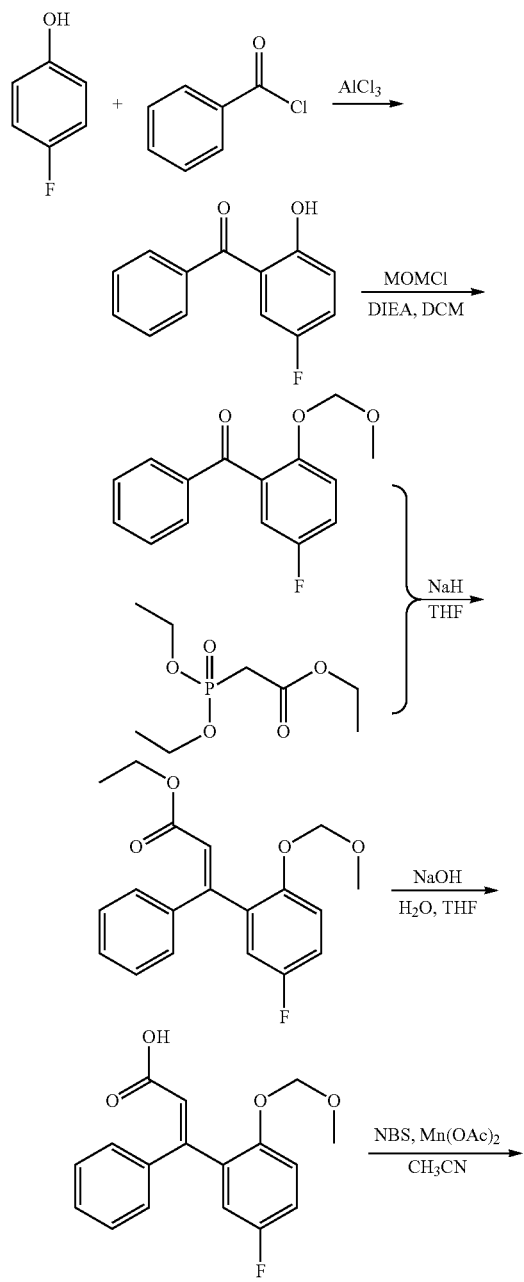

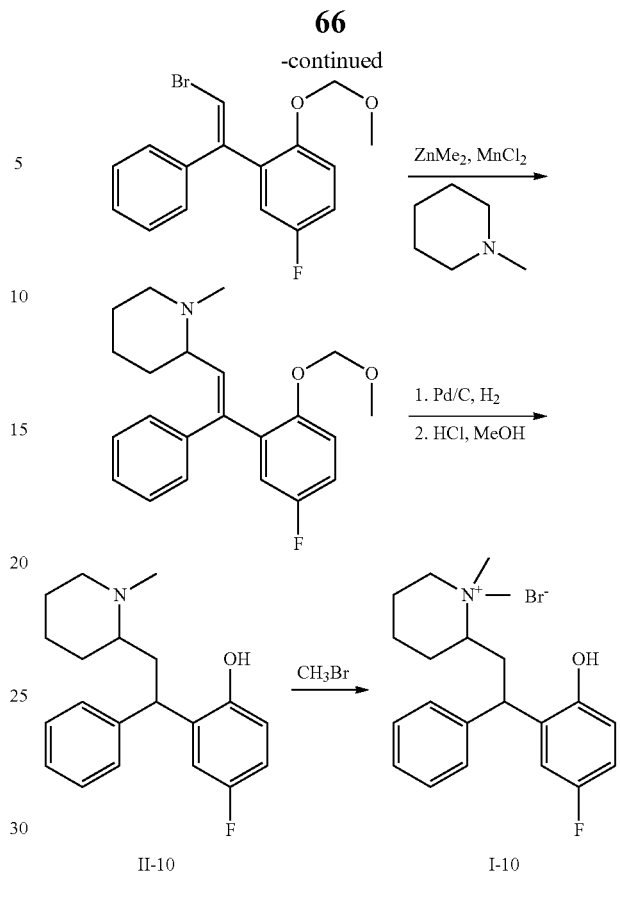

10.1 Synthesis of (2-hydroxy-5-fluorophenyl)(phenyl)-methanone

According to the steps described in 4.1.1 of embodiment 4, p-4-fluorophenol and benzoyl chloride are used as the raw materials to produce the brown solid pure product (2-hydroxy-5-fluorophenyl)(phenyl)-methanone with a yield of 83%. 1H-NMR (400 MHz, CDCl3), δ: 11.77 (s, 1H), 7.72-7.70 (m, 2H), 7.65-7.62 (m, 1H), 7.57-7.54 (m, 2H), 7.33-7.30 (m, 1H), 7.28-7.26 (m, 1H), 7.08 (q, J=4.4 Hz, 1H).

10.2 Synthesis of (2-methoxymethoxy-5-fluorophenyl)(phenyl)-methanone

According to the steps described in 2.1 of embodiment 2, (2-hydroxy-5-fluorophenyl)(phenyl)-methanone is used as the raw material to produce the brown oily product (2-methoxymethoxy-5-fluorophenyl)(phenyl)-methanone with a yield of 88%. 4 1-NMR (400 MHz, CDCl3), δ: 7.85-7.83 (m, 2H), 7.62 (t, J=7.6 Hz, 1H), 7.50 (t, J=7.6 Hz, 2H), 7.23-7.19 (m, 1H), 7.18-7.13 (m, 1H), 7.12-7.09 (m, 1H), 5.02 (s, 2H), 3.32 (s, 3H)

10.3 Synthesis of 3-(2-methoxymethoxy-5-fluorophenyl)-3-phenyl-ethyl Acrylate According to the steps described in 2.2 of embodiment 2, (2-methoxymethoxy-5-fluorophenyl)(phenyl)-methanone is used as the raw material to produce the brown oily product 3-(2-methoxymethoxy-5-fluorophenyl)-3-phenyl-ethyl acrylate with a yield of 72%, 1H-NMR spectrum shows that the product is mainly E-isomer, 1H NMR (400 MHz, CDCl₃), E-isomer, δ: 7.39-7.36 (m, 5H), 7.16-7.12 (m, 1H), 7.07-7.02 (m, 1H), 6.86-6.84 (m, 1H), 6.50 (m, 1H), 4.98 (s, 2H), 4.08 (q, J=7.2 Hz, 2H), 3.24 (s, 1H), 1.14 (t, J=7.2 Hz, 3H).

Z-isomer, δ: 7.39-7.36 (m, 5H), 7.16-7.12 (m, 1H), 7.07-7.02 (m, 1H), 6.86-6.84 (m, 1H), 6.50 (s, 1H), 4.98 (s, 2H), 4.09 (q, J=7.2 Hz, 2H), 3.25 (s, 1H), 1.15 (t, J=7.2 Hz, 3H).

10.4 Synthesis of 3-(2-methoxymethoxy-5-fluoro-phenyl)-3-phenyl-acrylic Acid According to the steps described in 2.3 of embodiment 2, 3-(2-methoxymethoxy-5-fluorophenyl)-3-phenyl-ethyl acrylate is used as the raw material to produce the brown solid product 3-(2-methoxymethoxy-5-fluorophenyl)-3-phenyl-acrylic acid with a yield of 91%. ¹H-NMR spectrum shows that the product is mainly E-isomer, ¹H NMR (400 MHz, CDCl₃), E-isomer δ: 12.15 (b, 1H), 7.38-7.36 (m, 3H), 7.33-7.29 (m, 3H), 6.93 (dd, J=3.2, 8.8 Hz, 1H), 6.49 (s, 1H), 4.99 (s, 2H), 3.08 (s, 3H).

10.5 Synthesis of 2-bromo-1 (2-methoxymethoxy-5-fluorophenyl)-1-(phenyl)-ethylene According to the steps described in 2.4 of embodiment 2, 3-(2-methoxymethoxy-5-fluorophenyl)-3-phenyl-acrylic acid is used as the raw material to produce the brown yellow oily product 2-bromo-1-(2-methoxymethoxy-5-fluorophenyl)-1-(phenyl)-ethylene with a yield of 66%. ¹H-NMR spectrum shows that the product is mainly the mixture of E,Z-isomers. ¹H NMR (400 MHz, CDCl₃), E-isomer, δ: 7.31-7.30 (m, 3H), 7.27-7.25 (m, 2H), 7.18-7.15 (m, 1H), 7.09-7.04 (m, 1H), 6.97-6.94 (m, 1H), 6.92 (s, 1H), 5.01 (s, 2H), 3.28 (s, 3H).

Z-isomer, δ: 7.31-7.30 (m, 3H), 7.27-7.25 (m, 2H), 7.18-7.15 (m, 1H), 7.09-7.04 (m, 1H), 6.97-6.94 (m, 1H), 6.92 (s, 1H), 5.03 (s, 2H), 3.30 (s, 3H)

10.6 Synthesis of 2-[2-(2-methoxymethoxy-5-fluorophenyl)-2-phenyl-vinyl]-N-methylpiperidine According to the steps described in 2.5 of embodiment 2, 2-bromo-1-(2-methoxymethoxy-5-fluorophenyl)-1-(phenyl)-ethylene and N-methylpiperidine are used as the raw materials to produce the light brown oily product 2-[2-(2-methoxymethoxy-5-fluorophenyl)-2-phenyl-vinyl]-N-methylpiperidine with a yield of 85%. ¹H-NMR spectrum shows that the product is mainly E-isomer. LC-MS (m/z): 356.4 [M+H]⁺. ¹H NMR (400 MHz, CDCl₃), δ: 7.28-7.27 (m, 6H), 7.17-7.15 (m, 1H), 7.07-7.05 (m, 1H), 6.84 (dd, J=3.2, 8.4 Hz, 1H), 4.98 (s, 2H), 3.22 (s, 3H), 2.40 (s, 3H), 2.04-2.03 (m, 1H), 1.79-1.77 (m, 3H), 1.66-1.59 (m, 5H).

10.7 Synthesis of 2-[2-(2-hydroxy-5-fluorophenyl)-2-phenyl-ethyl]-N-methylpiperidine (II-10)

According to the steps described in 2.6 of embodiment 2, 2-[2-(2-methoxymethoxy-5-fluorophenyl)-2-phenyl-vinyl]-N-methylpiperidine is used as the raw material to produce the white solid target product II-10 by double-bond hydrogenation and deoxidation of protecting group. The product is the two diastereomers II-10a and II-10b with II-10a/II-10b=2.5/1 and a total yield of 58.7%. LC-MS (m/z): 314.2 [M+H]⁺. ¹H NMR (400 MHz, CDCl₃), II-10a, δ: 7.37-7.32 (m, 3H), 7.30-7.24 (m, 2H), 6.88 (dd, J=5.2, 8.8 Hz, 1H), 6.76 (td, J=3.2, 8.4, 16.8 Hz, 1H), 6.40 (dd, J=3.2, 9.6 Hz, 1H), 4.52-4.83 (m, 1H), 3.01-2.98 (m, 1H), 2.87-2.81 (m, 1H), 2.56-2.53 (m, 1H), 2.40 (s, 3H), 2.22-2.14 (m, 1H), 2.04-1.98 (m, 1H), 1.83-1.80 (s, 1H), 1.72-1.64 (m, 1H), 1.60-1.54 (m, 1H), 1.45-1.43 (m, 1H), 1.37-1.31 (m, 2H).

II-10b, δ: 7.36-7.31 (m, 4H), 7.26-7.23 (m, 1H), 6.89-6.86 (m, 1H), 6.75 (td, J=3.2, 8.8 Hz, 1H), 6.50 (dd, J=3.2, 9.6 Hz, 1H), 4.55 (dd, J=3.2, 12.0 Hz, 1H), 3.15-3.13 (m, 1H), 2.57-2.54 (m, 1H), 2.49 (s, 3H), 2.40 (b, 1H), 2.26-2.15 (m, 2H), 1.59-1.54 (m, 3H), 1.31-1.28 (m, 2H), 1.15 (b, 1H).

HPLC chiral resolution is conducted to produce the two chiral isomers II-10a,b-1 and II-10a,b-2 of II-10a, II-10b (in the order of peak appearance). The resolution conditions are as follows: instrument: Waters 515-2996; chromatographic column: S-Chiral B (5 um, 10.0 mm*250 mm); mobile phase: n-hexane/isopropanol/diethylamine=100/3/0.1; flow rate: 1 ml/min; column temperature: room temperature; detection wavelength: 280 nm; and retention time: 8.426 min for chiral isomer II-10a-1 and 13.502 min for chiral isomer II-10a-2; 7.795 min for chiral isomer II-10b-1 and 12.267 min for chiral isomer II-10b-2.

10.8 Synthesis of 2-[2-(2-hydroxy-5-fluorophenyl)-phenethyl]-N,N-dimethylpiperidine Bromide (I-10)

According to the steps described in 2.7 of embodiment 2, II-10a or II-10b or the chiral monomer thereof is used as the raw material to react with bromomethane and produce the white solid target product I-10a or I-10b or the chiral monomers I-10a-1/2, I-10b-1/2 thereof by recrystallization of ethyl acetate with a yield of 83%. LC-MS (m/z): 328.3 [M+H]⁺. ¹H NMR (400 MHz, CD₃OD), I-10a, I-10a-1/2, δ: 7.46-7.38 (m, 4H), 7.31-7.27 (m, 1H), 6.95 (dd, J=10.4, 2.8 Hz, 1H), 6.78-6.75 (m, 2H), 4.59 (dd, J=10.8, 4.8 Hz, 1H), 3.48 (d, J=12.4 Hz, 1H), 3.31-3.26 (m, 1H), 3.04 (s, 3H), 3.03 (s, 3H), 3.02-2.99 (m, 1H), 2.85 (t, J=12.4 Hz, 1H), 2.28-2.24 (m, 1H), 2.10-2.00 (m, 1H), 1.98-1.85 (m, 3H), 1.82-1.75 (m, 1H), 1.53-1.42 (m, 1H).

I-10b, I-10b-1/2, δ: 7.41-7.38 (m, 2H), 7.35-7.30 (m, 2H), 7.24-7.20 (m, 1H), 6.95 (d, J=9.6 Hz, 1H), 6.84-6.82 (m, 2H), 4.55 (dd, J=10.8, 4.8 Hz, 1H), 3.50 (d, J=12.4 Hz, 1H), 3.09 (s, 3H), 3.04 (s, 3H), 3.09-3.04 (m, 1H), 2.94 (t, J=12.0 Hz, 1H), 2.23-2.19 (m, 1H), 2.10-2.05 (m, 1H), 1.99-1.94 (m, 1H), 1.91-1.85 (m, 1H), 1.81-1.75 (m, 2H), 1.49-1.44 (m, 1H), 1.35-1.30 (m, 1H).

Embodiment 11

Synthesis of 2-[2-(2,5-dihydroxy-phenyl)-phenethyl]-N-methylpiperidine (II-11)

Synthetic Route:

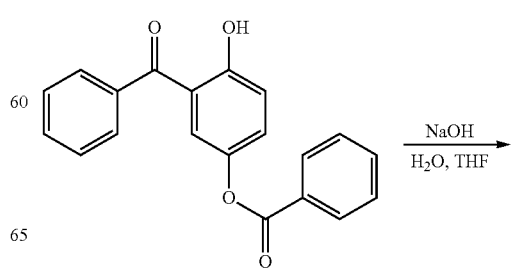

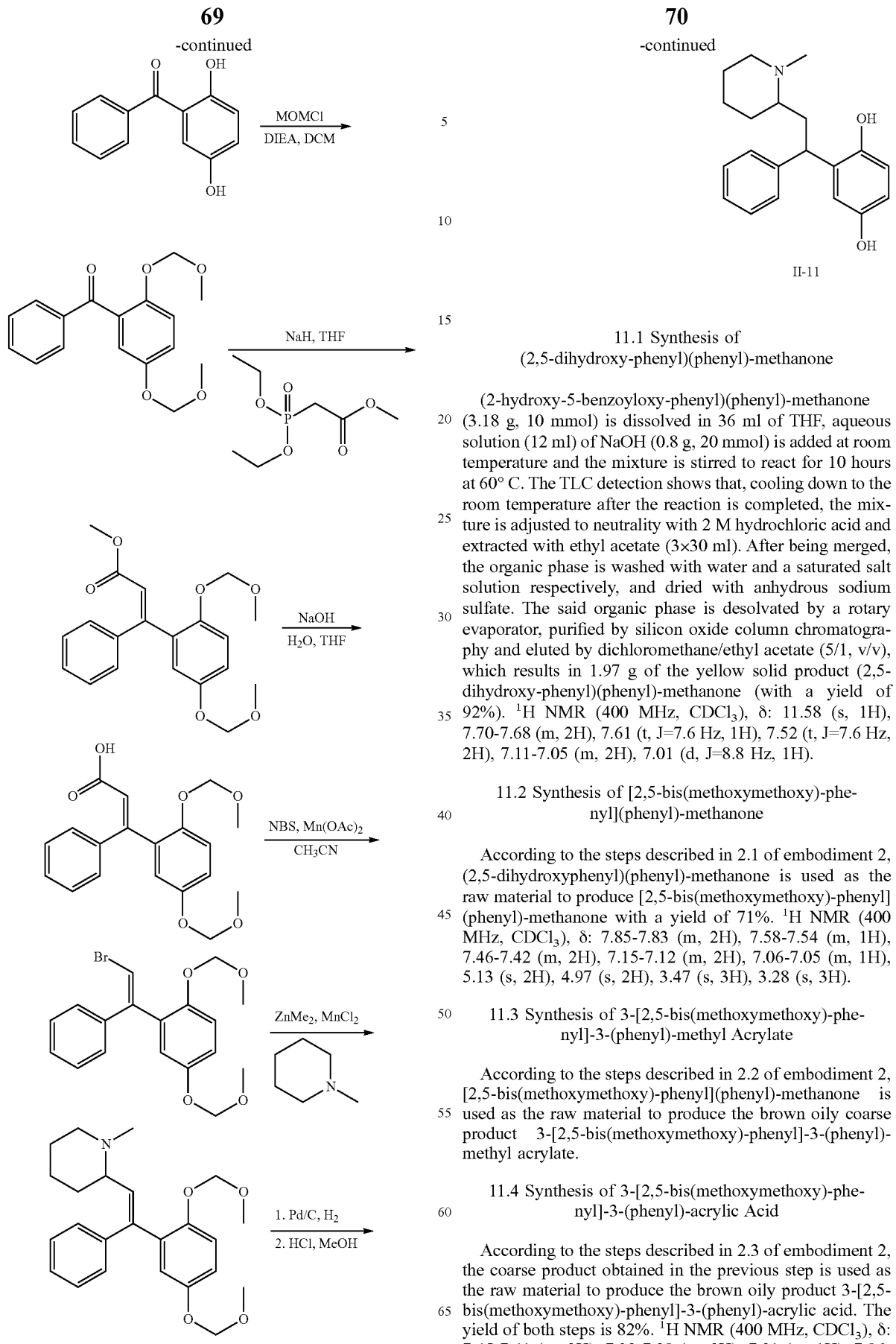

11.1 Synthesis of (2,5-dihydroxy-phenyl)(phenyl)-methanone (2-hydroxy-5-benzoyloxy-phenyl)(phenyl)-methanone (3.18 g, 10 mmol) is dissolved in 36 ml of THF, aqueous solution (12 ml) of NaOH (0.8 g, 20 mmol) is added at room temperature and the mixture is stirred to react for 10 hours at 60° C. The TLC detection shows that, cooling down to the room temperature after the reaction is completed, the mixture is adjusted to neutrality with 2 M hydrochloric acid and extracted with ethyl acetate (3×30 ml). After being merged, the organic phase is washed with water and a saturated salt solution respectively, and dried with anhydrous sodium sulfate. The said organic phase is desolvated by a rotary evaporator, purified by silicon oxide column chromatography and eluted by dichloromethane/ethyl acetate (5/1, v/v), which results in 1.97 g of the yellow solid product (2,5-dihydroxy-phenyl)(phenyl)-methanone (with a yield of 92%). $^1$H NMR (400 MHz, CDCl$_3$), δ: 11.58 (s, 1H), 7.70-7.68 (m, 2H), 7.61 (t, J=7.6 Hz, 1H), 7.52 (t, J=7.6 Hz, 2H), 7.11-7.05 (m, 2H), 7.01 (d, J=8.8 Hz, 1H).

11.2 Synthesis of [2,5-bis(methoxymethoxy)-phenyl](phenyl)-methanone

According to the steps described in 2.1 of embodiment 2, (2,5-dihydroxyphenyl)(phenyl)-methanone is used as the raw material to produce [2,5-bis(methoxymethoxy)-phenyl](phenyl)-methanone with a yield of 71%. $^1$H NMR (400 MHz, CDCl$_3$), δ: 7.85-7.83 (m, 2H), 7.58-7.54 (m, 1H), 7.46-7.42 (m, 2H), 7.15-7.12 (m, 2H), 7.06-7.05 (m, 1H), 5.13 (s, 2H), 4.97 (s, 2H), 3.47 (s, 3H), 3.28 (s, 3H).

11.3 Synthesis of 3-[2,5-bis(methoxymethoxy)-phenyl]-3-(phenyl)-methyl Acrylate According to the steps described in 2.2 of embodiment 2, [2,5-bis(methoxymethoxy)-phenyl](phenyl)-methanone is used as the raw material to produce the brown oily coarse product 3-[2,5-bis(methoxymethoxy)-phenyl]-3-(phenyl)-methyl acrylate.

11.4 Synthesis of 3-[2,5-bis(methoxymethoxy)-phenyl]-3-(phenyl)-acrylic Acid According to the steps described in 2.3 of embodiment 2, the coarse product obtained in the previous step is used as the raw material to produce the brown oily product 3-[2,5-bis(methoxymethoxy)-phenyl]-3-(phenyl)-acrylic acid. The yield of both steps is 82%. $^1$H NMR (400 MHz, CDCl$_3$), δ: 7.45-7.41 (m, 2H), 7.32-7.28 (m, 2H), 7.21 (m, 1H), 7.06-

7.02 (m, 1H), 6.90 (s, 1H), 6.81-6.79 (m, 1H), 6.65 (s, 1H), 5.05 (s, 2H), 4.91 (s, 2H), 3.45 (s, 3H), 3.25 (s, 3H).

11.5 Synthesis of 2-bromo-1-[2,5-bis(methoxymethoxy)-phenyl]-1-phenyl-ethylene According to the steps described in 2.4 of embodiment 2, 3-[2,5-bis(methoxymethoxy)-phenyl]-3-(phenyl)-acrylic acid is used as the raw material to produce the brown oily product 2-bromo-1-[2,5-bis(methoxymethoxy)-phenyl]-1-phenyl-ethylene with a yield of 59%. $^1$H NMR (400 MHz, CDCl$_3$), δ: 7.41-7.38 (m, 2H), 7.31-7.27 (m, 2H), 7.20-7.18 (m, 1H), 7.03-7.0 (m, 1H), 6.95 (s, 1H), 6.85 (s, 1H), 6.80-6.76 (m, 1H), 5.03 (s, 2H), 4.91 (s, 2H), 3.44 (s, 3H), 3.23 (s, 3H).

11.6 Synthesis of 2-{2-[2,5-bis(methoxymethoxy)-phenyl]-2-(phenyl)-vinyl}-N-methylpiperidine According to the steps described in 2.5 of embodiment 2, 2-bromo-1-[2,5-bis(methoxymethoxy)-phenyl]-1-phenyl-ethylene is used as the raw material to produce the light brown oily product 2-{2-[2,5-bis(methoxymethoxy)-phenyl]-2-(phenyl)-vinyl}-N-methylpiperidine with a yield of 51%. LC-MS (m/z): 398.3 [M+H]$^+$. $^1$H-NMR spectrum show's that the product is mainly the mixture of E,Z-isomers with E/Z 2.77/0.37. $^1$H NMR (400 MHz, CDCl$_3$), E-isomer, δ: 7.30-7.28 (m, 2H), 7.26-7.24 (m, 2H), 7.22-7.17 (m, 1H), 7.13 (d, J=8.8 Hz, 1H), 7.02 (dd, J=3.2, 8.8 Hz, 1H), 6.84 (d, J=2.8 Hz, 1H), 6.18 (d, J=9.2 Hz, 1H), 5.15 (s, 2H), 4.95 (s, 2H), 3.50 (s, 3H), 3.22 (s, 3H), 2.89-2.86 (m, 1H), 2.44-2.39 (m, 1H), 2.27 (s, 3H), 1.95-1.88 (m, 1H), 1.75-1.68 (m, 2H), 1.62-1.55 (m, 2H), 1.50-1.46 (m, 1H), 1.17-1.14 (m, 1H).

Z-isomer, δ: 7.30-7.28 (m, 2H), 7.26-7.24 (m, 2H), 7.22-7.17 (m, 1H), 7.13 (d, J=8.8 Hz, 1H), 7.02 (dd, J=3.2, 8.8 Hz, 1H), 6.84 (d, J=2.8 Hz, 1H), 6.18 (d, J=9.2 Hz, 1H), 5.12 (s, 2H), 4.94 (s, 2H), 3.49 (s, 3H), 3.21 (s, 3H), 2.89-2.86 (m, 1H), 2.44-2.39 (m, 1H), 2.27 (s, 3H), 1.95-1.88 (m, 1H), 1.75-1.68 (m, 2H), 1.62-1.55 (m, 2H), 1.50-1.46 (m, 1H), 1.17-1.14 (m, 1H).

11.7 Synthesis of 2-[2-(2,5-dihydroxy-phenyl)-2-phenyl-ethyl]-N-methylpiperidine (II-11)

According to the steps described in 2.6 of embodiment 2, 2-{2-[2,5-bis(methoxymethoxy)-phenyl]-2-(phenyl)-vinyl}-N-methylpiperidine is used as the raw material to produce the white solid target product II-11 by double-bond hydrogenation and deoxidation of protecting group with a yield of 25%. LC-MS (m/z): 312.3 [M+H]$^+$. $^1$H NMR (400 MHz, CDCl$_3$), δ: 12.03 (b, 1H), 7.31-7.28 (m, 3H), 7.25-7.20 (m, 2H), 7.03-7.0 (d, J=8.8 Hz, 1H), 6.72 (s, 1H), 6.68-6.66 (m, 1H), 4.50 (dd, J=3.2, 13.2 Hz, 1H), 3.01-2.98 (m, 1H), 2.87-2.84 (m, 1H), 2.55-2.52 (m, 1H), 2.40 (s, 3H), 2.22-2.14 (m, 1H), 2.04-1.98 (m, 1H), 1.82-1.80 (m, 1H), 1.70-1.62 (m, 1H), 1.57-1.52 (m, 1H), 1.42-1.38 (m, 1H), 1.33-1.27 (m, 2H).

Embodiment 12

2-[2-(2-hydroxy-5-pentyloxy-phenyl)-phenethyl]-N-methylpiperidine (II-12)

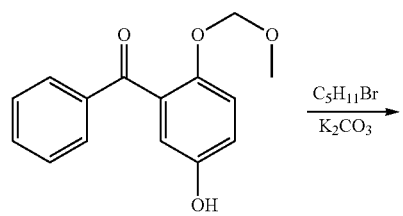

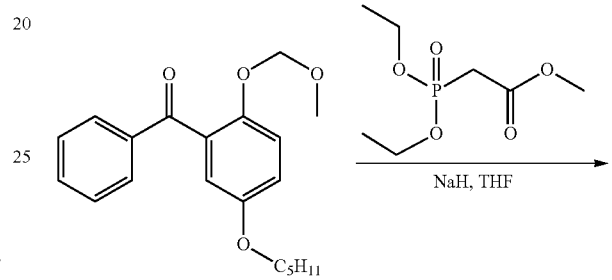

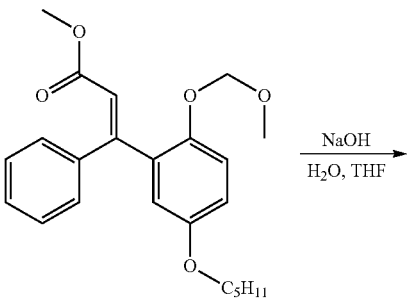

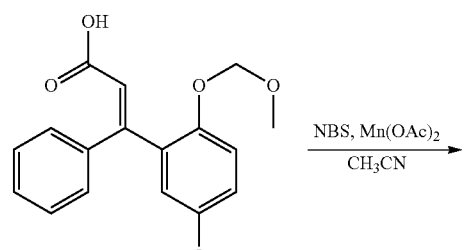

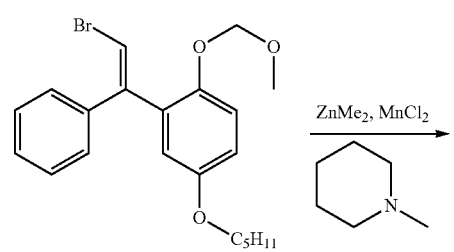

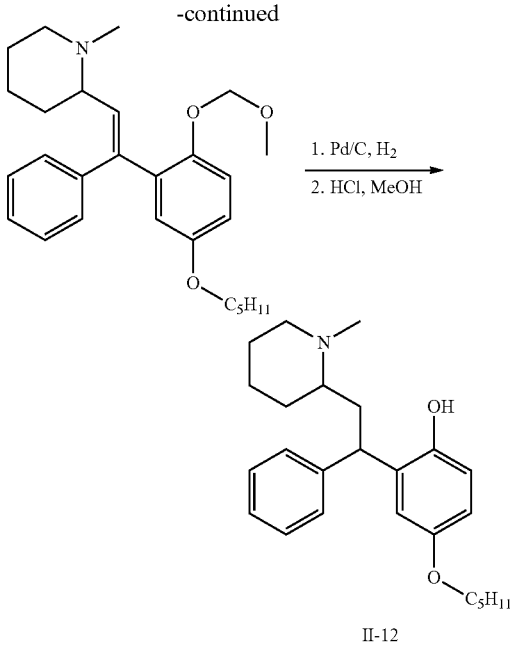

II-12

12.1 Synthesis of (2-methoxymethoxy-5-pentyloxy-phenyl)(phenyl)-methanone

According to the steps described in 9.4 of embodiment 9, (2-methoxymethoxy-5-hydroxy-phenyl)(phenyl)-methanone and bromopentane are used as the raw materials to produce the brown oily product (2-methoxymethoxy-5-pentyloxy-phenyl)(phenyl)-methanone with a yield of 83%. $^1$H NMR (400 MHz, CDCl$_3$), δ: 7.85-7.82 (m, 2H), 7.57-7.53 (m, 1H), 7.48-7.43 (m, 2H), 7.13 (d, J=9.2 Hz, 1H), 6.95 (dd, J=3.2, 9.2 Hz, 1H), 6.85 (d, J=3.2 Hz, 1H), 4.99 (s, 2H), 3.94 (t, J=6.4 Hz, 2H), 3.79 (s, 3H), 1.80-1.76 (m, 2H), 1.45-1.38 (m, 4H), 0.94 (t, J=7.2 Hz, 3H).

12.2 Synthesis of 3-(2-methoxymethoxy-5-pentyloxy-phenyl)-3-(phenyl)methyl Acrylate According to the steps described in 2.2 of embodiment 2, (2-methoxymethoxy-5-pentyloxy-phenyl)(phenyl)-methanone is used as the raw material to produce the brown oily coarse product 3-(2-methoxymethoxy-5-pentyloxy-phenyl)-3-(phenyl)-methyl acrylate, which can be directly used for the next step.

12.3 Synthesis of 3-(2-methoxymethoxy-5-pentyloxy-phenyl)-3-phenyl-acrylic Acid According to the steps described in 2.3 of embodiment 2, the coarse product obtained in the previous step is used as the raw material to produce the white solid product 3-(2-methoxymethoxy-5-pentyloxy-phenyl)-3-phenyl-acrylic acid. The yield of both steps is 86%. $^1$H NMR (400 MHz, CDCl$_3$), δ: 7.37-7.32 (m, 2H), 7.31-7.27 (m, 3H), 7.25-7.22 (m, 2H), 6.96 (s, 1H), 6.76 (s, 1H), 4.96 (s, 2H), 3.90 (t, J=6.4 Hz, 2H), 3.86 (s, 3H), 1.78-1.73 (m, 2H), 1.41-1.34 (m, 4H), 0.96 (t, J=7.2 Hz, 3H).

12.4 Synthesis of 2-bromo-1-(2-methoxymethoxy-5-pentyloxy-phenyl)-1-phenyl-ethylene According to the steps described in 2.4 of embodiment 2, 3-(2-methoxymethoxy-5-pentyloxy-phenyl)-3-(phenyl)-acrylic acid is used as the raw material to produce the brown yellow oily product 2-bromo-1-(2-methoxymethoxy-5-pentyloxy-phenyl)-1-phenyl-ethylene with a yield of 51%. $^1$H NMR (400 MHz, CDCl$_3$), δ: 7.31-7.27 (m, 5H), 7.14 (d, J=8.0 Hz, 1H), 6.91-6.88 (m, 2H), 6.76 (s, 1H), 4.96 (s, 2H), 3.95 (t, J=6.4 Hz, 2H), 3.79 (s, 3H), 1.85-1.80 (m, 2H), 1.48-1.35 (m, 4H), 0.96 (t, J=7.2 Hz, 3H).

12.5 Synthesis of 2-[2-(2-methoxymethoxy-5-pentyloxy-phenyl)-styryl]-N-methylpiperidine According to the steps described in 2.5 of embodiment 2, 2-bromo-1-(2-methoxymethoxy-5-pentyloxy-phenyl)-1-phenyl-ethylene is used as the raw material to produce the light brown oily product 2-[2-(2-methoxymethoxy-5-pentyloxy-phenyl)-styryl]-N-methylpiperidine with a yield of 53%. LC-MS (m/z): 424.3 [M+H]$^+$. $^1$H NMR (400 MHz, CDCl$_3$), δ: 7.27-7.15 (m, 5H), 7.13 (d, J=8.8 Hz, 1H), 6.84 (dd, J=3.2, 9.2 Hz, 1H), 6.64 (d, J=3.2 Hz, 1H), 6.13 (d, J=9.2 Hz, 1H), 4.95-4.73 (m, 2H), 3.92 (t, J 6.4 Hz, 2H), 3.80-3.73 (m, 2H), 2.85 (d, J=11.2 Hz, 1H), 2.42-2.38 (m, 1H), 2.25 (s, 3H), 1.93-1.86 (m, 1H), 1.72-1.65 (m, 4H), 1.61-1.55 (m, 2H), 1.54-1.34 (m, 5H), 1.20-0.92 (m, 4H).

12.6 Synthesis of 2-[2-(2-hydroxy-5-pentyloxy-phenyl)-phenethyl]-N-methylpiperidine (II-12)

According to the steps described in 2.6 of embodiment 2, 2-[2-(2-methoxymethoxy-5-pentyloxy-phenyl)-styryl-]-N-methylpiperidine is used as the raw material to produce the white solid target product II-12 by double-bond hydrogenation and deoxidation of protecting group with a yield of 42%. LC-MS (m/z): 382.2 [M+H]$^+$. $^1$H NMR (400 MHz, CDCl$_3$), δ: 12.43 (b, 1H), 7.32-7.29 (m, 3H), 7.22-7.19 (m, 2H), 6.89 (d, J=8.8 Hz, 1H), 6.52 (s, 1H), 6.39 (d, J=5.6 Hz, 1H), 4.50 (dd, J=3.2, 13.2 Hz, 1H), 3.93 (t, J=6.4 Hz, 2H), 2.95 (d, J=10.4 Hz, 1H), 2.85-2.77 (m, 1H), 2.59-2.50 (m, 1H), 2.32 (s, 3H), 2.16-2.11 (m, 1H), 2.02-1.95 (m, 1H), 1.78-1.70 (m, 3H), 1.69-1.64 (m, 1H), 1.60-1.50 (m, 2H), 1.42-1.28 (m, 6H), 0.93 (t, J=7.2 Hz, 3H).

Embodiment 13

2-[2-(2-hydroxy-5-trifluoromethyl-phenyl)-phenethyl]-N-methylpiperidine (II-13)

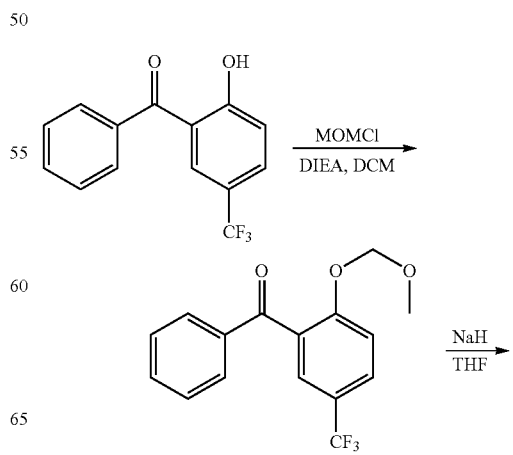

-continued

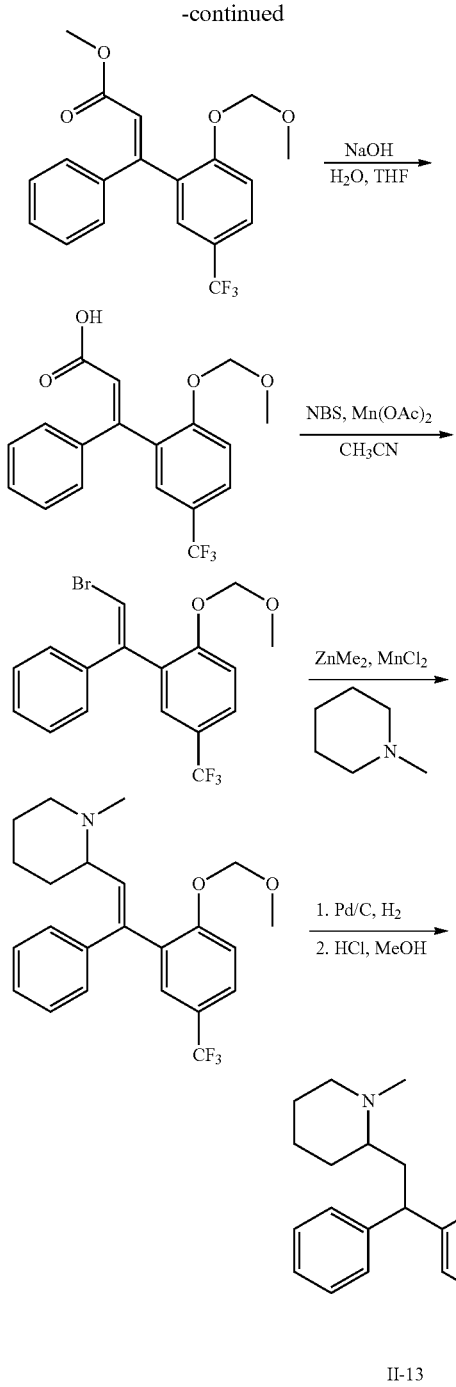

13.1 Synthesis of (2-methoxymethoxy-5-trifluoromethyl-phenyl)(phenyl)-methanone According to the steps described in 2.1 of embodiment 2, (2-hydroxy-5-trifluoromethyl-phenyl)(phenyl)-methanone is used as the raw material to produce the colorless oily product (2-methoxymethoxy-5-trifluoromethyl-phenyl)(phenyl)-methanone with a yield of 90%. $^1$H NMR (400 MHz, CDCl$_3$), δ: 8.04-7.92 (m, 2H), 7.87-7.63 (m, 1H), 7.49-7.38 (m, 3H), 7.30-7.22 (m, 1H), 7.18-7.15 (m, 1H), 5.05 (s, 2H), 3.58 (s, 3H).

13.2 Synthesis of 3-(2-methoxymethoxy-5-trifluoromethyl-phenyl)-3-phenyl-methyl Acrylate According to the steps described in 2.2 of embodiment 2, (2-methoxymethoxy-5-trifluoromethyl-phenyl)(phenyl)-methanone is used as the raw material to produce the brown oily coarse product 3-(2-methoxymethoxy-5-trifluoromethyl-phenyl)-3-phenyl-methyl acrylate, which can be directly used for the next step.

13.3 Synthesis of 3-(2-methoxymethoxy-5-trifluoromethyl-phenyl)-3-phenyl-acrylic Acid According to the steps described in 2.3 of embodiment 2, the coarse product obtained in the previous step is used as the raw material to produce the white solid product 3-(2-methoxymethoxy-5-trifluoromethyl-phenyl)-3-phenyl-acrylic acid. The yield of both steps is 82%. $^1$H NMR (400 MHz, CDCl$_3$), δ: 7.86-7.66 (m, 4H), 7.55-7.42 (m, 2H), 7.28-7.19 (m, 1H), 7.05-7.0 (m, 1H), 6.85 (s, 1H), 5.08 (s, 2H), 3.59 (s, 3H).

13.4 Synthesis of 2-bromo-1-(2-methoxymethoxy-5-trifluoromethyl-phenyl)-1-phenyl-ethylene According to the steps described in 2.4 of embodiment 2, 3-(2-methoxymethoxy-5-trifluoromethyl-phenyl)-3-phenyl-acrylic acid is used as the raw material to produce brown yellow oily product with a yield of 56%. 41 NMR (400 MHz, CDCl$_3$), δ: 7.51-7.39 (m, 3H), 7.35-7.28 (m, 2H), 7.18-7.15 (m, 1H), 7.11-7.09 (m, 1H), 7.05-7.0 (m, 1H), 6.55 (s, 1H), 5.01 (s, 2H), 3.51 (s, 3H).

13.5 Synthesis of 2-[2-(2-methoxymethoxy-5-trifluoromethyl-phenyl)-2-phenyl-vinyl]-N-methylpiperidine According to the steps described in 2.5 of embodiment 2, 2-bromo-1-(2-methoxymethoxy-5-trifluoromethyl-phenyl)-1-phenyl-ethylene is used as the raw material to produce the light brown oily product 2-[2-(2-methoxymethoxy-5-trifluoromethyl-phenyl)-2-phenyl-vinyl]-N-methylpiperidine with a yield of 60%. LC-MS (m/z): 406.3 [M+H]$^+$.

13.6 Synthesis of 2-[2-(2-hydroxy-5-trifluoromethyl-phenyl)-phenethyl]-N-methylpiperidine (II-13)

According to the steps described in 2.6 of embodiment 2, 2-[2-(2-methoxymethoxy-5-trifluoromethyl-phenyl)-styryl]-N-methylpiperidine is used as the raw material to produce the white solid target product II-13 by double-bond hydrogenation and deoxidation of protecting group with a yield of 49%. LC-MS (m/z): 408.3 $^1$H NMR (400 MHz, CDCl$_3$): δ: 12.25 (s, 1H), 7.32-7.28 (m, 4H), 7.22-7.18 (m, 1H), 6.88-6.85 (m, 2H), 6.63 (b, 1H), 4.50 (dd J=2.8, 12.8 Hz, 1H), 2.95 (d, J=13.6 Hz, 1H), 2.88-2.83 (m, 1H), 2.63-2.55 (m, 1H), 2.36-2.32 (m, 5H), 2.19-2.11 (m, 1H), 1.78-1.67 (m, 1H), 1.57-1.47 (m, 3H), 1.20-1.15 (m, 1H).

Embodiment 14

Synthesis of 2-[2-(4-chlorophenyl)-2-(2-hydroxy-5-methylphenyl)ethyl]-N-methylpiperidine (II-14) and 2-[2-(4-chlorophenyl)-2-(2-hydroxy-5-methylphenyl)-ethyl]-N,N-dimethylpiperidine Bromide (I-14)

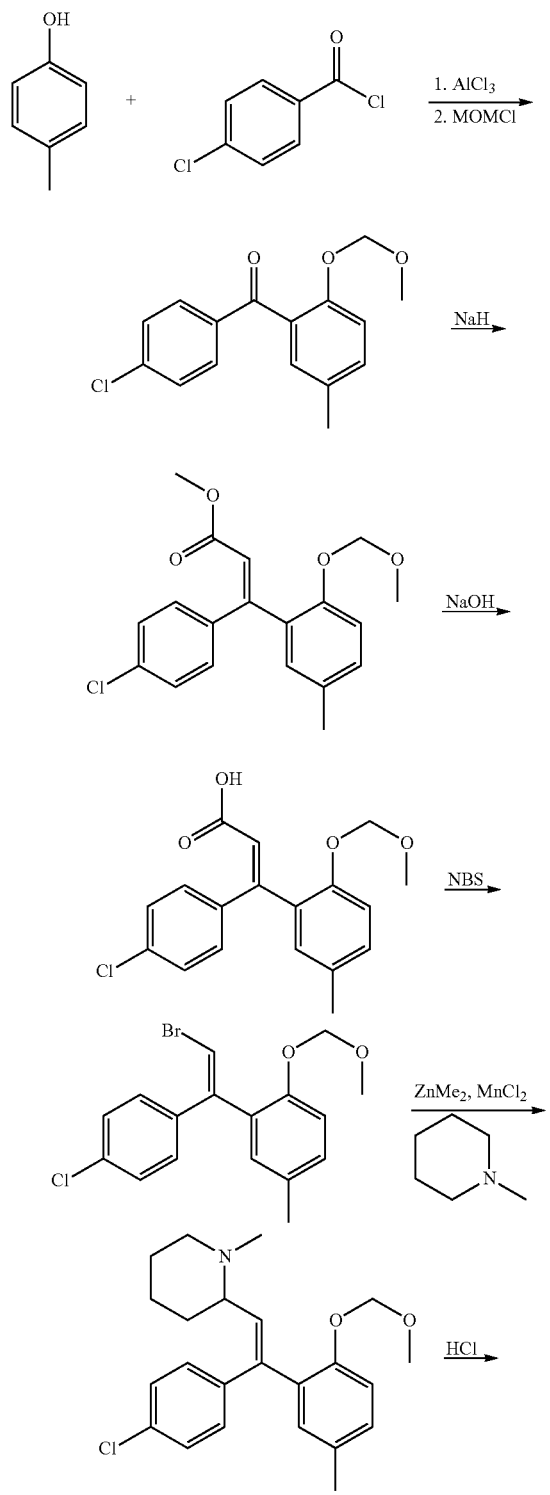

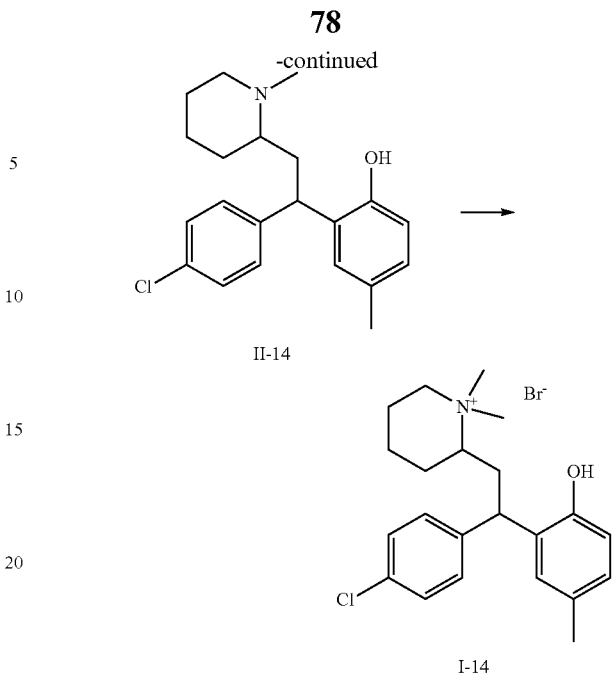

14.1 Synthesis of (4-chlorophenyl)(2-hydroxy-5-methylphenyl)-methanone

According to the steps described in 4.1.1 of embodiment 4, p-methylphenol and 4-chlorobenzoyl chloride are used as the raw materials to produce the brown solid coarse product (4-chlorophenyl) (2-hydroxy-5-methylphenyl)-methanone with a yield of 80%. $^1$H NMR (400 MHz, CDCl$_3$), δ: 11.70 (s, 1H), 7.65-7.62 (m, 2H), 7.51-7.48 (m, 2H), 7.35-7.32 (m, 1H), 7.31 (m, 1H), 7.0 (d, J=8.0 Hz, 1H), 2.26 (s, 3H).

14.2 Synthesis of (4-chlorophenyl)(2-methoxymethoxy-5-methylphenyl)-methanone According to the steps described in 2.1 of embodiment 2, (4-chlorophenyl)(2-hydroxy-5-methylphenyl)-methanone is used as the raw material to produce the brown oily product (4-chlorophenyl) (2-methoxymethoxy-5-methylphenyl)-methanone with a yield of 82%. $^1$H NMR (400 MHz, CDCl$_3$), δ: 7.78-7.76 (m, 2H), 7.42-7.39 (m, 2H), 7.26-7.24 (m, 1H), 7.17 (b, 1H), 7.11 (d, J=8.0 Hz, 1H), 5.0 (s, 2H), 3.28 (s, 3H), 2.33 (s, 3H).

14.3 Synthesis of 3-(4-chlorophenyl)-3-(2-methoxymethoxy-5-methylphenyl)-methyl Acrylate According to the steps described in 2.2 of embodiment 2, (4-chlorophenyl)(2-methoxymethoxy-5-methylphenyl)-methanone is used as the raw material to produce the brown oily product 3-(4-chlorophenyl)-3-(2-methoxymethoxy-5-methylphenyl)-methyl acrylate with a yield of 92%. $^1$H-NMR spectrum shows that the product is mainly E-isomer. $^1$H NMR (400 MHz, CDCl$_3$), δ: 7.28 (b, 4H), 7.15-7.12 (m, 1H), 7.06-7.04 (d, J=8.4 Hz, 1H), 6.85-6.43 (m, 1H), 6.42 (s, 1H), 4.99 (s, 2H), 3.61 (s, 3H), 3.22 (s, 3H), 2.29 (s, 3H).

14.4 Synthesis of 3-(4-chlorophenyl)-3-(2-methoxymethoxy-5-methylphenyl)-acrylic Acid According to the steps described in 2.3 of embodiment 2, 3-(4-chlorophenyl)-3-(2-methoxymethoxy-5-methylphenyl)-methyl acrylate is used as the raw material to produce the brown solid product 3-(4-chlorophenyl)-3-(2-methoxymethoxy-5-methylphenyl)-acrylic acid with a yield of 95%, NMR (400 MHz, CDCl$_3$), δ: 7.30-7.23 (m, 4H), 7.14-7.11 (m, 1H), 7.05 (d, J=8.4 Hz, 1H), 6.83-6.82 (m, 1H), 6.38 (s, 1H), 4.97 (s, 2H), 3.22 (s, 3H), 2.27 (s, 3H).

14.5 Synthesis of 2-bromo-1-(4-chlorophenyl)-1-(2-methoxymethoxy-5-methylphenyl)-ethylene According to the steps described in 2.4 of embodiment 2, 3-(4-chlorophenyl)-3-(2-methoxymethoxy-5-methylphenyl)-acrylic acid is used as the raw material to produce the brown yellow oily product 2-bromo-1-(4-chlorophenyl)-1-(2-methoxymethoxy-5-methylphenyl)-ethylene with a yield of 69%. $^1$H NMR (400 MHz, CDCl$_3$), δ: 7.25-7.22 (m, 2H), 7.18-7.13 (m, 3H), 7.09-7.07 (m, 1H), 6.97-6.96 (m, 1H), 6.87 (s, 1H), 5.02 (s, 2H), 3.27 (s, 3H), 2.32 (s, 3H).

14.6 Synthesis of 2-[2-(2-methoxymethoxy-5-methylphenyl)-2-(4-chlorophenyl)-vinyl]-N-methylpiperidine According to the steps described in 2.5 of embodiment 2, 2-bromo-1-(4-chlorophenyl)-1-(2-methoxymethoxy-5-methylphenyl)-ethylene is used as the raw material to produce the light brown oily product 2-[2-(2-methoxymethoxy-5-methylphenyl)-2-(4-methylphenyl)-vinyl]-N-methylpiperidine with a yield of 59%. $^1$H NMR (400 MHz, CDCl$_3$), δ: 7.20-7.16 (m, 4H), 7.13-7.10 (m, 1H), 7.07-7.05 (m, 1H), 6.86-6.85 (m, 1H), 6.14 (d, J=9.2 Hz, 1H), 4.96 (m, 2H), 3.24-3.17 (m, 3H), 2.86-2.85 (m, 1H), 2.42-2.38 (m, 1H), 2.31 (s, 3H), 2.25 (s, 3H), 1.95-1.85 (m, 1H), 1.75-1.55 (m, 1H), 1.50-1.42 (m, 1H), 1.18-1.10 (m, 1H).

14.7 Synthesis of 2-[2-(4-chlorophenyl)-2-(2-hydroxy-5-methylphenyl)-ethyl]-N-methylpiperidine (II-14)

According to the steps described in 2.6 of embodiment 2, 2-[2-(4-chlorophenyl)-2-(2-methoxymethoxy-5-methylphenyl)-vinyl]-N-methylpiperidine is used as the raw material to produce white solid target product by double-bond hydrogenation and deoxidation of protecting group with a yield of 58%. MS (m/z): 344.3 [M+H]$^+$. $^1$H NMR. (400 MHz, CDCl$_3$), δ: 10.58 (b, 1H), 7.50-7.45 (m, 4H), 7.22-7.13 (m, 1H), 7.07-7.04 (m, 1H), 6.86-6.83 (m, 1H), 4.54 (dd, J=2.8, 12.8 Hz, 1H), 3.06-3.04 (m, 1H), 2.47-2.45 (m, 1H), 2.38 (s, 3H), 2.26-2.24 (m, 1H), 2.20-2.08 (m, 2H), 2.11 (s, 3H), 1.56-1.46 (m, 3H), 1.20-1.15 (m, 3H).

14.8 Synthesis of 2-[2-(4-chlorophenyl)-2-(2-hydroxy-5-methylphenyl)-ethyl]-N,N-dimethylpiperidine Bromide (I-14)

According to the steps described in 2.7 of embodiment 2, II-14 and bromomethane are used as the raw materials to produce the white solid target product 1-14 with a yield of 91%. LC-MS (m/z): 346.3 [M+H]$^+$. $^1$H NMR (400 MHz, CD$_3$OD), δ: 7.65-7.60 (m, 2H), 7.45-7.39 (m, 2H), 7.20-7.17 (m, 1H), 7.11-7.06 (m, 1H), 6.96-6.93 (m, 1H), 4.34 (dd, J=4.0, 12.8 Hz, 1H), 3.73-3.70 (m, 1H), 3.44 (m, 1H), 3.26-3.22 (m, 1H), 3.03 (s, 3H), 3.01 (s, 3H), 2.84-2.81 (m, 1H), 2.20 (b, 1H), 2.13 (s, 3H), 2.09-2.02 (m, 1H), 1.96-1.91 (m, 1H), 1.88-1.82 (m, 2H), 1.80-1.71 (m, 1H), 1.46-1.39 (m, 1H).

Embodiment 15

Synthesis of 2-[2-(4-tolyl)-2-(2-hydroxy-5-methylphenyl)-ethyl]-N-methylpiperidine (II-15) and 2-[2-(4-tolyl)-2-(2-hydroxy-5-methyl-phenyl)-ethyl]-N,N-dimethylpiperidine Bromide (I-15)

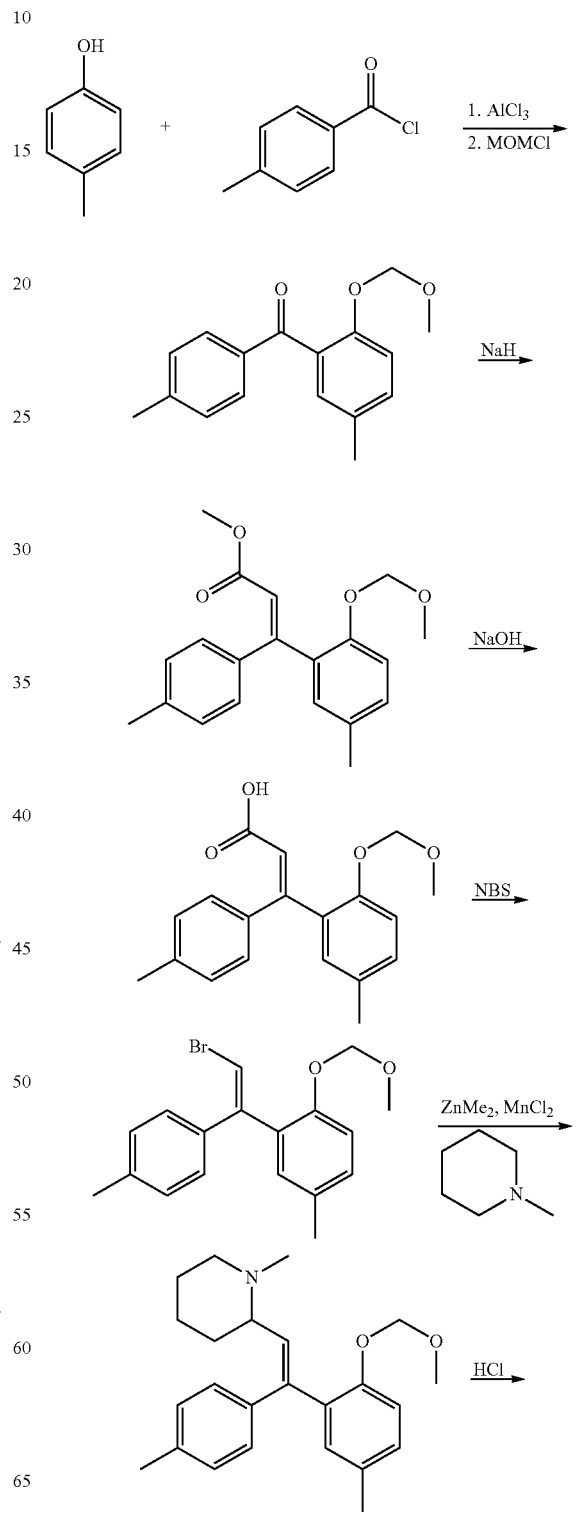

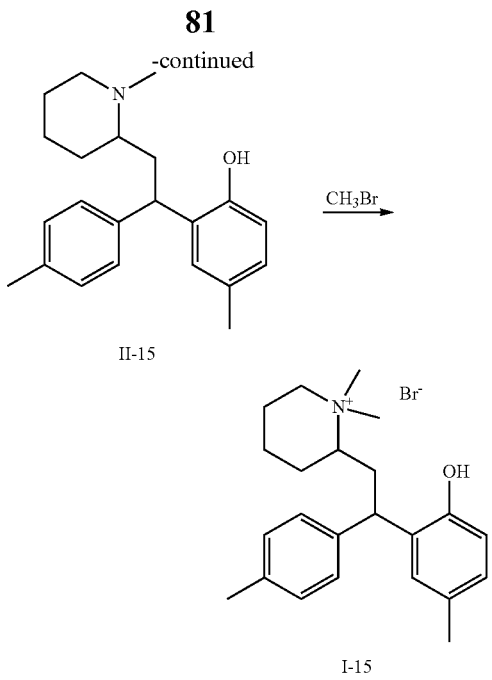

15.1 Synthesis of (4-methylphenyl)(2-hydroxy-5-methyl-phenyl)-methanone

According to the steps described in 4.1.1 of embodiment 4, p-methylphenol and 4-methylbenzoyl chloride are used as tire raw materials to produce the brown solid coarse product (4-methylphenyl) (2-hydroxy-5-methyl-phenyl)-methanone, which can be directly used for the next step.

15.2 Synthesis of (4-methylphenyl)(2-methoxymethoxy-5-methylphenyl)-methanone According to the steps described in 2.1 of embodiment 2, (4-methylphenyl)(2-hydroxy-5-methylphenyl)-methanone is used as the raw material to produce the brown oily product (4-methylphenyl) (2-methoxymethoxy-5-methylphenyl)-methanone. The yield of both steps is 72%. $^1$H NMR (400 MHz, CDCl$_3$), δ: 7.75 (d, J=8.0 Hz, 2H), 7.24-7.21 (m, 3H), 7.14 (b, 1H), 7.10 (d, J=12.0 Hz, 1H), 5.01 (s, 2H), 3.30 (s, 3H), 2.41 (s, 3H), 2.32 (s, 3H).

15.3 Synthesis of 3-(4-methylphenyl)-3-(2-methoxymethoxy-5-methylphenyl)-methyl Acrylate According to the steps described in 2.2 of embodiment 2, (4-methylphenyl)(2-methoxymethoxy-5-methylphenyl)-methanone is used as the raw material to produce the brown oily coarse product 3-(4-methylphenyl)-3-(2-methoxymethoxy-5-methylphenyl)-methyl acrylate, which can be directly used for the next step without purification.

15.4 Synthesis of 3-(4-methylphenyl)-3-(2-methoxymethoxy-5-methylphenyl)-acrylic Acid According to the steps described in 2.3 of embodiment 2, the coarse product 3-(4-methylphenyl)-3-(2-methoxymethoxy-5-methylphenyl)-methyl acrylate in the previous step is used as the raw material to produce the brown solid product 3-(4-methylphenyl)-3-(2-methoxymethoxy-5-methylphenyl)acrylic acid. The yield of both steps is 92%. $^1$H-NMR spectrum shows that the product is the mixture of E,Z-isomers with E/Z=2/1. $^1$H NMR (400 MHz, CDCl$_3$), E-isomer δ: 7.20 (d, J=8.0 Hz, 2H), 7.14-7.07 (m, 3H), 7.04 (d, J=8.0 Hz, 1H), 6.83 (b, 1H), 6.39 (s, 1H), 4.98 (s, 2H), 3.24 (s, 3H), 2.34 (s, 3H), 2.26 (s, 3H).

Z-isomer δ: 7.14-7.07 (m, 5H), 6.97-6.95 (m, 2H), 6.11 (s, 1H), 4.86 (s, 2H), 3.19 (s, 3H), 2.34 (s, 3H), 2.26 (s, 3H).

15.5 Synthesis of 2-bromo-1-(4-methylphenyl)-1-(2-methoxymethoxy-5-methylphenyl)-ethylene According to the steps described in 2.4 of embodiment 2, 3-(4-methylphenyl)-3-(2-methoxymethoxy-5-methylphenyl)acrylic acid is used as the raw material to produce the brown yellow oily product 2-bromo-1-(4-methylphenyl)-1-(2-methoxymethoxy-5-methylphenyl)-ethylene with a yield of 69%. $^1$H-NMR spectrum shows that the product is the mixture of E,Z-isomers with E/Z=2/1. $^1$H NMR (400 MHz, CDCl$_3$), E-isomer δ: 7.66 (s, 1H), 7.52 (d, J=8.0 Hz, 2H), 7.32 (b, 1H), 7.12 (d, J=8.0 Hz, 2H), 7.04 (m, 1H), 6.99 (d, J=8.0 Hz, 1H), 5.15 (dd, J=6.8, 25.6 Hz, 2H), 3.41 (s, 3H), 2.33 (s, 3H), 2.31 (s, 3H).

Z-isomer δ: 7.18 (d, J=8.0 Hz, 4H), 7.12-7.10 (m, 2H), 7.0 (b, 1H), 6.87 (s, 1H), 5.06 (s, 2H), 3.32 (s, 3H), 2.35 (s, 3H), 2.34 (s, 3H).

15.6 Synthesis of 2-[2-(2-methoxymethoxy-5-methylphenyl)-2-(4-methylphenyl)-vinyl]-N-methylpiperidine According to the steps described in 2.5 of embodiment 2, 2-bromo-1-(4-methylphenyl)-1-(2-methoxymethoxy-5-methyl-phenyl)-ethylene is used as the raw material to produce the light brown oily product 2-[2-(2-methoxymethoxy-5-methyl-phenyl)-2-(4-methylphenyl)-vinyl]-N-methylpiperidine with a yield of 69%.

15.7 Synthesis of 2-[2-(4-methylphenyl)-2-(2-hydroxy-5-methylphenyl)-ethyl]-N-methylpiperidine (II-15)

According to the steps described in 2.6 of embodiment 2, 2-[2-(4-methylphenyl)-2-(2-methoxymethoxy-5-methylphenyl)-vinyl]-N-methylpiperidine is used as the raw material to produce the white solid target product II-15 by double-bond hydrogenation and deoxidization of protecting group. $^1$H-NMR spectrum show's that II-15 is a pair of diastereomers with a ratio of 5/1 and a total yield of 53%. MS (m/z): 324.3 [M+H]$^+$. $^1$H NMR (400 MHz, CDCl$_3$), δ: 11.22 (b, 1H), 7.38 (d, J=8.0 Hz, 2H), 7.32 (d, J=8.0 Hz, 2H), 6.85 (m, 2H), 6.50 (s, 1H), 4.45 (dd, J=2.8, 12.8 Hz, 1H), 3.03-3.0 (m, 1H), 2.87-2.85 (m, 1H), 2.57-2.53 (m, 1H), 2.35 (s, 3H), 2.18-2.13 (m, 1H), 2.11 (s, 3H), 2.09 (s, 3H), 2.01-1.93 (m, 1H), 1.79-1.56 (m, 4H), 1.50-1.30 (m, 2H).

15.8 Synthesis of 2-[2-(4-methylphenyl)-2-(2-hydroxy-5-methylphenyl)-ethyl-]-N,N-dimethylpiperidine Bromide (I-15)

According to the steps described in 2.7 of embodiment 2, II-15 and bromomethane are used as the raw materials to produce the white solid target product I-15 with a yield of 92%. LC-MS (m/z): 326.3 [M+H]$^+$. $^1$H NMR (400 MHz, CD$_3$OD), δ: 7.42-7.39 (m, 2H), 7.32-7.28 (m, 2H), 6.97 (m, 1H), 6.82-6.79 (m, 1H), 6.67-6.64 (m, 1H), 4.43 (dd, J=3.2, 12.0 Hz, 1H), 3.51-3.48 (m, 1H), 3.34-3.30 (m, 1H), 2.99 (s, 3H), 2.96 (s, 3H), 2.87-2.83 (m, 1H), 2.26-2.20 (m, 1H), 2.16 (s, 3H), 2.14 (s, 3H), 2.08-2.01 (m, 1H), 1.96-1.91 (m, 1H), 1.89-1.76 (m, 2H), 1.52-1.44 (m, 1H), 1.36-1.31 (m, 2H).

Embodiment 16

2-[2-(2-hydroxy-3-methyl-5-isopropyl phenyl)-2-(3-ethyl phenyl)-ethyl]-N-methylpiperidine (II-16)

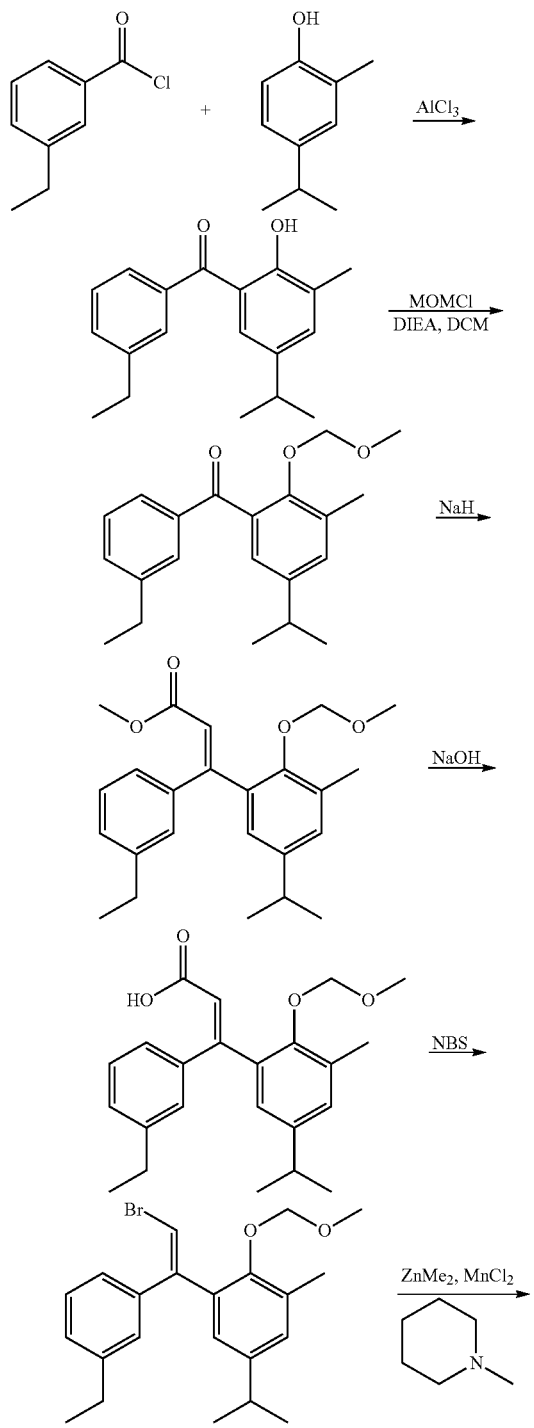

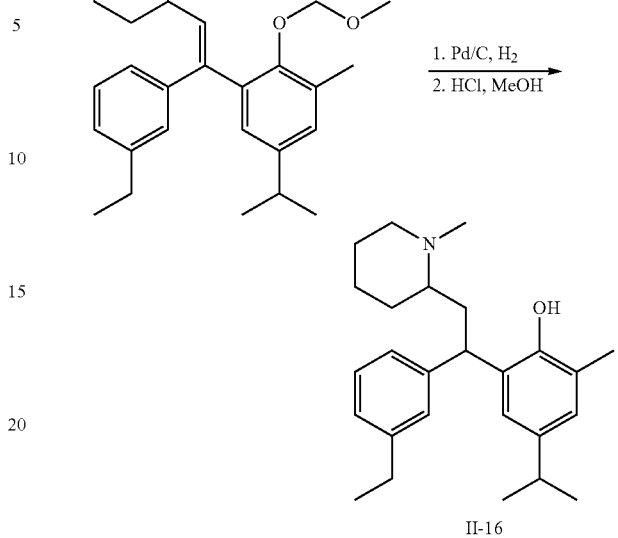

16.1 Synthesis of (2-hydroxy-3-methyl-5-isopropyl phenyl)(3-ethyl phenyl)-methanone According to the steps described in 4.1.1 of embodiment 4, 2-methyl-3-isopropyl-phenol and 3-ethylbenzoyl chloride are used as the raw materials to produce the brown solid coarse product (2-hydroxy-3-methyl-5-isopropyl-phenyl)(3-ethyl phenyl)-methanone, and the coarse product can be used in the next step directly.

16.2 Synthesis of (2-methoxymethoxy-3-methyl-5-isopropyl phenyl)(3-ethyl phenyl)-methanone According to the steps described in 2.1 of embodiment 2, the coarse product obtained in the previous step is used as the raw material to produce colorless oily product (2-methoxymethoxy-3-methyl-5-isopropyl phenyl)(3-ethyl phenyl)-methanone. The yield of both steps is 78%. $^1$H NMR (400 MHz, CDCl$_3$), δ: 7.52-7.47 (m, 2H), 7.42-7.38 (m, 2H), 7.26-7.23 (m, 1H), 7.04 (s, 1H), 4.99 (s, 2H), 3.30 (s, 3H), 3.18 (m, 1H), 2.62 (q, J=8.0 Hz, 2H), 1.29 (d. J=6.8 Hz, 6H), 1.24 (t, J=8.0 Hz, 3H).

16.3 Synthesis of 3-(2-methoxymethoxy-3-methyl-5-isopropyl phenyl)-3-(3-ethyl phenyl)-methyl Acrylate According to the steps described in 2.2 of embodiment 2, (2-methoxymethoxy-3-methyl-5-isopropyl phenyl)(3-ethyl phenyl)-methanone is used as the raw material, and the yellow oily product obtained can be directly used for hydrolysis in the next step.

16.4 Synthesis of 3-(2-methoxymethoxy-3-methyl-5-isopropyl phenyl)-3-(3-ethyl phenyl)-acrylic Acid According to the steps described in 2.3 of embodiment 2, the coarse product obtained in the previous step is used as the raw material to produce the white solid product 3-(2-methoxymethoxy-3-methyl-3-isopropyl phenyl)-3-(3-ethyl phenyl)acrylic acid. The yield of both steps is 81%. $^1$H NMR (400 MHz, CDCl$_3$), δ: 7.24-7.16 (m, 4H), 7.06-7.04 (m, 1H), 6.77 (s, 1H), 6.36 (s, 1H), 4.97 (s, 2H), 3.21 (s, 3H), 3.16 (m, 1H), 2.57 (q, J=8.0 Hz, 2H), 1.28 (d, J=6.8 Hz, 614), 1.25 (t, J=8.0 Hz, 3H).

16.5 Synthesis of 2-bromo-1-(2-methoxymethoxy-3-methyl-5-isopropyl phenyl)-1-(3-ethyl phenyl)-ethylene According to the steps described in 2.4 of embodiment 2, 3-(2-methoxymethoxy-3-methyl-5-isopropyl phenyl)-3-(3-ethyl phenyl)-acrylic acid is used as the raw material to produce the brown yellow oily product 2-bromo-1-(2-methoxymethoxy-3-methyl-5-isopropyl phenyl)-1-(3-ethyl phenyl)-ethylene with a yield of 61%. $^1$H-NMR spectrum shows that the product is mainly E-isomer and no obvious Z-isomer is found. $^1$H NMR (400 MHz, CDCl$_3$), δ: 7.23-7.18 (m, 4H), 7.10-7.08 (m, 1H), 7.02 (s, 1H), 6.91 (s, 1H), 5.12 (m, 2H), 3.40 (s, 3H), 3.16 (m, 1H), 2.56 (q, J=8.0 Hz, 2H), 2.09 (s, 3H), 1.29 (d, J=6.8 Hz, 6H), 1.22 (t, J=8.0 Hz, 3H).

16.6 Synthesis of 2-[2-(2-methoxymethoxy-3-methyl-5-isopropyl phenyl)-2-(3-ethyl phenyl)-vinyl]-N-methylpiperidine According to the steps described in 2.5 of embodiment 2, 2-bromo-1-(2-methoxymethoxy-3-methyl-5-isopropyl phenyl)-1-(3-ethyl phenyl)-ethylene is used as the raw material to produce the light brown oily product 2-[2-(2-methoxymethoxy-3-methyl-5-isopropyl phenyl)-2-(3-ethyl phenyl)-vinyl]-N-methylpiperidine. LC-MS (m/z): 422.2 [M+H]$^+$. The product can be used directly for the next reaction.

16.7 Synthesis of 2-[2-(2-hydroxy-3-methyl-5-isopropyl phenyl)-2-(3-ethyl phenyl)-ethyl]-N-methylpiperidine (II-16)

According to the steps described in 2.6 of embodiment 2, the coarse product obtained in the previous step is used as the raw material to produce the white solid target product II-16 by double-bond hydrogenation reduction, deoxidization of protecting group and separation by using silica gel column with a yield of 32%. LC-MS (m/z): 380.3 [M+H]$^+$. $^1$H NMR (400 MHz, CDCl$_3$), δ: 11.83 (b, 1H), 7.29-7.20 (m, 4H), 7.10-7.05 (m, 1H), 6.67 (b, 1H), 4.45 (dd, J=4.0 Hz, 16 Hz, 1H), 3.0-2.96 (m, 4H), 2.85-2.82 (m, 1H), 2.59-2.53 (m, 3H), 2.40 (s, 3H), 2.17-2.10 (m, 4H), 2.01-1.93 (m, 1H), 1.80-1.50 (m, 3H), 1.45-1.34 (m, 3H), 1.30-1.20 (m, 9H).

Embodiment 17

2-[2-(2-methoxyphenyl)-phenethyl]-N-methylpiperidine (II-17)

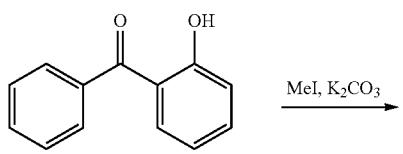

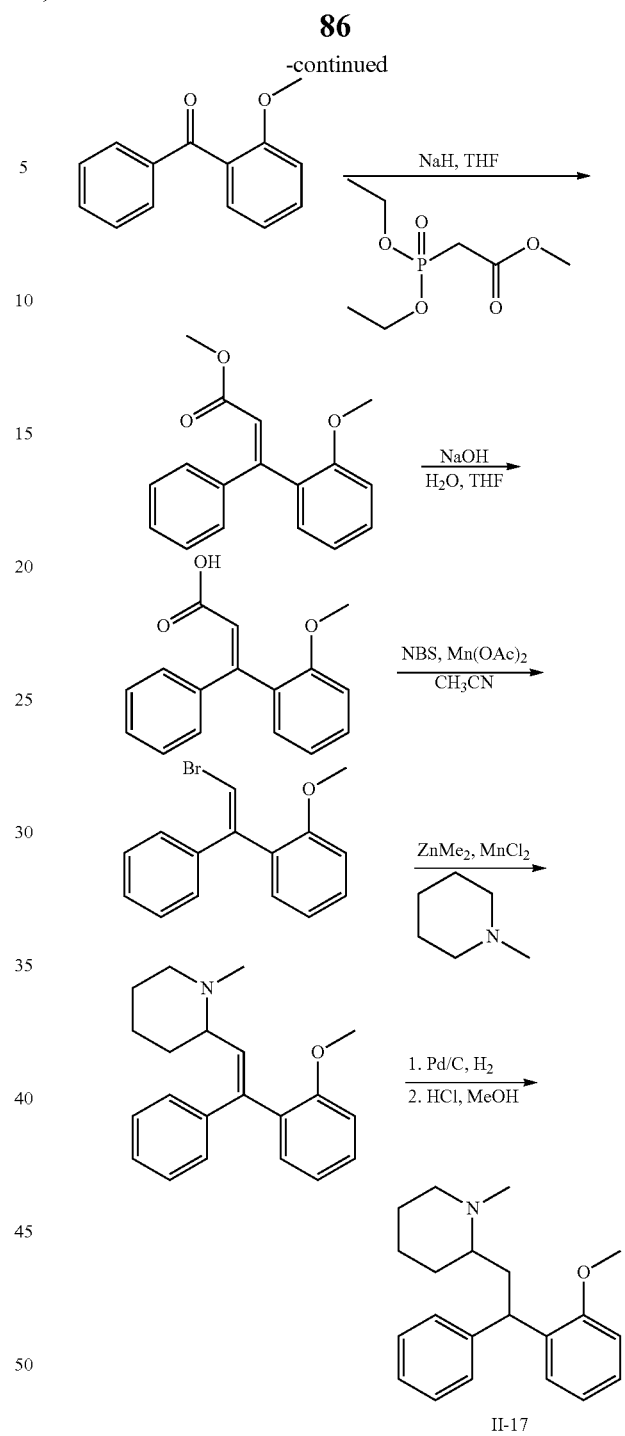

II-17

17.1 Synthesis of (2-methoxyphenyl)(phenyl)-methanone (2-hydroxy-phenyl)(phenyl)-methanone (1.98 g, 10 mmol) is dissolved in N,N-dimethylformamide (30 ml); anhydrous potassium carbonate (2.76 g, 20 mmol) is added; the above materials are stirred at room temperature; then iodomethane (2.84 g, 20 mmol) is dropped; and the reaction is carried out for 6 h at room temperature. TLC is used for monitoring; after the reaction is completed, the materials are quenched by addition of water and extracted with dichloromethane (3×30 ml). After being merged, the organic phase is washed with water and a saturated salt solution, dried with anhydrous sodium sulfate, desolvated by the rotary evaporator, purified by silicon oxide column chromatography and eluted by ligroin/dichloromethane (4/1) to obtain 2.01 g of the brown solid product, with a yield of 95%. $^1$H NMR (400 MHz, CDCl$_3$), δ: 7.82-7.80 (m, 2H), 7.57-7.53 (m, 1H), 7.49-7.41 (m, 3H), 7.37 (dd, J=1.6, 7.6 Hz, 1H), 7.04 (t, J=7.6 Hz, 1H), 6.98 (d, J=8.4 Hz, 1H), 3.73 (s, 3H).

17.2 Synthesis of 3-(2-methoxyphenyl)-3-(phenyl)-methyl Acrylate

According to tire steps described in 2.2 of embodiment 2, (2-methoxyphenyl)(phenyl)-methanone is used as the raw material to produce the brown oily coarse product of 3-(2-methoxyphenyl)-3-(phenyl)methyl acrylate and the coarse product can be used in the next step directly.

17.3 Synthesis of 3-(2-methoxyphenyl)-3-(phenyl)-acrylic Acid

According to the steps described in 2.3 of embodiment 2, 3-(2-methoxyphenyl)-3-(phenyl)-methyl acrylate is used as the raw material to produce the white solid product of 3-(2-methoxyphenyl)-3-(phenyl)-acrylic acid. The yield of both steps is 76%.

17.4 Synthesis of 2-bromo-1-(2-methoxyphenyl)-styrene

According to the steps described in 2.4 of embodiment 2, 3-(2-methoxyphenyl)-3-(phenyl)-acrylic acid is used as the raw material to produce the brown yellow oily product of 2-bromo-1-(2-methoxyphenyl)-styrene with a yield of 59%. $^1$H NMR (400 MHz, CDCl$_3$), δ: 7.40-7.33 (m, 1H), 7.27-7.20 (m, 5H), 7.18-7.15 (m, 1H), 7.05-6.95 (m, 2H), 6.88 (s, 1H), 3.72 (s, 3H).

17.5 Synthesis of 2-[2-(2-methoxyphenyl)-styryl]-N-methylpiperidine

According to the steps described in 2.5 of embodiment 2, 2-bromo-1-(2-methoxyphenyl)-styrene is used as the raw material to produce the light brown oily product of 2-[2-(2-methoxyphenyl)-styryl]-N-methylpiperidine with a yield of 42%. $^1$H NMR show's that the product is mainly E-isomer, LC-MS (m/z): 308.6 [M+H]$^+$, $^1$H NMR (400 MHz, CDCl$_3$), δ: 7.36-7.31 (m, 1H), 7.25-7.23 (m, 3H), 7.20-7.15 (m, 1H), 7.05 (dd, J=2.5, 7.6 Hz, 1H), 6.99 (dd, J=0.8, 7.2 Hz, 1H), 6.95 (d, 7.2 Hz, 1H), 6.17 (d, J=9.6 Hz, 1H), 3.69 (s, 3H), 2.85 (d, J=12. Hz, 1H), 2.41-2.25 (m, 1H), 2.22 (s, 3H), 1.88-1.81 (m, 3H), 2.69-1.53 (m, 2H), 1.49-1.39 (m, 1H), 1.15-1.04 (m, 1H).

17.6 Synthesis of 2-[2-(2-methoxyphenyl)-phenethyl]-N-methylpiperidine (II-17)

According to the steps described in 2.6 of embodiment 2, 2-[2-(2-methoxyphenyl)-styryl-]-N-methylpiperidine is used as the raw material and stirred to react at 40° C. for 12 h under 0.1 Mpa of hydrogen pressure to obtain the white solid target product II-17, with a yield of 79%. $^1$H NMR shows that the product is a pair of diastereomers with D-17a/II-17b=2.6/1. LC-MS (m/z): 310.6 [M+H]$^+$. $^1$H NMR (400 MHz, CDCl$_3$), II-17a, δ: 7.29-7.27 (m, 3H), 7.25-7.23 (m, 1H), 7.19-7.14 (m, 2H), 7.12-7.09 (m, 1H), 6.88-6.86 (m, 1H), 6.83-6.81 (d, J=8.4 Hz, 1H), 4.51-4.47 (dd, J=4.4, 10.4 Hz, 1H), 3.80 (s, 3H), 2.79-2.74 (m, 1H), 2.59-2.47 (m, 1H), 2.26 (s, 3H), 2.09-2.00 (m, 1H), 1.87-1.61 (m, 1H), 1.59-1.50 (m, 2H), 1.35-1.22 (m, 1H), 1.20-1.10 (m, 1H).

II-17b, δ: 7.30-7.27 (m, 2H), 7.25-7.23 (m, 2H), 7.23-7.20 (m, 1H), 7.19-7.14 (m, 1H), 7.12-7.09 (m, 1H), 6.93-6.89 (m, 1H), 6.85-6.84 (m, 1H), 4.56-4.52 (dd, J=5.6, 10.4 Hz, 1H), 3.78 (s, 3H), 2.79-2.74 (m, 1H), 2.59-2.47 (m, 1H), 2.30 (s, 3H), 2.09-2.00 (m, 1H), 1.87-1.61 (m, 4H), 1.59-1.50 (m, 2H), 1.35-1.22 (m, 1H), 1.20-1.10 (m, 1H).

Embodiment 18

2-[2-(2-hydroxy-5-methyl-phenyl)-phenethyl]-N-ethylpiperidine (II-18)

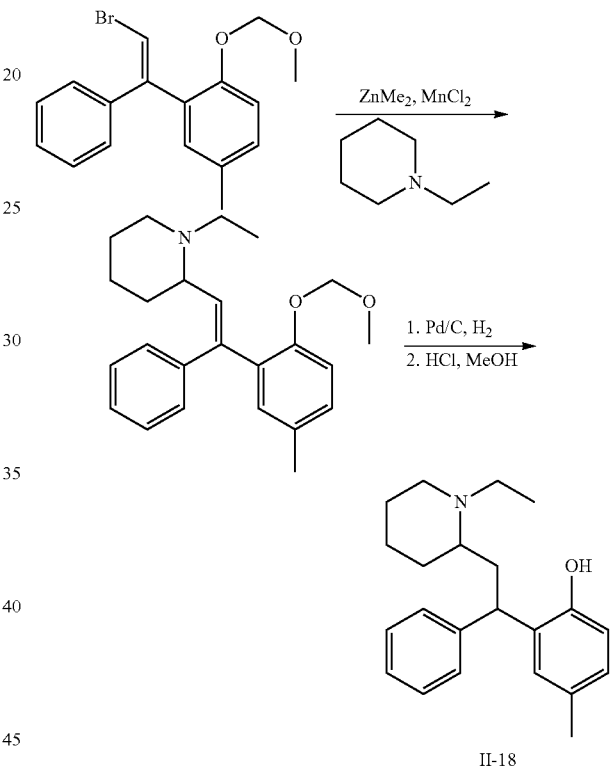

18.1 Synthesis of 2-[2-(2-methoxymethoxy-5-methylphenyl)-styryl]N-ethylpiperidine According to the steps described in 2.5 of embodiment 2, 2-bromo-1-(2-methoxymethoxy-5-methyl-phenyl)-N-phenyl-ethylene and N-ethylpiperidine are used as the raw materials to produce the light brown oily product 2-[2-(2-methoxymethoxy-5-methyl-phenyl)-styryl]-N-ethylpiperidine with a yield of 63%, LC-MS (m/z): 366.2 [M+H]$^+$.

18.2 Synthesis of 2-[2-(2-hydroxy-5-methyl-phenyl)-phenethyl]-N-ethylpiperidine (II-18)

According to the steps described in 2.6 of embodiment 2, 2-[2-(2-methoxymethoxy-5-methyl-phenyl)-styryl-]-N-ethylpiperidine is used as the raw material to produce the brown solid target product II-18 by double-bond hydrogenation and deoxidization of protecting group with a yield of 51%. 44 NMR shows that only one diastereomer product is obtained.

LC-MS (m/z): 324.2, [M+H]⁺. ¹H NMR (400 MHz, CDCl₃), δ: 12.18 (s, 1H), 7.31 (d, J=4.4 Hz, 4H), 7.23-7.20 (m, 1H), 6.90-6.84 (m, 2H), 6.47 (d, J=1.6 Hz, 1H), 4.48 (dd, J=3.2, 12.8 Hz, 1H), 2.98 (d, J=13.6 Hz, 1H), 2.85 (t, J=0.1-0.8 Hz, 1H), 2.60-2.54 (m, 1H), 2.41-2.36 (m, 5H), 2.16-2.11 (m, 1H), 2.01-1.93 (m, 1H), 1.78-1.75 (m, 1H), 1.69-1.66 (m, 1H), 1.60-1.50 (m, 2H), 1.45-1.37 (m, 1H), 1.32-1.22 (m, 3H), 1.04 (t, J=7.6 Hz, 3H).

Embodiment 19

2-[2-(2-hydroxy-5-methyl-phenyl)-phenethyl]-N-methylpyrrolidine (II-19) and 2-[2-(2-hydroxy-5-methyl-phenyl)-phenethyl]-N,N-dimethylpyrrolidine Bromide (I-19)

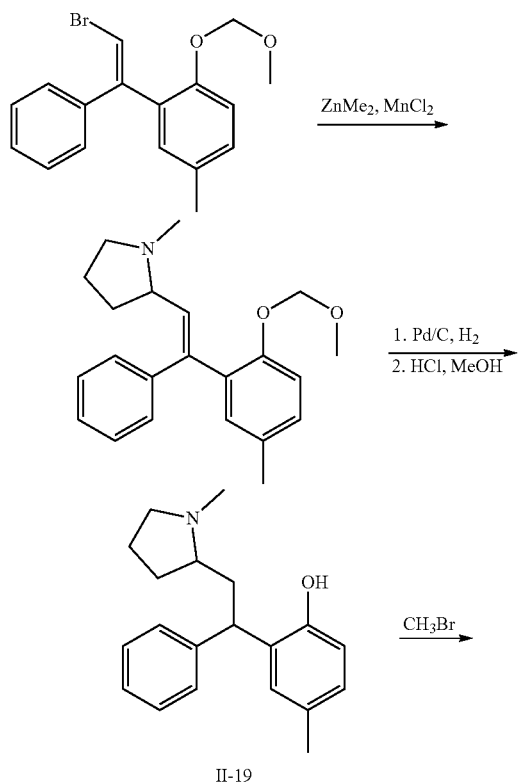

19.1 Synthesis of 2-[2-(2-methoxymethoxy-5-methyl-phenyl)-2-phenyl-vinyl]-N-methylpyrrolidine According to the steps described in 2.5 of embodiment 2, 2-bromo-1-(2-methoxymethoxy-5-methyl-phenyl)-1-phenyl-ethylene and N-methylpyrrolidine are used as the raw materials to produce the light brown oily coarse product which can be used in the next step directly, with a yield of 75%. LC-MS (m/z): 338.3 [M+H]⁺.

19.2 Synthesis of 2-[2-(2-hydroxy-5-methyl-phenyl)-phenethyl]-N-methylpyrrolidine (II-19)

According to the steps described in 2.6 of embodiment 2, 2-[2-(2-methoxymethoxy-5-methyl-phenyl)-styryl-]-N-methylpyrrolidine is used as the raw material to produce the white solid product II-19 by double-bond hydrogenation and deoxidization of protecting group with a yield of 45%. ¹H NMR shows that the product is a pair of diastereomers with II-19a/II-19b=3/1. LC-MS (m/z): 296.3 [M+H]⁺. ¹H NMR (400 MHz, CDCl₃), isomer II-19a, δ: 7.33-7.32 (m, 4H), 7.24-7.20 (m, 1H), 6.83 (dd, J=1.6, 8.0 Hz, 1H), 6.77 (d, J=8.0 Hz, 1H), 6.57 (d, J=1.6 Hz, 1H), 4.37 (dd, J=3.2, 7.2 Hz, 1H), 3.20-3.15 (m, 1H), 2.57-2.50 (m, 1H), 2.48-2.38 (m, 2H), 2.23 (s, 3H), 2.22-2.15 (m, 1H), 2.10 (s, 3H), 2.0-1.72 (m, 4H).

Isomer II-19b, δ: 7.32-7.31 (m, 4H), 7.25-7.20 (m, 1H), 6.84-6.78 (m, 2H), 6.53 (d, J=2.0 Hz, 1H), 4.45 (dd, J=4.4, 11.6 Hz, 1H), 3.25-3.21 (m, 1H), 2.54-2.48 (m, 1H), 2.45 (s, 3H), 2.48-2.38 (m, 1H), 2.33-2.29 (m, 1H), 2.10 (s, 3H), 2.0-1.50 (m, 5H).

19.3 Synthesis of 2-[2-(2-hydroxy-5-methyl-phenyl)-phenethyl]-N,N-dimethylpyrrolidine Bromide (I-19)

According to the steps described in 2.7 of embodiment 2, the isomer 1 of II-19a and bromomethane are used as the raw materials to produce the white solid target product I-19a with a yield of 95%. LC-MS (m/z): 310.2 [M+H]⁺. ¹H NMR (400 MHz, DMSO-d₆), δ: 9.29 (s, 1H), 7.39 (d, J=7.2 Hz, 2H), 7.32 (t, J=7.6 Hz, 2H), 7.21 (t, J=7.2 Hz, 1H), 7.04 (d, J=1.6 Hz, 1H), 6.81 (dd, J=1.6, 8.0 Hz, 1H), 6.67 (d, J 8.0 Hz, 1H), 4.26 (dd, J=2.8, 11.2 Hz, 1H), 3.57-3.53 (m, 1H), 3.47-3.39 (m, 1H), 3.17-3.09 (m, 1H), 3.06 (s, 3H), 2.88-2.83 (m, 4H), 2.25-2.18 (m, 1H), 2.16 (s, 3H), 2.02-1.84 (m, 4H).

Embodiment 20

2-[2-(2-hydroxy-5-ethyl-phenyl)-phenethyl]-N-methylpyrrolidine (II-20) and 2-[2-(2-hydroxy-5-ethyl-phenyl)-phenethyl]-N,N-dimethylpyrrolidine Bromide (I-20)

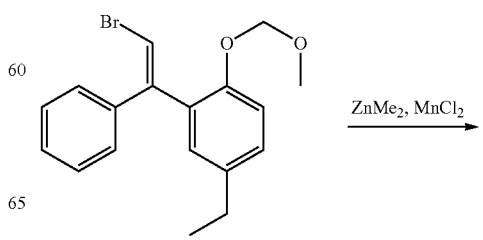

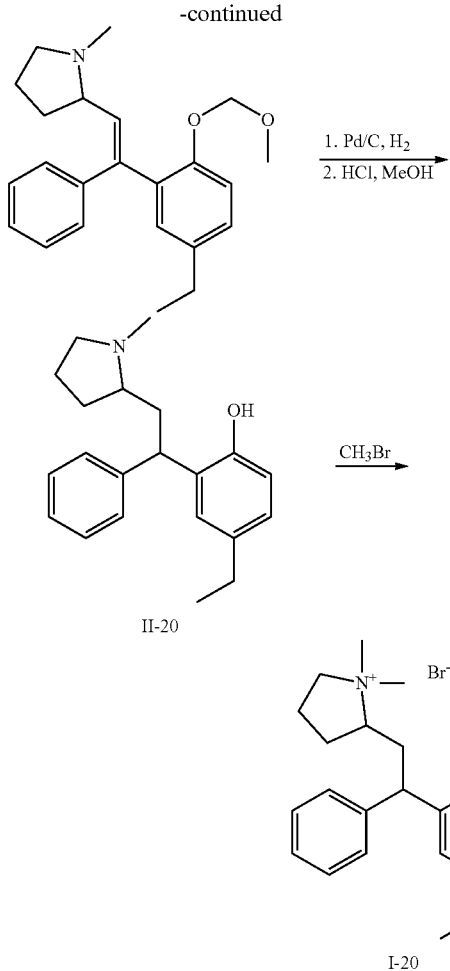

20.1 Synthesis of 2-[2-(2-methoxymethoxy-5-ethyl-phenyl)-styryl]-N-methylpyrrolidine According to the steps described in 2.5 of embodiment 2, 2-bromo-1-(2-methoxymethoxy-5-ethyl-phenyl)-1-phenyl-ethylene and N-methylpyrrolidine are used as the raw materials to produce the light brown oily coarse product which can be used in the next step directly, with a yield of 80%, LC-MS (m/z): 352.3 [M+H]$^+$.

20.2 Synthesis of 2-[2-(2-hydroxy-5-ethyl-phenyl)-phenethyl]-N-methylpyrrolidine (II-20)

According to the steps described in 2.6 of embodiment 2, 2-[2-(2-methoxymethoxy-5-ethyl-phenyl)-styryl-]-N-methylpyrrolidine is used as the raw material to produce the white solid target product II-20 by double-bond hydrogenation and deoxidization of protecting group with a yield of 32%. $^1$H NMR shows that the product is a pair of diastereomers with II-20a/II-20b-2/1. LC-MS (m/z): 310.3 [M+H]$^+$. $^1$H NMR (400 MHz, CDCl$_3$), isomer II-20a, δ: 11.16 (b, 1H), 7.33-7.31 (m, 4H), 7.24-7.21 (m, 1H), 6.86 (dd, J=2.0, 8.4 Hz, 1H), 6.78 (d, J=8.0 Hz, 1H), 6.58 (d, J=2.0 Hz, 1H), 4.36 (dd, J=4.8, 7.2 Hz, 1H), 3.16 (t, J=8.0 Hz, 1H), 2.53-2.49 (m, 1H), 2.46-2.37 (m, 4H), 2.23 (s, 3H), 2.24-2.15 (m, 1H), 1.98-1.74 (m, 4H), 1.05 (t, J=7.6 Hz, 3H).

Isomer II-20b, δ: 11.16 (b, 1H), 7.33-7.29 (m, 4H), 7.24-7.18 (m, 1H), 6.88-6.84 (m, 1H), 6.81 (d, J=8.4 Hz, 1H), 6.55 (d, J=2.0 Hz, 1H), 4.46 (dd, J=4.4, 7.2 Hz, 1H), 3.25-3.19 (m, 1H), 2.54-2.48 (m, 1H), 2.45 (s, 3H), 2.43-2.36 (m, 3H), 2.32-2.24 (m, 2H), 2.22 (s, 3H), 2.21-2.14 (m, 1H), 1.62-1.55 (m, 3H), 1.04 (t, J=7.6 Hz, 3H).

20.3 Synthesis of 2-[2-(2-hydroxy-5-ethyl-phenyl)-phenethyl]-N,N-dimethylpyrrolidine Bromide (I-20)

According to the steps described in 2.7 of embodiment 2, II-20 and bromomethane are used as the raw materials to produce the white solid target product I-20 with a yield of 96%. LC-MS (m/z): 323.3 [M+H]$^+$. $^1$H NMR (400 MHz, Acetone-d$_6$), isomer I-20a, δ: 7.40-7.27 (m, 4H), 7.25-7.17 (m, 1H), 7.14 (d, J=2.0 Hz, 1H), 7.04 (s, 1H), 6.88 (dd, J=2.4, 8.4 Hz, 1H), 6.78 (d, J=8.4 Hz, 1H), 4.31 (dd, J=4.8, 10.8 Hz, 1H), 3.56-3.49 (m, 1H), 3.34-3.14 (m, 2H), 2.98 (s, 3H), 2.82 (s, 3H), 2.77-2.70 (m, 1H), 2.53 (m, 2H), 2.35-2.25 (m, 1H), 2.13-2.08 (m, 1H), 2.06-1.99 (m, 2H), 1.91-1.82 (m, 1H), 1.14 (t, J=7.6 Hz, 3H).

Isomer I-20b, δ: 7.40-7.27 (m, 4H), 7.25-7.17 (m, 1H), 7.12 (d, J=2.0 Hz, 1H), 7.10 (s, 1H), 6.94 (dd, J=2.4, 8.4 Hz, 1H), 6.83 (d, J=8.4 Hz, 1H), 4.36 (dd, J=4.8, 12.0 Hz, 1H), 3.56-3.49 (m, 1H), 3.34-3.14 (m, 2H), 3.01 (s, 3H), 2.90-2.87 (m, 1H), 2.82 (s, 3H), 2.53 (m, 2H), 2.35-2.25 (m, 1H), 2.13-2.08 (m, 1H), 2.06-1.99 (m, 2H), 1.91-1.82 (m, 1H), 1.15 (t, J=7.6 Hz, 3H).

Embodiment 21

2-[2-(2-thienyl)-phenethyl]-N-methylpiperidine (II-21)

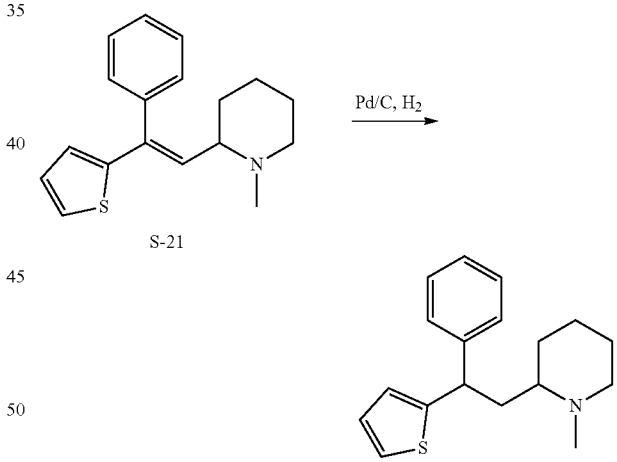

21.1 Synthesis of 2-[2-(2-thienyl)-phenethyl]-N-methylpiperidine (II-21)

According to the reaction described in embodiment 2, phenyl-2-thienyl-methanone is used as the raw material to produce S-21.

According to the steps described in 2.6 of embodiment 2, 2-[2-(2-thienyl)-styryl]-N-methylpiperidine is used as the raw material and stirred to react at 40° C. for 24 h under 4 Mpa of hydrogen pressure to obtain the yellow brown oily target product II-21. LC-MS (m/z): 285.3 [M+H]$^+$. $^1$H NMR (400 MHz, CDCl$_3$), δ: 7.24-7.15 (m, 5H), 7.04 (d, J=5.2, 1H), 6.81-6.79 (m, 1H), 6.48 (d, J=3.2 Hz, 1H), 3.98-3.93 (m, 1H), 2.74-2.70 (m, 1H), 2.38-2.19 (m, 4H), 1.91-1.86 (m, 1H), 1.87-1.76 (m, 2H), 1.72-1.65 (m, 1H), 1.60-1.55 (m, 1H), 1.50-1.43 (m, 2H), 1.25-1.16 (m, 2H).

Embodiment 22

2-[2-(3-thienyl)-2-(2-hydroxy-5-methyl-phenyl)-ethyl]-N-methylpiperidine (II-22) and 2-[2-(3-thienyl)-2-(2-hydroxy-5-methyl-phenyl)-ethyl]-N,N-dimethylpiperidine Bromide (I-22)

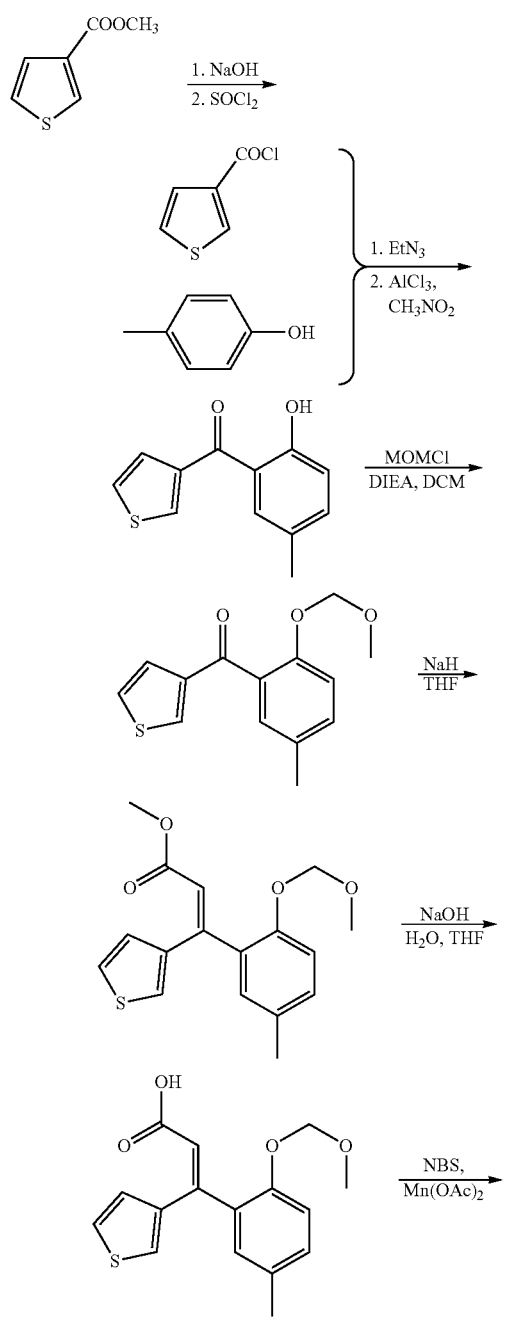

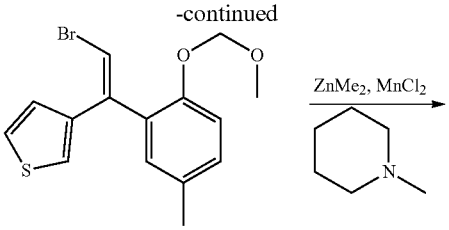
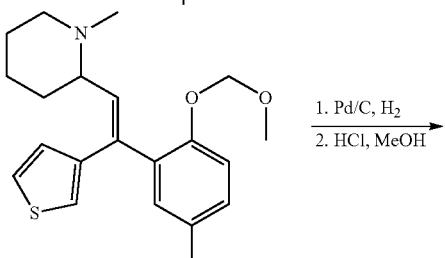
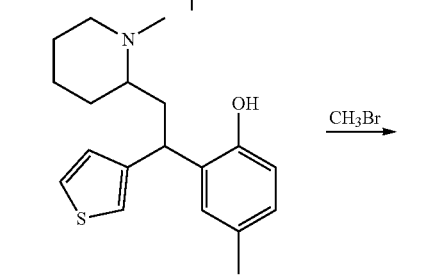

22.1 Synthesis of 3-thiophenecarbonyl Chloride 3-thiophenecarboxylate (1.42 g, 10 mmol) is dissolved in 30 ml of THF, aqueous solution (10 ml) of NaOH (0.8 g, 20 mmol) is added and the above materials are stirred to react at 60° C. TLC is used for monitoring; after the reaction is completed, the materials are cooled to room temperature, adjusted to acidity with 2 M hydrochloric acid and extracted with ethyl acetate (3×30 ml). After being merged, the organic phase is washed with water and a saturated salt solution respectively, dried with anhydrous sodium sulfate, and desolvated by the rotary evaporator to obtain the coarse product of 3-thiophenecarbonyl chloride which can be used in the next step directly.

22.2 Synthesis of (3-thienyl)(2-hydroxy-5-methyl-phenyl)-methanone

According to the steps described in 4.1.1 of embodiment 4, 3-thiophenecarbonyl chloride (10 mmol) and benzoyl chloride (12 mmol) are used as the raw materials to produce the brown yellow solid pure product (3-thienyl)(2-hydroxy-5-methyl-phenyl)-methanone (The yield of both steps is 43%). $^1$H NMR (400 MHz, CDCl$_3$), δ: 11.73 (s, 1H), 7.95 (dd, J=1.2, 3.2 Hz, 1H), 7.61 (d, J=1.6 Hz, 1H), 7.54 (dd, J 1.2, 5.2 Hz, 1H), 7.45 (dd, J=3.2, 5.2 Hz, 1H), 7.35 (dd, J=2.0, 8.4 Hz, 1H), 7.00 (d, J=8.4 Hz, 1H), 2.33 (s, 3H).

22.3 Synthesis of (3-thienyl)(2-methoxymethoxy-5-methyl-phenyl)-methanone

According to the steps described in 2.1 of embodiment 2, (3-thienyl)(2-hydroxy-5-methyl-phenyl)-methanone is used as the raw material to produce the brown yellow solid product (3-thienyl)(2-methoxymethoxy-5-methyl-phenyl)-methanone (with a yield of 80%). $^1$H NMR (400 MHz, CDCl$_3$), δ: 7.95 (dd, J=1.2, 2.8 Hz, 1H), 7.71 (d, J=1.6 Hz, 1H), 7.63 (dd, J=1.2, 4.8 Hz, 1H), 7.55 (dd, J=2.8, 5.2 Hz, 1H), 7.35 (dd, J=2.0, 8.4 Hz, 1H), 6.98 (d, J=8.4 Hz, 1H), 5.10 (s, 2H), 3.37 (s, 3H), 2.33 (s, 3H).

22.4 Synthesis of 3-(3-thienyl)-3-(2-methoxymethoxy-5-methyl-phenyl)-methyl Acrylate According to the steps described in 2.2 of embodiment 2, (3-thienyl)(2-methoxymethoxy-5-methyl-phenyl)-methanone is used as the raw material to produce the brown yellow oily product 3-(3-thienyl)-3-(2-methoxymethoxy-5-methyl-phenyl)-methyl acrylate with a yield of 68%. $^1$H NMR (400 MHz, CDCl$_3$), δ: 7.29-7.28 (m, 2H), 7.13-7.10 (m, 1H), 7.08-7.04 (m, 2H), 6.90 (d, J=3.6 Hz, 1H), 6.46 (d, J=3.6 Hz, 1H), 5.02 (s, 2H), 3.59 (s, 3H), 3.26 (s, 3H), 2.30 (s, 3H).

22.5 Synthesis of 3-(3-thienyl)-3-(2-methoxymethoxy-5-methyl-phenyl)-acrylic Acid According to the steps described in 2.3 of embodiment 2, 3-(3-thienyl)-3-(2-methoxymethoxy-5-methyl-phenyl)-methyl acrylate is used as the raw material to produce the brown solid product 3-(3-thienyl)-3-(2-methoxymethoxy-5-methyl-phenyl)-acrylic acid with a yield of 86%. $^1$H-NMR spectrum shows that the product is the mixture of E/Z isomer with E:Z=1.73:1. E-isomer: $^1$H NMR (400 MHz, CDCl$_3$), δ: 7.32-7.30 (m, 1H), 7.29-2.28 (m, 1H), 7.15-7.10 (m, 1H), 7.06-7.04 (m, 1H), 7.01-6.99 (m, 1H), 6.90 (s, 1H), 6.45 (d, J=3.6 Hz, 1H), 5.02 (s, 2H), 3.27 (s, 3H), 2.29 (s, 3H).
Z-isomer: $^1$H NMR (400 MHz, CDCl$_3$), δ: 7.32-7.30 (m, 1H), 7.29-2.28 (m, 1H), 7.15-7.10 (m, 1H), 7.06-7.04 (m, 1H), 7.01-6.99 (m, 1H), 6.90 (s, 1H), 6.05 (d, J=3.6 Hz, 1H), 4.90 (s, 2H), 3.22 (s, 3H), 2.29 (s, 3H).

22.6 Synthesis of 2-bromo-1-(3-thienyl)-1-(2-methoxymethoxy-5-methyl-phenyl)-ethylene According to the steps described in 2.4 of embodiment 2, 3-(3-thienyl)-3-(2-methoxymethoxy-5-methyl-phenyl)-acrylic acid is used as the raw material to produce the brown yellow oily product 2-bromo-1-(3-thienyl)-1-(2-methoxymethoxy-3-methyl-phenyl)ethylene with a yield of 41%. $^1$H NMR (400 MHz, CDCl$_3$), δ: 7.30-7.28 (m, 1H), 7.18-7.17 (m, 2H), 7.11 (d, J=8.4 Hz, 1H), 7.00-6.99 (m, 1H), 6.95 (s, 1H), 6.91-6.90 (m, 1H), 5.09 (s, 2H), 3.35 (s, 3H), 3.25 (s, 3H).

22.7 Synthesis of 2-[2-(3-thienyl)-2-(2-methoxymethoxy-5-methylphenyl)-vinyl]N-methylpiperidine According to the steps described in 2.5 of embodiment 2, 2-bromo-1-(3-thienyl)-1-(2-methoxymethoxy-5-methyl-phenyl)-ethylene is used as the raw material to produce the light brown oily product 2-[2-(3-thienyl)-2-(2-methoxymethoxy-5-methyl-phenyl)-vinyl]-N-methylpiperidine with a yield of 62%. LC-MS (m/z): 358.1 [M+H]$^+$. $^1$H NMR (400 MHz, CDCl$_3$): δ 7.27-7.24 (m, 1H), 7.09-7.07 (m, 2H), 7.03-7.01 (m, 1H), 6.93 (s, 1H), 6.67 (d, J=3.2 Hz, 1H), 6.08 (d, J=12.8 Hz, 1H), 5.06-5.01 (m, 2H), 3.31 (s, 3H), 2.94-2.85 (m, 2H), 2.49-2.43 (m, 1H), 2.33 (s, 3H), 2.32 (s, 3H), 1.75-1.70 (m, 2H), 1.63-1.58 (m, 3H), 1.56-1.49 (m, 1H).

22.8 Synthesis of 2-[2-(3-thienyl)-2-(2-hydroxy-5-methyl-phenyl)-ethyl]-N-methylpiperidine (II-22)

According to the steps described in 2.6 of embodiment 2, 2-[2-(3-thienyl)-2-(2-methoxymethoxy-5-methyl-phenyl)-vinyl]-N-methylpiperidine is used as the raw material to produce the white solid target product II-22 by double-bond hydrogenation and deoxidization of protecting group with a yield of 32%. LC-MS (m/z): 316.2 [M+H]$^+$. $^1$H NMR (400 MHz, CDCl$_3$), δ: 7.30-7.28 (m, 1H), 7.10-7.04 (m, 2H), 7.02-7.0 (m, 1H), 6.92 (s, 1H), 6.71 (d, J=3.2 Hz, 1H), 4.40-4.35 (m, 1H), 3.0-2.95 (m, 1H), 2.86-2.83 (m, 1H), 2.61-2.55 (m, 1H), 2.40 (s, 3H), 2.19-2.12 (m, 1H), 2.10 (s, 3H), 2.01-1.92 (m, 1H), 1.77-1.51 (m, 4H), 1.47-1.35 (m, 2H).

22.9 Synthesis of 2-[2-(3-thienyl)-2-(2-hydroxy-5-methyl-phenyl)-ethyl]-N,N-dimethylpiperidine Bromide (I-22)

According to the steps described in 2.7 of embodiment 2, II-22 and bromomethane are used as the raw materials to produce the brown solid target product I-22 with a yield of 96%. LC-MS (m/z): 330.3 [M+H]$^+$. $^1$H NMR (400 MHz, CD$_3$OD), δ: 7.25-7.24 (m, 1H), 7.16-7.11 (m, 2H), 7.08-7.05 (m, 1H), 6.89 (s, 1H), 6.85-6.82 (m, 1H), 4.29 (b, 1H), 3.64-3.60 (m, 1H), 3.39-3.35 (m, 1H), 3.24-3.20 (m, 1H), 2.94 (s, 3H), 2.91 (s, 3H), 2.83-2.80 (m, 1H), 2.29-2.24 (m, 1H), 2.12 (s, 3H), 2.07-2.01 (m, 1H), 1.95-1.73 (m, 4H), 1.43-1.35 (m, 1H).

Embodiment 23

2-[2-(2-isobutyryl ester group-5-methyl-phenyl)-phenethyl]-N-methylpiperidine (II-23) and 2-[2-(2-isobutyryl ester group-5-methyl-phenyl)-phenethyl]-N,N-dimethylpiperidine Bromide (I-23)

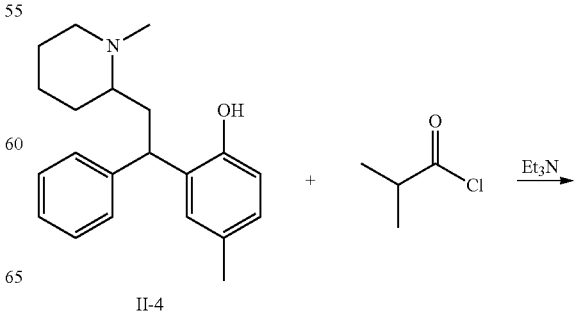

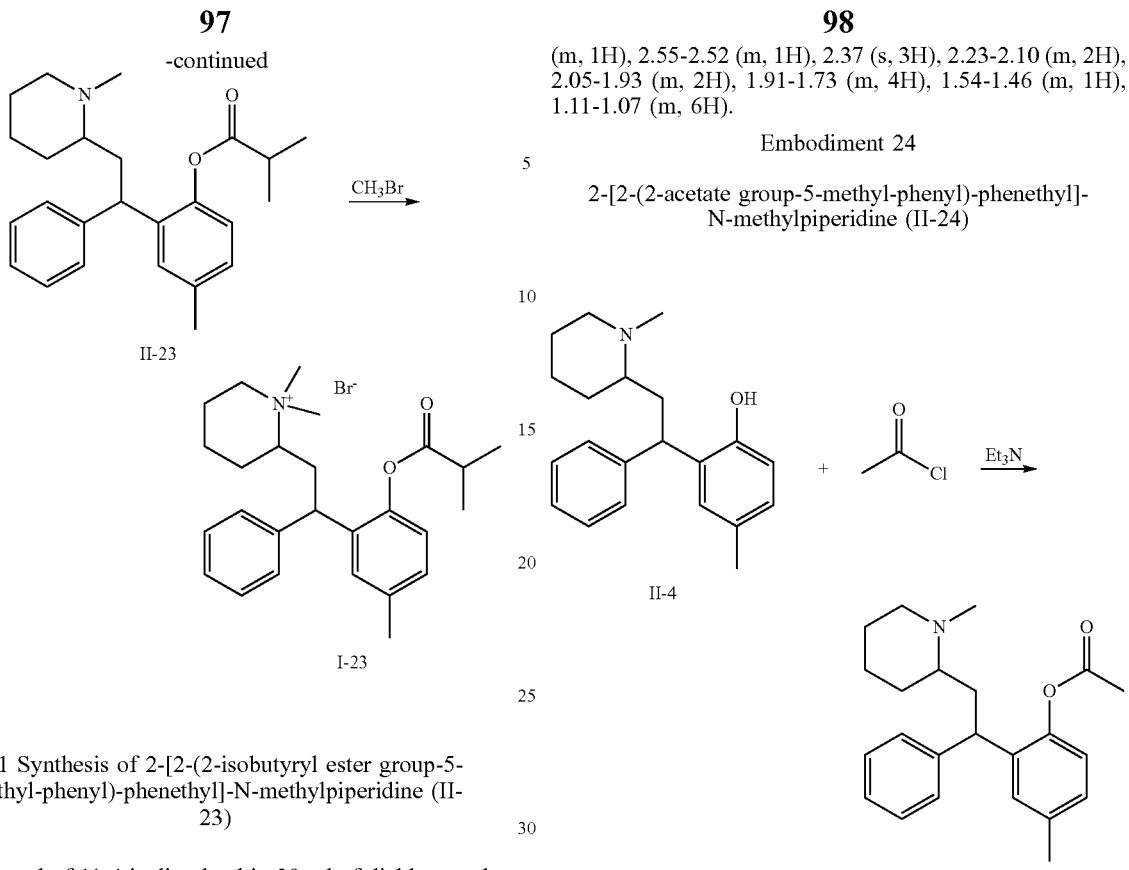

23.1 Synthesis of 2-[2-(2-isobutyryl ester group-5-methyl-phenyl)-phenethyl]-N-methylpiperidine (II-23)

1.0 mmol of 11-4 is dissolved in 20 ml of dichloromethane, and stirred at room temperature. 1.2 mmol of isobutyryl chloride and 2 mmol of triethylamine are added. The materials are stirred for reaction, and TLC is used for monitoring. After the reaction is finished, the materials are washed with water and neutralized to neutral with $NaHCO_3$. After being merged, the organic phase is dried with $Na_2SO_4$ and desolvated by decompressed pressure, and the residues are purified by silicon oxide column chromatography to obtain 285 mg of the brown solid target product II-23 with a yield of 75%.

LC-MS (m/z): 380.3 [M+H]$^+$. $^1$H NMR (400 MHz, $CDCl_3$), δ: 7.32-7.18 (m, 5H), 7.05 (b, 1H). 7.02-6.99 (m, 1H), 6.89 (d, J=8.0 Hz, 1H), 4.18 (dd, J=5.2, 10.4 Hz, 1H), 2.82-2.77 (m, 1H), 2.55-2.48 (m, 1H), 2.48-2.44 (m, 1H), 2.30 (s, 3H), 2.28 (s, 3H), 2.28-2.23 (m, 1H), 2.13-2.06 (m, 1H), 1.95-1.88 (m, 1H), 1.87-1.78 (m, 1H), 1.73-1.62 (m, 3H), 1.58-1.52 (m, 2H), 1.10-1.07 (m, 6H).

23.2 Synthesis of 2-[2-(2-isobutyryl ester group-5-methyl-phenyl)-phenethyl]-N,N-dimethylpiperidine Bromide (I-23)

0.1 mmol of II-23 is placed in a 25 ml round-bottom flask and dissolved by addition of 5 ml of dried THF. 0.5 mmol of bromomethane is dropped at room temperature and stirred for reaction, and TLC is used for monitoring. After the reaction is completed, a large number of solid products are separated out, desolvated by suction filtration, and washed by a little of THF to produce the brown solid target product 1-23 with a yield of 95%. LC-MS (m/z): 394.3 [M+H]$^+$. $^1$H NMR (400 MHz, $CDCl_3$), δ: 7.42 (b, 1H), 7.38-7.35 (m, 4H), 7.29-7.25 (m, 1H), 7.11-7.08 (m, 1H), 6.90-6.87 (d, J=8.0 Hz, 1H), 4.30 (dd, J=4.0, 8.4 Hz, 1H), 3.50-3.45 (m, 1H), 3.30-3.26 (m, 1H), 3.04 (s, 3H), 2.99 (s, 3H), 2.96-2.89 (m, 1H), 2.55-2.52 (m, 1H), 2.37 (s, 3H), 2.23-2.10 (m, 2H), 2.05-1.93 (m, 2H), 1.91-1.73 (m, 4H), 1.54-1.46 (m, 1H), 1.11-1.07 (m, 6H).

Embodiment 24

2-[2-(2-acetate group-5-methyl-phenyl)-phenethyl]-N-methylpiperidine (II-24)

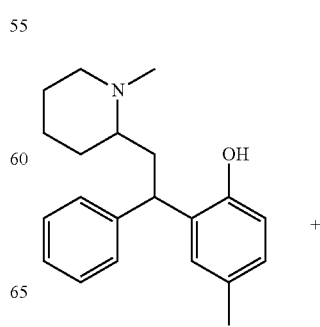

24.1 Synthesis of 2-[2-(2-acetate group-5-methyl-phenyl)-phenethyl]-N-methylpiperidine (II-24)

According to the steps described in 23.1 of embodiment 23, II-4 and acetyl chloride are used as the raw materials to produce the brown solid target product II-24 with a yield of 72%. LC-MS (m/z): 352.3 [M+H]$^+$. $^1$H NMR (400 MHz, $CDCl_3$), δ: 7.34-7.28 (m, 2H), 7.26-7.19 (m, 3H), 7.06 (b, 1H), 7.03-7.0 (m, 1H), 6.91-6.89 (m, 1H), 4.20 (dd, J=5.2, 10.4 Hz, 1H), 2.82-2.77 (m, 1H), 2.55-2.48 (m, 1H), 2.31 (s, 3H), 2.29 (s, 3H), 2.28 (s, 3H), 2.13-2.07 (m, 1H), 1.95-1.88 (m, 1H), 1.87-1.74 (m, 2H), 1.72-1.65 (m, 1H), 1.59-1.52 (m, 2H), 1.32-1.18 (m, 2H).

Embodiment 25

2-[2-(2-benzoate Group-5-methyl-phenyl)-phenethyl]-N-methylpiperidine (II-25) and 2-[2-(2-benzoate Group-5-methyl-phenyl)-phenethyl]-N,N-dimethylpiperidine Bromide (I-25)

99

-continued

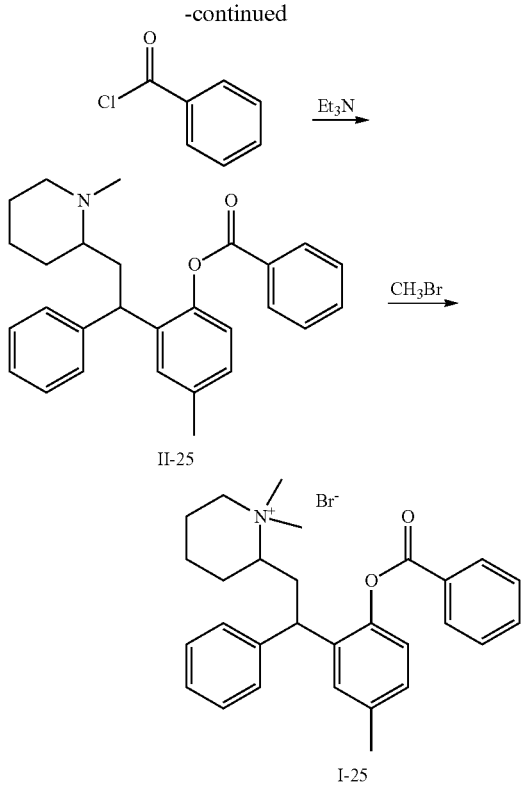

25.1 Synthesis of 2-[2-(2-benzoate group-5-methyl-phenyl)-phenethyl]-N-methylpiperidine (II-25)

According to the steps described in 23.1 of embodiment 23, II-4 and benzoyl chloride are used as the raw materials to produce the brown solid target product II-25 with a yield of 70%. LC-MS (m/z): 414.3 [M+H]$^+$. $^1$H NMR (400 MHz, CDCl$_3$), δ: 8.22 (d, J=7.6 Hz, 2H), 7.70 (t, J=6.8 Hz, 1H), 7.58 (t, J=7.6 Hz, 2H), 7.39-7.21 (m, 1H), 7.21-7.07 (m, 3H), 7.0 (d, J=8.0 Hz, 1H), 4.12 (dd, J=4.8, 10.8 Hz, 1H), 3.43-3.38 (m, 1H), 3.22-3.05 (m, 1H), 2.97-2.78 (m, 1H), 2.66-2.49 (m, 2H), 2.62 (s, 3H), 2.35 (s, 3H), 2.23-2.08 (m, 1H), 2.20-1.86 (m, 2H), 1.85-1.65 (m, 2H), 1.62-1.42 (m, 1H).

25.2 Synthesis of 2-[2-(2-benzoate group-5-methyl-phenyl)-phenethyl]-N,N-dimethylpiperidine Bromide (I-25)

According to the steps described in 23.2 of embodiment 23, II-25 and bromomethane are used as the raw materials to produce the brown solid target product 1-25 with a yield of 95%. LC-MS (m/z): 428.3 [M+H]$^+$. $^1$H NMR (400 MHz, CD$_3$OD), δ: 8.23-8.19 (m, 2H), 7.77 (t, J=7.6 Hz, 1H), 7.63 (t, J=7.6 Hz, 2H), 7.35-7.25 (m, 6H), 7.17 (d, J=8.4 Hz, 1H), 7.05-7.01 (m, 1H), 4.22 (m, 1H), 3.45-3.38 (m, 1H), 3.28-3.20 (m, 1H), 2.96 (s, 3H), 2.94 (s, 3H), 2.62 (s, 3H), 2.11-2.0 (m, 2H), 1.84-1.65 (m, 1H), 1.40-1.30 (m, 3H).

100

Embodiment 26

2-[2-(2-methyl p-toluenesulfonate group-5-methyl-phenyl)-phenethyl]-N-methylpiperidine (II-26) and 2-[2-(2-methyl p-toluenesulfonate group-5-methyl-phenyl)-phenethyl]-N,N-dimethylpiperidine Bromide (I-26)

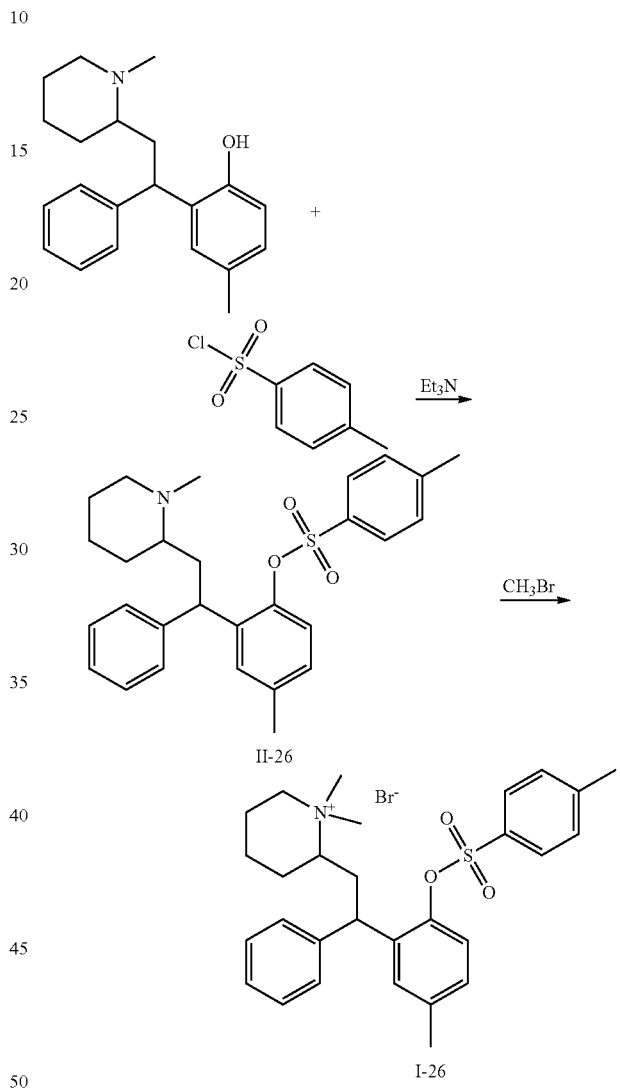

26.1 Synthesis of 2-[2-(2-methyl p-toluenesulfonate Group-5-methyl-phenyl)phenethyl]N-methylpiperidine (II-26)

According to the steps described in 23.1 of embodiment 23, II-4 and p-toluenesulfonyl chloride are used as the raw materials to produce the brown solid target product II-26 with a yield of 57%. LC-MS (m/z): 464.3 [M+H]$^+$. $^1$H NMR (400 MHz, CDCl$_3$), δ: 7.85 (d, J=8.4 Hz, 2H), 7.42 (d, J=8.4 Hz, 2H), 7.38-7.21 (m, 4H), 7.21-7.07 (m, 3H), 6.90-6.87 (m, 1H), 4.13 (dd, J=4.8, 11.2 Hz, 1H), 3.43-3.37 (m, 1H), 3.21-3.06 (m, 1H), 2.97 (s, 3H), 2.96-2.78 (m, 4H), 2.66-2.48 (m, 2H), 2.45 (s, 3H), 2.22-2.08 (m, 1H), 2.20-1.85 (m, 2H), 1.85-1.64 (m, 2H), 1.62-1.40 (m, 1H).

26.2 Synthesis of 2-[2-(2-benzoate group-5-methyl-phenyl)-phenethyl]-N,N-dimethylpiperidine Bromide (I-26)

According to the steps described in 23.2 of embodiment 23, II-26 and bromomethane are used as the raw materials to produce the brown solid target product 1-26 with a yield of 91%, LC-MS (m/z): 476.3 [M+H]$^+$. $^1$H NMR (400 MHz, CDCl$_3$), δ: 7.82-7.78 (m, 2H), 7.35-7.32 (m, 2H), 7.28-7.15 (m, 4H), 7.12 (m, 1H), 6.96-6.87 (m, 2H), 6.73-6.69 (m, 1H), 4.28-4.24 (m, 1H), 3.40-3.36 (m, 1H), 3.28-3.21 (m, 1H), 2.98 (s, 3H), 2.96 (s, 3H), 2.47 (s, 3H), 2.32 (s, 3H), 2.12-2.03 (m, 2H), 1.84-1.75 (m, 2H), 1.75-1.60 (m, 3H), 1.39-1.29 (m, 2H).

Embodiment of Activity Test:

The present invention relates to the antagonistic activity of the compound against the muscarinic receptor, which is primarily assessed by a cell-level dynamic mass redistribution (DMR) assay method. All tests are carried out on Epic platform, wherein the target model of the muscarinic receptor M1 is the CHO-K1 ceil model stably transfecting the M1 receptor, the target model of M3 is the HT-29 cell model endogenously highly expressing the M3 receptor, and the selected probe molecule is acetylcholine. Tire probe molecule acetylcholine is dissolved in water, while all other compounds are dissolved in DMSO.

Embodiment 1 of activity test: The CHO-K1 cell model stably transfecting the M1 receptor is used to preliminarily evaluate the antagonistic effect of some compounds of the present invention on the M1 receptor subtype of the muscarine in vitro.

Experimental scheme 1: Firstly, CHO-K1-M1 cells at the logarithmic growth stage are inoculated in a biocompatible 384-orifice plate at a density of 15,000 units/orifice, and each orifice has an inoculation volume of 40 μL. The inoculated cell plate is placed in a cell incubator for culture for 12 h until the cell growth and fusion degree reaches about 95%, and the activity assay is carried out. The culture medium is sucked from the cultured ceils, the buffer salt specified by the test is added with a volume of 30 μL per orifice and is stabilized for 1 h. After the baseline is stable, a 2-min baseline is established, and different concentrations of compounds to be tested are added to test the cultured cells for 1 h. After the cells are pretreated with the compounds to be tested for 1 h, the 2-min baseline is re-established, and acetylcholine having a concentration of 1 μM is added to test the cultured cells for 1 h. If the compounds do not produce DMR signal and reduce the DMR response signal of acetylcholine in a dose-dependent manner, it indicates that the compounds have an antagonistic effect on the receptor. The time point used to calculate IC$_{50}$ values is the point where the DMR response signal is maximum (5 min).

Experimental result 1: After the activity assay is completed, it is found that the DMR characteristic spectra of the test compound s in the present invention is consistent, wherein the DMR signal of the compound II-5, the influence of the compound on the DMR response signal of acetylcholine and tire corresponding dose curve are shown in FIG. 1. As shown in FIG. 1, the DMR response signal of the compound II-5 is almost zero, can antagonize the DMR response signal of acetylcholine in a dose-dependent manner and has a S-shaped dose response signal curve, indicating that all the compounds tested in the present invention have antagonistic effects on the M1 receptor subtype of the muscarine. See table 2 for the IC$_{50}$ values corresponding to the test compounds. According to the structures and IC$_{50}$ values of compounds, the following structure-activity relationship between this kind of compound and the M1 receptor is found: when the compound II-1 (3130±2 40 nM) becomes II-2 (29.2±6.5 nM) by introducing hydroxy into the ortho position of phenyl of the compound II-1 (3130±240 nM), the antagonistic activity is increased by more than 100 times; and when the compound II-1 (3130±240 nM) becomes II-3 (43.4±10.6 nM) by introducing dihydroxy into the ortho position of phenyl of the compound II-1 (3130±240 nM), the antagonistic activity is increased by more than 70 times. Therefore, the introduction of hydroxy on phenyl significantly increases the antagonistic activity of the compound against the M1 receptor. For most other compounds, the effect is consistent. When II-2 (29.2±6.5 nM) becomes II-4 (11.7±1.6 nM) or II-5 (9.4±1.3 nM) by introducing methyl or ethyl into the cytoskeletal structure of II-2 (29.2±6.5 nM), the activity is further increased by about 4 times; and when II-2 (29.2±6.5 nM) becomes II-6 (73.2±12.5 nM) by introducing propyl into the cytoskeletal structure of II-2 (29.2±6.5 nM), the activity is decreased. Therefore, the introduction of methyl or ethyl is beneficial to improve the antagonistic activity against the M1 receptor, while the introduction of propyl will result in the decrease of activity. When atom F (II-7: 320±20 nM; II-8: 350±30 nM) and atom Cl (II-14: 129.2±29.8) are introduced into the structure of II-4 (11.7±1.6 nM), methyl becomes methoxyl or hydroxy (II-9: 73.2±12.5 nM; II-11: 120.4±35.8) and N-methyl becomes N-ethyl (II-18: 295.8±62.9 nM), the activity is decreased; when phenyl becomes sulfur heterocyclic ring, the activity of the compound II-22 (9.7±0.6 nM) remains basically unchanged; and when hydroxy in the structure is esterified into prodrugs (II-23, II-24, II-25 and II-26), the activity is greatly decreased, but II-4 with high activity may be released after hydrolysis by esterase in vivo. When nitrogenous six-membered ring (II-4: 11.7±1.6 nM; II-5: 9.4±1.3 nM) becomes nitrogenous five-membered ring (II-19: 74.5±6 nM; II-20: 63±7.5 nM), the activity is decreased by 5 times. When the compound reacts with bromomethane or iodomethane to generate quaternary ammonium, salts (I-2-10-Br, I-14-Br, I-15-Br, I-19-Br, I-20-Br and I-22-26-Br), the antagonistic activity of the compound against M1 is affected in different ways, but the higher activity is maintained; and when the compound reacts with hydrochloric acid, bromic acid or glacial acetic acid to generate salts (I-2-Cl, I-3-Cl, I-4-Cl, I-5-Cl, I-4-HBr and I-5-Ac), the antagonistic activity of the compounds against M1 is decreased. In the compounds determined by the present invention, the antagonistic activity of II-5 against the M1 receptor of the muscarine is the highest.

Embodiment 2 of activity test: The HT-29 ceil model endogenously highly expressing the M3 receptor is used to preliminarily evaluate the antagonistic effect of some compounds of the present invention on the M3 receptor subtype of the muscarine in vitro.

Experimental scheme 2: Firstly, HT-29 cells at the logarithmic growth stage are inoculated in a biocompatible 384-orifice plate at a density of 32,000 units/orifice, and each orifice has an inoculation volume of 40 μL. The inoculated cell plate is placed in a cell incubator for culture for 20 h until the cell growth and fusion degree reaches about 95%, and the activity assay is carried out. The culture medium is sucked from the cultured cells, the buffer salt specified by the test is added with a volume of 30 μL per orifice and is stabilized for 1 h. After the baseline is stable, a 2-min baseline is established, and different concentrations of compounds to be tested are added to test the cultured cells for 1 h. After the cells are pretreated, with the compounds to be tested for 1 h, the 2-min baseline is re-established, and acetylcholine having a concentration of 16 µM is added to test the cultured cells for 1 h. If the compounds do not produce DMR signal and reduce the DMR response signal of acetylcholine in a dose-dependent manner, it indicates that the compounds have an antagonistic effect on the receptor. The time point used to calculate $IC_{50}$ values is the point where the DMR response signal is maximum (30 min).

Figure 2:
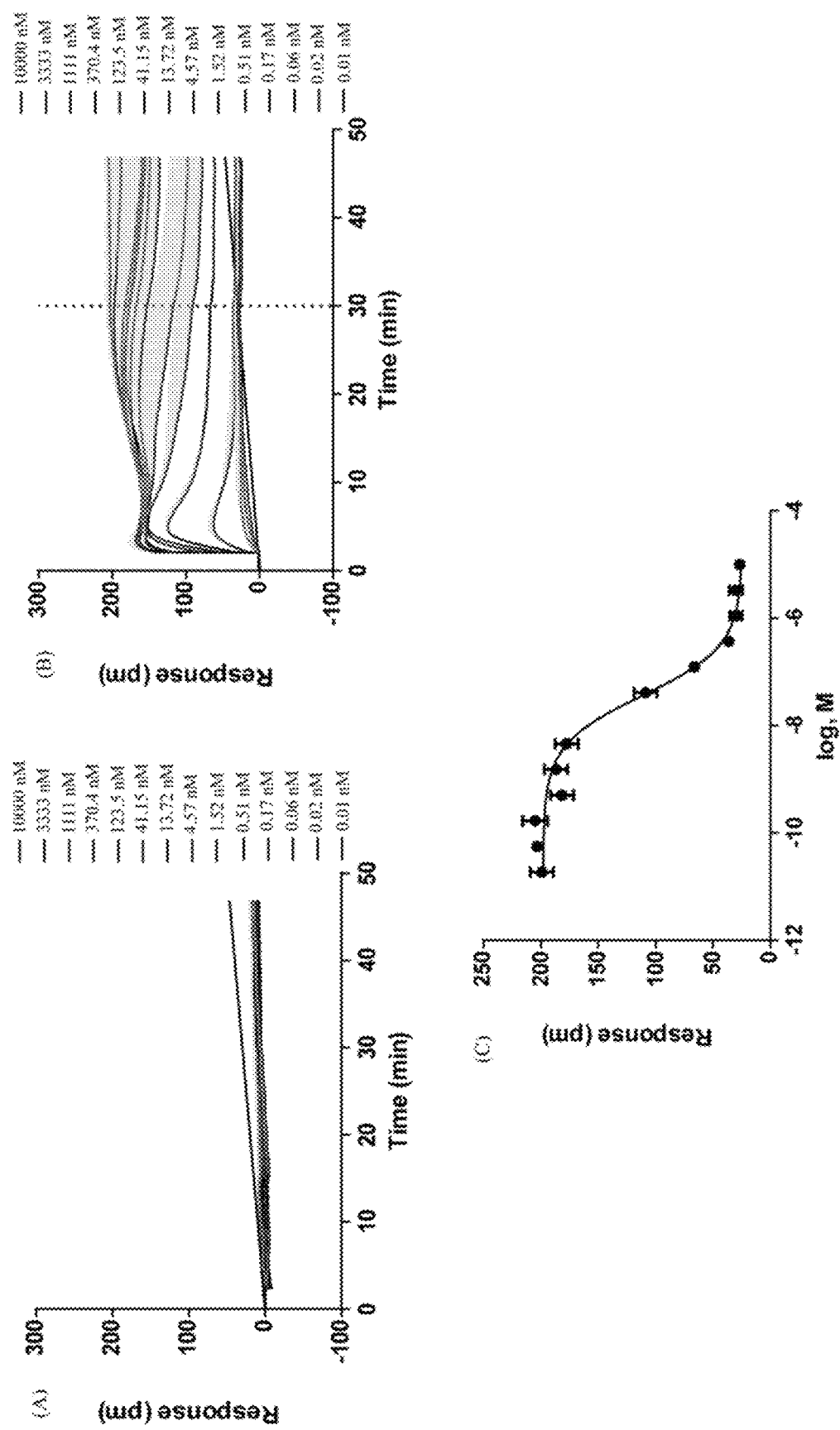
FIG. 2 shows the DMR signal of compound II-2 on HT-29 cells (A), the effect of the compound on DMR response signal of acetylcholine (B) and the corresponding dose curves (C).

Experimental result 2: After the activity assay is completed, it is found that the DMR characteristic spectra of the test compounds in the present invention is consistent, wherein the DMR signal of the compound II-2, the influence of the compound on the DMR response signal of acetylcholine and the corresponding dose curve are shown in FIG. 2. As shown in FIG. 2, the DMR response signal of the compound II-2, is almost zero, can antagonize the DMR response signal of acetylcholine in a dose-dependent manner and has a S-shaped dose response signal curve, indicating that all the compounds tested in the present invention have antagonistic effects on the M3 receptor subtype of the muscarine. See table 2 for the $IC_{50}$ values corresponding to the test compounds. According to the structures and $IC_{50}$ values of compounds, the following structure-activity relationship between this kind of compound and the M3 receptor is found: when the compound II-1 (>10000 nM) becomes the compound II-2 (36.5±5 nM) by introducing hydroxy into the ortho position of phenyl of the compound II-1 (>10000 nM), the antagonistic activity against the M3 receptor is greatly increased; and when the compound II-1 (>10000 nM) becomes II-3 (13.1±1.9 nM) by introducing dihydroxy into the ortho position of phenyl of the compound II-1 (>10000 nM), the antagonistic activity against the M3 receptor is increased continuously. Therefore, the introduction of hydroxy in this kind of compound structure is beneficial to improve the antagonistic activity against the M3 receptor. When II-2 (36.5±5 nM) becomes II-4 (40.7±10.6 nM) by introducing methyl into phenyl of II-2 (36.5±5 nM), the activity remains basically unchanged; and when ethyl (II-5: 108.6±9 nM) and propyl (II-6: 110.3±13.9 nM) are introduced into phenyl of II-2 (36.5±5 nM), the activity is decreased. When atom F is (II-8: 150±10 nM; II-10: 49.3 nM) introduced into the meta-position and para position of II-2 phenolic hydroxyl group, the antagonistic activity against the M3 receptor is decreased. When atom F (II-7: 210±30 nM), methyl or ethyl (II-15: 212±20 nM; II-16: 371±67.8) are introduced into the benzene ring of II-4 (40.7±10.6 nM), or methyl is changed into methoxy, hydroxy or pentyloxy (II-9: 320.4±41.4 nM; II-11: 370.4±159.4; II-12: 920.4±49.4), the activity is decreased significantly; when N-methyl becomes N-ethyl (II-12: 238.9±33.2 nM), the activity is decreased by 6 times; when benzene ring becomes sulfur heterocyclic ring II-22 (20.7±3.6 nM), the activity is increased by 3 times; and when hydroxy in the structure is esterified into prodrugs (II-23, II-24, II-25 and II-26), the activity is greatly decreased. When nitrogenous six-membered ring (II-4: 40.7±10.6 nM; II-5: 108.6±9 nM) becomes nitrogenous five-membered ring (II-19: 137.4±22.9 nM; II-20: 258.2±30.4 nM), the activity is decreased. When the compound reacts with bromomethane or iodomethane to generate quaternary ammonium salts (I-2-10-Br, I-14-Br, I-15-Br, I-19-Br, I-20-Br and I-22-26-Br), the antagonistic activity of the compound against M3 is increased obviously, and some compounds are even as active as tiotropium bromide with the exception of I-4-PrOPh which shows a significant decrease in activity; and when the free alkali of the compound II (II-2-5) reacts with hydrochloric acid, hydrobromic acid or glacial acetic acid to generate salt, the antagonistic activity of the compounds (I-2-Cl, I-3-Cl, I-4-Cl, I-5-Cl, I-4-HBr and I-5-Ac) against M3 is decreased.

For the diastereomer compounds, the antagonistic activity of type a against the M3 receptor is generally higher than that of type b against the M3 receptor, for example, the antagonistic activity of II-4a (40.7±10.6 nM), I-4a-Br (35.5±13.9 nM) and I-10a (49.3±9.3 nM) against the M3 receptor are all higher than that of II-4b (119.7±35.9), I-4b-Br (47.7±11.9) and I-10B (109.4±39.4 nM) against the M3 receptor. In terms of the activity comparison of enantiomers, the activity of No. 1 isomers such as I-2a-1-Br (5.7±1.1 nM), I-3-1-Br (6.0±1.1 nM) and I-4a-1-Br (39.3±10.9 nM) are almost significantly higher than that of the corresponding No. 2 isomers such as I-2a-2-Br (28.4±6.1 nM), I-3-2-Br (11.0±3.6 nM) and I-4a-2-Br (1210±120.5 nM).

TABLE 2

Antagonistic Activity of Compounds Involved in the Present Invention against M1 and M3 Receptors ($IC_{50}$)

| Number | Structure | M1 Receptor $IC_{50}$ (nM) | M3 Receptor $IC_{50}$ (nM) |
| --- | --- | --- | --- |
| II-1 | 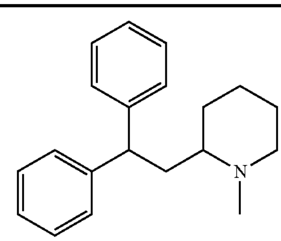 | 3130 ± 240 | >10000 |
| II-2a | 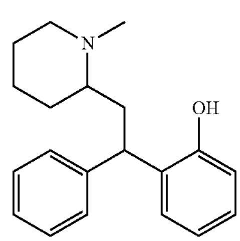 [SMILES: CN1CCCCC1CC(c1ccccc1)c1ccccc1O] | 29.2 ± 6.5 | 36.5 ± 5.0 |

TABLE 2-continued
Antagonistic Activity of Compounds Involved in the Present Invention against M1 and M3 Receptors (IC$_{50}$)
| Number | Structure | M1 Receptor IC$_{50}$ (nM) | M3 Receptor IC$_{50}$ (nM) |
| --- | --- | --- | --- |
| II-2a-1 | Chiral Monomer-1 | 22.4 ± 6.7 | 32.2 ± 2.9 |
| II-2a-2 | Chiral Monomer-2 | 38.8 ± 10.5 | 49.1 ± 6.6 |
| I-2a-Cl | 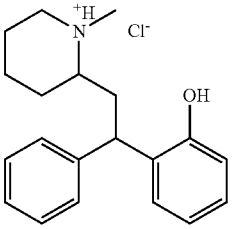 | 249.5 ± 176.1 | 74.6 ± 33.9 |
| I-2a-Br | 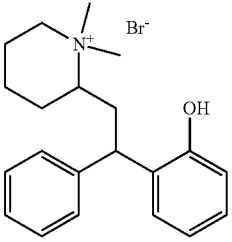 [SMILES: C[N+]1(C)CCCCC1CC(c1ccccc1)c1ccccc1O ; [Br-]] | 53.8 ± 4.6 | 33.8 ± 3.6 |
| I-2a-1-Br | Chiral Monomer-1 | 8.8 ± 2.6 | 5.7 ± 1.1 |
| I-2a-2-Br | Chiral Monomer-2 | 33.8 ± 8.6 | 28.4 ± 6.1 |
| I-2a-I | 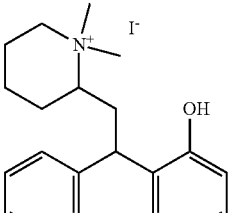 | 16.5 ± 1.8 | 25.6 ± 1.9 |
| II-3 | 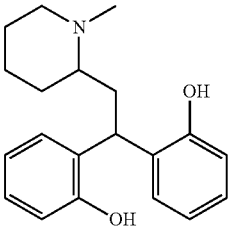 [SMILES: CN1CCCCC1CC(c1ccccc1O)c1ccccc1O]<br>Raceme | 43.4 ± 10.6 | 13.1 ± 1.9 |
| II-3-1 | Chiral Monomer-1 | 30.4 ± 12.6 | 15.4 ± 2.9 |
| II-3-2 | Chiral Monomer-2 | 53.4 ± 16.2 | 67.3 ± 6.6 |
| I-3-Cl | 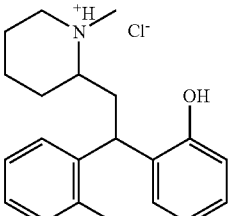 | 401.8 ± 185 | 66.2 ± 51.8 |

TABLE 2-continued

Antagonistic Activity of Compounds Involved in the Present Invention against M1 and M3 Receptors (IC$_{50}$)

| Number | Structure | M1 Receptor IC$_{50}$ (nM) | M3 Receptor IC$_{50}$ (nM) |
|---|---|---|---|
| I-3-Br | [structure] | 23.4 ± 6.6 | 15.4 ± 2.9 |
| I-3-1-Br | Chiral Monomer-1 | 18.5 ± 3.6 | 6.0 ± 1.1 |
| I-3-2-Br | Chiral Monomer-2 | 43.7 ± 15.3 | 11.0 ± 3.6 |
| I-3-I | [structure] | 63.5 ± 15.1 | 6.9 ± 1.3 |
| II-4a | [structure] Diastereomer a | 11.7 ± 1.6 | 40.7 ± 10.6 |
| II-4a-1 | Chiral Monomer-1 | 8.8 ± 0.6 | 53 ± 6.8 |
| II-4a-2 | Chiral Monomer-2 | 276.7 ± 45.9 | 1244.5 ± 472.6 |
| II-4b | [structure] Diastereomer b | 31.7 ± 11.6 | 119.7 ± 35.9 |
| II-4b-1 | Chiral Monomer-1 of Diastereomer b | 29.7 ± 7.5 | 57.7 ± 15.3 |
| II-4b-2 | Chiral Monomer-2 of Diastereomer b | 347.6 ± 11.9 | 871.2 ± 315.9 |

TABLE 2-continued

Antagonistic Activity of Compounds Involved in the Present Invention against M1 and M3 Receptors (IC$_{50}$)

| Number | Structure | M1 Receptor IC$_{50}$ (nM) | M3 Receptor IC$_{50}$ (nM) |
|---|---|---|---|
| I-4a-Cl | 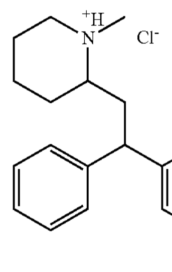 | 70.8 ± 9.2 | 290.4 ± 32.8 |
| I-4a-HBr | 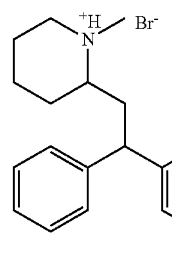 | 26.5 ± 2.5 | 151.4 ± 15.3 |
| I-4a-Br | Diastereomer a | 36.2 ± 6.1 | 35.5 ± 13.9 |
| I-4a-1-Br | Chiral Monomer-1 of Diastereomer a | 28.8 ± 11.3 | 39.3 ± 10.9 |
| I-4a-2-Br | Chiral Monomer-2 of Diastereomer a | 832 ± 131.6 | 1210 ± 120.5 |
| I-4b-Br | Diastereomer b | 61.0 ± 21.8 | 47.7 ± 11.9 |
| I-4b-1-Br | Chiral Monomer-1 of Diastereomer b | 47.5 ± 13.5 | 27.1 ± 5.3 |
| I-4B-2-Br | Chiral Monomer-2 of Diastereomer b | 156.6 ± 61.6 | 217.3 ± 37.9 |

TABLE 2-continued
Antagonistic Activity of Compounds Involved in the Present Invention against M1 and M3 Receptors ($IC_{50}$)
| Number | Structure | M1 Receptor $IC_{50}$ (nM) | M3 Receptor $IC_{50}$ (nM) |
|---|---|---|---|
| I-4a-I | 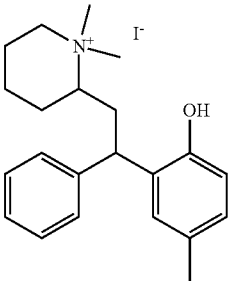 [SMILES: Cc1ccc(O)c(C(CC2CCCC[N+]2(C)C)c2ccccc2)c1 ; [I-]] | 13.8 ± 1.5 | 9.3 ± 1.0 |
| I-4a-PrOPh | 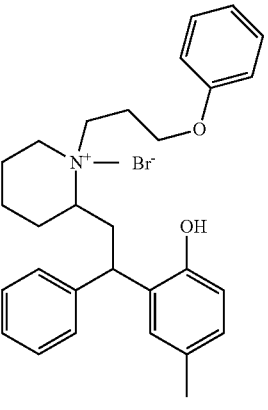 [SMILES: Cc1ccc(O)c(C(CC2CCCC[N+]2(C)CCCOc2ccccc2)c2ccccc2)c1 ; [Br-]] | 295.3 ± 136.0 | 278.7 ± 128.0 |
| II-5 | 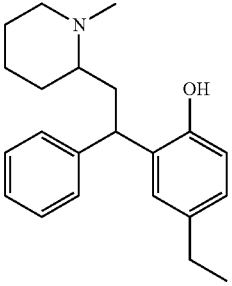 [SMILES: CCc1ccc(O)c(C(CC2CCCCN2C)c2ccccc2)c1] | 9.4 ± 1.3 | 108.6 ± 9.0 |
| I-5-Cl | 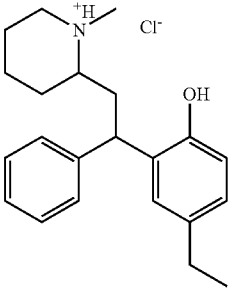 | 46.9 ± 3.3 | 274.8 ± 247.5 |

TABLE 2-continued
Antagonistic Activity of Compounds Involved in the Present Invention against M1 and M3 Receptors (IC$_{50}$)
| Number | Structure | M1 Receptor IC$_{50}$ (nM) | M3 Receptor IC$_{50}$ (nM) |
|---|---|---|---|
| I-5-HBr | 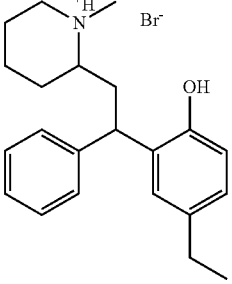 | 45.6 ± 7.8 | 10.5 ± 1.1 |
| I-5-Br | 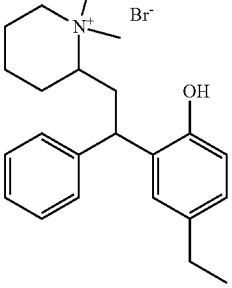 | 45.6 ± 7.8 | 10.5 ± 1.1 |
| I-5-I | 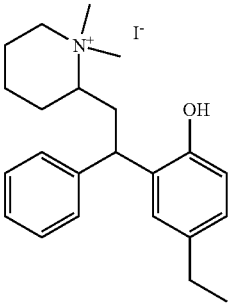 [SMILES: CCc1ccc(O)c(C(CC2CCCC[N+]2(C)C)c2ccccc2)c1 ; [I-]] | 20.0 ± 2.3 | 18.8 ± 2.3 |
| II-6 | 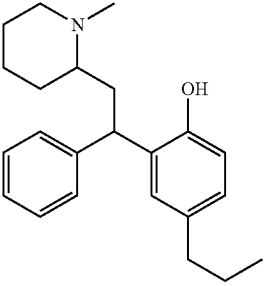 [SMILES: CCCc1ccc(O)c(C(CC2CCCCN2C)c2ccccc2)c1] | 73.2 ± 12.5 | 110.3 ± 13.9 |
| I-6 | 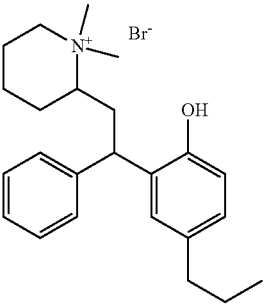 [SMILES: CCCc1ccc(O)c(C(CC2CCCC[N+]2(C)C)c2ccccc2)c1 ; [Br-]] | 133.2 ± 22.8 | 20.3 ± 3.6 |

TABLE 2-continued

Antagonistic Activity of Compounds Involved in the Present Invention against M1 and M3 Receptors ($IC_{50}$)

| Number | Structure | M1 Receptor $IC_{50}$ (nM) | M3 Receptor $IC_{50}$ (nM) |
|---|---|---|---|
| II-7 | 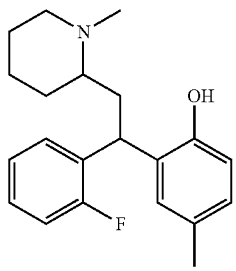 [SMILES: Cc1ccc(O)c(C(CC2CCCCN2C)c2ccccc2F)c1] | 230.0 ± 10.0 | 210.0 ± 30.0 |
| I-7 | 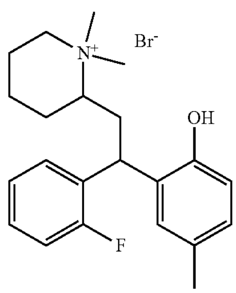 [SMILES: Cc1ccc(O)c(C(CC2CCCC[N+]2(C)C)c2ccccc2F)c1 ; [Br-]] | 320.0 ± 20.0 | 103.0 ± 10.0 |
| II-8 | 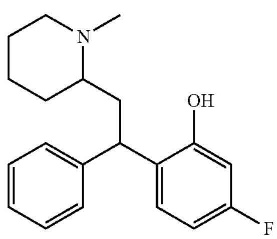 [SMILES: CN1CCCCC1CC(c1ccccc1)c1ccc(F)cc1O] | 42.0 ± 8.0 | 430.0 ± 70.0 |
| I-8 | 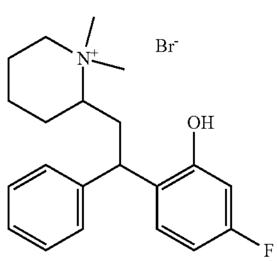 [SMILES: C[N+]1(C)CCCCC1CC(c1ccccc1)c1ccc(F)cc1O ; [Br-]] | 113.0 ± 41.2 | 97.2 ± 21.1 |
| II-9 | 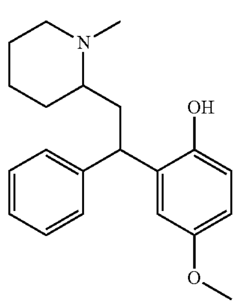 [SMILES: COc1ccc(O)c(C(CC2CCCCN2C)c2ccccc2)c1] | 73.2 ± 12.5 | 320.4 ± 41.4 |

TABLE 2-continued

Antagonistic Activity of Compounds Involved in the Present Invention against M1 and M3 Receptors ($IC_{50}$)

| Number | Structure | M1 Receptor $IC_{50}$ (nM) | M3 Receptor $IC_{50}$ (nM) |
|---|---|---|---|
| I-9 | 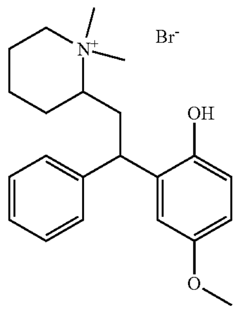 [SMILES: COc1ccc(O)c(C(CC2CCCC[N+]2(C)C)c2ccccc2)c1 ; [Br-]] | 100.3 ± 10.2 | 160.2 ± 20.3 |
| II-10a | Diastereomer a | 53.2 ± 12.5 | 49.3 ± 9.3 |
| II-10b | Diastereomer b | 83.2 ± 22.8 | 109.4 ± 39.4 |
| I-10a | Diastereomer a | 13.2 ± 1.2 | 11.7 ± 2.3 |
| I-10a-1 | Chiral Monomer-1 | — | 37.04 ± 4.3 |
| I-10a-2 | Chiral Monomer-2 | — | 82.91 ± 11.7 |

TABLE 2-continued

Antagonistic Activity of Compounds Involved in the Present Invention against M1 and M3 Receptors (IC$_{50}$)

| Number | Structure | M1 Receptor IC$_{50}$ (nM) | M3 Receptor IC$_{50}$ (nM) |
| --- | --- | --- | --- |
| I-10b | [structure] Diastereomer b | 23.2 ± 12.1 | 12.1 ± 5.3 |
| I-10b-1 | Chiral Monomer-1 | — | 35.2 ± 6.3 |
| I-10b-2 | Chiral Monomer-2 | — | 163.9 ± 12.6 |
| II-11 | [structure] | 190.4 ± 35.8 | 370.4 ± 159.4 |
| II-12 | [structure] | — | 620.4 ± 49.4 |
| II-13 | [structure] | — | 249.2 ± 9.8 |
| II-14 | [structure] | 129.2 ± 29.8 | 149.2 ± 39.5 |

TABLE 2-continued

Antagonistic Activity of Compounds Involved in the Present Invention against M1 and M3 Receptors (IC$_{50}$)

| Number | Structure | M1 Receptor IC$_{50}$ (nM) | M3 Receptor IC$_{50}$ (nM) |
|---|---|---|---|
| I-14 | 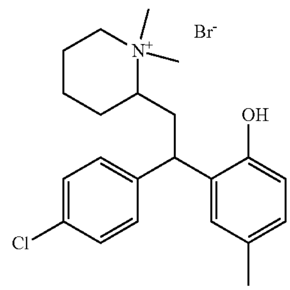 [SMILES: Cc1ccc(O)c(C(CC2CCCC[N+]2(C)C)c2ccc(Cl)cc2)c1 ; [Br-]] | 79.2 ± 36.9 | 87.2 ± 36.5 |
| II-15 | 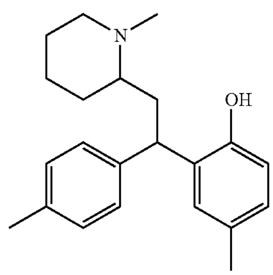 [SMILES: Cc1ccc(C(CC2CCCCN2C)c2cc(C)ccc2O)cc1] | 65.1 ± 11.7 | 112.3 ± 20.0 |
| I-15 | 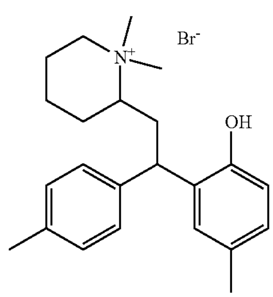 [SMILES: Cc1ccc(C(CC2CCCC[N+]2(C)C)c2cc(C)ccc2O)cc1 ; [Br-]] | 48.3 ± 11.0 | 78 ± 31.0 |
| II-16 | 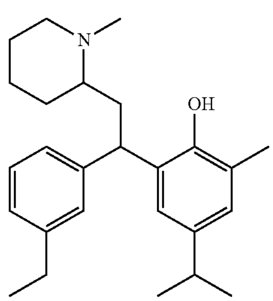 [SMILES: CCc1cccc(C(CC2CCCCN2C)c2cc(C(C)C)cc(C)c2O)c1] | — | 371 ± 67.8 |
| II-17 | 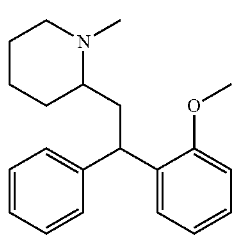 [SMILES: COc1ccccc1C(CC1CCCCN1C)c1ccccc1] | 6700.0 ± 810.0 | 3420.0 ± 330.0 |

TABLE 2-continued
Antagonistic Activity of Compounds Involved in the Present Invention against M1 and M3 Receptors (IC$_{50}$)
| Number | Structure | M1 Receptor IC$_{50}$ (nM) | M3 Receptor IC$_{50}$ (nM) |
|---|---|---|---|
| II-18 | 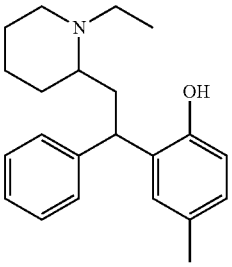 [SMILES: CCN1CCCCC1CC(c1ccccc1)c1cc(C)ccc1O] | 295.8 ± 62.9 | 238.9 ± 33.2 |
| II-19 | 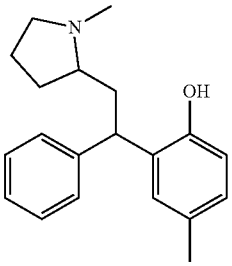 [SMILES: Cc1ccc(O)c(C(CC2CCCN2C)c2ccccc2)c1] | 74.5 ± 6.0 | 137.4 ± 22.9 |
| I-19 | 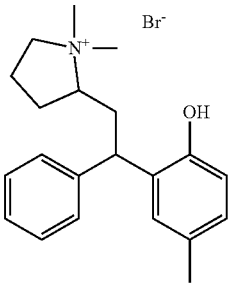 [SMILES: Cc1ccc(O)c(C(CC2CCC[N+]2(C)C)c2ccccc2)c1 ; [Br-]] | 41.0 ± 9.2 | 29.9 ± 4.7 |
| II-20 | 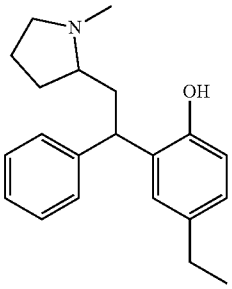 [SMILES: CCc1ccc(O)c(C(CC2CCCN2C)c2ccccc2)c1] | 63.0 ± 7.5 | 258.2 ± 30.4 |
| I-20 | 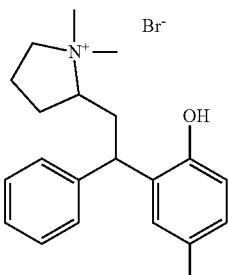 | 89.0 ± 7.3 | 53.2 ± 9.3 |

TABLE 2-continued

Antagonistic Activity of Compounds Involved in the Present Invention against M1 and M3 Receptors (IC$_{50}$)

| Number | Structure | M1 Receptor IC$_{50}$ (nM) | M3 Receptor IC$_{50}$ (nM) |
| --- | --- | --- | --- |
| II-21 | 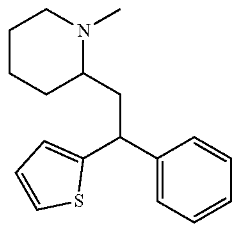 [SMILES: CN1CCCCC1CC(c1ccccc1)c1cccs1] | 3680.0 ± 810.0 | 2420.0 ± 330.0 |
| II-22 | 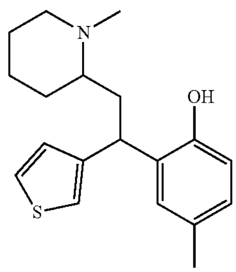 [SMILES: Cc1ccc(O)c(C(CC2CCCCN2C)c2ccsc2)c1] | 19.7 ± 0.6 | 20.7 ± 3.6 |
| I-22 | 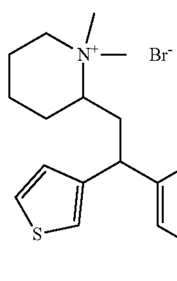 | 25.7 ± 0.8 | 10.7 ± 1.6 |
| II-23 | 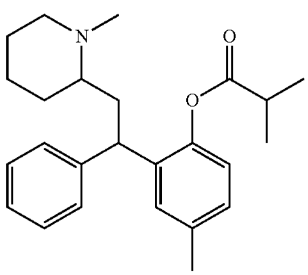 [SMILES: Cc1ccc(OC(=O)C(C)C)c(C(CC2CCCCN2C)c2ccccc2)c1] | 1900.0 ± 500.0 | 690.0 ± 160.0 |
| I-23 | 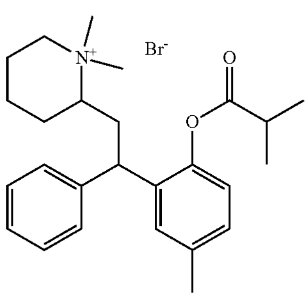 [SMILES: Cc1ccc(OC(=O)C(C)C)c(C(CC2CCCC[N+]2(C)C)c2ccccc2)c1 ; [Br-]] | 2530.0 ± 480.0 | 790.0 ± 75.0 |

TABLE 2-continued

Antagonistic Activity of Compounds Involved in the Present Invention against M1 and M3 Receptors ($IC_{50}$)

| Number | Structure | M1 Receptor $IC_{50}$ (nM) | M3 Receptor $IC_{50}$ (nM) |
|---|---|---|---|
| II-24 | 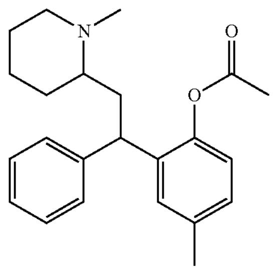 [SMILES: CC(=O)Oc1ccc(C)cc1C(CC1CCCCN1C)c1ccccc1] | 3340.0 ± 210.0 | 1210.0 ± 120.0 |
| II-25 | 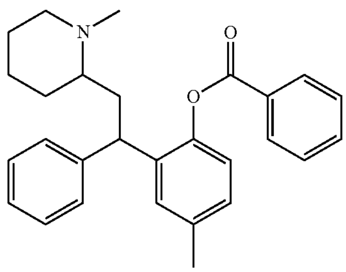 [SMILES: Cc1ccc(OC(=O)c2ccccc2)c(C(CC2CCCCN2C)c2ccccc2)c1] | 1600.0 ± 200.0 | 2970.0 ± 700.0 |
| I-25 | 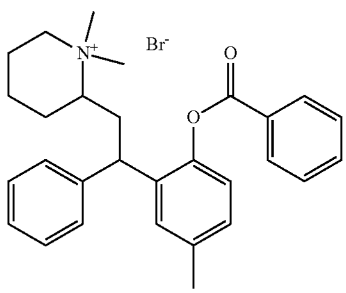 [SMILES: Cc1ccc(OC(=O)c2ccccc2)c(C(CC2CCCC[N+]2(C)C)c2ccccc2)c1 ; [Br-]] | 997.0 ± 60.0 | 2310.0 ± 600.0 |
| II-26 | 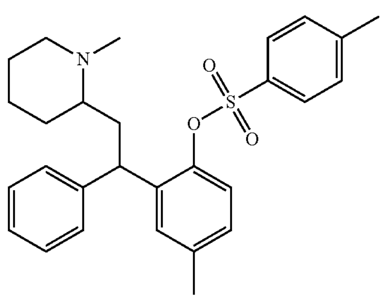 [SMILES: Cc1ccc(S(=O)(=O)Oc2ccc(C)cc2C(CC2CCCCN2C)c2ccccc2)cc1] | — | 2617.4 ± 425.3 |
| I-26 | 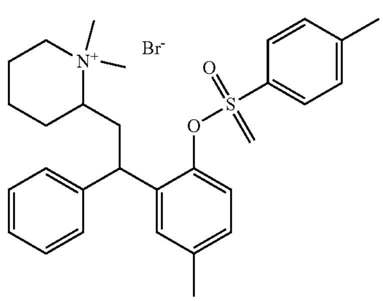 [SMILES: C=S(=O)(Oc1ccc(C)cc1C(CC1CCCC[N+]1(C)C)c1ccccc1)c1ccc(C)cc1 ; [Br-]] | — | 793.3 ± 69.7 |

TABLE 2-continued

Antagonistic Activity of Compounds Involved in the Present Invention against M1 and M3 Receptors ($IC_{50}$)

| Number | Structure | M1 Receptor $IC_{50}$ (nM) | M3 Receptor $IC_{50}$ (nM) |
|---|---|---|---|
| Tiotropium Bromide | 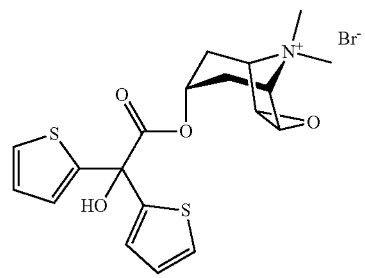 | — | 8.7 ± 0.8 |

Example of Activity Assay of Isolated Organs in Animals

1. Experimental Materials

Compositions of perfusate (mM): containing 135 of NaCl, 5.4 of KCl, 0.33 of $NaH_2PO_4$, 5 of HEPES, 1.7 of $MgCL_2.6H_2O$, 1.8 of $CaCl_2$ and 10 of glucose, and is adjusted to pH 7.3 with NaOH.

RM6240B/C (4-Channel) Multi-Channel Physiology Recorder (Chengdu Instrument Factory).

SQG-4J Four-Cavity Organ Bath System (Chengdu Instrument Factory).

2. Preparation of Tracheal Strip

The guinea pig is put to death by hammering it on the head, the chest cavity is quickly opened, and trachea is carefully isolated. The complete tracheal segment from the lower thyroid cartilage to the bifurcation of the trachea is cut out, and immersed in 4° C. perfusate with saturated oxygen (95% $O_2$, 5% $CO_2$). The connective tissue and fat around the trachea are gently removed, and the trachea segment is quickly suspended and cut into tracheal strips with a blade (2-3 mm in width and 20 mm in length). The tracheal strip is fixed with one suture line at each end and quickly moved to a constant temperature (37.2° C.) Magnus' bath containing 15 mL of perfusate, and 5% $CO_2$ and 95% $O_2$ are continuously injected. The upper end of the tracheal strip is connected to a muscle tension transducer, and the load is adjusted to 1.5 g. The biological signal processing system is used to record the changes in muscular tension of tracheal smooth muscle. The perfusate is replaced once every 15 min, and the experiment is started after the tension is stabilized for 1 h. After each experiment, the smooth muscle is rinsed 3 to 5 times, and the next experiment is carried out after stabilization to the baseline.

3. Effects of Compounds Tested on Contraction of Isolated Tracheal Strip in Guinea Pig After incubation of isolated tracheal for 1 h, 10 μm/L of carbachol is added to induce the minimum concentration (the concentration obtained from the dose-effect curve of carbachol) of the maximum tracheal smooth muscle contraction, and the changes in tension of the tracheal strip within 5 min are recorded. When the tension of the tracheal smooth muscle reaches the highest point, the compounds tested with a concentration of 1 nm/L are added, and the changes in tension of the tracheal strip within 5 min are recorded. Observe that the tension of the tracheal smooth muscle shows a downward trend. If there is no obvious trend, the above administration is repeated at a concentration which equals to the multiple of 10, namely 10 um/L, 100 nm/L and 1000 nm/L, until the tension of the tracheal smooth muscle shows a downward trend. Then, the concentration difference is decreased, that is, the concentration is increased by three or four times to repeat the above administration, which makes the tension decrease continuously to the base value (initial load). The changes in tension of the tracheal stop within 5 min are recorded. The dose-effect relationship between the compounds tested and the contractile activity of the isolated tracheal smooth muscle in the guinea pig is obtained. The curve of the changes in tension of the tracheal smooth muscle in each group is recorded and the inhibition rate is calculated. After repeated experiments, $IC_{50}$ value of each compound tested is calculated by taking points respectively.

In addition, the above experiments are repeated to record the dose-effect relationship between the positive drug tiotropium bromide and the contractile activity of the isolated tracheal smooth muscle in the guinea pig, and the $IC_{50}$ values are calculated and compared with that of the compounds tested. The dose-effect relationship between solvent (DMSO) control group and the contractile activity of the isolated tracheal smooth muscle in the guinea pig is recorded.

Figure 3:
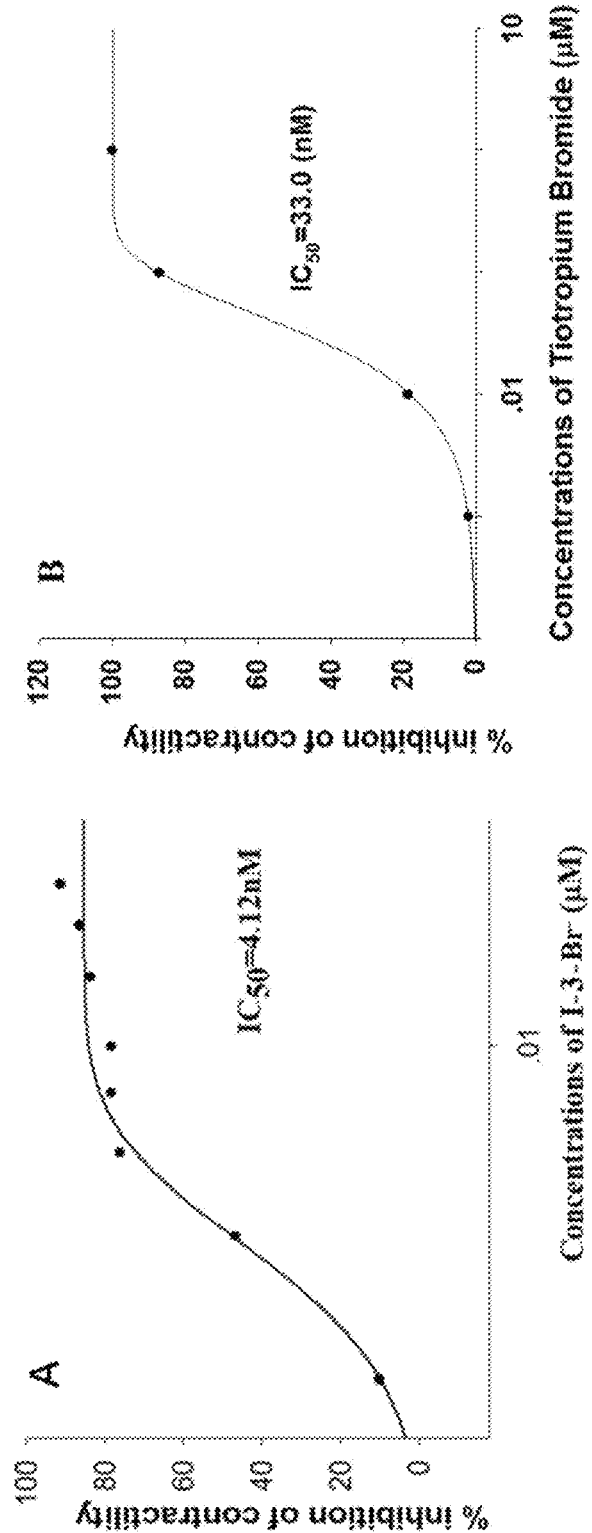
FIG. 3 shows the diastolic effect curves of compound I-3-Br (A) and tiotropium bromide (B) on the isolated tracheal model of guinea pigs.
Figure 4:
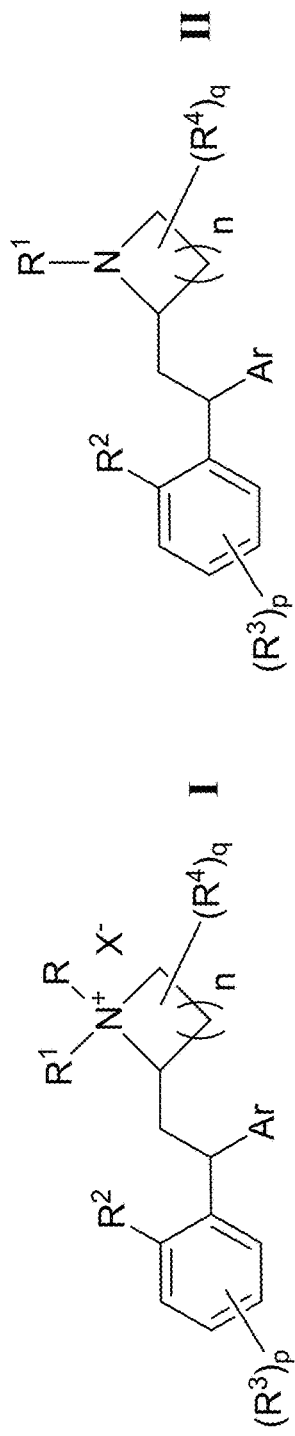
FIG. 4 shows the general formulas I and II of the 2-(2,2-diarylethyl)-cyclic amine derivative or pharmaceutically acceptable salts thereof.

Inhibition Rate=(Tension before Administration−Tension after Administration)/Tension before Administration The test results show that the 2-(2,2-diarylethyl)-cyclic amine derivative has a good vasodilatation effect on the tracheal smooth muscle. Taking the compound I-3-Br as an example, I-3-Br ($IC_{50}$=4.1 nM) shows a similar or better tracheal vasodilatation effect than that of tiotropium bromide ($IC_{50}$=33.0 nM), as shown in FIG. 3.

In a similar experiment with an isolated trachea, other compounds, such as I-2a-Br (IC50=6.4 nM), I-4a-Br (IC50=13.3 nM) and 1-7 (33.4 nM), also show a good vasodilatation effect on the isolated tracheal. These results are the same as that of the above cell activity assay.

Example of Efficacy Evaluation in Animal:

1. Screening of Animal

On the first day, guinea pigs are placed in a 38×38×38 cm (about 55 L) of home-made container with an atomizing nozzle having a diameter of about 3 cm above the side wall. Ultrasonic atomizer (YUWELL, model 402AI) is used to spray normal saline containing acetylcholine chloride (20 g/L) and histamine (1 g/L) for 15 s. The incubation period of asthma of guinea pigs (also is called asthma incubation period, which is the time from the end of the spray to asthma attack, extreme breathing difficulty until convulsion and fall)

is recorded after the cessation of spraying. Animals with an incubation period of less than 120 s are qualified sensitive animals.

2. Experimental Processes

On the second day, the qualified animals are selected for experiments, wherein one group (comprising 4 guinea pigs) is used as the control group, one group (comprising 4 guinea pigs) is experimented with positive medicine thiamethoxam bromide and one group (comprising 10 guinea pigs) is experimented with the drug to be tested. The animals are placed in a container, and sprayed with normal saline, tiotropium bromide and the compound to be tested. Both tiotropium bromide and the compound to be tested are soluble in normal saline at a concentration of 0.2 mM. After spraying for 10 min, the guinea pigs are taken out and put into another container of the same size. After 10 min, normal saline containing acetylcholine chloride (20 g/L) and histamine (1 g/L) is sprayed into the container for 15 s. The incubation periods of asthma of the guinea pigs are observed and recorded. If there is no convulsion and fall after 240 s, the incubation period is recorded as 240 s.

3. Experimental Results

The experimental results show that the asthma incubation period is 125.8±45.1 s in the control group and 238.9±5.0 s in the positive tiotropium bromide group. No asthma-induced convulsion and fall occurs in administration groups I-4a-1-Br, I-3-1-Br and I-10a-1 within 2.40 s, that is, the asthma, incubation period is 240 s. In addition, the asthma incubation periods of administration groups I-2a-1-Br and I-3-2-Br are 228.9±4.7 s and 233.1±21.8 s respectively. It can be seen that I-4a-1-Br, I-3-1-Br, I-10a-1, I-2a-1-Br and I-3-2-Br all show good efficacy.

Therefore, this kind of compound can be used to treat muscarine receptor-mediated or regulated diseases, including asthma, COPD, OAB, bronchospasm with chronic obstructive pulmonary disease, visceral spasm, irritable bowel syndrome, Parkinson's disease, depression or anxiety, schizophrenia and related mental diseases. This kind of compound show good prospects for patent medicines.

The compound and pharmaceutically acceptable salt thereof of the present invention can be taken in accordance with pharmacologically acceptable administration methods, including oral administration, percutaneous administration, parenteral administration, nasal and pulmonary administration, or by inhalation and blowing. The compound of the present invention uses a pharmaceutically acceptable carrier or diluent material which may be any inert, organic or inorganic material suitable for administration, such, as water, gelatin, arabic gum, lactose, microcrystal line cellulose, starch, sodium starch glycolate, calcium hydrogen phosphate, magnesium stearate, talcum powder and colloidal silicon dioxide. The drug composition also includes other pharmaceutically active agents and conventional additives, for example, stabilizers, wetting agents, emulsifiers, flavoring agents, buffers and the like. The compound of the present invention can be prepared into solid or liquid form, such as tablets, capsules, powders, syrups, aerosols, sterile solutions, suspensions or emulsions.

The above only describes preferred embodiments of the patent of the present invention and is not intended to limit the patent of the present invention. Any equivalent replacement or modification or other changes in the technical solution and technical content disclosed in the patent of the present invention made by any of those skilled in the art on the premise of not deviating from the technical solution of the patent of the present invention shall belong to the content not deviating from, the technical solution of the patent of the present invention and shall remain within the protection scope of the patent of the present invention.

The invention claimed is:

1. A 2-(2,2-diarylethyl)-cyclic amine derivative of formula I or pharmaceutically acceptable salt thereof of formula II,

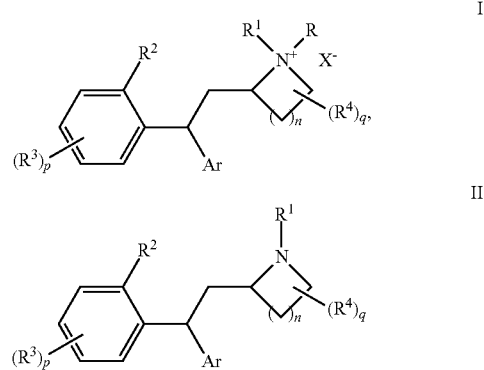

wherein,

X– is a pharmaceutically acceptable anion;

R is hydrogen, substituted or unsubstituted $C_{1-10}$ alkyl;

$R^1$ is substituted or unsubstituted $C_{1-10}$ alkyl;

n is 1, 2, 3, 4, or 5;

$R^2$ is —OH, —$CF_3$, —CN, halogen, nitro, amino, substituted or unsubstituted $C_{1-10}$ alkyl, or —O-Pg, wherein Pg is an oxygen protective group;

$R^3$ is independently —OH, —$CF_3$, —CN, halogen, substituted or unsubstituted $C_{1-10}$ alkyl, —O-Pg', substituted or unsubstituted $C_{1-10}$ alkoxy, substituted or unsubstituted $C_{3-10}$ cycloalkyl, or substituted or unsubstituted $C_{3-10}$ cycloalkyloxy at each occurrence, wherein Pg' is an oxygen protective group;

p is 0, 1, 2, 3, or 4;

$R^4$ is independently halogen, or substituted or unsubstituted $C_{1-10}$ alkyl at each occurrence;

q is 0, 1, 2, 3, or 4;

Ar is substituted or unsubstituted aryl or substituted or unsubstituted heterocyclic aryl, with the proviso that, when Ar is unsubstituted phenyl, the compound of formula II satisfies at least one of the following conditions: (1) $R^2$ is not hydrogen, (2) p is not 0, (3) q is not 0, (4) n is not 2, and (5) $R^1$ is not methyl.

2. The 2-(2,2-diarylethyl)-cyclic amine derivative or pharmaceutically acceptable salt thereof according to claim 1, wherein $R^2$ is hydroxy.

3. The 2-(2,2-diarylethyl)-cyclic amine derivative or pharmaceutically acceptable salt thereof according to claim 1, wherein $R^2$ is hydroxy, —OH, —$CF_3$, —CN, halogen, nitro, amino, substituted or unsubstituted $C_{1-10}$ alkyl, or —O-Pg, wherein Pg is selected from —$C_{1-10}$ alkyl, —$C_{1-4}$ alkylene-(substituted or unsubstituted phenyl), —$C_{1-4}$ alkylene-($C_{1-4}$ alkoxy), —$SiR^{2a}R^{2a'}R^{2a''}$, —$COR^{2b}$, —CO—$OR^{2b}$, —CO—$NR^{2b}R^{2b'}$, —$SO_2$$NR^{2b}R^{2b'}$, —$COAr'$, and —CO—$OAr'$, wherein $R^{2a}$, $R^{2a'}$ and $R^{2a''}$ are each independently —$C_{1-4}$ alkyl or phenyl; $R^{2b}$ and $R^{2b'}$ are each independently hydrogen, or substituted or unsubstituted —$C_{1-4}$ alkyl, provided that $R^{2b}$ is not hydrogen when directly connected to an oxygen atom; or $R^{2b}$, $R^{2b'}$ together with the nitrogen atom connected thereto, form a 4-8 membered heterocyclic ring; and Ar' is substituted or unsubstituted phenyl, or substituted or unsubstituted naphthyl.

4. The 2-(2,2-diarylethyl)-cyclic amine derivative or pharmaceutically acceptable salt thereof according to claim 1, wherein $R^2$ is —O-Pg, and Pg is selected from methyl, ethyl, allyl, benzyl, substituted benzyl, methoxymethyl (MOM), benzyloxymethyl (BOM), 2-methoxyethoxymethyl (MEM), trimethylsilyl (TMS), triethylsilyl (TES), triisopropylsilyl(TIPS), t-butyldimethylsilyl (TBDMS), —Si(Ph)$_2$C(CH$_3$)$_3$, tetrahydropyranyl (THP), formyl, acetyl, chloracetyl, dichloroacetyl, trichloroacetyl, trifluoroacetyl, propionyl, methoxyacetyl, benzoyl, methylsulfonyl, —CO—OCH$_3$, —CO—OCH$_2$CH$_3$, —CO—OPh, benzenesulfonyl, and p-toluenesulfonyl;

or $R^2$ is —OH, methoxyl, formyloxy, acetoxy, propionyloxy, benzoyloxy, —O—CO—OCH$_3$, —O—CO—OCH$_2$CH$_3$, or —O—CO—OPh.

5. The 2-(2,2-diarylethyl)-cyclic amine derivative or pharmaceutically acceptable salt thereof according to claim 1, wherein $R^3$ is independently —OH, —CF$_3$, —CN, halogen, C$_{1-10}$ alkyl, C$_{1-10}$ alkoxy, —(C$_{1-4}$ alkylene)-OH, —(C$_{1-4}$ alkylene)-O—CO—(C$_{1-10}$ alkyl), —(C$_{1-4}$ alkylene)-O—(C$_{1-10}$ alkyl), or —O-Pg', wherein Pg' is selected from —COR$^{2b}$, —CO—OR$^{2b}$, —CO—NR$^{2b}$R$^{2b'}$, —SO$_2$—NR$^{2b}$R$^{2b'}$, —COAr', and —CO—OAr' at each occurrence;

wherein $R^{2b}$ and $R^{2b'}$ are each independently hydrogen or optionally substituted C$_{1-4}$ alkyl, provided that $R^{2b}$ is not hydrogen when directly connected to the oxygen atom, or $R^{2b}$, $R^{2b'}$, together with the nitrogen atom connected thereto, form a 4-8 membered substituted or unsubstituted heterocyclic ring; and Ar' is substituted or unsubstituted phenyl, or substituted or unsubstituted naphthyl.

6. The 2-(2,2-diarylethyl)-cyclic amine derivative or pharmaceutically acceptable salt thereof according to claim 5, wherein $R^3$ is independently —OH, —F, —CF$_3$, —CN, methyl, ethyl, propyl, butyl, isopropyl, isobutyl, tert-butyl, methoxyl, ethoxyl, hydroxymethyl, or 2-hydroxyethyl at each occurrence.

7. The 2-(2,2-diarylethyl)-cyclic amine derivative or pharmaceutically acceptable salt thereof of claim 1, wherein p is 0 or 1; or, p is 1, and $R^3$ is connected to the meta position of $R^2$; or, p is 1, and $R^3$ is connected to the para position of $R^2$.

8. The 2-(2,2-diarylethyl)-cyclic amine derivative or pharmaceutically acceptable salt thereof of claim 1, wherein the

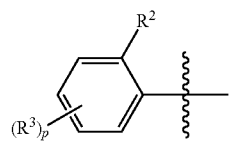

groups in the formulas I and II are selected from:

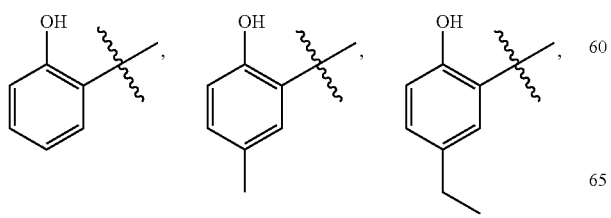

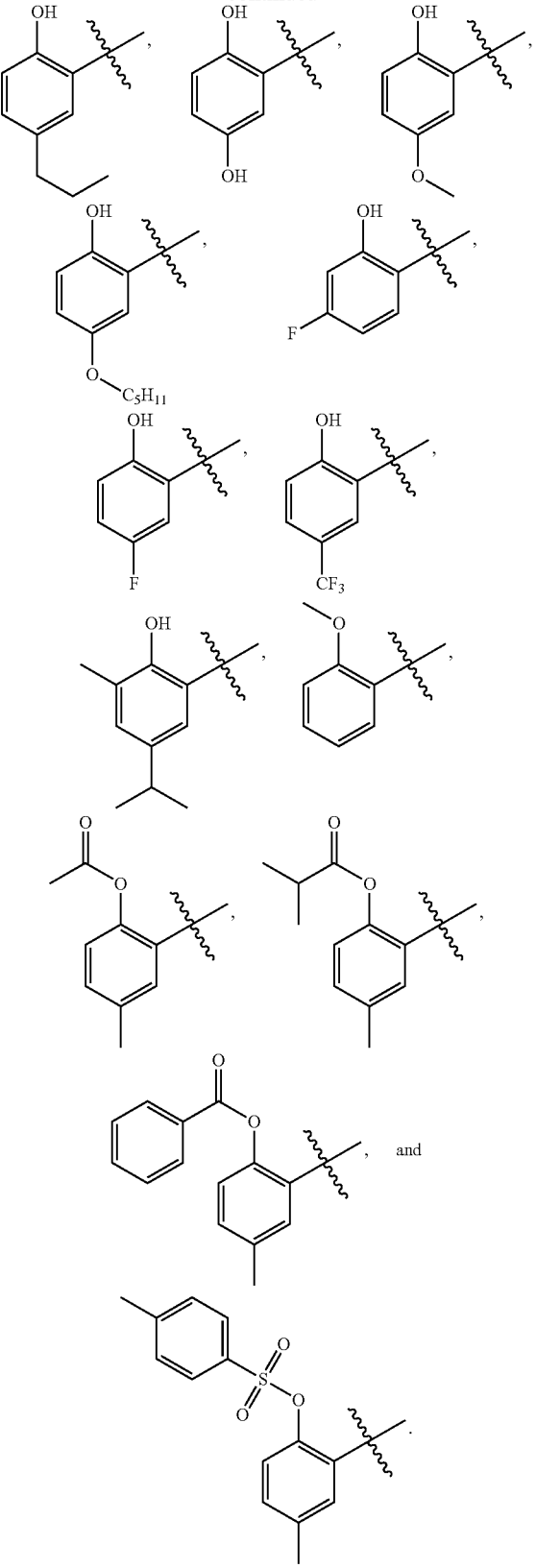

9. The 2-(2,2-diarylethyl)-cyclic amine derivative or pharmaceutically acceptable salt thereof of claim 1, wherein n is 2 or 3.

10. The 2-(2,2-diarylethyl)-cyclic amine derivative or pharmaceutically acceptable salt thereof of claim 1, wherein $R^4$ is independently F or $C_{1-4}$ alkyl at each occurrence.

11. The 2-(2,2-diarylethyl)-cyclic amine derivative or pharmaceutically acceptable salt thereof of claim 1, wherein q is 0, 1, or 2.

12. The 2-(2,2-diarylethyl)-cyclic amine derivative or pharmaceutically acceptable salt thereof of claim 1, wherein R is hydrogen or substituted or unsubstituted $C_{1-10}$ alkyl; and $R^1$ is substituted or unsubstituted $C_{1-10}$ alkyl, wherein "substituted or unsubstituted $C_{1-10}$ alkyl" means that $C_{1-10}$ alkyl is not substituted or is optionally substituted by one or more substituents, wherein each substituent is independently selected from $C_{3-6}$ cycloalkyl, $C_{1-6}$ alkoxy, —OH, halogen, and substituted or unsubstituted phenyl.

13. The 2-(2,2-diarylethyl)-cyclic amine derivative or pharmaceutically acceptable salt thereof of claim 1, wherein Ar is aryl or heterocyclic aryl optionally substituted by one or more substituents, wherein each substituent is independently selected from —OH, —$CF_3$, —CN, halogen, $C_{1-10}$ alkyl, $C_{3-10}$ cycloalkyl, and $C_{1-10}$ alkoxy.

14. The 2-(2,2-diarylethyl)-cyclic amine derivative or pharmaceutically acceptable salt thereof of claim 1, wherein Ar is selected from

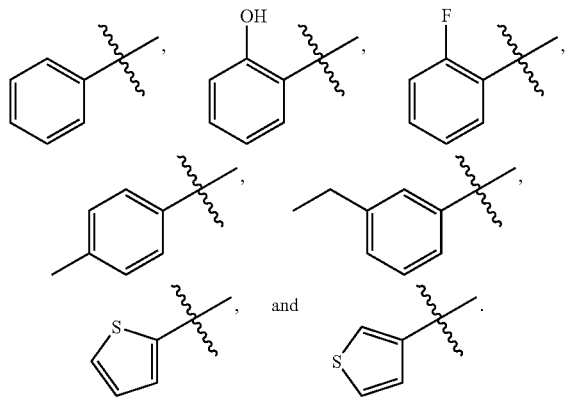

15. The 2-(2,2-diarylethyl)-cyclic amine derivative or pharmaceutically acceptable salt thereof of claim 1, wherein X– is the pharmaceutically acceptable anion selected from Cl⁻, Br⁻, I⁻, acetate ion, butanedioic acid ion, fumaric acid ion, and toluene-p-sulfonic acid ion.

16. The 2-(2,2-diarylethyl)-cyclic amine derivative or pharmaceutically acceptable salt thereof of claim 1 is one or more selected from:
- 2-[2-(2-hydroxy-phenyl)-phenethyl-]-N,N-dimethylpiperidine bromide/iodide (I-2a-Br or I-2a-I, and chiral monomers I-2a-1-Br and I-2a-2-Br),
- 2-[2-(2-hydroxy-phenyl)-phenethyl-]-N-methylpiperidine (diastereomer II-2a, and chiral monomers II-2a-1 and II-2a-2),
- 2-[2,2-bis (2-hydroxy-phenyl)-ethyl-]-N,N-dimethylpiperidine bromide/iodide (I-3-Br or I-3-I, and chiral monomers 1-3-1-Br, 1-3-2-Br, 1-3-1-I and I-3-2-I),
- 2-[2,2-bis (2-hydroxy-phenyl)-ethyl-]-N-methylpiperidine (II-3, and chiral monomers II-3-1 and II-3-2),
- 2-[2-(2-hydroxy-5-methyl-phenyl)-phenethyl-]-N,N-dimethylpiperidine bromide (diastereomers I-4a-Br and I-4b-Br; and chiral monomers I-4a-1-Br, I-4a-2-Br, I-4b-1-Br and I-4b-2-Br),
- 2-[2-(2-hydroxy-5-methyl-phenyl)-phenethyl-]-N,N-dimethylpiperidine iodide (I-4a-I, and chiral monomers I-4a-1-I and I-4a-2-I),
- 2-[2-(2-hydroxy-5-methyl-phenyl)-phenethyl-]-N-methyl, N-phenoxypropyl piperidine bromide (I-4a-PrOPh racemate, and chiral monomers I-4a-1-PrOPh and I-4a-2-PrOPh),
- 2-[2-(2-hydroxy-5-methyl-phenyl)-phenethyl-]-N-methylpiperidine (diastereomers II-4a and II-4b, and chiral monomers II-4a-1, II-4a-2, II-4b-1 and II-4b-2),
- 2-[2-(2-hydroxy-5-ethyl-phenyl)-phenethyl-]-N,N-dimethylpiperidine bromide/iodide (I-5-Br and I-5-I),
- 2-[2-(2-hydroxy-5-ethyl-phenyl)-phenethyl-]-N-methylpiperidine (II-5),
- 2-[2-(2-hydroxy-5-propyl-phenyl)-phenethyl-]-N,N-dimethylpiperidine bromide (I-6),
- 2-[2-(2-hydroxy-5-propyl-phenyl)-phenethyl-]-N-methylpiperidine (II-6),
- 2-[2-(2-fluorophenyl)-2-(2-hydroxy-5-methyl-phenyl)-ethyl-]-N,N-dimethylpiperidine bromide (I-7),
- 2-[2-(2-fluorophenyl)-2-(2-hydroxy-5-methyl-phenyl)-ethyl-]-N-methylpiperidine (II-7),
- 2-[2-(2-hydroxy-4-fluorophenyl)-phenethyl-]-N,N-dimethylpiperidine bromide (I-8),
- 2-[2-(2-hydroxy-4-fluorophenyl)-phenethyl-]-N-methylpiperidine (II-8),
- 2-[2-(2-hydroxy-5-methoxyl-phenyl)-phenethyl-]-N,N-dimethylpiperidine bromide (I-9),
- 2-[2-(2-hydroxy-5-methoxyl-phenyl)-phenethyl-]-N-methylpiperidine (II-9),
- 2-[2-(2-hydroxy-5-fluorophenyl)-phenethyl-]-N,N-dimethylpiperidine bromide (diastereomers I-10a and I-10b, and chiral monomers I-10a-1, I-10a-2, I-10b-1 and I-10b-2),
- 2-[2-(2-hydroxy-5-fluorophenyl)-phenethyl-]-N-methylpiperidine (diastereomers II-10a and II-10b,
- and chiral monomers II-10a-1, II-10a-2, II-10b-1 and II-10b-2),
- 2-[2-(2,5-dihydroxy-phenyl)-phenethyl-]-N-methylpiperidine (II-11),
- 2-[2-(2-hydroxy-5-pentyloxy-phenyl)-phenethyl-]-N-methylpiperidine (II-12),
- 2-[2-(2-hydroxy-5-trifluoromethyl-phenyl)-phenethyl-]-N-methylpiperidine (II-13),
- 2-[2-(4-chlorphenyl)-2-(2-hydroxy-5-methylphenyl)-ethyl-]-N-methylpiperidine (II-14),
- 2-[2-(4-chlorphenyl)-2-(2-hydroxy-5-methylphenyl)-ethyl-]-N,N-dimethylpiperidine bromide (I-14),
- 2-[2-(4-tolyl)-2-(2-hydroxy-5-methyl-phenyl)-ethyl-]-N-methylpiperidine (II-15),
- 2-[2-(4-tolyl)-2-(2-hydroxy-5-methyl-phenyl)-ethyl-]-N,N-dimethylpiperidine bromide (I-15),
- 2-[2-(2-hydroxy-3-methyl-5-isopropyl phenyl)-2-(3-ethyl phenyl)-ethyl-]-N-methylpiperidine (II-16),
- 2-[2-(2-methoxyl-phenyl)-phenethyl-]-N-methylpiperidine (II-17),
- 2-[2-(2-hydroxy-5-methyl-phenyl)-phenethyl-]-N-ethylpiperidine (II-18),
- 2-[2-(2-hydroxy-5-methyl-phenyl)-phenethyl-]-N,N-dimethylpyrrolidine bromide (I-19),
- 2-[2-(2-hydroxy-5-methyl-phenyl)-phenethyl-]-N-methylpyrrolidine (II-19),
- 2-[2-(2-hydroxy-5-ethyl-phenyl)-phenethyl-]-N,N-dimethylpyrrolidine bromide (I-20),
- 2-[2-(2-hydroxy-5-ethyl-phenyl)-phenethyl-]-N-methylpyrrolidine (II-20),
- 2-[2-(2-thienyl)-phenethyl]-N-methylpiperidine (II-21), 2-[2-(3-thienyl)-2-(2-hydroxy-5-methyl-phenyl)-ethyl-]-N,N-dimethylpiperidine bromide (I-22), 2-[2-(3-thienyl)-2-(2-hydroxy-5-methyl-phenyl)-ethyl-]-N-methylpiperidine (II-22), 2-[2-(2-isobutyryl ester group-5-methyl-phenyl)-phenethyl-]-N,N-dimethylpiperidine bromide (I-23), 2-[2-(2-isobutyryl ester group-5-methyl-phenyl)-phenethyl-]-N-methylpiperidine (II-23), 2-[2-(2-acetate group-5-methyl-phenyl)-phenethyl-]-N-methylpiperidine (II-24), 2-[2-(2-benzoate group-5-methyl-phenyl)-phenethyl-]-N,N-dimethylpiperidine bromide (I-25), 2-[2-(2-benzoate group-5-methyl-phenyl)-phenethyl-]-N-methylpiperidine (II-25), 2-[2-(2-methyl p-toluenesulfonate group-5-methyl-phenyl)-phenethyl-]-N,N-dimethylpiperidine bromide (I-26), and 2-[2-(2-methyl p-toluenesulfonate group-5-methyl-phenyl)-phenethyl-]-N-methylpiperidine (II-26).

17. The 2-(2,2-diarylethyl)-cyclic amine derivative or pharmaceutically acceptable salt thereof of claim 1 comprising on or more than one of the corresponding diastereomer mixtures, diastereomer monomers, enantiomer mixtures, enantiomer monomers, pharmaceutically acceptable salts, solvates, hydrates, and crystal forms thereof.

18. A pharmaceutical composition comprising one or more than one of the 2-(2,2-diarylethyl)-cyclic amine derivatives or pharmaceutically acceptable salts thereof of claim 1, pharmaceutically acceptable adjuvants.

19. A synthesis method of the 2-(2,2-diarylethyl)-cyclic amine derivative or pharmaceutically acceptable salt thereof of claim 1, comprising:

hydrogenating a compound of S-1 to form the compound of formula II:

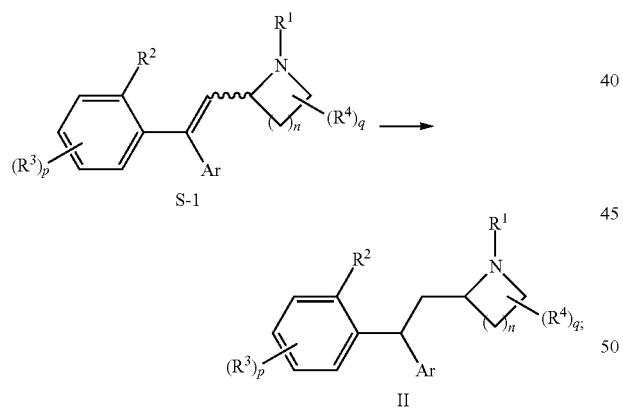

S-1 or synthesizing the compound of formula I by reacting the compound of formula II with an organic reagent R-L, wherein L is a leaving group:

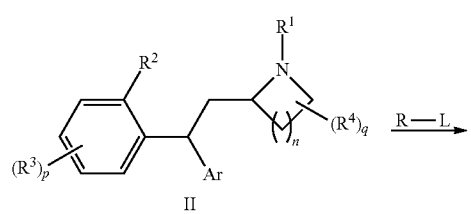

II

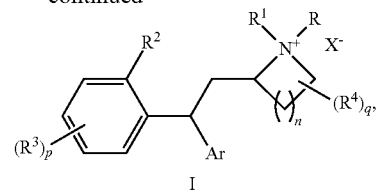

I

20. The synthetic method of claim 19, wherein R-L is an organic or inorganic acid or an alkylation reagent selected from organic halide, dialkyl sulfate, and dialkyl carbonate.

21. The synthetic method of claim 19, wherein $R^1$, $R^2$, $R^3$, and $R^4$ in the compound of formula S-1, the compound of formula II, and the compound of formula I are the same, respectively.

22. The synthetic method of claim 19, wherein $R^1$, $R^3$, and $R^4$ in the compound of formula II and the compound of formula I are the same, respectively, and $R^2$ is different.

23. The synthetic method of claim 19, wherein $R^2$ in the compound of formula II is —O-Pg, and Pg represents the oxygen protective group, and the oxygen protective group Pg is removed from $R^2$ in the compound of formula II to obtain a compound of formula S-2,

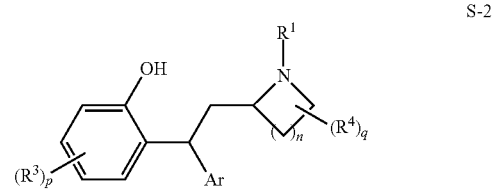

S-2

24. The synthetic method of claim 19, wherein $R^2$ in the compound of formula II is —OH, and the oxygen protective group is added to $R^2$ in the compound of formula II to obtain a compound of formula S-3,

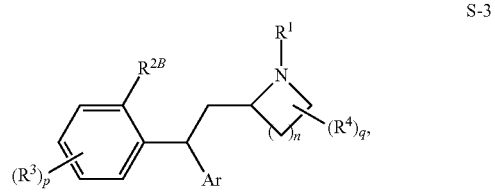

S-3 wherein $R^{2B}$ is —O-$Pg^B$, $Pg^B$ is the oxygen protective group, and the compound of formula S-3 is optionally reacted with the organic reagent R-L to produce the compound of formula I, wherein $R^2$ in the compound of formula I is the same as $R^{2B}$ in the compound of formula S-3.

25. A method for treating a disease or disorder mediated by muscarine receptors, comprising administering to a subject in need thereof an effective amount of a pharmaceutical composition, wherein the pharmaceutical composition comprises one or more than one of the 2-(2,2-diarylethyl)-cyclic amine derivatives or pharmaceutically acceptable salts thereof of claim 1.

26. A method for treating asthma, chronic obstructive pulmonary disease (COPD), overactive bladder (OAB), bronchospasm with chronic obstructive pulmonary disease, visceral spasm, irritable bowel syndrome, Parkinson's disease, depression, anxiety, or schizophrenia, comprising administering to a subject in need thereof an effective amount of a pharmaceutical composition, wherein the pharmaceutical composition comprises one or more than one of the 2-(2,2-diarylethyl)-cyclic amine derivatives or pharmaceutically acceptable salts thereof of claim 1.

* * * * *